US007342147B2

(12) United States Patent
Keetman et al.

(10) Patent No.: US 7,342,147 B2
(45) Date of Patent: Mar. 11, 2008

(54) EXPRESSION CASSETTES FOR ROOT-PREFERENTIAL EXPRESSION IN PLANTS

(75) Inventors: Ulrich Keetman, Quedlinburg (DE); Ute Linemann, Gatersleben (DE); Karin Herbers, Neustadt (DE); Helke Hillebrand, Mannheim (DE)

(73) Assignee: SunGene GmbH (DE)

( * ) Notice: Subject to any disclaimer, the term of this patent is extended or adjusted under 35 U.S.C. 154(b) by 0 days.

(21) Appl. No.: 11/285,701

(22) Filed: Nov. 22, 2005

(65) Prior Publication Data

US 2006/0117415 A1 Jun. 1, 2006

(30) Foreign Application Priority Data

Nov. 27, 2004 (EP) .................................. 04028202
Feb. 3, 2005 (EP) .................................. 05002261
Feb. 11, 2005 (EP) .................................. 05002849

(51) Int. Cl.
*C12N 15/82* (2006.01)
*A01H 5/10* (2006.01)
*C07H 21/04* (2006.01)

(52) U.S. Cl. .................. 800/287; 536/24.1; 435/320.1; 435/419; 435/468; 800/298

(58) Field of Classification Search ..................... None
See application file for complete search history.

(56) References Cited

U.S. PATENT DOCUMENTS 5,459,252 A 10/1995 Conkling et al.
5,466,785 A 11/1995 de Framond
5,633,363 A 5/1997 Colbert et al.
5,750,386 A 5/1998 Conkling et al.
5,837,848 A 11/1998 Ely et al.
6,018,099 A 1/2000 de Framond

FOREIGN PATENT DOCUMENTS

WO WO-02/38588 5/2002
WO WO-03/074688 9/2003

OTHER PUBLICATIONS

Oommenn et al 1994, The Plant Cell 6:1789-1803.*
Fourgoux-Nicol et al. 1999, Plant Molecular Biology 40 :857-872.*
Kim et al. 1994, Plant Molecular Biology 24: 105-117.*
Suzuki et al. 1993, Plant Mol. Biol. 21:109-119.*
Lin et al. 1999, Genbank accession: AC011765.*
Hass et al. 2002, Genbank accession: AY088286.*
Padgette et al 1995, Crop Sci. 35:1451-1461.*
An et al 1986, Plant Physiol. 81:301-305.*
Malboobi, M.A. et al., "A phosphate-starvation inducible β-glucosidase gene (*psr* 3.2) isolated from *Arabidopsis thaliana* is a member of a distinct subfamily of the BGA family", Plant Molecular Biology, 1997, vol. 34, pp. 57-68.

Nitz, I. et al., "*Pyk* 10, a seedling and root specific gene and promoter from *Arabidopsis thaliana*", Plant Science, 2001, vol. 161, pp. 337-346.

Müssig, C. et al., "Changes in gene expression in response to altered *SHL* transcript levels", Plant Molecular Biology, 2003, vol. 53, pp. 805-820.

Ahn, Y.O. et al., "Furcatin hydrolase from *Viburnum furcatum* blume is a novel disaccharide-specific acuminosidase in glycosyl hydrolase family 1", The Journal of Biological Chemistry, 2004, vol. 279, No. 22, pp. 23405-23414.

"Beta-glucosidase, putative; 11384-8406", Jun. 1, 2001, GenBank Accession No. Q9C8Y9.

"*Arabidopsis thaliana* chromosome 1 BAC T27F4 genomic sequence, complete sequence", Jan. 11, 2000, GenBank Accession No. AC020665.

"*Arabidopsis thaliana* hydrolase, hydrolyzing o-glycosyl compounds AT1G66280 mRNA, complete cds.", May 13, 2003, GenBank Accession No. NM_105299.

"*Arabidopsis thaliana* DNA binding / transcription factor AT1G74500 mRNA, complete cds.", Nov. 4, 2005, GenBank Accession No. NM_106110.

"Hydrolase, hydrolyzing o-glycosyl compounds [*Arabidopsis thaliana*].", Nov. 4, 2005, GenBank Accession NP_176802.

"DNA binding / transcription factor [*Arabidopsis thaliana*].", Nov. 4, 2005, GenBank Accession No. NP_177590.

"*Arabidopsis thaliana* peroxidase AT1G49570 mRNA, complete cds.", May 13, 2003, GenBank Accession No. NM_103845.

"Peroxidase [*Arabidopsis thaliana*]." May 13, 2003, GenBank Accession No. NP_175380.

"*Arabidopsis thaliana* CEL1; hydrolase, hydrolyzing o-glycosyl compounds AT1G70710 (CEL1) mRNA, complete cds.", May 14, 2003, GenBank Accession No. NM_105739.

"CEL1; hydrolase, hydrolyzing o-glycosyl compounds [*Arabidopsis thaliana*].", Nov. 4, 2005, GenBank Accession No. NP_177228.

"*Arabidopsis thaliana* UDP-glycosyltransferase/ transferase, transferring glycosyl groups AT5G66690 mRNA, complete cds.", May 13, 2003, GenBank Accession No. NM_126067.

"UDP-glycosyltransferase/transferase, transferring glycosyl groups [*Arabidopsis thaliana*].", Nov. 4, 2005, GenBank Accession No. NP_201470.

(Continued)

*Primary Examiner*—Aswin Mehta
*Assistant Examiner*—Li Zheng
(74) *Attorney, Agent, or Firm*—Connolly Bove Lodge & Hutz LLP

(57) ABSTRACT

The present invention relates to expression cassettes comprising transcription regulating sequences with root-preferential or root-specific expression profiles in plants obtainable from *Arabidopsis thaliana* genes At1g66280, At1g74500, At1g49570, At1g70710, At5g66690, At3g29630, At5g48070, or At4g17800.

15 Claims, No Drawings

OTHER PUBLICATIONS

"*Arabidopsis thaliana* transferase, transferring glycosyl groups AT3G29630 mRNA, complete cds." May 13, 2003, GenBank Accession No. NM_113884.

"Transferase, transferring glycosyl groups [*Arabidopsis thaliana*].", Nov. 4, 2005, GenBank Accession No. NP_189604.

"*Arabidopsis thaliana* ATXTH20; hydrolase, acting on glycosyl bonds / hydrolase, hydrolyzing o-glycosyl compounds AT5G48070 (ATXTH20) mRNA, complete cds.", May 13, 2003, GenBank Accession No. NM_124181.

"ATXTH20; hydrolase, acting on glycosyl bonds / hydrolase, hydrolyzing o-glycosyl compounds [*Arabidopsis thaliana*].", Nov. 4, 2005, GenBank Accession No. NP_199618.

"*Arabidopsis thaliana* unknown protein AT4G17800 mRNA, complete cds.", Feb. 17, 2004, GenBank Accession No. NM_117890.

"Unknown protein [*Arabidopsis thaliana*].", Nov. 4, 2005, GenBank Accession No. NP_193515.

Hwang I. et al., "*Arabidopsis thaliana* root-specific kinase homolog is induced by dehydration, ABA, and NaCI.", The Plant Journal, 1995, vol. 8(1), pp. 37-43.

* cited by examiner

SEQUENCE LISTING

```
<160> NUMBER OF SEQ ID NOS: 69

<210> SEQ ID NO 1
<211> LENGTH: 1656
<212> TYPE: DNA
<213> ORGANISM: Arabidopsis thaliana
<220> FEATURE:
<221> NAME/KEY: promoter
<222> LOCATION: (1)..(1656)
<223> OTHER INFORMATION: transcription regulating sequence from
      Arabidopsis thaliana gene At1g66280

<400> SEQUENCE: 1

gtttggccta aatgtgtaat gctgttactt cttttgactc aaagacatgt ttttgctcat     60

tagtaattca gacttcgagt agaaaaatag ataatggatt acaaaaacga aaaataaaat    120

aaagatgctt caaatttaac ctaaaatagt attagatctt tgtaagacac taagacccaa    180

ggattaaaca ttctaggaac taaattataa ttaaactctt ggaaaattaa gatctatttg    240

tttaggagct tttaagatat acatgtctag gctttaatga gctttacgac cgaagaaaat    300

tagagagctt gtgattttga tcatgatctg agtgagtctc aaaaactaaa aggaggacaa    360

taatgaagat tcgaattgaa ttctttaaac tagttaacta ggttaattgt tttatgggcc    420

tgttatgtta agttaataat ttttggggcc ttttatcttc aacatataaa gggctcttct    480
```

```
attgtttttt tccaactcca acaactaaaa tacaaacaaa ttttggacct tttattgtgg    540

accgtaggca gatgcccatg tttccatggg tgagagacgg acctgaggtg gtcgcaactc    600

gcaaccgacg ttcagaggga gaagcggagg tggtggtgga agcaaagaga gttagatgat    660

ggctgtggtg aggactatgt aaagtgtaaa catgtgtcac ttatctttgc ttattttaca    720

gttggaggaa atgccgaaat tgtatgtacc aagaaaatat acatgtatct gtttttatac    780

ttgttttaat gtctacagtg ttcgataaag ataccctgat caacttcata atgtaacaaa    840

aatgaagtca tgtatcaccg tagtggagtt aggtttgatg aattttaaaa ataaaactaa    900

ttcaactagc ttaaaattaa ttatcgccaa ataagtacca aacgtagccc gggctaaacc    960

ttagtatttt aaatatgcta aaaatctatt tacagataga tggtgcatcg ccatcaagta   1020

gcaaaataag cgtcagcgca atactatcaa cgaaaaaaga tggtatgtta aaaaaaggtt   1080

tctagctact acatattcga tttaaatatt tatcaaagta ataataatct acaatgtgat   1140

ttactgatca taatgcgtgg aaggtggaac atattatatt gttaatactt aacaatatta   1200

tcaaagtaca ataatgtgat tgctgatgca tcgtgacgta aaacaagaac accttcaaag   1260

tcaaacacca agagagattg tcgttacatg tgtttttaat gatatataag gaagcttcat   1320

tattttggag ttatacaacg actttcattc agtcacattt aatatatatt tgttgcttaa   1380

tcgtgacaca tgtcgaattt attttatttt ttagtattaa atagttttat atttaattgg   1440

aagtttccat ttccttgact acgccataaa gatacacaaa gactcttaac tgatccagat   1500

cattgaagta accaagggta agtaattgaa ctggccatag ttagtaaaag attgtaccaa   1560

ccgtttcttc attcttagga gagcaaaaaa aaactagtcg cagtgtattc ttcttctatg   1620

acgactagac gagagtagtg agtcgcaatg tgcttt                              1656
```

```
<210> SEQ ID NO 2
<211> LENGTH: 3293
<212> TYPE: DNA
<213> ORGANISM: Arabidopsis thaliana
<220> FEATURE:
<221> NAME/KEY: promoter
<222> LOCATION: (1)..(3293)
<223> OTHER INFORMATION: transcription regulating sequence from
      Arabidopsis thaliana gene
      At1g66280

<400> SEQUENCE: 2

gtttggccta aatgtgtaat gctgttactt cttttgactc aaagacatgt ttttgctcat     60

tagtaattca gacttcgagt agaaaaatag ataatggatt acaaaaacga aaaataaaat    120

aaagatgctt caaatttaac ctaaaatagt attagatctt tgtaagacac taagacccaa    180

ggattaaaca ttctaggaac taaattataa ttaaactctt ggaaaattaa gatctatttg    240

tttaggagct tttaagatat acatgtctag gctttaatga gctttacgac cgaagaaaat    300

tagagagctt gtgattttga tcatgatctg agtgagtctc aaaaactaaa aggaggacaa    360

taaggaagat tcggattgaa ttctttaaac tagttaacta ggttaattgt tttatgggcc    420

tgttatgtta agttaataat ttttggggcc ttttatcttc aacatataaa gggctcttct    480

attgtttttt tccaactcca acaactaaaa tacaaacaaa ttttggacct tttaatttgt    540

ggaccgtagc agatgcccat gtttccatgg gtgagagacg gacctgaggt ggtcgcaact    600

cgcaaccgac gttcagaggg agaagcggag gtggtggtgg aagcaaagag agttagatga    660

tggctgtggt gaggactatg taaagtgtaa acatgtgtca cttatctttg cttattttac    720

agttggagga aatgccgaaa ttgtatgtac caagaaaata tacatgtatc tgtttttata    780
```

-continued

```
cttgttttaa tgtctacagt gttcgataaa gataccctga tcaacttcat aatgtaacaa    840
aaatgaagtc atgtatcacc gtagtggagt taggtttgat gaattttaaa aataaaacta    900
attcaactag cttaaaatta attatcgcca aataagtacc aaacgtagcc cgggctaaac    960
cttagtattt taaatatgct aaaaatctat ttacagatag atggtgcatc gccatcaagt   1020
agcaaaataa gcgtcagcgc aatactatca acgaaaaaag atggtatgtt aaaaaaaggt   1080
ttctagctac tacatattcg atttaaatat ttatcaaagt aataataatc tacaatgtga   1140
tttactgatc ataatgcgtg gaaggtggaa cctattatat tgttaatact taacaatatt   1200
atcaaagtac aataatgtga ttgctgatgc atcgtgacgt aaaacaagaa caccttcaaa   1260
gtcaaacacc aagagagatt gtcgttacat gtgtttttaa tgatatataa ggaagcttca   1320
ttattttgga gttatacaac gactttcatt cagtcacatt taatatatat ttgttgctta   1380
atcgtgacac atgtcgaatt tattttattt tttagtattt aatagtttta tatttaattg   1440
gaagtttcca tttccttgac tacgccataa agatacacaa agactcttaa ctgatccaga   1500
tcattgaagt aaccaagggt aagtaattga actggccata gttagtaaaa gattgtacca   1560
accgtttctt cattcttagg agagcaaaaa aaactagtcg cagtgtattc ttcttctatg   1620
acgactagac gagagtagtg agtcgcaatg tgctttggta gggcatcagc taagaggaat   1680
acacatattt ttaagttgct ttcttccaag gtacaatatt tgacatatat atggacttgt   1740
aaacttacca gattttctga tcatgtaaat agtagctttc aatgtcctcg atcacaaagg   1800
ccatgaagtg tagcattttg agaaatggtc attccaaatc taaatggact ttctcattga   1860
gttgtttgaa agaaaaataa tcaattacac caccaattga tcgaccaaga aaaatgtttg   1920
gtgaataata gttaccccaa tttgtgtttt tttgggcaaa aaagttgccc cacatttata   1980
ttttaatttt gatgcctaaa tttcgttgat cttaattagg ctttaccgca ctgtcctgac   2040
agcagtcagc atgcgactag aatgtgacca attgtttgtc cgaaaccgaa gattactcat   2100
tccaaactcc cagtctaatt ggaggttgtg tcttgatatc taataacttg tttgataacc   2160
attataaggt cttttgctta ggttttacgg tccataagtt accaatgtat cctatgatca   2220
ggacgactac tacaggttca agattttgaa gatataggtc atacactaga ttttcttatt   2280
tataattgta tagtttagct tagtcacccg ggatctctca tcgaatgaat catcctattt   2340
aaataatagt caagcggaaa ccaataatga aagattatat taagttatga aaacgtcaat   2400
aataatcatg attaagataa gatcgaaaac accatttgga tgattagatc tatctatata   2460
gtaaaataaa ataaacatta tcaacgaggc ctggttgtgg catattaaaa acaagacatt   2520
aatgagagat cagtatcgct ataaaaaacg acactaacat ataaatgaac catcctaaaa   2580
ttgttttctt aatcaagaca aaagaaaaaa aagaaaacta aaaaccaaaa tgtcattgca   2640
aaagtttctc atggggacac gttgctccta accaccatcg tatacaatag ttaaataatt   2700
gtatactatc ttagtgggat aagtaaatga aagtttattc aataaatatt aatatcttaa   2760
acgtcaataa tacctaaagt aagatccaaa aactcgatct ggatcattac tatagaaaat   2820
taaagaaaat gattaacgag gccttgttgg catatctttt tcttttcttg taaaacagat   2880
ctggttgcat atttgaaagt agacattaaa tgagagatcc gttgattatg gaagattaaa   2940
tgttaatatt gttgctcgtt aaacacgaga aatattatta agacgaaggt gcaacaatag   3000
atgaagactt cagttatagg acatacacga tttttttttt tttttgatag gatacactat   3060
ttatttaaag gcacgttttt attatatgtt ccacgcgtaa tataatatgt tccaaacttt   3120
```

-continued

```
gaaaaataag taagaacaca cctatatata aaataaattt attaaacaaa tatagtttag   3180

tgacttattt gtcattacca aacaatcaaa atcactatat aattaagaac tctgtttaga   3240

tgtaaacaaa tcatcacaaa cttgttctct tccaaaagac caaaaattag aaa          3293
```

<210> SEQ ID NO 3
<211> LENGTH: 3246
<212> TYPE: DNA
<213> ORGANISM: Arabidopsis thaliana
<220> FEATURE:
<221> NAME/KEY: promoter
<222> LOCATION: (1)..(3246)
<223> OTHER INFORMATION: transcription regulating sequence from Arabidopsis thaliana gene At1g66280

<400> SEQUENCE: 3

```
gtttggccta aatgtgtaat gctgttactt cttttgactc aaagacatgt ttttgctcat     60

tagtaattca gacttcgagt agaaaaatag ataatggatt acaaaaacga aaaataaaat    120

aaagatgctt caaatttaac ctaaaatagt attagatctt tgtaagacac taagacccaa    180

ggattaaaca ttctaggaac taaattataa ttaaactctt ggaaaattaa gatctatttg    240

tttaggagct tttaagatat acatgtctag gctttaatga gctttacgac cgaagaaaat    300

tagagagctt gtgattttga tcatgatctg agtgagtctc aaaaactaaa aggaggacaa    360

taaggaagat tcggattgaa ttctttaaac tagttaacta ggttaattgt tttatgggcc    420

tgttatgtta agttaataat ttttggggcc ttttatcttc aacatataaa gggctcttct    480

attgtttttt tccaactcca acaactaaaa tacaaacaaa ttttggacct tttaatttgt    540

ggaccgtagc agatgcccat gtttccatgg gtgagagacg gacctgaggt ggtcgcaact    600

cgcaaccgac gttcagaggg agaagcggag gtggtggtgg aagcaaagag agttagatga    660

tggctgtggt gaggactatg taaagtgtaa acatgtgtca cttatctttg cttattttac    720

agttggagga aatgccgaaa ttgtatgtac caagaaaata tacatgtatc tgtttttata    780

cttgttttaa tgtctacagt gttcgataaa gataccctga tcaacttcat aatgtaacaa    840

aaatgaagtc atgtatcacc gtagtggagt taggtttgat gaattttaaa aataaaacta    900

attcaactag cttaaaatta attatcgcca aataagtacc aaacgtagcc cgggctaaac    960

cttagtattt taaatatgct aaaaatctat ttacagatag atggtgcatc gccatcaagt   1020

agcaaaataa gcgtcagcgc aatactatca acgaaaaaag atggtatgtt aaaaaaaggt   1080

ttctagctac tacatattcg atttaaatat ttatcaaagt aataataatc tacaatgtga   1140

tttactgatc ataatgcgtg gaaggtggaa cctattatat tgttaatact taacaatatt   1200

atcaaagtac aataatgtga ttgctgatgc atcgtgacgt aaaacaagaa caccttcaaa   1260

gtcaaacacc aagagagatt gtcgttacat gtgtttttaa tgatatataa ggaagcttca   1320

ttattttgga gttatacaac gactttcatt cagtcacatt taatatatat ttgttgctta   1380

atcgtgacac atgtcgaatt tattttattt tttagtattt aatagtttta tatttaattg   1440

gaagtttcca tttccttgac tacgccataa agatacacaa agactcttaa ctgatccaga   1500

tcattgaagt aaccaagggt aagtaattga actggccata gttagtaaaa gattgtacca   1560

accgtttctt cattcttagg agagcaaaaa aaactagtcg cagtgtattc ttcttctatg   1620

acgactagac gagagtagtg agtcgcaatg tgctttggta gggcatcagc taagaggaat   1680

acacatattt ttaagttgct ttcttccaag gtacaatatt tgacatatat atggacttgt   1740

aaacttacca gattttctga tcatgtaaat agtagctttc aatgtcctcg atcacaaagg   1800
```

-continued

```
ccatgaagtg tagcattttg agaaatggtc attccaaatc taaatggact ttctcattga   1860

gttgtttgaa agaaaaataa tcaattacac caccaattga tcgaccaaga aaaatgtttg   1920

gtgaataata gttaccccaa tttgtgtttt tttgggcaaa aaagttgccc cacatttata   1980

ttttaatttt gatgcctaaa tttcgttgat cttaattagg ctttaccgca ctgtcctgac   2040

agcagtcagc atgcgactag aatgtgacca attgtttgtc cgaaaccgaa gattactcat   2100

tccaaactcc cagtctaatt ggaggttgtg tcttgatatc taataacttg tttgataacc   2160

attataaggt cttttgctta ggttttacgg tccataagtt accaatgtat cctatgatca   2220

ggacgactac tacaggttca agattttgaa gatataggtc atacactaga ttttcttatt   2280

tataattgta tagtttagct tagtcacccg ggatctctca tcgaatgaat catcctattt   2340

aaataatagt caagcggaaa ccaataatga aagattatat taagttatga aaacgtcaat   2400

aataatcatg attaagataa gatcgaaaac accatttgga tgattagatc tatctatata   2460

gtaaaataaa ataaacatta tcaacgaggc ctggttgtgg catattaaaa acaagacatt   2520

aatgagagat cagtatcgct ataaaaaacg acactaacat ataaatgaac catcctaaaa   2580

ttgttttctt aatcaagaca aaagaaaaaa aagaaaacta aaaaccaaaa tgtcattgca   2640

aaagtttctc atggggacac gttgctccta accaccatcg tatacaatag ttaaataatt   2700

gtatactatc ttagtgggat aagtaaatga aagtttattc aataaatatt aatatcttaa   2760

acgtcaataa tacctaaagt aagatccaaa aactcgatct ggatcattac tatagaaaat   2820

taaagaaaat gattaacgag gccttgttgg catatctttt tcttttcttg taaaacagat   2880

ctggttgcat atttgaaagt agacattaaa tgagagatcc gttgattatg gaagattaaa   2940

tgttaatatt gttgctcgtt aaacacgaga aatattatta agacgaaggt gcaacaatag   3000

atgaagactt cagttatagg acatacacga tttttttttt tttttgatag gatacactat   3060

ttatttaaag gcacgttttt attatatgtt ccacgcgtaa tataatatgt tccaaacttt   3120

gaaaaataag taagaacaca cctatatata aaataaattt attaaacaaa tatagtttag   3180

tgacttattt gtcattacca aacaatcaaa atcactatat aattaagaac tctgtttaga   3240

tgtaaa                                                              3246
```

<210> SEQ ID NO 4
<211> LENGTH: 1656
<212> TYPE: DNA
<213> ORGANISM: Arabidopsis thaliana
<220> FEATURE:
<221> NAME/KEY: promoter
<222> LOCATION: (1)..(1656)
<223> OTHER INFORMATION: transcription regulating sequence from
      Arabidopsis thaliana gene At1g66280

<400> SEQUENCE: 4

```
gtttggccta aatgtgtaat gctgttactt cttttgactc aaagacatgt ttttgctcat     60

tagtaattca gacttcgagt agaaaaatag ataatggatt acaaaaacga aaaataaaat    120

aaagatgctt caaatttaac ctaaaatagt attagatctt tgtaagacac taagacccaa    180

ggattaaaca ttctaggaac taaattataa ttaaactctt ggaaaattaa gatctatttg    240

tttaggagct tttaagatat acatgtctag gctttaatga gctttacgac cgaagaaaat    300

tagagagctt gtgattttga tcatgatctg agtgagtctc aaaaactaaa aggaggacaa    360

taaggaagat tcggattgaa ttctttaaac tagttaacta ggttaattgt tttatgggcc    420

tgttatgtta agttaataat ttttggggcc ttttatcttc aacatataaa gggctcttct    480
```

-continued

```
attgtttttt tccaactcca acaactaaaa tacaaacaaa ttttggacct tttaatttgt    540

ggaccgtagc agatgcccat gtttccatgg gtgagagacg gacctgaggt ggtcgcaact    600

cgcaaccgac gttcagaggg agaagcggag gtggtggtgg aagcaaagag agttagatga    660

tggctgtggt gaggactatg taaagtgtaa acatgtgtca cttatctttg cttattttac    720

agttggagga aatgccgaaa ttgtatgtac caagaaaata tacatgtatc tgtttttata    780

cttgttttaa tgtctacagt gttcgataaa gataccctga tcaacttcat aatgtaacaa    840

aaatgaagtc atgtatcacc gtagtggagt taggtttgat gaattttaaa aataaaacta    900

attcaactag cttaaaatta attatcgcca aataagtacc aaacgtagcc cgggctaaac    960

cttagtattt taaatatgct aaaaatctat ttacagatag atggtgcatc gccatcaagt   1020

agcaaaataa gcgtcagcgc aatactatca acgaaaaaag atggtatgtt aaaaaaaggt   1080

ttctagctac tacatattcg atttaaatat ttatcaaagt aataataatc tacaatgtga   1140

tttactgatc ataatgcgtg gaaggtggaa cctattatat tgttaatact taacaatatt   1200

atcaaagtac aataatgtga ttgctgatgc atcgtgacgt aaaacaagaa caccttcaaa   1260

gtcaaacacc aagagagatt gtcgttacat gtgtttttaa tgatatataa ggaagcttca   1320

ttattttgga gttatacaac gactttcatt cagtcacatt taatatatat ttgttgctta   1380

atcgtgacac atgtcgaatt tattttattt tttagtattt aatagtttta tatttaattg   1440

gaagtttcca tttccttgac tacgccataa agatacacaa agactcttaa ctgatccaga   1500

tcattgaagt aaccaagggt aagtaattga actggccata gttagtaaaa gattgtacca   1560

accgtttctt cattcttagg agagcaaaaa aaactagtcg cagtgtattc ttcttctatg   1620

acgactagac gagagtagtg agtcgcaatg tgcttt                              1656
```

```
<210> SEQ ID NO 5
<211> LENGTH: 1870
<212> TYPE: DNA
<213> ORGANISM: Arabidopsis thaliana
<220> FEATURE:
<221> NAME/KEY: CDS
<222> LOCATION: (49)..(1623)
<223> OTHER INFORMATION: codinf for glycosyl hydrolase family 1 protein

<400> SEQUENCE: 5

aaatcatcac aaacttgttc tcttccaaaa gaccaaaaat tagaaacc atg gca ttg      57
                                                     Met Ala Leu
                                                     1

caa aag ttc cct ctc ctg ggg ctt ctt ttt ctc ata acc att gtc gtc      105
Gln Lys Phe Pro Leu Leu Gly Leu Leu Phe Leu Ile Thr Ile Val Val
    5                   10                  15

tct tcg aca ata gcc gtc gat gat cct gtg tgc cca acg acg tcc aaa      153
Ser Ser Thr Ile Ala Val Asp Asp Pro Val Cys Pro Thr Thr Ser Lys
20                  25                  30                  35

cta agc cga gca agt ttc cct aat ggg ttt gtg ttt ggc aca gct act      201
Leu Ser Arg Ala Ser Phe Pro Asn Gly Phe Val Phe Gly Thr Ala Thr
                40                  45                  50

gct gcg ttt cag gtt gaa ggt gca att aat gaa act tgt cgt gga cct      249
Ala Ala Phe Gln Val Glu Gly Ala Ile Asn Glu Thr Cys Arg Gly Pro
            55                  60                  65

gct cta tgg gat atc ttc tgt aag aga aat cca gag aga tgt agt ggc      297
Ala Leu Trp Asp Ile Phe Cys Lys Arg Asn Pro Glu Arg Cys Ser Gly
        70                  75                  80

cac aac gcc gat gtg gcc gtt gat ttc ttc cat cgt tat aag gaa gat      345
His Asn Ala Asp Val Ala Val Asp Phe Phe His Arg Tyr Lys Glu Asp
    85                  90                  95
```

-continued

```
att caa cta atg aag aat cta aac aca gac gca ttc aga ctc tca atc      393
Ile Gln Leu Met Lys Asn Leu Asn Thr Asp Ala Phe Arg Leu Ser Ile
100                 105                 110                 115

gca tgg tca aga ata ttt cct cat ggg aga aag gag aag gga gtg agt      441
Ala Trp Ser Arg Ile Phe Pro His Gly Arg Lys Glu Lys Gly Val Ser
                120                 125                 130

caa gct ggt gtg aaa ttc tac cac gac ctg atc gat gag ctc ctt aaa      489
Gln Ala Gly Val Lys Phe Tyr His Asp Leu Ile Asp Glu Leu Leu Lys
            135                 140                 145

aat ggt ata att ccg ttt gtg act gtt ttc cat tgg gac act cca caa      537
Asn Gly Ile Ile Pro Phe Val Thr Val Phe His Trp Asp Thr Pro Gln
        150                 155                 160

gat tta gaa gac gaa tat ggc ggt ttc tta agc gag aac att gtg aaa      585
Asp Leu Glu Asp Glu Tyr Gly Gly Phe Leu Ser Glu Asn Ile Val Lys
    165                 170                 175

gat ttc cga gaa tat gca gat tat gtt ttc act gaa tac ggt gga aaa      633
Asp Phe Arg Glu Tyr Ala Asp Tyr Val Phe Thr Glu Tyr Gly Gly Lys
180                 185                 190                 195

gtg aaa aac tgg atc act ttc aac gag cca tgg gtc ttc gct cat gca      681
Val Lys Asn Trp Ile Thr Phe Asn Glu Pro Trp Val Phe Ala His Ala
                200                 205                 210

ggt tac gac gta ggc aag aag gcg cca gga cgt tgt tct cgc tac ctt      729
Gly Tyr Asp Val Gly Lys Lys Ala Pro Gly Arg Cys Ser Arg Tyr Leu
            215                 220                 225

aaa ggt tgt gaa gac cga gat gga cga tca ggt tat gag gct tat cta      777
Lys Gly Cys Glu Asp Arg Asp Gly Arg Ser Gly Tyr Glu Ala Tyr Leu
        230                 235                 240

gtt agt cac aac ctc ctc aac gct cat gca gaa gct gtt gaa gtt ttc      825
Val Ser His Asn Leu Leu Asn Ala His Ala Glu Ala Val Glu Val Phe
    245                 250                 255

cgc caa aag gtt aaa ggt ggg aaa att gga atc gca cat agt ccg gct      873
Arg Gln Lys Val Lys Gly Gly Lys Ile Gly Ile Ala His Ser Pro Ala
260                 265                 270                 275

tgg ttc gaa cca cat gat ctt aaa gat tca aat gac gtt cca act gtt      921
Trp Phe Glu Pro His Asp Leu Lys Asp Ser Asn Asp Val Pro Thr Val
                280                 285                 290

agc cgt gta ctt gac ttt atg ttg gga tgg cat cta gac cca act act      969
Ser Arg Val Leu Asp Phe Met Leu Gly Trp His Leu Asp Pro Thr Thr
            295                 300                 305

ttt gga gat tat cca caa atc atg aaa gac ctt ctt ggt cac aga ttg     1017
Phe Gly Asp Tyr Pro Gln Ile Met Lys Asp Leu Leu Gly His Arg Leu
        310                 315                 320

ccc aaa ttc act tct tca caa aaa gca aaa ttg aaa gat tcg acc gat     1065
Pro Lys Phe Thr Ser Ser Gln Lys Ala Lys Leu Lys Asp Ser Thr Asp
    325                 330                 335

ttc gta ggg ctt aac tac tat act tca aca ttt tca aac cat aat gaa     1113
Phe Val Gly Leu Asn Tyr Tyr Thr Ser Thr Phe Ser Asn His Asn Glu
340                 345                 350                 355

aag cca gat ccg tct aca cca agt tgg aag caa gat tct ctt gtt gct     1161
Lys Pro Asp Pro Ser Thr Pro Ser Trp Lys Gln Asp Ser Leu Val Ala
                360                 365                 370

tgg gaa cct aag aat gta gat cac agc gcc att ggt agc cag cct ctt     1209
Trp Glu Pro Lys Asn Val Asp His Ser Ala Ile Gly Ser Gln Pro Leu
            375                 380                 385

acc gct gca ttg ccc gtc tac gct aaa ggt ttt aga agt ctt tta aag     1257
Thr Ala Ala Leu Pro Val Tyr Ala Lys Gly Phe Arg Ser Leu Leu Lys
        390                 395                 400

tac atc aaa gat aaa tac gca aac ccg gaa att atg atc atg gaa aat     1305
Tyr Ile Lys Asp Lys Tyr Ala Asn Pro Glu Ile Met Ile Met Glu Asn
```

```
    405                 410                 415

gga tat gga gat aaa ctt aag gac aaa gat tcg gtt gag gtt ggt act      1353
Gly Tyr Gly Asp Lys Leu Lys Asp Lys Asp Ser Val Glu Val Gly Thr
420                 425                 430                 435

gct gat tat aac agg aaa tac tat ctt cag agg cat ctt cta gct atg      1401
Ala Asp Tyr Asn Arg Lys Tyr Tyr Leu Gln Arg His Leu Leu Ala Met
                440                 445                 450

aac gaa gct att tgc att gac aaa gtg aga gtt acg gga tac ttt gta      1449
Asn Glu Ala Ile Cys Ile Asp Lys Val Arg Val Thr Gly Tyr Phe Val
            455                 460                 465

tgg tca tta tta gat aac ttt gaa tgg caa gat ggt tat aat aac aga      1497
Trp Ser Leu Leu Asp Asn Phe Glu Trp Gln Asp Gly Tyr Asn Asn Arg
        470                 475                 480

ttc gga ctc tat tac gtc gat ttc aaa aat aac ctc aca cgt tat gag      1545
Phe Gly Leu Tyr Tyr Val Asp Phe Lys Asn Asn Leu Thr Arg Tyr Glu
    485                 490                 495

aaa gaa tca gcc aag tac tac aaa gat ttc ctc ggt caa ggt gtt cgt      1593
Lys Glu Ser Ala Lys Tyr Tyr Lys Asp Phe Leu Gly Gln Gly Val Arg
500                 505                 510                 515

cca tcc gcg ctc aag aag gat gag ctt taa gttatatttt gaggatttgg       1643
Pro Ser Ala Leu Lys Lys Asp Glu Leu
                520

ttttctgttc aatgcttctt tcctatgttt tagtttgtga ttgatcatga ttcatgaagt   1703

cttggttaat aataataaaa gtgttttgta ttccttcagt ttctagctta tttgacatga   1763

tcaagaatgc tttagtataa atatattatc cttatatgaa ggtatcttta ccttcaaaac   1823

atgaagaaat attgtattat atatattaaa aaaagtctta aatttac                 1870


<210> SEQ ID NO 6
<211> LENGTH: 524
<212> TYPE: PRT
<213> ORGANISM: Arabidopsis thaliana

<400> SEQUENCE: 6

Met Ala Leu Gln Lys Phe Pro Leu Leu Gly Leu Leu Phe Leu Ile Thr
1               5                   10                  15

Ile Val Val Ser Ser Thr Ile Ala Val Asp Asp Pro Val Cys Pro Thr
            20                  25                  30

Thr Ser Lys Leu Ser Arg Ala Ser Phe Pro Asn Gly Phe Val Phe Gly
        35                  40                  45

Thr Ala Thr Ala Ala Phe Gln Val Glu Gly Ala Ile Asn Glu Thr Cys
    50                  55                  60

Arg Gly Pro Ala Leu Trp Asp Ile Phe Cys Lys Arg Asn Pro Glu Arg
65                  70                  75                  80

Cys Ser Gly His Asn Ala Asp Val Ala Val Asp Phe Phe His Arg Tyr
                85                  90                  95

Lys Glu Asp Ile Gln Leu Met Lys Asn Leu Asn Thr Asp Ala Phe Arg
            100                 105                 110

Leu Ser Ile Ala Trp Ser Arg Ile Phe Pro His Gly Arg Lys Glu Lys
        115                 120                 125

Gly Val Ser Gln Ala Gly Val Lys Phe Tyr His Asp Leu Ile Asp Glu
    130                 135                 140

Leu Leu Lys Asn Gly Ile Ile Pro Phe Val Thr Val Phe His Trp Asp
145                 150                 155                 160

Thr Pro Gln Asp Leu Glu Asp Glu Tyr Gly Gly Phe Leu Ser Glu Asn
                165                 170                 175
```

-continued

```
Ile Val Lys Asp Phe Arg Glu Tyr Ala Asp Tyr Val Phe Thr Glu Tyr
            180                 185                 190

Gly Gly Lys Val Lys Asn Trp Ile Thr Phe Asn Glu Pro Trp Val Phe
        195                 200                 205

Ala His Ala Gly Tyr Asp Val Gly Lys Lys Ala Pro Gly Arg Cys Ser
    210                 215                 220

Arg Tyr Leu Lys Gly Cys Glu Asp Arg Asp Gly Arg Ser Gly Tyr Glu
225                 230                 235                 240

Ala Tyr Leu Val Ser His Asn Leu Leu Asn Ala His Ala Glu Ala Val
                245                 250                 255

Glu Val Phe Arg Gln Lys Val Lys Gly Gly Lys Ile Gly Ile Ala His
            260                 265                 270

Ser Pro Ala Trp Phe Glu Pro His Asp Leu Lys Asp Ser Asn Asp Val
        275                 280                 285

Pro Thr Val Ser Arg Val Leu Asp Phe Met Leu Gly Trp His Leu Asp
    290                 295                 300

Pro Thr Thr Phe Gly Asp Tyr Pro Gln Ile Met Lys Asp Leu Leu Gly
305                 310                 315                 320

His Arg Leu Pro Lys Phe Thr Ser Ser Gln Lys Ala Lys Leu Lys Asp
                325                 330                 335

Ser Thr Asp Phe Val Gly Leu Asn Tyr Tyr Thr Ser Thr Phe Ser Asn
            340                 345                 350

His Asn Glu Lys Pro Asp Pro Ser Thr Pro Ser Trp Lys Gln Asp Ser
        355                 360                 365

Leu Val Ala Trp Glu Pro Lys Asn Val Asp His Ser Ala Ile Gly Ser
    370                 375                 380

Gln Pro Leu Thr Ala Ala Leu Pro Val Tyr Ala Lys Gly Phe Arg Ser
385                 390                 395                 400

Leu Leu Lys Tyr Ile Lys Asp Lys Tyr Ala Asn Pro Glu Ile Met Ile
                405                 410                 415

Met Glu Asn Gly Tyr Gly Asp Lys Leu Lys Asp Lys Asp Ser Val Glu
            420                 425                 430

Val Gly Thr Ala Asp Tyr Asn Arg Lys Tyr Tyr Leu Gln Arg His Leu
        435                 440                 445

Leu Ala Met Asn Glu Ala Ile Cys Ile Asp Lys Val Arg Val Thr Gly
    450                 455                 460

Tyr Phe Val Trp Ser Leu Leu Asp Asn Phe Glu Trp Gln Asp Gly Tyr
465                 470                 475                 480

Asn Asn Arg Phe Gly Leu Tyr Tyr Val Asp Phe Lys Asn Asn Leu Thr
                485                 490                 495

Arg Tyr Glu Lys Glu Ser Ala Lys Tyr Tyr Lys Asp Phe Leu Gly Gln
            500                 505                 510

Gly Val Arg Pro Ser Ala Leu Lys Lys Asp Glu Leu
        515                 520
```

<210> SEQ ID NO 7
<211> LENGTH: 3360
<212> TYPE: DNA
<213> ORGANISM: Arabidopsis thaliana
<220> FEATURE:
<221> NAME/KEY: promoter
<222> LOCATION: (1)..(3360)
<223> OTHER INFORMATION: transcription regulating sequence of Arabidopsis thaliana gene At1g74500

<400> SEQUENCE: 7

-continued

```
cgaaacaagt agcaaaacga ataaacaaaa cggatttgga ggttttaaca aaaaaaataa     60
gactgtaata agaatagaat gctcgtgaaa taaagcttaa tcttcgctgt cgattgatta    120
gtgatcatgt gccgcgagag acacgctgac cacaatttaa cacatctgag ctctttgttt    180
atgttccttt ctttagaaat aaaactcata tcaaatctta cctaaaataa aaaaaactta    240
caattagatc ttttctctct aatgtaatca cttttagact tatttaactt tgttttttta    300
tagcgaagaa aagttatgat tgattgtttt ggttgacctt gtgtgtatat actatctatt    360
tatgttcacc cgcaattatt atttaagtcc cctattcgaa ctttttatct ctagatatta    420
ttagttctct catgatcatg ttcaatccta tccacacaga tatatcatat ttgttgatga    480
ttcgatatag aactatcgag atgtctctaa ttttttttcat tatcttttgt aattcctgtt    540
atcttggaaa cgttttaaag ctatgtctga tatgtttatc aaataaagga aaaagggaaa    600
gaaaaaataa ctatgcctga tattgactct ccgacgaaaa cttggtgaga agaccattca    660
tgtcatttaa atggaacaca cgaagaagat aaatagtgaa attcggttgg agctaggtcc    720
ccatacctat cactagacta ccatctaatt atatatgata tatagtatat aaaaccacat    780
ttgatatgat cttataaatt aatattatac aataattttg acttttaata atttatcgct    840
catttaccat ttcaaaaatt gtgaaggtat atatacaata gtaggagtac aaaattttgt    900
atcattaaca ttttattttg ttatcgccaa ttttctaccg tttcaatgag ctagtgagaa    960
atggagttga gaatttgtac aacagcctac agcagtacaa ttaagttctt ctagaagatt   1020
ttactgaaat ggtcgctact tttcaacata caaggaattt gcatctaatg aatcaaaagt   1080
aaattgcatt accatatatt tctccaatgt attaaaatct gagattttgt gtttcgtcct   1140
ccacagctca ctcttcgagt ttacattttt tctttgtcgt cttatacttt ctctttttga   1200
aacatatctc cttattttct tggcttattt taactatata agaaagtacg taatttttac   1260
tatacaagaa tttgtagttt tcacttttca ggctcgaaac tacaaggatc tcagaattat   1320
tataaaaaag gcgtaagaaa tacaaagttg gcgaatattt ttctctgtaa actattgtcc   1380
taacattcgt tacaaagaaa aacaacgaat aagaaaatgc agaggtagat atgggtctaa   1440
aattttggat tgttgacgta acaaaaatat ctaaatttta accaatatat atctaaacga   1500
cttctgtgta ttgatacaaa aaataacaaa taaagataaa atattgatga gaataaattt   1560
tcctcaagtt tccaaacgat aggcaaatgt tggttttaat atttgctgtt aaaatcattt   1620
tagcatagtg gttaaattaa aaatgctttt agttagaaac atttagtgaa tacttgttgt   1680
tgttaaagaa acgttaagtg gatacggtag ttcaatactt taagtatgtt tctattctct   1740
tttttattct tattcatcat aatttttata ttttcctgtt ttctcttttc aataataata   1800
ttaattcata attaacttag atacattttc tatatcttta ggcctatgag tttctaaata   1860
cggccctagc tacgtgtttt tgtggtgcag ctgattagtg catatagcta aataaataac   1920
taaacaatga gatgaccgat gaagtgttca acgtcggtcg gtgcaagtga acgcgcctcc   1980
cgaaatgcca cgtgtgtgtt gttttgttga tcaaagaaca tgggcgtgtg tgtgatctct   2040
ttgaccagtc aaatcactca tactttggct ctttcctcat acacacaaaa tgtatacgta   2100
tattaattaa aagaattact gtgtgtagat tttttcttat acgtcgtcat gtattttttt   2160
tttaaaattt ggtcatgtat gtttttttat attctgcatt aaaaatacca aaacaattct   2220
tatattagag tagagggagt aaaaaaacaa aaaaaaaaac aaattgaatt acattgttaa   2280
ttaaatttct attttttttt ttatataact aattggctgt tcggtcattt ttgataaaaa   2340
cacactaaaa atgcttcaga aataatctga ttttgtattg tataaaatgc cggtttaaat   2400
```

-continued

```
aacaatgcca taaattataa gttggtagta ttaaaaaaaa tataaggtac atgtgtggac   2460
gtggtagagc gaaatcccaa acatcgataa tgtgaatttg tatcttaata gaagttgtgt   2520
ttcgaggaat ggataggctt attttactta taaagtatat ataaaaaaaa agtataatac   2580
tttcttcctt gataaacgca caaaattcag ttcaatatct tctttagttt aacattactc   2640
accacagaag taacaatact ctaccatctt tataaccttt caatatatac aaatgtttat   2700
ttctgttaca tgacgtccat gtctgttcgt ataaaataaa aaatattaaa atgtttcttt   2760
tcacttccta tttttttcgt aataaaaaaa ctaagttgaa gatatataaa ttattaaggt   2820
aatgaagaat gttaaaaata gaccttagaa gttagaactc taatatatga actgcaaggt   2880
ccgagtgtca aattcaaagc tcgaaacata ttaataaatt ttacggtata gggtaatttt   2940
tcatatatgt tttggctaga ttcaacgata tatattatta tacctagcaa atttagatct   3000
atgtacattt aaaatacgag attctctgaa atcgttctat tataacaaaa gttgtcagga   3060
gagggggcat ataattcaat atttgaaaaa taagattcgc aatatatttt tttctaacta   3120
aaataagaaa gcaattttat atatttttca taaacaaata ataaaaagac ctacataaat   3180
acaaccgtca cttcacttgt ttccttcata ctatcaactt ttctctatct atctctctct   3240
cttctttttc cggcataact tctgtgttac cctaaactcc ataacctgtt tcatcgataa   3300
agtgcctttg cttctatctc tgtcactctt actacttgtt gaacaatatt ctacaaaaaa   3360
```

<210> SEQ ID NO 8
<211> LENGTH: 3207
<212> TYPE: DNA
<213> ORGANISM: Arabidopsis thaliana
<220> FEATURE:
<221> NAME/KEY: promoter
<222> LOCATION: (1)..(3207)
<223> OTHER INFORMATION: transcription regulating sequence of
      Arabidopsis thaliana gene At1g74500

<400> SEQUENCE: 8

```
cgaaacaagt agcaaaacga ataaacaaaa cggatttgga ggttttaaca aaaaaaataa     60
gactgtaata agaatagaat gctcgtgaaa taaagcttaa tcttcgctgt cgattgatta    120
gtgatcatgt gccgcgagag acacgctgac cacaatttaa cacatctgag ctctttgttt    180
atgttccttt ctttagaaat aaaactcata tcaaatctta cctaaaataa aaaaaactta    240
caattagatc ttttctctct aatgtaatca cttttagact tatttaactt tgttttttta    300
tagcgaagaa aagttatgat tgattgtttt ggttgacctt gtgtgtatat actatctatt    360
tatgttcacc cgcaattatt atttaagtcc cctattcgaa ctttttatct ctagatatta    420
ttagttctct catgatcatg ttcaatccta tccacacaga tatatcatat ttgttgatga    480
ttcgatatag aactatcgag atgtctctaa ttttttttcat tatcttttgt aattcctgtt    540
atcttggaaa cgttttaaag ctatgtctga tatgtttatc aaataaagga aaaagggaaa    600
gaaaaaataa ctatgcctga tattgactct ccgacgaaaa cttggtgaga agaccattca    660
tgtcatttaa atggaacaca cgaagaagat aaatagtgaa attcggttgg agctaggtcc    720
ccatacctat cactagacta ccatctaatt atatatgata tatagtatat aaaaccacat    780
ttgatatgat cttataaatt aatattatac aataattttg acttttaata atttatcgct    840
catttaccat ttcaaaaatt gtgaaggtat atatacaata gtaggagtac aaaattttgt    900
atcattaaca ttttattttg ttatcgccaa ttttctaccg tttcaatgag ctagtgagaa    960
atggagttga gaatttgtac aacagcctac agcagtacaa ttaagttctt ctagaagatt   1020
```

-continued

```
ttactgaaat ggtcgctact tttcaacata caaggaattt gcatctaatg aatcaaaagt   1080
aaattgcatt accatatatt tctccaatgt attaaaatct gagattttgt gtttcgtcct   1140
ccacagctca ctcttcgagt ttacattttt tctttgtcgt cttatacttt ctctttttga   1200
aacatatctc cttattttct tggcttattt taactatata agaaagtacg taatttttac   1260
tatacaagaa tttgtagttt tcacttttca ggctcgaaac tacaaggatc tcagaattat   1320
tataaaaaag gcgtaagaaa tacaaagttg gcgaatattt ttctctgtaa actattgtcc   1380
taacattcgt tacaaagaaa aacaacgaat aagaaaatgc agaggtagat atgggtctaa   1440
aattttggat tgttgacgta acaaaaatat ctaaatttta accaatatat atctaaacga   1500
cttctgtgta ttgatacaaa aaataacaaa taaagataaa atattgatga gaataaattt   1560
tcctcaagtt tccaaacgat aggcaaatgt tggttttaat atttgctgtt aaaatcattt   1620
tagcatagtg gttaaattaa aaatgctttt agttagaaac atttagtgaa tacttgttgt   1680
tgttaaagaa acgttaagtg gatacggtag ttcaatactt taagtatgtt tctattctct   1740
tttttattct tattcatcat aatttttata ttttcctgtt ttctcttttc aataataata   1800
ttaattcata attaacttag atacattttc tatatcttta ggcctatgag tttctaaata   1860
cggccctagc tacgtgtttt tgtggtgcag ctgattagtg catatagcta aataaataac   1920
taaacaatga gatgaccgat gaagtgttca acgtcggtcg gtgcaagtga acgcgcctcc   1980
cgaaatgcca cgtgtgtgtt gttttgttga tcaaagaaca tgggcgtgtg tgtgatctct   2040
ttgaccagtc aaatcactca tactttggct ctttcctcat acacacaaaa tgtatacgta   2100
tattaattaa aagaattact gtgtgtagat tttttcttat acgtcgtcat gtattttttt   2160
tttaaaattt ggtcatgtat gtttttttat attctgcatt aaaaatacca aaacaattct   2220
tatattagag tagagggagt aaaaaaacaa aaaaaaaaac aaattgaatt acattgttaa   2280
ttaaatttct attttttttt ttatataact aattggctgt tcggtcattt ttgataaaaa   2340
cacactaaaa atgcttcaga aataatctga ttttgtattg tataaaatgc cggtttaaat   2400
aacaatgcca taaattataa gttggtagta ttaaaaaaaa tataaggtac atgtgtggac   2460
gtggtagagc gaaatcccaa acatcgataa tgtgaatttg tatcttaata gaagttgtgt   2520
ttcgaggaat ggataggctt attttactta taaagtatat ataaaaaaaa agtataatac   2580
tttcttcctt gataaacgca caaaattcag ttcaatatct tctttagttt aacattactc   2640
accacagaag taacaatact ctaccatctt tataaccttt caatatatac aaatgtttat   2700
ttctgttaca tgacgtccat gtctgttcgt ataaaataaa aaatattaaa atgtttcttt   2760
tcacttccta tttttttcgt aataaaaaaa ctaagttgaa gatatataaa ttattaaggt   2820
aatgaagaat gttaaaaata gaccttagaa gttagaactc taatatatga actgcaaggt   2880
ccgagtgtca aattcaaagc tcgaaacata ttaataaatt ttacggtata gggtaatttt   2940
tcatatatgt tttggctaga ttcaacgata tatattatta tacctagcaa atttagatct   3000
atgtacattt aaaatacgag attctctgaa atcgttctat tataacaaaa gttgtcagga   3060
gagggggcat ataattcaat atttgaaaaa taagattcgc aatatatttt tttctaacta   3120
aaataagaaa gcaattttat atatttttca taaacaaata ataaaaagac ctacataaat   3180
acaaccgtca cttcacttgt ttccttc                                        3207
```

<210> SEQ ID NO 9
<211> LENGTH: 3363
<212> TYPE: DNA

```
<213> ORGANISM: Arabidopsis thaliana
<220> FEATURE:
<221> NAME/KEY: promoter
<222> LOCATION: (1)..(3363)
<223> OTHER INFORMATION: transcription regulating sequence of
      Arabidopsis thaliana gene At1g74500

<400> SEQUENCE: 9

cgaaacaagt agcaaaacga ataaacaaaa cggatttgga ggttttaaca aaaaaaataa     60

gactgtaata agaatagaat gctcgtgaaa taaagcttaa tcttcgctgt cgattgatta    120

gtgatcatgt gccgcgagag acacgctgac cacaatttaa cacatctgag ctctttgttt    180

atgttccttt ctttagaaat aaaactcata tcaaatctta cctaaaataa aaaaaactta    240

caattagatc ttttctctct aatgtaatca cttttagact tatttaactt tgtttttta     300

tagcgaagaa aagttatgat tgattgtttt ggttgacctt gtgtgtatat actatctatt    360

tatgttcacc cgcaattatt atttaagtcc cctattcgaa ctttttatct ctagatatta    420

ttagttctct catgatcatg ttcaatccta tccacacaga tatatcatat ttgttgatga    480

ttcgatatag aactatcgag atgtctctaa tttttttcat tatcttttgt aattcctgtt    540

atcttggaaa cgttttaaag ctatgtctga tatgtttatc aaataaagga aaaagggaaa    600

gaaaaaataa ctatgcctga tattgactct ccgacgaaaa cttggtgaga agaccattca    660

tgtcatttaa atggaacaca cgaagaagat aaatagtgaa attcggttgg agctaggtcc    720

ccatacctat cactagacta ccatctaatt atatatgata tatattatat aaaaccacat    780

ttgatatgat cttataaatt aatattatac aataattttg acttttaata atttatcgct    840

catttaccat ttcaaaaatt gtgaaggtat atatacaata gtaggagtac aaaattttgt    900

atcattaaca ttatattttg ttatcgccaa ttttctaccg tttcaatgag ctagtgagaa    960

atggagttga aaatttgtac aacagcctac agcagtacaa ttaagttctt ctagaagatt   1020

ttactgaaat ggtcgctact tttcaacata caaggaattt gcatttaatg aatcaaaagt   1080

aaattgcatt accatatatt tctccaatgt attaaaatct gagattttgt gtttcgtcct   1140

ccacagctca ctcttcgagt ttacattttt tctttgtcgt cttatacttt ctctttttga   1200

aacatatctc cttattttct tggcttattt taactatata agaaagtacg taatttttac   1260

tatacaagaa tttgtagttt tcacttttca ggctcgaaac tacaaggatc tcagaattat   1320

tataaaaaag gcgtaagaaa tacaaagttg gcgaatattt ttctctgtaa actattgtcc   1380

taacattcgt tacaaagaaa aacaacgaat aagaaaatgc agaggtagat atgggtctaa   1440

aattttggat tgttgacgta acaaaaatat ctaaatttta accaatatat atctaaacga   1500

cttctgtgta ttgatacaaa aaataacaaa taaagataaa atattgatga aaataaattt   1560

tcctcaagtt tccaaacgat aggcaaatgt tggttttaat atttgctgtt aaaatcattt   1620

tagcatagtg gttaaattaa aaatgctttt agttagaaac atttagtgaa tacttgttgt   1680

tgttaaagaa acgttaagtg gatacggtag ttcaatactt taagtatgtt tctattctct   1740

tttttattct tattcatcat aatttttata ttttcctgtt ttctcttttc aataataata   1800

ttaattcata attaacttag atacattttc tatatcttta ggcctatgag tttctaaata   1860

cggccctagc tacgtgtttt tgtggtgcag ctgattagtg catatagcta aataaataac   1920

taaacaatga gatgaccgat gaagtgttca acgtcggtcg gtgcaagtga acgcgcctcc   1980

cgaaatgcca cgtgtgtgtt gttttgttga tcaaagaaca tgggcgtgtg tgtgatctct   2040

ttgaccagtc aaatcactca tactttggct ctttcctcat acacacaaaa tgtatacgta   2100
```

-continued

```
tattaattaa aagaattact gtgtgtagat tttttcttat acgtcgtcat gtattttttt   2160

ttaaatttgg tcatgtatgt ttttttatat tctgcattaa aaataccaaa acaattctta   2220

tattagagta gagggagtaa aaaaacaaaa aaaaaacaaa acaaattgaa ttacattgtt   2280

aattaaattt cttttttttt ttttatataa ctaattggct gttcggtcat ttttgataaa   2340

aacacactaa aaatgcttca gaaataatct gattttgtat tgtataaaat gccggtttaa   2400

ataacaatgc cataaattat aagttggtag tattaaaaaa aatataaggt acatgtgtgg   2460

acgtggtaga gcgaaatccc aaacatcgat aatgtgaatt tgtatcttaa tagaagttgt   2520

gtttcgagga atggataggc ttattttact tataaagtat atataaaaaa aaaagtataa   2580

tactttcttc cttgataaac gcacaaaatt cagttcaata tcttctttag tttaacatta   2640

ctcaccacag aagtaacaat actctaccat ctttataacc tttcaatata tacaaatgtt   2700

tatttctgtt acatgacgtc catgtctgtt cgtataaaat aaaaaatatt aaaatgtttc   2760

ttttcacttc ctattttttt cgtaataaaa aaactaagtt gaagatatat aaattattaa   2820

ggtaatgaag aatgttaaaa atagacctta gaagttagaa ctctaatata tgaactgcaa   2880

ggtccgagtg tcaaattcaa agctcgaaac atattaataa attttacggt atagggtaat   2940

ttttcatata tgttttggct agattcaacg atatatatta ttatacctag caaatttaga   3000

tctatgtaca tttaaaatac gagattctct gaaatcgttc tattataaca aaagttgtca   3060

ggagaggggg catataattc aatatttgaa aaataagatt cgcaatatat ttttttctaa   3120

ctaaaataag aaagcaattt tatatatttt tcataaacaa ataataaaaa gacctacata   3180

aatacaaccg tcacttcact tgtttccttc atactatcaa cttttctcta tctatctctc   3240

tctcttcttt ttccggcata acttctgtgt taccctaaac tccataacct gtttcaccga   3300

taaagtgcct ttgcttctat ctctgtcact cttactactt gttgaacaat attctacaaa   3360

aaa                                                                 3363


<210> SEQ ID NO 10
<211> LENGTH: 1291
<212> TYPE: DNA
<213> ORGANISM: Arabidopsis thaliana
<220> FEATURE:
<221> NAME/KEY: promoter
<222> LOCATION: (1)..(1291)
<223> OTHER INFORMATION: transcription regulating sequence of
      Arabidopsis thaliana gene At1g74500

<400> SEQUENCE: 10

tctttcctca tacacacaaa atgtatacgt atattaatta aaagaattac tgtgtgtaga     60

tttttttctta tacgtcgtca tgtatttttt ttttaaaatt tggtcatgta tgttttttta    120

tattctgcat taaaaatacc aaaacaattc ttatattaga gtagagggag taaaaaaaca    180

aaaaaaaaaa caaattgaat tacattgtta attaaatttc tatttttttt tttatataac    240

taattggctg ttcggtcatt tttgataaaa acacactaaa aatgcttcag aaataatctg    300

attttgtatt gtataaaatg ccggtttaaa taacaatgcc ataaattata agttggtagt    360

attaaaaaaa atataaggta catgtgtgga cgtggtagag cgaaatccca aacatcgata    420

atgtgaattt gtatcttaat agaagttgtg tttcgaggaa tggataggct tattttactt    480

ataaagtata tataaaaaaa aagtataata ctttcttcct tgataaacgc acaaaattca    540

gttcaatatc ttctttagtt taacattact caccacagaa gtaacaatac tctaccatct    600

ttataacctt tcaatatata caaatgttta tttctgttac atgacgtcca tgtctgttcg    660
```

```
tataaaataa aaaatattaa aatgtttctt ttcacttcct attttttttcg taataaaaaa    720

actaagttga agatatataa attattaagg taatgaagaa tgttaaaaat agaccttaga    780

agttagaact ctaatatatg aactgcaagg tccgagtgtc aaattcaaag ctcgaaacat    840

attaataaat tttacggtat agggtaattt ttcatatatg ttttggctag attcaacgat    900

atatattatt atacctagca aatttagatc tatgtacatt taaaatacga gattctctga    960

aatcgttcta ttataacaaa agttgtcagg agagggggca tataattcaa tatttgaaaa   1020

ataagattcg caatatattt ttttctaact aaaataagaa agcaatttta tatatttttc   1080

ataaacaaat aataaaaaga cctacataaa tacaaccgtc acttcacttg tttccttcat   1140

actatcaact tttctctatc tatctctctc tcttcttttt ccggcataac ttctgtgtta   1200

ccctaaactc cataacctgt ttcatcgata aagtgccttt gcttctatct ctgtcactct   1260

tactacttgt tgaacaatat tctacaaaaa a                                 1291
```

```
<210> SEQ ID NO 11
<211> LENGTH: 1294
<212> TYPE: DNA
<213> ORGANISM: Arabidopsis thaliana
<220> FEATURE:
<221> NAME/KEY: promoter
<222> LOCATION: (1)..(1294)
<223> OTHER INFORMATION: transcription regulating sequence of
      Arabidopsis thaliana gene At1g74500

<400> SEQUENCE: 11
```

```
tctttcctca tacacacaaa atgtatacgt atattaatta aaagaattac tgtgtgtaga     60

tttttttctta tacgtcgtca tgtatttttt tttaaatttg gtcatgtatg ttttttttata    120

ttctgcatta aaaataccaa aacaattctt atattagagt agagggagta aaaaaacaaa    180

aaaaaaacaa aacaaattga attacattgt taattaaatt tcttttttttt tttttatata    240

actaattggc tgttcggtca tttttgataa aaacacacta aaaatgcttc agaaataatc    300

tgattttgta ttgtataaaa tgccggttta aataacaatg ccataaatta taagttggta    360

gtattaaaaa aaatataagg tacatgtgtg gacgtggtag agcgaaatcc caaacatcga    420

taatgtgaat ttgtatctta atagaagttg tgtttcgagg aatggatagg cttattttac    480

ttataaagta tatataaaaa aaaaagtata atactttctt ccttgataaa cgcacaaaat    540

tcagttcaat atcttcttta gtttaacatt actcaccaca gaagtaacaa tactctacca    600

tctttataac ctttcaatat atacaaatgt ttatttctgt tacatgacgt ccatgtctgt    660

tcgtataaaa taaaaaaatat taaaatgttt cttttcactt cctatttttt tcgtaataaa    720

aaaactaagt tgaagatata taaattatta aggtaatgaa gaatgttaaa aatagacctt    780

agaagttaga actctaatat atgaactgca aggtccgagt gtcaaattca aagctcgaaa    840

catattaata aattttacgg tatagggtaa tttttcatat atgttttggc tagattcaac    900

gatatatatt attataccta gcaaatttag atctatgtac atttaaaata cgagattctc    960

tgaaatcgtt ctattataac aaaagttgtc aggagagggg gcatataatt caatatttga   1020

aaaataagat tcgcaatata ttttttttcta actaaaataa gaaagcaatt ttatatattt   1080

ttcataaaca aataataaaa agacctacat aaatacaacc gtcacttcac ttgtttcctt   1140

catactatca acttttctct atctatctct ctctcttctt tttccggcat aacttctgtg   1200

ttaccctaaa ctccataacc tgtttcaccg ataaagtgcc tttgcttcta tctctgtcac   1260

tcttactact tgttgaacaa tattctacaa aaaa                              1294
```

-continued

```
<210> SEQ ID NO 12
<211> LENGTH: 557
<212> TYPE: DNA
<213> ORGANISM: Arabidopsis thaliana
<220> FEATURE:
<221> NAME/KEY: CDS
<222> LOCATION: (154)..(435)
<223> OTHER INFORMATION: coding for bHLH family protein

<400> SEQUENCE: 12

atactatcaa cttttctcta tctatctctc tctcttcttt ttccggcata acttctgtgt      60

taccctaaac tccataacct gtttcaccga taaagtgcct ttgcttctat ctctgtcact     120

cttactactt gttgaacaat attctacaaa aaa atg tcg gga aga aga tca cgt      174
                                     Met Ser Gly Arg Arg Ser Arg
                                     1               5

tcg agg caa tca tca gga act tca agg atc tca gaa gat caa atc aat      222
Ser Arg Gln Ser Ser Gly Thr Ser Arg Ile Ser Glu Asp Gln Ile Asn
        10                  15                  20

gat ctg att atc aag ttg caa cag ctt ctt cct gag ctc agg gac agt      270
Asp Leu Ile Ile Lys Leu Gln Gln Leu Leu Pro Glu Leu Arg Asp Ser
    25                  30                  35

cgt cgt tcc gac aag gtt tca gca gcg agg gtg tta caa gat acg tgc      318
Arg Arg Ser Asp Lys Val Ser Ala Ala Arg Val Leu Gln Asp Thr Cys
40                  45                  50                  55

aac tac ata cgg aat ctg cat aga gag gtt gat gat cta agt gag agg      366
Asn Tyr Ile Arg Asn Leu His Arg Glu Val Asp Asp Leu Ser Glu Arg
                60                  65                  70

cta tct gag tta cta gca aac tca gac act gca caa gct gct tta atc      414
Leu Ser Glu Leu Leu Ala Asn Ser Asp Thr Ala Gln Ala Ala Leu Ile
            75                  80                  85

aga agc tta ctt acc caa taa ttcctatcta tctttttctt cttcttcttt         465
Arg Ser Leu Leu Thr Gln
        90

tttttgttta ctataataat aataatagtt tgcgggtttt tttttctata gatgttgatg    525

accttataaa cgtttaatga tacgagttcg tc                                  557


<210> SEQ ID NO 13
<211> LENGTH: 93
<212> TYPE: PRT
<213> ORGANISM: Arabidopsis thaliana

<400> SEQUENCE: 13

Met Ser Gly Arg Arg Ser Arg Ser Arg Gln Ser Ser Gly Thr Ser Arg
1               5                   10                  15

Ile Ser Glu Asp Gln Ile Asn Asp Leu Ile Ile Lys Leu Gln Gln Leu
            20                  25                  30

Leu Pro Glu Leu Arg Asp Ser Arg Arg Ser Asp Lys Val Ser Ala Ala
        35                  40                  45

Arg Val Leu Gln Asp Thr Cys Asn Tyr Ile Arg Asn Leu His Arg Glu
    50                  55                  60

Val Asp Asp Leu Ser Glu Arg Leu Ser Glu Leu Leu Ala Asn Ser Asp
65                  70                  75                  80

Thr Ala Gln Ala Ala Leu Ile Arg Ser Leu Leu Thr Gln
                85                  90


<210> SEQ ID NO 14
<211> LENGTH: 2831
<212> TYPE: DNA
<213> ORGANISM: Arabidopsis thaliana
```

-continued

<400> SEQUENCE: 14

```
atttgcagag attatactta gccttgtttt tgtaaacggc tttttttggt tgggttttta      60
tttttcttga ggcattatcc aatattcaag taataatttt gatgtttttg tttcataatt     120
ttgtgtgtgt agtttacaaa aagagcataa taataggagg gacataagca tgtgtttggt     180
catttattca gattcatagt agagatgctt tgaatttttt gttcataagc tttgaaataa     240
tgttcttcaa cgctcaccta atcattcggt cgttcgttca attgactaaa aggtctttag     300
ctttgaccga cagatgcgta ttacatatgg tattatttta aattatgttt tttttgggtg     360
aatttataat aacaaaaaaa atcaacaagc agaaaagttt gggcattttg ggtatatata     420
tatatatatg cctcatgcta cccagccggc ccacctcatg ttttcagccc aatgatacat     480
atgagcaaga aaaacactgc atagcaaatg attttcattt gcacaaaaaa aaaaaaaaaa     540
gcaaatgatt ttcaatttta tttttgaaat gaatttgaaa ggtttgagac tatcgtgaat     600
atatataaaa ttaaaaaaca acttaaatga ataatcttgg aactggaaaa cagattaata     660
atgagttttt agtttgaaac tacacaaaat agataccttg gacttggaca gtaaaatatc     720
tgattttttt acaaacttca tgacattttc cgataatttt accaatattt tgccacataa     780
ttaaaaaaac ttatctcaat tcgtatcatc agttttttta aacaactgca catgtatatc     840
gtttgctaca aattcatagt aatggttcac aaaaatttat agaaatttca gtacttttgt     900
tatagatata aattttgaaa cgacaaaatg ttttgctact ttctaccgca atactgttat     960
ctaattgtaa ttaattattt ctaactttga cctaagttat aactcaacga cgatactata    1020
gtacaagctt attactaaac tacaaattta aacaggggtg tgactctagc tagctagttt    1080
ataataaatg agacgcaatg atggatatgc agctacaagt gggttcataa aatattacat    1140
atccactttg gttgtggaaa ctggaaagtt atgtaaattt tggccaacca aaggaagcaa    1200
agactttgct tctcaactct tcgagtacac ttccgagtaa gcttccaaca tgggcacgta    1260
gtggaatatg ttgcgcaatc ctcttgatgt cataaacata atggacaaaa ataatttaaa    1320
atttacgtac acatgtttct taaaactcca aattttatcc ggaaaaatga atgttttgaa    1380
aagtctaaga acaagtgcga tattatgtga caaacagaac aaatacaaga acaagagtta    1440
gatcgtaagt ataagttaca ttttccatca tttggttgtg gtttggatga aatgttctac    1500
cgagcataat ggcagcgctt gtctaaaggt ttcccccaaa atccaaatat cattttaaat    1560
cgagagggat cggagtatca tgatcacagt tgaatactcc ttcttttatc aattagacct    1620
cgagtaaatt ataaattcca ccatccataa gaaggtgata ccatctttgg gatcgatatt    1680
atcgaccttt agaatccgtt tcaagtttgg catatatggt atatagttaa attccaaagt    1740
atatttgcaa cggaccatct aatgaaatcc tcgtttatac tatgaagaag ttggaaacat    1800
tacttaacat atgtatgtag acgagagcaa taaatttcat caaagcctac ttttctattt    1860
tggagacaaa tttggctgat aatctattaa tttggccttt gaagtgtttc tactttctac    1920
gtataagcaa atttctttta acctccctaa actttctgga agacttaaag taactaatat    1980
cccattcctc cttctttgga tatttacaaa aatttcttta gttcgtctat tttaggattc    2040
tagacttgta tttgaacaaa cccgtagata atttattatt tatgatttga atattgatcc    2100
gaagccactc cctataaatg atgagtcttg catgagaact agttcacatt gactttgatc    2160
agcttggtac gtacctaata acttaaaaag cttggtaatt accttataac ttacatccat    2220
tgaagagata aagggagatt gatggcggaa tttagaccga tattttctcc aatagatcat    2280
```

```
tataaaccga attacatttt tgctgtacat aggctgcgct aaacacccca aatgcgcaca   2340

acgttatcaa taaaaatgaa aaagtaaggg catgagatga ttagtttaga ttatttacat   2400

gcactaattc tcccactatt caaaacttat gagtatacat ttaacattta ctaggttttg   2460

gtttttattt gaatgtttgt atgacgttta caaggaaaag ttcgtatgac ttggtataat   2520

atatggcatt ttaattctag ataaaatcac atgctcacat gggtaataac aaatcattta   2580

ttttgccaag tgactgaact atctgacaaa aacctaatat tacaaaaacc tcaaaattta   2640

tcccactata ttatcttatt tatagtggca ttcccacttt cttaattatg catgcatctc   2700

cgaggcgcac ccttgttaag gcaaatatct attttttaaa aatacacctt gtttttggtg   2760

tataaataca agctaaaatc atcatagcaa tacactatca atctacgatc atatatcttt   2820

catttcatca t                                                        2831
```

<210> SEQ ID NO 15
<211> LENGTH: 2791
<212> TYPE: DNA
<213> ORGANISM: Arabidopsis thaliana

<400> SEQUENCE: 15

```
atttgcagag attatactta gccttgtttt tgtaaacggc tttttttggt tgggttttta     60

tttttcttga ggcattatcc aatattcaag taataatttt gatgtttttg tttcataatt    120

ttgtgtgtgt agtttacaaa aagagcataa taataggagg gacataagca tgtgtttggt    180

catttattca gattcatagt agagatgctt tgaatttttt gttcataagc tttgaaataa    240

tgttcttcaa cgctcaccta atcattcggt cgttcgttca attgactaaa aggtctttag    300

ctttgaccga cagatgcgta ttacatatgg tattatttta aattatgttt tttttgggtg    360

aatttataat aacaaaaaaa atcaacaagc agaaaagttt gggcattttg ggtatatata    420

tatatatatg cctcatgcta cccagccggc ccacctcatg ttttcagccc aatgatacat    480

atgagcaaga aaaacactgc atagcaaatg attttcattt gcacaaaaaa aaaaaaaaaa    540

gcaaatgatt ttcaatttta tttttgaaat gaatttgaaa ggtttgagac tatcgtgaat    600

atatataaaa ttaaaaaaca acttaaatga ataatcttgg aactggaaaa cagattaata    660

atgagttttt agtttgaaac tacacaaaat agataccttg gacttggaca gtaaaatatc    720

tgattttttt acaaacttca tgacattttc cgataatttt accaatattt tgccacataa    780

ttaaaaaaac ttatctcaat tcgtatcatc agttttttta aacaactgca catgtatatc    840

gtttgctaca aattcatagt aatggttcac aaaaatttat agaaatttca gtacttttgt    900

tatagatata aattttgaaa cgacaaaatg ttttgctact ttctaccgca atactgttat    960

ctaattgtaa ttaattattt ctaactttga cctaagttat aactcaacga cgatactata   1020

gtacaagctt attactaaac tacaaattta aacaggggtg tgactctagc tagctagttt   1080

ataataaatg agacgcaatg atggatatgc agctacaagt gggttcataa aatattacat   1140

atccactttg gttgtggaaa ctggaaagtt atgtaaattt tggccaacca aaggaagcaa   1200

agactttgct tctcaactct tcgagtacac ttccgagtaa gcttccaaca tgggcacgta   1260

gtggaatatg ttgcgcaatc ctcttgatgt cataaacata atggacaaaa ataatttaaa   1320

atttacgtac acatgtttct taaaactcca aattttatcc ggaaaaatga atgttttgaa   1380

aagtctaaga acaagtgcga tattatgtga caaacagaac aaatacaaga acaagagtta   1440

gatcgtaagt ataagttaca ttttccatca tttggttgtg gtttggatga aatgttctac   1500

cgagcataat ggcagcgctt gtctaaaggt ttcccccaaa atccaaatat cattttaaat   1560
```

```
cgagagggat cggagtatca tgatcacagt tgaatactcc ttcttttatc aattagacct   1620

cgagtaaatt ataaattcca ccatccataa gaaggtgata ccatctttgg gatcgatatt   1680

atcgaccttt agaatccgtt tcaagtttgg catatatggt atatagttaa attccaaagt   1740

atatttgcaa cggaccatct aatgaaatcc tcgtttatac tatgaagaag ttggaaacat   1800

tacttaacat atgtatgtag acgagagcaa taaatttcat caaagcctac ttttctattt   1860

tggagacaaa tttggctgat aatctattaa tttggccttt gaagtgtttc tactttctac   1920

gtataagcaa atttctttta acctccctaa actttctgga agacttaaag taactaatat   1980

cccattcctc cttctttgga tatttacaaa aatttcttta gttcgtctat tttaggattc   2040

tagacttgta tttgaacaaa cccgtagata atttattatt tatgatttga atattgatcc   2100

gaagccactc cctataaatg atgagtcttg catgagaact agttcacatt gactttgatc   2160

agcttggtac gtacctaata acttaaaaag cttggtaatt accttataac ttacatccat   2220

tgaagagata aagggagatt gatggcggaa tttagaccga tattttctcc aatagatcat   2280

tataaaccga attacatttt tgctgtacat aggctgcgct aaacacccca aatgcgcaca   2340

acgttatcaa taaaaatgaa aaagtaaggg catgagatga ttagtttaga ttatttacat   2400

gcactaattc tcccactatt caaaacttat gagtatacat ttaacattta ctaggttttg   2460

gtttttattt gaatgtttgt atgacgttta caaggaaaag ttcgtatgac ttggtataat   2520

atatggcatt ttaattctag ataaaatcac atgctcacat gggtaataac aaatcattta   2580

ttttgccaag tgactgaact atctgacaaa aacctaatat tacaaaaacc tcaaaattta   2640

tcccactata ttatcttatt tatagtggca ttcccacttt cttaattatg catgcatctc   2700

cgaggcgcac ccttgttaag gcaaatatct attttttaaa aatacacctt gtttttggtg   2760

tataaataca agctaaaatc atcatagcaa t                                  2791
```

<210> SEQ ID NO 16
<211> LENGTH: 2830
<212> TYPE: DNA
<213> ORGANISM: Arabidopsis thaliana

<400> SEQUENCE: 16

```
atttgcagag attatactta gccttgtttt tgtaaacggc ttttttggt tgggttttta      60

tttttcttga ggcattatcc aatattcaag taataatttt gatgtttttg tttcataatt    120

ttgtgtgttt agtttacaaa aagagcataa taataggagg gacataagca tgtgtttggt    180

catttattca gattcatagt agagatgctt tgaatttttt gttcataagc tttgaaataa    240

tgttcttcaa cgctcaccta atcattcggt cgttcgttca attgactaaa aggtctttag    300

ctttgaccga cagatgcgta ttacatatgg tattatttta aattatgttt tttttgggtg    360

aatttataat aacaaaaaaa atcaacaagc agaaaagttt gggcattttg ggtatatata    420

tatatatatg cctcatgcta cccagccggc ccacctcatg ttttcagccc aatgatacat    480

atgagcaaga aaaaccctgc atagcaaatg attttcattt gcacaaaaaa aaaaaaaaag    540

caaatgattt tcaattttat ttttgaaatg aatttgaaag gtttgagact atcgtgaata    600

tatataaaat taaaaaacaa cttaaatgaa taatcttgga actggaaaac agattaataa    660

tgagttttta gtttgaaact acacaaaata gataccttgg acttggacag taaaatatct    720

gatttttttta caaacttcat gacattttcc gataatttta ccaatatttt gccacataat    780

taaaaagact tgtctcaatt cgtatcatca gttttttttaa acaactgcac atgtatatcg    840
```

-continued

```
tttgctacaa attcatagta atggttcaca aaaatttata gaaatttcag tacttttgtt     900

atagatataa attttgaaac gacaaaatgt tttgctactt tctaccgcaa tactgttatc     960

taattgtaat taattatttc taactttgac ctaagttata actcaacgac gatactatag    1020

tacaagctta ttactaaact acaaatttaa acaggggtgt gactctagct agctagttta    1080

taataaatga gacgcaatga tggatatgca gctacaagtg ggttcataaa atattacata    1140

tccactttgg ttgtggaaac tggaaagtta tgtaaatttt ggccaaccaa aggaagcaaa    1200

gactttgctt ctcaactctt cgagtacact tccgagtaag cttccaacat gggcacgtag    1260

tggaatatgt tgcgcaatcc tcttgatgtc ataaacataa tggacaaaaa taatttaaaa    1320

tttacgtaca catgtttctt aaaactccaa attttatccg gaaaaatgaa tgttttgaaa    1380

agtctaagaa caagtgcgat attatgtgac aaacagaaca aatacaagaa caagagttag    1440

atcgtaagta taagttacat tttccatcat ttggttgtgg tttggatgaa atgttctacc    1500

gagcataatg gcagcgcttg tctaaaggtt tcccccaaaa tccaaatatc attttaaatc    1560

gagagggatc ggagtatcat gatcacagtt gaatactcct tcttttatca attagacctc    1620

gagtaaatta taaattccac catccataag aaggtgatac catctttggg atcgatatta    1680

tcgaccttta gaatccgttt caagtttggc atatatgata tatagttaaa ttccaaagta    1740

tatttgcaac ggaccatcta atgaaatcct cgtttatact atgaagaagt tggaaacatt    1800

acttaacata tgtatgtaga cgagagcaat aaatttcatc aaagcctact tttctatttt    1860

ggagacaaat ttggctgata atctattaat ttggcctttg aagtgtttct actttctacg    1920

tataagcaaa tttcttttaa cctccctaaa ctttctggaa gacttaaagt aactaatatc    1980

ccattcctcc ttctttggat atttacaaaa atttctttag ttcgtctaat ttaggattct    2040

agacttgtat ttgaacaaac ccgtagataa tttattattt aggatttgaa tattgatccg    2100

aagccacccc ctataaatga tgagtcttgc atgagaacta gttcacattg actttgatca    2160

gcttggtacg tacctaataa cttaaaaagc ttgctaatta ccttataact tacatccatt    2220

gaagagataa agggagattg atggcggaat ttagaccgat attttctcca atagatcatt    2280

ataaaccgga ttacattttt gctgtacata ggctgcgcta aacaccccaa atgcgcacaa    2340

cgttatcaat aaaaatgaaa aagtaagggc atgagatgat tagtttagat tatttacatg    2400

cactaattct cccactattc aaaacttatg agtatacatt taacatttac taggttttgg    2460

tttttatttg aatgtttgta tgacgtttac aaggaaaagt tcgtatgact tggtataata    2520

tatggcattt taattctaga taaaatcaca tgctcacatg ggtaataaca aatcatttat    2580

tttgccaagt gactgaacta tctgacaaaa acctaatatt acaaaaacct caaaatttat    2640

cccactatat tatcttattt atagtggcat tcccactttc ttaattatgc atgcatctcc    2700

gaggcgcacc cttgttaagg caaatatcta ttttttaaaa atacaccttg tttttggtgt    2760

ataaatacaa gctaaaatca tcatagcaat acactatcaa tctacgatca tatatctttc    2820

atttcatcat                                                           2830
```

<210> SEQ ID NO 17
<211> LENGTH: 1333
<212> TYPE: DNA
<213> ORGANISM: Arabidopsis thaliana
<220> FEATURE:
<221> NAME/KEY: CDS
<222> LOCATION: (42)..(1094)
<223> OTHER INFORMATION: coding for peroxidase ATP5a protein

<400> SEQUENCE: 17

```
acactatcaa tctacgatca tatatctttc atttcatcat c atg gac cac aaa atg      56
                                              Met Asp His Lys Met
                                              1               5

tca atg tat ttg ttt gtg tct tac cta gca atc ttt act ctt ttc ttc      104
Ser Met Tyr Leu Phe Val Ser Tyr Leu Ala Ile Phe Thr Leu Phe Phe
                10                  15                  20

aaa ggc ttt gtc tcc tcg ttt cct tcg gga tat aac aat ggt tac aac      152
Lys Gly Phe Val Ser Ser Phe Pro Ser Gly Tyr Asn Asn Gly Tyr Asn
            25                  30                  35

aat ggt cac gga cat gga cta act agc aat ctc aac tat cga ttc tat      200
Asn Gly His Gly His Gly Leu Thr Ser Asn Leu Asn Tyr Arg Phe Tyr
        40                  45                  50

gac cgg tct tgt ccg cgt ctt caa acg att gtt aag tcc gga gtt tgg      248
Asp Arg Ser Cys Pro Arg Leu Gln Thr Ile Val Lys Ser Gly Val Trp
    55                  60                  65

aga gct ttt aaa gat gat tct cga atc gct gca tct ctt ctt cga ctc      296
Arg Ala Phe Lys Asp Asp Ser Arg Ile Ala Ala Ser Leu Leu Arg Leu
70                  75                  80                  85

cat ttc cac gat tgt ttt gtc aat gga tgt gat gga tct ata ctt ctg      344
His Phe His Asp Cys Phe Val Asn Gly Cys Asp Gly Ser Ile Leu Leu
                90                  95                  100

aac gat tca gag gat ttc aaa gga gag aag aac gct cag cca aac cga      392
Asn Asp Ser Glu Asp Phe Lys Gly Glu Lys Asn Ala Gln Pro Asn Arg
            105                 110                 115

aac tca gtc cgt gga ttc gaa gtc att gaa gac att aaa tct gat atc      440
Asn Ser Val Arg Gly Phe Glu Val Ile Glu Asp Ile Lys Ser Asp Ile
        120                 125                 130

gaa agt tct tgt ccc tta aca gtt tca tgc gct gac ata gtt gct ctc      488
Glu Ser Ser Cys Pro Leu Thr Val Ser Cys Ala Asp Ile Val Ala Leu
    135                 140                 145

gcg gct aga gaa gct gtc gtc ctc act gga gga ccg ttt tgg ccc gtg      536
Ala Ala Arg Glu Ala Val Val Leu Thr Gly Gly Pro Phe Trp Pro Val
150                 155                 160                 165

cct ttg gga cga agg gac tca tta acg gcg agt gag caa gcg gcg aat      584
Pro Leu Gly Arg Arg Asp Ser Leu Thr Ala Ser Glu Gln Ala Ala Asn
                170                 175                 180

aca aat ctg cca tct ccg ttt gag gcg ttg gag aat ata aca gcc aag      632
Thr Asn Leu Pro Ser Pro Phe Glu Ala Leu Glu Asn Ile Thr Ala Lys
            185                 190                 195

ttc gtg acc ctt gga ctc gac ctc aag gac gtt gtt gtc ctc tca gga      680
Phe Val Thr Leu Gly Leu Asp Leu Lys Asp Val Val Val Leu Ser Gly
        200                 205                 210

gca cat act ata gga ttt gct caa tgt ttc gtg atc aag cat aga ctc      728
Ala His Thr Ile Gly Phe Ala Gln Cys Phe Val Ile Lys His Arg Leu
    215                 220                 225

ttc aac ttc aag ggc tca ggc cag cct gac cca aac cta gcc gct tcc      776
Phe Asn Phe Lys Gly Ser Gly Gln Pro Asp Pro Asn Leu Ala Ala Ser
230                 235                 240                 245

tca gca ctt ctc tct aag cta aag gac acg tgt cct aac gtg gac tcc      824
Ser Ala Leu Leu Ser Lys Leu Lys Asp Thr Cys Pro Asn Val Asp Ser
                250                 255                 260

tca gac tct aag ctc gct gct ctt gac gca gct agc tca gtc aag ttt      872
Ser Asp Ser Lys Leu Ala Ala Leu Asp Ala Ala Ser Ser Val Lys Phe
            265                 270                 275

gac aat gct tac tac gtg aac tta atg aac aac ata gga ctg ttg gat      920
Asp Asn Ala Tyr Tyr Val Asn Leu Met Asn Asn Ile Gly Leu Leu Asp
        280                 285                 290

tct gat caa acc cta atg aca gat cct acg gct gcc gcc ttg gtg aag      968
Ser Asp Gln Thr Leu Met Thr Asp Pro Thr Ala Ala Ala Leu Val Lys
```

-continued

```
    295                 300                 305

tcg tac agc gag aat ccg tac ttg ttc tcg agg gat ttc gca gtt tca     1016
Ser Tyr Ser Glu Asn Pro Tyr Leu Phe Ser Arg Asp Phe Ala Val Ser
310                 315                 320                 325

atg gtt aaa atg ggg aat atc gga gtt atg acc gga agt gat gga gta     1064
Met Val Lys Met Gly Asn Ile Gly Val Met Thr Gly Ser Asp Gly Val
                330                 335                 340

att cga gga aaa tgt gga ttt cca ggt taa gttatatata gactcttcac       1114
Ile Arg Gly Lys Cys Gly Phe Pro Gly
            345                 350

aaaatccaaa tcagtctatt atatatctag agctaatcta gctttaatga ggaatcaaat   1174

aaaccaaagt ctatgaataa aatatgtttt atatatatgg tgtaaaagcg tccttatgta   1234

tcaatatata tatatatgga tcccataaac aaaaatactt ggacttgtat gtgtgttacg   1294

tttgtgtgta atggaaaatg tatttgtctt tgtattttt                          1333


<210> SEQ ID NO 18
<211> LENGTH: 350
<212> TYPE: PRT
<213> ORGANISM: Arabidopsis thaliana

<400> SEQUENCE: 18

Met Asp His Lys Met Ser Met Tyr Leu Phe Val Ser Tyr Leu Ala Ile
1               5                   10                  15

Phe Thr Leu Phe Phe Lys Gly Phe Val Ser Ser Phe Pro Ser Gly Tyr
            20                  25                  30

Asn Asn Gly Tyr Asn Asn Gly His Gly His Gly Leu Thr Ser Asn Leu
        35                  40                  45

Asn Tyr Arg Phe Tyr Asp Arg Ser Cys Pro Arg Leu Gln Thr Ile Val
    50                  55                  60

Lys Ser Gly Val Trp Arg Ala Phe Lys Asp Asp Ser Arg Ile Ala Ala
65                  70                  75                  80

Ser Leu Leu Arg Leu His Phe His Asp Cys Phe Val Asn Gly Cys Asp
                85                  90                  95

Gly Ser Ile Leu Leu Asn Asp Ser Glu Asp Phe Lys Gly Glu Lys Asn
            100                 105                 110

Ala Gln Pro Asn Arg Asn Ser Val Arg Gly Phe Glu Val Ile Glu Asp
        115                 120                 125

Ile Lys Ser Asp Ile Glu Ser Ser Cys Pro Leu Thr Val Ser Cys Ala
    130                 135                 140

Asp Ile Val Ala Leu Ala Ala Arg Glu Ala Val Val Leu Thr Gly Gly
145                 150                 155                 160

Pro Phe Trp Pro Val Pro Leu Gly Arg Arg Asp Ser Leu Thr Ala Ser
                165                 170                 175

Glu Gln Ala Ala Asn Thr Asn Leu Pro Ser Pro Phe Glu Ala Leu Glu
            180                 185                 190

Asn Ile Thr Ala Lys Phe Val Thr Leu Gly Leu Asp Leu Lys Asp Val
        195                 200                 205

Val Val Leu Ser Gly Ala His Thr Ile Gly Phe Ala Gln Cys Phe Val
    210                 215                 220

Ile Lys His Arg Leu Phe Asn Phe Lys Gly Ser Gly Gln Pro Asp Pro
225                 230                 235                 240

Asn Leu Ala Ala Ser Ser Ala Leu Leu Ser Lys Leu Lys Asp Thr Cys
                245                 250                 255

Pro Asn Val Asp Ser Ser Asp Ser Lys Leu Ala Ala Leu Asp Ala Ala
```

-continued

```
            260                 265                 270

Ser Ser Val Lys Phe Asp Asn Ala Tyr Tyr Val Asn Leu Met Asn Asn
        275                 280                 285

Ile Gly Leu Leu Asp Ser Asp Gln Thr Leu Met Thr Asp Pro Thr Ala
    290                 295                 300

Ala Ala Leu Val Lys Ser Tyr Ser Glu Asn Pro Tyr Leu Phe Ser Arg
305                 310                 315                 320

Asp Phe Ala Val Ser Met Val Lys Met Gly Asn Ile Gly Val Met Thr
                325                 330                 335

Gly Ser Asp Gly Val Ile Arg Gly Lys Cys Gly Phe Pro Gly
            340                 345                 350


<210> SEQ ID NO 19
<211> LENGTH: 3142
<212> TYPE: DNA
<213> ORGANISM: Arabidopsis thaliana
<220> FEATURE:
<221> NAME/KEY: promoter
<222> LOCATION: (1)..(3142)
<223> OTHER INFORMATION: transcription regulating sequence from
      Arabidopsis thaliana gene At1g70710

<400> SEQUENCE: 19

gatccaaatg ataatttacc acaacatccg gtcctaaaca agcaaatcaa tgagagcaaa     60

tgttgttagt gcgtaactga cgaaaaaagt ggtactcaac ttgtgaaaaa atactgtgga    120

tactaagtat taaccatata taaaacgtaa aaaaaaactg atactatcaa attttgacta    180

attggttatt caacatatag gattctgaat gaccgaaata tattttttct aatataattg    240

tattggctga tagaaactta tacaaacctt ttaaaagttt ttaaattaac atcaatatat    300

acaaaacatg attacactta cgacatcatg tgtgctgcat aattacgtcc acctttgtta    360

caacattgct ttgtttgtac tgtaattcga agcaaaatta ccctcgttat ttcttctgtc    420

tacagcatca tatatataca acattttcta ttcttacaaa ccattgataa ttatgaagta    480

atgaactaag cgcatcatgt tcatgccttt tgcggttgat tattgaaata taaacaaaat    540

aaaatgatat ggttgtttcg cactgcatga tgatcttaca agtcaatttc acccaaaaag    600

ctacaaacat agcaaaagta ggagtttcac gtcttcttgc catcacacag aatcaatatg    660

ttgaaacgta tcaaaagttt cttacattat atggtgcata cggaattaac atctggacct    720

atatcatgca tgtttaatat gatgtcgtgt tctaggaacg ctagtggcaa cgaatatatg    780

atgatggttc atgcatatca ccgataaatg aacaaattat ccattctgta ttatattgat    840

atatatagag taagttgtta tctgattgtg gttggtccaa aaaatacatg aatgtttatt    900

tcgatcacac tactacctct accatcttgg ttttttccaa ttttttagca tgatttttta    960

tttacgatta gatatatttc ttaaaaaaaa catgaacatg catatgagtg aaagtaaatt   1020

gacttgttag aatcgtcaat atttagttct aataattata tccattgctt taatcacttt   1080

ctatgttgat attattgttt gatcaaaacc atcagtataa cctattatac aatagttttg   1140

attcgttttg atctcttagg tttcttttta gctattagaa acaaattcat agagactata   1200

gacattagac aatgataatg tagaacaaca attaatgttc ctcaaatatc ccataaaacc   1260

tattgaatca actggtccaa aaccaataca acgagaactt attgtctacg tttatatgac   1320

ccaaagacac taatcaatcg gcctcaatta gaggcggatt taaagacatc acggtatcat   1380

aatatccatg ttacttttc tgttctcttt tttacttacc cgtccatttc tttcttttgg   1440

caaaataatt ttgctaaatt acgtggcaaa ataattttgc taaattacag cgaagaggat   1500
```

```
cacatgcatc agcactattt acaacaatcc tttagggtat atgttagtca accccgtaac   1560

accattcgta cccattaatc atgaacattt cgcaaagttt tcccaccaaa aacggcgtcg   1620

gataaggttt ttggcatttt gtgtttcttt ttttgtgtgc atagcataat ttcattttaa   1680

ccgtactatt cgaagatttt taaattggat aaagatgatt cattcattac atagtcgctt   1740

tgttgttact agtgataaat tcatgttaat gattctatga ttttcggcca gctatctcat   1800

taattattaa gacgtttaag tggagctatt agcaatcgtg tatgacataa tgattagcat   1860

tttcatgtgc catgcccatg catgaggcta tttttttgttt aaaattttat tctattatat   1920

ccgaattttg ttatatacta aatgaacatt tgtctctgat ttggtctact agttaattaa   1980

cctttagctt cactaataaa aaatctcatg attttgatac ttaaacccaa aacatattaa   2040

aaacaattag cagtctttta aatcgataat gtgcttagat gattatacgt tcgtaggaaa   2100

ctcttttgtt tccaatgcat gttaagaact aagaactcgt atccttaagc accaatgctt   2160

tatgcttaat gcctcattag agatataaac tgagattgac tgtgttctga atcatcataa   2220

tataaggcac acaaagaaca gaacaggaaa tacttagcaa tataataggt ttccaataaa   2280

agtgaagaag aatacaataa acttttataa aaaaaaaagt atataataat ttcacactcg   2340

aatcaaccaa atgtaagatg tcttgtccat ttacacatca catgagtaag tggattacag   2400

attgcaattg atgaaatttg gatcttagct aaaaatttat tacgttacta tatacatcga   2460

gttttaagat gttcataatc acaaccacaa ccacaagttt gaagaaataa gaaacagagt   2520

aataatatat caaataaaat ttcatggctg atggaatctt ttttctaatt gtaggtccaa   2580

aaaagcctaa attaatgggg aaacaaaaac caaaattcaa tagtaatttt actaattatg   2640

tcttggttaa atagagtaaa aagaaaatta atcacaaacc tccaaaaatc aactaattga   2700

gatcaaaaca cgtgtcgcat gccaataggg cggtggatca catggtaaaa aaattcactt   2760

taatttttgt ctttcttcat aattcatctc acagatttca acttctcttt tggattctct   2820

caccgtacac cgacggcgta ccactcccct tccacaccgt ccgcattaaa aatctcaaac   2880

cctaaaaccc gtatccaata acccacccgg tccaaccggt tattcaaacc cggtcaatcc   2940

aaaattcgcc tcggaatcca aacctccata cccaatctaa catggaaaaa cctccaatca   3000

caaacctcca cgtggtgatc actcattggc tcttattctg gaatccaaga ggaccttttt   3060

agtataaaga gccccttcgt tggtcctatc accttctctc tctcacacac taacagaaag   3120

cacaaaaaac agagacaaaa ga                                            3142
```

```
<210> SEQ ID NO 20
<211> LENGTH: 3104
<212> TYPE: DNA
<213> ORGANISM: Arabidopsis thaliana
<220> FEATURE:
<221> NAME/KEY: promoter
<222> LOCATION: (1)..(3104)
<223> OTHER INFORMATION: transcription regulating sequence from
      Arabidopsis thaliana gene At1g70710

<400> SEQUENCE: 20

gatccaaatg ataatttacc acaacatccg gtcctaaaca agcaaatcaa tgagagcaaa     60

tgttgttagt gcgtaactga cgaaaaaagt ggtactcaac ttgtgaaaaa atactgtgga    120

tactaagtat taaccatata taaaacgtaa aaaaaaactg atactatcaa attttgacta    180

attggttatt caacatatag gattctgaat gaccgaaata tattttttct aatataattg    240

tattggctga tagaaactta tacaaacctt ttaaaagttt ttaaattaac atcaatatat    300
```

-continued

```
acaaaacatg attacactta cgacatcatg tgtgctgcat aattacgtcc acctttgtta    360
caacattgct ttgtttgtac tgtaattcga agcaaaatta ccctcgttat ttcttctgtc    420
tacagcatca tatatataca acattttcta ttcttacaaa ccattgataa ttatgaagta    480
atgaactaag cgcatcatgt tcatgccttt tgcggttgat tattgaaata taaacaaaat    540
aaaatgatat ggttgtttcg cactgcatga tgatcttaca agtcaatttc acccaaaaag    600
ctacaaacat agcaaaagta ggagtttcac gtcttcttgc catcacacag aatcaatatg    660
ttgaaacgta tcaaaagttt cttacattat atggtgcata cggaattaac atctggacct    720
atatcatgca tgtttaatat gatgtcgtgt tctaggaacg ctagtggcaa cgaatatatg    780
atgatggttc atgcatatca ccgataaatg aacaaattat ccattctgta ttatattgat    840
atatatagag taagttgtta tctgattgtg gttggtccaa aaaatacatg aatgtttatt    900
tcgatcacac tactacctct accatcttgg ttttttccaa tttttagca tgatttttta    960
tttacgatta gatatatttc ttaaaaaaaa catgaacatg catatgagtg aaagtaaatt   1020
gacttgttag aatcgtcaat atttagttct aataattata tccattgctt taatcacttt   1080
ctatgttgat attattgttt gatcaaaacc atcagtataa cctattatac aatagttttg   1140
attcgttttg atctcttagg tttcttttta gctattagaa acaaattcat agagactata   1200
gacattagac aatgataatg tagaacaaca attaatgttc ctcaaatatc ccataaaacc   1260
tattgaatca actggtccaa aaccaataca acgagaactt attgtctacg tttatatgac   1320
ccaaagacac taatcaatcg gcctcaatta gaggcggatt taaagacatc acggtatcat   1380
aatatccatg ttacttttc tgttctcttt tttacttacc cgtccatttc tttcttttgg    1440
caaaataatt ttgctaaatt acgtggcaaa ataattttgc taaattacag cgaagaggat   1500
cacatgcatc agcactattt acaacaatcc tttagggtat atgttagtca accccgtaac   1560
accattcgta cccattaatc atgaacattt cgcaaagttt tcccaccaaa aacggcgtcg   1620
gataaggttt ttggcatttt gtgtttcttt ttttgtgtgc atagcataat ttcattttaa   1680
ccgtactatt cgaagatttt taaattggat aaagatgatt cattcattac atagtcgctt   1740
tgttgttact agtgataaat tcatgttaat gattctatga ttttcggcca gctatctcat   1800
taattattaa gacgtttaag tggagctatt agcaatcgtg tatgacataa tgattagcat   1860
tttcatgtgc catgcccatg catgaggcta tttttttgttt aaaattttat tctattatat   1920
ccgaattttg ttatatacta aatgaacatt tgtctctgat ttggtctact agttaattaa   1980
cctttagctt cactaataaa aaatctcatg attttgatac ttaaacccaa aacatattaa   2040
aaacaattag cagtcttttta aatcgataat gtgcttagat gattatacgt tcgtaggaaa   2100
ctcttttgtt tccaatgcat gttaagaact aagaactcgt atccttaagc accaatgctt   2160
tatgcttaat gcctcattag agatataaac tgagattgac tgtgttctga atcatcataa   2220
tataaggcac acaaagaaca gaacaggaaa tacttagcaa tataataggt ttccaataaa   2280
agtgaagaag aatacaataa acttttataa aaaaaaaagt atataataat ttcacactcg   2340
aatcaaccaa atgtaagatg tcttgtccat ttacacatca catgagtaag tggattacag   2400
attgcaattg atgaaatttg gatcttagct aaaaatttat tacgttacta tatacatcga   2460
gttttaagat gttcataatc acaaccacaa ccacaagttt gaagaaataa gaaacagagt   2520
aataatatat caaataaaat ttcatggctg atggaatctt ttttctaatt gtaggtccaa   2580
aaaagcctaa attaatgggg aaacaaaaac caaaattcaa tagtaatttt actaattatg   2640
```

-continued

```
tcttggttaa atagagtaaa aagaaaatta atcacaaacc tccaaaaatc aactaattga   2700

gatcaaaaca cgtgtcgcat gccaataggg cggtggatca catggtaaaa aaattcactt   2760

taatttttgt ctttcttcat aattcatctc acagatttca acttctcttt tggattctct   2820

caccgtacac cgacggcgta ccactcccct tccacaccgt ccgcattaaa aatctcaaac   2880

cctaaaaccc gtatccaata acccacccgg tccaaccggt tattcaaacc cggtcaatcc   2940

aaaattcgcc tcggaatcca aacctccata cccaatctaa catggaaaaa cctccaatca   3000

caaacctcca cgtggtgatc actcattggc tcttattctg gaatccaaga ggaccttttt   3060

agtataaaga gcccccttcgt tggtcctatc accttctctc tctc                   3104
```

```
<210> SEQ ID NO 21
<211> LENGTH: 3180
<212> TYPE: DNA
<213> ORGANISM: Arabidopsis thaliana
<220> FEATURE:
<221> NAME/KEY: promoter
<222> LOCATION: (1)..(3180)
<223> OTHER INFORMATION: transcription regulating sequence from
      Arabidopsis thaliana gene At1g70710

<400> SEQUENCE: 21

gatccaaatg ataatttacc acaacatccg gtcctaaaca agcaaatcaa tgagagcaaa     60

tgttgttagt gcgtaactga cgaaaaaagt ggtactcaac ttgtgaaaaa atactgtgga    120

tactaagtat taaccatata taaaacgtaa aaaaaaactg atactatcaa attttgacta    180

attggttatt caacatatag gattctgaat gaccgaaata tattttttct aatataattg    240

tattggctga tagaaactta tacaaacctt ttaaaagttt ttaaattaac atcaatatat    300

acaaaacatg attacactta cgacatcatg tgtgctgcat aattacgtcc acctttgtta    360

caacattgct ttgtttgtac tgtaattcga atcaaaatta ccctcgttat ttcttctgtc    420

tacagcatca tatatataca acattttcta ttcttacaaa ccattgataa ttatgaagta    480

atgaactaag cgcatcatgt tcatgccttt tgcggttgat tattgaaata taaacaaaat    540

aaaatgatat ggttgtttcg cactgcatga tgatcttaca agtcaatttc acccaaaaag    600

ctacaaacat agcaaaagta ggagtttcac gtcttcttgc catcacacag aatcaatatg    660

ttgaaacgta tcaaaagttt cttacattat atggtgcata cggaattaac atctggacct    720

atatcatgca tgtttaatat gatgtcgtgt tctaggaacg ctagtggcaa cgaatatatg    780

atgatggttc atgcatatca ccgataaatg aacaaattat ccattctgta ttatattgat    840

atatatagag taagttgtta tctgattgtg gttggtccaa aaaatacatg aatgtttatt    900

tcgatcacac tactacctct accatcttgg ttttttccaa ttttttagca tgattttttta    960

tttacgatta gatatatttc tttaaaaaaa catgaacatg catatgagtg aaagtaaatt   1020

gacttgttag aatcgtcaat atttagttct aataattata tccattgctt taatcacttt   1080

ctatgttgat attattgttt gatcaaaacc atcagtataa cctattatac aatagtttga   1140

tcaaaaccat cagtataacc tattatacaa tagttttgat tcgttttgat ctcttaggtt   1200

tctttttagc tattagaaac aaattcatag agactataga cattagacaa tgataatgta   1260

gaacaacaat taatgttcct caaatatccc ataaaaccta ttgaatcaac tggtccaaaa   1320

ccaatacaac gagaacttat tgtctacgtt tatatgaccc aaagacacta atcaatcggc   1380

ctcaattaga ggcggattta aagacatcac ggtatcatca tatccatgtt actttttctg   1440

ttctcttttt tacttacccg tccatttctt tcttttggca aaataatttt gctaaattac   1500
```

-continued gtggcaaaat aattttgcta aattacagcg aagaggatca catgcatcag cactatttac 1560
aacaatcctt tagggtatat gttagtcaac cccgtaacac cattcgtacc cattaatcat 1620
gaacatttcg caaagttttc ccaccaaaaa cggcgtcgga taaggttttt ggcatttttgt 1680 gtttcttttt ttgtgtgcat agcataattt cattttaacc gtactattcg aagattttta 1740
aattggataa agatgattca ttcattacat agtcgctttg ttgttactag tgataaattc 1800
atgttaatga ttctatgatt ttcggccagc tatctcatta attattaaga cgtttaagtg 1860
gagctattag caatcgtgta tgacataatg attagcattt tcatgtgcca tgcccatgca 1920
tgaggctttt ttttgtttaa aattttattc tattatatcc gaattttgtt atatactaaa 1980
tgaacatttg tctctgattt ggtctactag ttaattaacc tttagcttca ctaataaaaa 2040
atctcatgat tttgatactt aaacccaaaa catattaaaa acaattagca gtcttttaaa 2100
tcgataatgt gcttagatga ttatacgttc gtaggaaact cttttgtttc caatgcatgt 2160
taagaactaa gaactcgtat ccttaagcac caatgcttta tgcttaatgc ctcattagag 2220
atataaactg agattgactg tgttctgaat catcataata taaggcacac aaagaacaga 2280
acaggaaata cttagcaata taataggttt ccaataaaag tgaagaagaa tacaataaac 2340
ttttataaaa aaaaaagtat ataataattt cacactcgaa tcaaccaaat gtaagatgtc 2400
ttgtccattt acacatcaca tgagtaagtg gattacagat tgcaattgat gaaatctgga 2460
tcttagctaa aaatttatta cgttactata tacatcgagt tttaagatgt tcataatcac 2520
aaccacaacc acaagtttga agaaataaga aacagagtaa taatatatca aataaaattt 2580
catggctgat ggaatctttt ttctaattgt aggtccaaaa aagcctaaat taatggggaa 2640
acaaaaacca aaattcaata gtaattttac taattatgtc ttggttaaat agagtaaaaa 2700
gaaaattaat cacaaacctc caaaaatcaa ctaattgaga tcaaaacacg tgtcgcatgc 2760
caatagggcg gtggatcaca tggtaaaaaa attcacttta atttttgtct ttcttcataa 2820
ttcatctcac agatttcaac ttctcttttg gattctctca ccgtacaccg tcggcgtacc 2880
actccccttc cacaccgtcg gcattaaaaa tctcaaaccc taaaacccgt atccaataac 2940
ccacccggtc caaccggtta ttcaaacccg gtcaatccaa aattcgcctc ggaatccaaa 3000
cctccatacc caatctaaca tggaaaaacc tccaatcaca aacctccacg tggtgatcac 3060
tcattggctc ttattctgga atccaagagg accttttttag tataaagagc cccttcgttg 3120
gtcctatcac cttctctctc tcacacacta acagaaagca caaaaaacag agacaaaaga 3180

<210> SEQ ID NO 22
<211> LENGTH: 1741
<212> TYPE: DNA
<213> ORGANISM: Arabidopsis thaliana
<220> FEATURE:
<221> NAME/KEY: CDS
<222> LOCATION: (39)..(1517)
<223> OTHER INFORMATION: codinf for endo-1,4-beta-glucanase protein

<400> SEQUENCE: 22

```
acacactaac agaaagcaca aaaaacagag acaaaaga atg gcg cga aaa tcc cta      56
                                          Met Ala Arg Lys Ser Leu
                                          1               5

att ttc ccg gtg att ttg ctc gcc gtt ctt ctc ttc tct ccg ccg att       104
Ile Phe Pro Val Ile Leu Leu Ala Val Leu Leu Phe Ser Pro Pro Ile
            10                  15                  20

tac tcc gcc ggt cac gat tac cgc gac gct ctc cgt aaa agc att ctc       152
Tyr Ser Ala Gly His Asp Tyr Arg Asp Ala Leu Arg Lys Ser Ile Leu
        25                  30                  35
```

-continued

```
ttc ttc gaa ggt caa cgt tcc ggt aaa ctc cct cca gat caa cgc tta      200
Phe Phe Glu Gly Gln Arg Ser Gly Lys Leu Pro Pro Asp Gln Arg Leu
    40                  45                  50

aaa tgg cgc cgt gac tca gca tta cgc gac ggt tcc tcc gcc ggc gtt      248
Lys Trp Arg Arg Asp Ser Ala Leu Arg Asp Gly Ser Ser Ala Gly Val
55                  60                  65                  70

gac tta tcc ggt ggt tac tac gac gcc gga gac aac atc aag ttc ggt      296
Asp Leu Ser Gly Gly Tyr Tyr Asp Ala Gly Asp Asn Ile Lys Phe Gly
                75                  80                  85

ttt ccg atg gcg ttc aca aca acg atg ctt tca tgg agt ata atc gat      344
Phe Pro Met Ala Phe Thr Thr Thr Met Leu Ser Trp Ser Ile Ile Asp
            90                  95                  100

ttc ggt aaa acc atg gga cct gag ctt aga aac gcc gtg aaa gct gtt      392
Phe Gly Lys Thr Met Gly Pro Glu Leu Arg Asn Ala Val Lys Ala Val
        105                 110                 115

aaa tgg gga aca gat tac ctc ctt aaa gcg acg gcg att ccc gga gta      440
Lys Trp Gly Thr Asp Tyr Leu Leu Lys Ala Thr Ala Ile Pro Gly Val
    120                 125                 130

gtc ttc gtc caa gtc gga gac gct tac tcc gat cat aac tgt tgg gaa      488
Val Phe Val Gln Val Gly Asp Ala Tyr Ser Asp His Asn Cys Trp Glu
135                 140                 145                 150

agg cct gaa gat atg gac act ctc cgt act gtt tac aaa atc gat aga      536
Arg Pro Glu Asp Met Asp Thr Leu Arg Thr Val Tyr Lys Ile Asp Arg
                155                 160                 165

gct cat cct ggt tct gac gtc gct ggt gaa acc gca gcc gct tta gcc      584
Ala His Pro Gly Ser Asp Val Ala Gly Glu Thr Ala Ala Ala Leu Ala
            170                 175                 180

gcc gct tca atc gtt ttt aga aaa cgc gat cct gct tat tcc aga ctt      632
Ala Ala Ser Ile Val Phe Arg Lys Arg Asp Pro Ala Tyr Ser Arg Leu
        185                 190                 195

cta ctt gac cgt gcc act agg gta ttc gcg ttt gct aac aga tat cgc      680
Leu Leu Asp Arg Ala Thr Arg Val Phe Ala Phe Ala Asn Arg Tyr Arg
    200                 205                 210

ggc gcg tat agt aac agt ctc tac cac gcg gtt tgt cct ttt tac tgt      728
Gly Ala Tyr Ser Asn Ser Leu Tyr His Ala Val Cys Pro Phe Tyr Cys
215                 220                 225                 230

gat ttc aac ggt tac cag gat gag tta ctg tgg gga gcg gca tgg cta      776
Asp Phe Asn Gly Tyr Gln Asp Glu Leu Leu Trp Gly Ala Ala Trp Leu
                235                 240                 245

cac aaa gcc tcg agg aaa cga gcg tac aga gaa ttc att gtg aag aac      824
His Lys Ala Ser Arg Lys Arg Ala Tyr Arg Glu Phe Ile Val Lys Asn
            250                 255                 260

gag gtc att ctt aag gct gga gat acc att aat gag ttt ggt tgg gac      872
Glu Val Ile Leu Lys Ala Gly Asp Thr Ile Asn Glu Phe Gly Trp Asp
        265                 270                 275

aat aag cat gct ggg att aat gtc tta atc tcc aag gaa gtg tta atg      920
Asn Lys His Ala Gly Ile Asn Val Leu Ile Ser Lys Glu Val Leu Met
    280                 285                 290

gga aaa gca gag tat ttt gag tct ttc aag cag aac gca gat ggg ttt      968
Gly Lys Ala Glu Tyr Phe Glu Ser Phe Lys Gln Asn Ala Asp Gly Phe
295                 300                 305                 310

atc tgt tct ata ttg cct gga att tct cac ccc caa gtc caa tac tct     1016
Ile Cys Ser Ile Leu Pro Gly Ile Ser His Pro Gln Val Gln Tyr Ser
                315                 320                 325

cga gga ggg cta cta gtg aag act gga ggg agt aac atg caa cat gta     1064
Arg Gly Gly Leu Leu Val Lys Thr Gly Gly Ser Asn Met Gln His Val
            330                 335                 340

aca tca cta tct ttc ctc cta ttg gct tac tct aat tat ctg agc cat     1112
Thr Ser Leu Ser Phe Leu Leu Leu Ala Tyr Ser Asn Tyr Leu Ser His
```

-continued

```
        345                 350                 355

gcc aaa aag gtt gtg cct tgt ggc gaa tta act gct tcc cca tct ctc      1160
Ala Lys Lys Val Val Pro Cys Gly Glu Leu Thr Ala Ser Pro Ser Leu
    360                 365                 370

ctc cgt caa atc gcc aag cgt cag gtg gat tac att ctc gga gac aac      1208
Leu Arg Gln Ile Ala Lys Arg Gln Val Asp Tyr Ile Leu Gly Asp Asn
375                 380                 385                 390

ccg atg gga ctg tct tac atg gtt gga tac ggt caa aag ttt cca cgt      1256
Pro Met Gly Leu Ser Tyr Met Val Gly Tyr Gly Gln Lys Phe Pro Arg
                395                 400                 405

agg att cat cac cgt ggt agc tcg gtt cct tcg gtt tca gcc cat cca      1304
Arg Ile His His Arg Gly Ser Ser Val Pro Ser Val Ser Ala His Pro
            410                 415                 420

agc cac ata ggg tgc aaa gaa ggc tct cgc tat ttc cta agc cca aat      1352
Ser His Ile Gly Cys Lys Glu Gly Ser Arg Tyr Phe Leu Ser Pro Asn
        425                 430                 435

cct aac cca aac ctt ttg gtt ggt gct gta gtc ggt gga cct aat gtc      1400
Pro Asn Pro Asn Leu Leu Val Gly Ala Val Val Gly Gly Pro Asn Val
    440                 445                 450

act gat gct ttt ccg gat tca aga cct tac ttt cag cag tct gag ccc      1448
Thr Asp Ala Phe Pro Asp Ser Arg Pro Tyr Phe Gln Gln Ser Glu Pro
455                 460                 465                 470

acg act tat atc aat gca cca cta gtg ggc ctt ctc ggt tac ttc tcc      1496
Thr Thr Tyr Ile Asn Ala Pro Leu Val Gly Leu Leu Gly Tyr Phe Ser
                475                 480                 485

gcc cat tct act tgg cga tga gggagggcct tattacttat tactctctat        1547
Ala His Ser Thr Trp Arg
            490

cctattagag gtgtgctgga aactttaggc caccctaaaa cccttttttt tctttttttaa   1607

tgttattgcc actctttatt ttctactact taaccaattg tattgtaagc ccgtaattag   1667

tgaagaagag aaagagttat gtcggtgtct aaacttatta tatttgcagt caattacttg   1727

aattatttgt ttgc                                                      1741


<210> SEQ ID NO 23
<211> LENGTH: 492
<212> TYPE: PRT
<213> ORGANISM: Arabidopsis thaliana

<400> SEQUENCE: 23

Met Ala Arg Lys Ser Leu Ile Phe Pro Val Ile Leu Leu Ala Val Leu
1               5                   10                  15

Leu Phe Ser Pro Pro Ile Tyr Ser Ala Gly His Asp Tyr Arg Asp Ala
            20                  25                  30

Leu Arg Lys Ser Ile Leu Phe Phe Glu Gly Gln Arg Ser Gly Lys Leu
        35                  40                  45

Pro Pro Asp Gln Arg Leu Lys Trp Arg Arg Asp Ser Ala Leu Arg Asp
    50                  55                  60

Gly Ser Ser Ala Gly Val Asp Leu Ser Gly Gly Tyr Tyr Asp Ala Gly
65                  70                  75                  80

Asp Asn Ile Lys Phe Gly Phe Pro Met Ala Phe Thr Thr Thr Met Leu
                85                  90                  95

Ser Trp Ser Ile Ile Asp Phe Gly Lys Thr Met Gly Pro Glu Leu Arg
            100                 105                 110

Asn Ala Val Lys Ala Val Lys Trp Gly Thr Asp Tyr Leu Leu Lys Ala
        115                 120                 125

Thr Ala Ile Pro Gly Val Val Phe Val Gln Val Gly Asp Ala Tyr Ser
```

```
    130                 135                 140

Asp His Asn Cys Trp Glu Arg Pro Glu Asp Met Asp Thr Leu Arg Thr
145                 150                 155                 160

Val Tyr Lys Ile Asp Arg Ala His Pro Gly Ser Asp Val Ala Gly Glu
                165                 170                 175

Thr Ala Ala Ala Leu Ala Ala Ala Ser Ile Val Phe Arg Lys Arg Asp
            180                 185                 190

Pro Ala Tyr Ser Arg Leu Leu Leu Asp Arg Ala Thr Arg Val Phe Ala
        195                 200                 205

Phe Ala Asn Arg Tyr Arg Gly Ala Tyr Ser Asn Ser Leu Tyr His Ala
    210                 215                 220

Val Cys Pro Phe Tyr Cys Asp Phe Asn Gly Tyr Gln Asp Glu Leu Leu
225                 230                 235                 240

Trp Gly Ala Ala Trp Leu His Lys Ala Ser Arg Lys Arg Ala Tyr Arg
                245                 250                 255

Glu Phe Ile Val Lys Asn Glu Val Ile Leu Lys Ala Gly Asp Thr Ile
            260                 265                 270

Asn Glu Phe Gly Trp Asp Asn Lys His Ala Gly Ile Asn Val Leu Ile
        275                 280                 285

Ser Lys Glu Val Leu Met Gly Lys Ala Glu Tyr Phe Glu Ser Phe Lys
    290                 295                 300

Gln Asn Ala Asp Gly Phe Ile Cys Ser Ile Leu Pro Gly Ile Ser His
305                 310                 315                 320

Pro Gln Val Gln Tyr Ser Arg Gly Gly Leu Leu Val Lys Thr Gly Gly
                325                 330                 335

Ser Asn Met Gln His Val Thr Ser Leu Ser Phe Leu Leu Leu Ala Tyr
            340                 345                 350

Ser Asn Tyr Leu Ser His Ala Lys Lys Val Val Pro Cys Gly Glu Leu
        355                 360                 365

Thr Ala Ser Pro Ser Leu Leu Arg Gln Ile Ala Lys Arg Gln Val Asp
    370                 375                 380

Tyr Ile Leu Gly Asp Asn Pro Met Gly Leu Ser Tyr Met Val Gly Tyr
385                 390                 395                 400

Gly Gln Lys Phe Pro Arg Arg Ile His His Arg Gly Ser Ser Val Pro
                405                 410                 415

Ser Val Ser Ala His Pro Ser His Ile Gly Cys Lys Glu Gly Ser Arg
            420                 425                 430

Tyr Phe Leu Ser Pro Asn Pro Asn Pro Asn Leu Leu Val Gly Ala Val
        435                 440                 445

Val Gly Gly Pro Asn Val Thr Asp Ala Phe Pro Asp Ser Arg Pro Tyr
    450                 455                 460

Phe Gln Gln Ser Glu Pro Thr Thr Tyr Ile Asn Ala Pro Leu Val Gly
465                 470                 475                 480

Leu Leu Gly Tyr Phe Ser Ala His Ser Thr Trp Arg
                485                 490
```

<210> SEQ ID NO 24
<211> LENGTH: 3208
<212> TYPE: DNA
<213> ORGANISM: Arabidopsis thaliana
<220> FEATURE:
<221> NAME/KEY: promoter
<222> LOCATION: (1)..(3208)
<223> OTHER INFORMATION: transcription regulating sequence from Arabidopsis thaliana gene At5g66690

<400> SEQUENCE: 24

```
ttcctccaaa cctaaactcg gacccaatat ttacctatct agatggcaag taacatcaat      60
tattcaatct tatgcattac atatataata tgaaattatc attgtggcag gtgagagaat     120
gattggacca cgtaacattg tgacatgtga tgagtttatt taacttgtcg cgccaattaa     180
atattctaat agtaatatca attattcact ttaattggta aaaaagaaga agataaaaaa     240
cagttcatat aatacattat caaatacgaa gtcagaacaa gattaagatc gtatcacgta     300
agacggagat cgactttctt cgttccagcc ttgacttacc atataacaag ttaaatatat     360
ttgtctcatt agaatcacgg gattaatgtt acgtaactac ggagatagcg tgataagaaa     420
tttggttaca aaacattgta tataaaaaaa ctaaatagag ctagttaagt ttcaaatcta     480
attttatttt ttgattaatt tgatgatttc cttccataga accataaata aaattcaatc     540
atttcctcta ttatgaaatt taattatata ttttgtttta ttagagagca ggaagaatat     600
attacgtaat atcaagaaaa tttagtcata agaccatatc ataataagcg gaattttcaa     660
caacaaacat ccaattttga tttactatta actgattatt ttctctgacc ggagtgaccg     720
ccattattta gaataatgtt ctttgaatga atcaaatttt atggcaccca aaagacagaa     780
gccacggcat ccgtttggca ttttatagtg atcttgcatt ttataatttt gatttgtatt     840
ttcttataac cgctattata agtttaacgt ttaaagctct gtatgttcac ctgacaaaaa     900
tgataagtaa aaaaaaacaa taattttcgt gaatctcaat attttcattg gtggtcgtaa     960
agccatgtga tggaatagtt accaacgtga gtcgtgatat atgggattag aaaatgtgac    1020
caattggtta ccagcaatca aacaaacgat aatccatggt tgatgaagaa agtagggtta    1080
ggtttgtaaa aaaaagaaat ggttgtgtgg tgatctaata atacatgggc tataagttta    1140
taattgcatt cctgcttatt aaggtacttt catcatagaa tcaaaacagt tactatcttt    1200
cttttctcct cactttttgt ttttcttctt ccttttttcga tagaatgtct gaatgtgtat    1260
acaattcttt tcaccattgg aatatgtgct ggtcaatatt aattactgat ttacataaaa    1320
tataatatcg ggcatgtgat ccaccatctc caacgtgagc ccgatcatgt ggtgattaat    1380
tggtcatttt tctatagatt cctcagaaga tattttatga aatacatgat cataatattg    1440
agttgtatac gacaattgag ggggtagcta gctcttacga tggaccaatc atctctaaga    1500
aaactatata tataattaaa gtaaaccaat taattacgat tactaaatac taacaaacaa    1560
aaccatatat atagggaacg cgaaaaaaat attagatata tatttgattg gtttaacttt    1620
gaatttttaa ttataaccca aaaaatactc atagttaatt tctttttttgg tgatatctgt    1680
ttacttttta ctctacttca cgtttttttt ttcttttact ctacttcacg ttaagttaga    1740
caaactcttg ttccattttt cattttatac aaaataaatat aattacatta ctaatatatg    1800
tatcgttatg ctgctatgtt actcaaaatg taaacaaaaa aaagagactc ggactggtct    1860
ttacgccaga tctaaatagg gtcaaccatc gtgctatgca ctctgctcaa tctgttaaaa    1920
aaatacagtc tacatacacc gacaataagg tttgtataat atacattatc tcaaaaatca    1980
aaaacaggaa acttgggcaa aatctttgaa attttaatta tgtatcgttc ctacaagttt    2040
ttttttttta aatggattca atatgtaaca tgttagtcga gtcttaaaaa aatatcatat    2100
aggtaacagg gaaacgattt aacgataata ggttccacaa attatataag tttcagctaa    2160
gttaaataaa tcattatgcc ttttcataat tactttattt agtttctgat tctaaaagca    2220
acttcattag gggtgtgaga aaggatatct aattctcaaa acaaataaaa attggttttt    2280
actaaacaag tttaagaacc atctttcact tgggagattt tcagaatcat tgagtctctt    2340
```

```
ccttattggt tctaattttt tattaatcaa aaaatattac ttttgtttta gctaaaatta   2400

ctattatatt gtttagatac ttaaccaatg gatgctcaaa attagatgag tttctcaatt   2460

taatttaaac taaacataat attattctag taattatact tagtgggtat ctaaactaat   2520

aaagatgctc taatatacta tatactaaaa caatatcgac ttctacaaac attgatccca   2580

taattcaact ataaataatg tacagtaatt tcttgaccaa acagtatagt gtacctctag   2640

aatattgctc aagcatctct gcatatataa tattactaat cgccatttag tgtcttcgta   2700

acaccatgtg cacccttagc agacaaaaaa atacaactca cacgcaaacc aaacaagcgg   2760

ttaaactgta taatcgcaat tggtatcact tattctagaa tgtttccaca ccacttcttt   2820

aacttaatta gtttttaaaa aaaactaatc aagttttaac tacttattta gaaaattaca   2880

aaactttaaa ctaaatatat ataattcaat gaagattcag atatgttatt gcttttgtct   2940

caatacttaa atttgcctaa aatacaaggt aagaatatta gattacatat acagtataat   3000

tactttattt cattgtttgt ctttcaaata atatacaact attaaactac aatttatagt   3060

ctatatcaat atttttattt ataaatgtta taaatctgcc tataaataag taagtaaccc   3120

atatacaacg accatagaaa cacatcatta acaaaacaaa gcctctctaa ataaaaacaa   3180

aaagctaact gaataagaag aagtagtg                                       3208
```

<210> SEQ ID NO 25
<211> LENGTH: 3141
<212> TYPE: DNA
<213> ORGANISM: Arabidopsis thaliana
<220> FEATURE:
<221> NAME/KEY: promoter
<222> LOCATION: (1)..(3141)
<223> OTHER INFORMATION: transcription regulating sequence from Arabidopsis thaliana gene At5g66690

<400> SEQUENCE: 25

```
ttcctccaaa cctaaactcg gacccaatat ttacctatct agatggcaag taacatcaat     60

tattcaatct tatgcattac atatataata tgaaattatc attgtggcag gtgagagaat    120

gattggacca cgtaacattg tgacatgtga tgagtttatt taacttgtcg cgccaattaa    180

atattctaat agtaatatca attattcact ttaattggta aaaaagaaga agataaaaaa    240

cagttcatat aatacattat caaatacgaa gtcagaacaa gattaagatc gtatcacgta    300

agacggagat cgactttctt cgttccagcc ttgacttacc atataacaag ttaaatatat    360

ttgtctcatt agaatcacgg gattaatgtt acgtaactac ggagatagcg tgataagaaa    420

tttggttaca aaacattgta tataaaaaaa ctaaatagag ctagttaagt ttcaaatcta    480

attttatttt ttgattaatt tgatgatttc cttccataga accataaata aaattcaatc    540

atttcctcta ttatgaaatt taattatata ttttgtttta ttagagagca ggaagaatat    600

attacgtaat atcaagaaaa tttagtcata agaccatatc ataataagcg gaattttcaa    660

caacaaacat ccaattttga tttactatta actgattatt ttctctgacc ggagtgaccg    720

ccattattta gaataatgtt ctttgaatga atcaaatttt atggcaccca aaagacagaa    780

gccacggcat ccgtttggca ttttatagtg atcttgcatt ttataatttt gatttgtatt    840

ttcttataac cgctattata agtttaacgt ttaaagctct gtatgttcac ctgacaaaaa    900

tgataagtaa aaaaaaacaa taattttcgt gaatctcaat attttcattg gtggtcgtaa    960

agccatgtga tggaatagtt accaacgtga gtcgtgatat atgggattag aaaatgtgac   1020

caattggtta ccagcaatca aacaaacgat aatccatggt tgatgaagaa agtagggtta   1080
```

-continued

```
ggtttgtaaa aaaaagaaat ggttgtgtgg tgatctaata atacatgggc tataagttta   1140
taattgcatt cctgcttatt aaggtacttt catcatagaa tcaaaacagt tactatcttt   1200
cttttctcct cactttttgt ttttcttctt cctttttcga tagaatgtct gaatgtgtat   1260
acaattcttt tcaccattgg aatatgtgct ggtcaatatt aattactgat ttacataaaa   1320
tataatatcg ggcatgtgat ccaccatctc caacgtgagc ccgatcatgt ggtgattaat   1380
tggtcatttt tctatagatt cctcagaaga tattttatga aatacatgat cataatattg   1440
agttgtatac gacaattgag ggggtagcta gctcttacga tggaccaatc atctctaaga   1500
aaactatata tataattaaa gtaaaccaat taattacgat tactaaatac taacaaacaa   1560
aaccatatat atagggaacg cgaaaaaaat attagatata tatttgattg gtttaacttt   1620
gaatttttaa ttataaccca aaaaatactc atagttaatt tctttttgg tgatatctgt   1680
ttacttttta ctctacttca cgtttttttt ttcttttact ctacttcacg ttaagttaga   1740
caaactcttg ttccattttt cattttatac aaaataatat aattacatta ctaatatatg   1800
tatcgttatg ctgctatgtt actcaaaatg taaacaaaaa aaagagactc ggactggtct   1860
ttacgccaga tctaaatagg gtcaaccatc gtgctatgca ctctgctcaa tctgttaaaa   1920
aaatacagtc tacatacacc gacaataagg tttgtataat atacattatc tcaaaaatca   1980
aaaacaggaa acttgggcaa aatctttgaa attttaatta tgtatcgttc ctacaagttt   2040
ttttttttta aatggattca atatgtaaca tgttagtcga gtcttaaaaa aatatcatat   2100
aggtaacagg gaaacgattt aacgataata ggttccacaa attatataag tttcagctaa   2160
gttaaataaa tcattatgcc ttttcataat tactttattt agtttctgat tctaaaagca   2220
acttcattag gggtgtgaga aaggatatct aattctcaaa acaaataaaa attggttttt   2280
actaaacaag tttaagaacc atctttcact tgggagattt tcagaatcat tgagtctctt   2340
ccttattggt tctaattttt tattaatcaa aaaatattac ttttgtttta gctaaaatta   2400
ctattatatt gtttagatac ttaaccaatg gatgctcaaa attagatgag tttctcaatt   2460
taatttaaac taaacataat attattctag taattatact tagtgggtat ctaaactaat   2520
aaagatgctc taatatacta tatactaaaa caatatcgac ttctacaaac attgatccca   2580
taattcaact ataaataatg tacagtaatt tcttgaccaa acagtatagt gtacctctag   2640
aatattgctc aagcatctct gcatatataa tattactaat cgccatttag tgtcttcgta   2700
acaccatgtg caccccttagc agacaaaaaa atacaactca cacgcaaacc aaacaagcgg   2760
ttaaactgta taatcgcaat tggtatcact tattctagaa tgtttccaca ccacttcttt   2820
aacttaatta gtttttaaaa aaaactaatc aagttttaac tacttattta gaaaattaca   2880
aaactttaaa ctaaatatat ataattcaat gaagattcag atatgttatt gcttttgtct   2940
caatacttaa atttgcctaa aatacaaggt aagaatatta gattacatat acagtataat   3000
tactttattt cattgtttgt ctttcaaata atatacaact attaaactac aatttatagt   3060
ctatatcaat atttttattt ataaatgtta taaatctgcc tataaataag taagtaaccc   3120
atatacaacg accatagaaa c                                              3141
```

<210> SEQ ID NO 26
<211> LENGTH: 3208
<212> TYPE: DNA
<213> ORGANISM: Arabidopsis thaliana
<220> FEATURE:
<221> NAME/KEY: promoter
<222> LOCATION: (1)..(3208)

<223> OTHER INFORMATION: transcription regulating sequence from Arabidopsis thaliana gene At5g66690

<400> SEQUENCE: 26

```
ttcctccaaa cctaaactcg gacccaatat ttacctatct agatggcaag taacatcaat     60
tattcaatct tatgcattac atatataata tgaaattatc attgtggcag gtgagagaat    120
gattggacca cgtaacattg tgacatgtga tgagtttatt taacttgtcg cgccaattaa    180
atattctaat agtaatatca attattcact ttaattggta aaaaagaaga agataaaaaa    240
cagttcatat aatacattat caaatacgaa gtcagaacaa gattaagatc gtatcacgta    300
agacggagat cgactttctt cgttccagcc ttgacttacc atataacaag ttaaatatat    360
ttgtctcatt agaatcacgg gattaatgtt acgtaactac ggagatagcg tgataagaaa    420
tttggttaca aaacattgta tataaaaaaa ctaaatagag ctagttaagt ttcaaatcta    480
attttatttt ttgattaatt tgatgatttc cttccataga accataaata aaattcaatc    540
atttcctcta ttatgaaatt taattatata ttttgtttta ttagagagca ggaagaatat    600
attacgtaat atcaagaaaa tttagtcata agaccatatc ataataagcg gaattttcaa    660
caacaaacat ccaattttga tttactatta actgattatt ttctctgacc ggagtgaccg    720
ccattattta gaataatgtt ctttgaatga atcaaatttt atggcaccca aaagacagaa    780
gccacggcat ccgtttggca ttttatagtg atcttgcatt ttataatttt gatttgtatt    840
ttcttataac cgctattata agtttaacgt ttaaagctct gtatgttcac ctgacaaaaa    900
tgataagtaa aaaaaaacaa taattttcgt gaatctcaat attttcattg gtggtcgtaa    960
agccatgtga tggaatagtt accaacgtga gtcgtgatat atgggattag aaaatgtgac   1020
caattggtta ccagcaatca aacaaacgat aatccatggt tgatgaagaa agtagggtta   1080
ggtttgtaaa aaaaagaaat ggttgtgtgg tgatctaata atacatgggc tataagttta   1140
taattgcatt cctgcttatt aaggtacttt catcatagaa tcaaaacagt tactatcttt   1200
cttttctcct cactttttgt ttttcttctt cctttttcga tagaatgtct gaatgtgtat   1260
acaattcttt tcaccattgg aatatgtgct ggtcaatatt aattactgat ttacataaaa   1320
tataatatcg ggcatgtgat ccaccatctc caacgtgagc ccgatcatgt ggtgattaat   1380
tggtcatttt tctatagatt cctcagaaga tattttatga aatacatgat cataaatattg  1440
agttgtatac gacaattgag ggggtagcta gctcttacga tggaccaatc atctctaaga   1500
aaactatata tataattaaa gtaaaccaat taattacgat tactaaatac taacaaacaa   1560
aaccatatat atagggaacg cgaaaaaaat attagatata tatttgattg gtttaacttt   1620
gaatttttaa ttataaccca aaaaatactc atagttaatt tctttttttgg tgatatctgt  1680
ttacttttta ctctacttca cgtttttttt ttcttttact ctacttcacg ttaagttaga   1740
caaactcttg ttccattttt cattttatac aaaataatat aattacatta ctaatatatg   1800
tatcgttatg ctgctatgtt actcaaaatg taaacaaaaa aaagagactc ggactggtct   1860
ttacgccaga tctaaatagg gtcaaccatc gtgctatgca ctctgctcaa tctgttaaaa   1920
aaatacagtc tacatacacc gacaataagg tttgtataat atacattatc tcaaaaatca   1980
aaaacaggaa acttgggcaa aatctttgaa attttaatta tgtatcgttc ctacaagttt   2040
ttttttttta aatggattca atatgtaaca tgttagtcga gtcttaaaaa aatatcatat   2100
aggtaacagg gaaacgattt aacgataata ggttccacaa attatataag tttcagctaa   2160
gttaaataaa tcattatgcc ttttcataat tactttattt agtttctgat tctaaaagca   2220
```

-continued

```
acttcattag gggtgtgaga aaggatatct aattctcaaa acaaataaaa attggttttt   2280

actaaacaag tttaagaacc atctttcact tgggagattt tcagaatcat tgagtctctt   2340

ccttattggt tctaattttt tattaatcaa aaaatattac ttttgtttta gctaaaatta   2400

ctattatatt gtttagatac ttaaccaatg gatgctcaaa attagatgag tttctcaatt   2460

taatttaaac taaacataat attattctag taattatact tagtgggtat ctaaactaat   2520

aaagatgctc taatatacta tatactaaaa caatatcgac ttctacaaac attgatccca   2580

taattcaact ataaataatg tacagtaatt tcttgaccaa acagtatagt gtacctctag   2640

aatattgctc aagcatctct gcatatataa tattactaat cgccatttag tgtcttcgta   2700

acaccatgtg cacccttagc agacaaaaaa atacaactca cacgcaaacc aaacaagcgg   2760

ttaaactgta taatcgcaat tggtatcact tattctagaa tgtttccaca ccacttcttt   2820

aacttaatta gtttttaaa aaaactaatc aagttttaac tacttattta gaaaattaca   2880

aaactttaaa ctaaatatat ataattcaat gaagattcag atatgttatt gcttttgtct   2940

caatacttaa atttgcctaa aatacaaggt aagaatatta gattacatat acagtataat   3000

tactttattt cattgtttgt ctttcaaata atatacaact attaaactac aatttatagt   3060

ctatatcaat atttttattt ataaatgtta taaatctgcc tataaataag taagtaaccc   3120

atatacaacg accatagaaa cacatcatta acaaaacaaa gcctctctaa ataaaaacaa   3180

aaagctaact gaataagaag aagtagtg                                      3208
```

<210> SEQ ID NO 27
<211> LENGTH: 1714
<212> TYPE: DNA
<213> ORGANISM: Arabidopsis thaliana
<220> FEATURE:
<221> NAME/KEY: CDS
<222> LOCATION: (76)..(1521)
<223> OTHER INFORMATION: coding for UDP-glucose glycosyltransferase
      protein

<400> SEQUENCE: 27

```
atagaaacac atcattaaca aaacaaagcc tctctaaata aaaacaaaaa gctaactgaa     60

taagaagaag tagtg atg cat atc aca aaa cca cac gcc gcc atg ttt tcc     111
                 Met His Ile Thr Lys Pro His Ala Ala Met Phe Ser
                 1               5                   10

agt ccc gga atg ggc cat gtc atc ccg gtg atc gag ctt gga aag cgt       159
Ser Pro Gly Met Gly His Val Ile Pro Val Ile Glu Leu Gly Lys Arg
        15                  20                  25

ctc tcc gct aac aac ggc ttc cac gtc acc gtc ttc gtc ctc gaa acc       207
Leu Ser Ala Asn Asn Gly Phe His Val Thr Val Phe Val Leu Glu Thr
    30                  35                  40

gac gca gcc tcc gct caa tcc aag ttc cta aac tca acc ggc gtc gac       255
Asp Ala Ala Ser Ala Gln Ser Lys Phe Leu Asn Ser Thr Gly Val Asp
45                  50                  55                  60

atc gtc aaa ctt cca tcg ccg gac att tat ggt tta gtg gac ccc gac       303
Ile Val Lys Leu Pro Ser Pro Asp Ile Tyr Gly Leu Val Asp Pro Asp
                65                  70                  75

gac cat gta gtg acc aag atc gga gtc att atg cgt gca gca gtt cca       351
Asp His Val Val Thr Lys Ile Gly Val Ile Met Arg Ala Ala Val Pro
            80                  85                  90

gcc ctc cga tcc aag atc gct gcc atg cat caa aag cca acg gct ctg       399
Ala Leu Arg Ser Lys Ile Ala Ala Met His Gln Lys Pro Thr Ala Leu
        95                  100                 105

atc gtt gac ttg ttt ggc aca gat gcg tta tgt ctc gca aag gaa ttt       447
Ile Val Asp Leu Phe Gly Thr Asp Ala Leu Cys Leu Ala Lys Glu Phe
```

-continued

```
    110                 115                 120

aac atg ttg agt tat gtg ttt atc cct acc aac gca cgt ttt ctc gga      495
Asn Met Leu Ser Tyr Val Phe Ile Pro Thr Asn Ala Arg Phe Leu Gly
125                 130                 135                 140

gtt tcg att tat tat cca aat ttg gac aaa gat atc aag gaa gag cac      543
Val Ser Ile Tyr Tyr Pro Asn Leu Asp Lys Asp Ile Lys Glu Glu His
                145                 150                 155

aca gtg caa aga aac cca ctc gct ata ccg ggg tgt gaa ccg gtt agg      591
Thr Val Gln Arg Asn Pro Leu Ala Ile Pro Gly Cys Glu Pro Val Arg
            160                 165                 170

ttc gaa gat act ctg gat gca tat ctg gtt ccc gac gaa ccg gtg tac      639
Phe Glu Asp Thr Leu Asp Ala Tyr Leu Val Pro Asp Glu Pro Val Tyr
        175                 180                 185

cgg gat ttt gtt cgt cat ggt ctg gct tac cca aaa gcc gat gga att      687
Arg Asp Phe Val Arg His Gly Leu Ala Tyr Pro Lys Ala Asp Gly Ile
    190                 195                 200

ttg gta aat aca tgg gaa gag atg gag ccc aaa tca ttg aag tcc ctt      735
Leu Val Asn Thr Trp Glu Glu Met Glu Pro Lys Ser Leu Lys Ser Leu
205                 210                 215                 220

cta aac cca aag ctc ttg ggc cgg gtt gct cgt gta ccg gtc tat cca      783
Leu Asn Pro Lys Leu Leu Gly Arg Val Ala Arg Val Pro Val Tyr Pro
                225                 230                 235

atc ggt ccc tta tgc aga ccg ata caa tca tcc gaa acc gat cac ccg      831
Ile Gly Pro Leu Cys Arg Pro Ile Gln Ser Ser Glu Thr Asp His Pro
            240                 245                 250

gtt ttg gat tgg tta aac gaa caa ccg aac gag tcg gtt ctc tat atc      879
Val Leu Asp Trp Leu Asn Glu Gln Pro Asn Glu Ser Val Leu Tyr Ile
        255                 260                 265

tcc ttc ggg agt ggt ggt tgt cta tcg gcg aaa cag tta act gaa ttg      927
Ser Phe Gly Ser Gly Gly Cys Leu Ser Ala Lys Gln Leu Thr Glu Leu
    270                 275                 280

gcg tgg gga ctc gag cag agc cag caa cgg ttc gta tgg gtg gtt cga      975
Ala Trp Gly Leu Glu Gln Ser Gln Gln Arg Phe Val Trp Val Val Arg
285                 290                 295                 300

cca ccg gtc gac ggt tcg tgt tgt agc gag tat gtc tcg gct aac ggt     1023
Pro Pro Val Asp Gly Ser Cys Cys Ser Glu Tyr Val Ser Ala Asn Gly
                305                 310                 315

ggt gga acc gaa gac aac acg cca gag tat cta ccg gaa ggg ttc gtg     1071
Gly Gly Thr Glu Asp Asn Thr Pro Glu Tyr Leu Pro Glu Gly Phe Val
            320                 325                 330

agt cgt act agt gat aga ggt ttc gtg gtc ccc tca tgg gcc cca caa     1119
Ser Arg Thr Ser Asp Arg Gly Phe Val Val Pro Ser Trp Ala Pro Gln
        335                 340                 345

gct gaa atc ctg tcc cat cgg gcc gtt ggt ggg ttt ttg acc cat tgc     1167
Ala Glu Ile Leu Ser His Arg Ala Val Gly Gly Phe Leu Thr His Cys
    350                 355                 360

ggt tgg agc tcg acg ttg gaa agc gtc gtt ggc ggc gtt ccg atg atc     1215
Gly Trp Ser Ser Thr Leu Glu Ser Val Val Gly Gly Val Pro Met Ile
365                 370                 375                 380

gca tgg cca ctt ttt gcc gag cag aat atg aat gcg gcg ttg ctc agc     1263
Ala Trp Pro Leu Phe Ala Glu Gln Asn Met Asn Ala Ala Leu Leu Ser
                385                 390                 395

gac gaa ctg gga atc gca gtc aga ttg gat gat cca aag gag gat att     1311
Asp Glu Leu Gly Ile Ala Val Arg Leu Asp Asp Pro Lys Glu Asp Ile
            400                 405                 410

tct agg tgg aag att gag gcg ttg gtg agg aag gtt atg act gag aag     1359
Ser Arg Trp Lys Ile Glu Ala Leu Val Arg Lys Val Met Thr Glu Lys
        415                 420                 425

gaa ggt gaa gcg atg aga agg aaa gtg aag aag ttg aga gac tcg gcg     1407
```

-continued

```
Glu Gly Glu Ala Met Arg Arg Lys Val Lys Lys Leu Arg Asp Ser Ala
    430                 435                 440

gag atg tca ctg agc att gac ggt ggt ggt ttg gcg cac gag tcg ctt     1455
Glu Met Ser Leu Ser Ile Asp Gly Gly Gly Leu Ala His Glu Ser Leu
445                 450                 455                 460

tgc aga gtc acc aag gag tgt caa cgg ttt ttg gaa cgt gtc gtg gac     1503
Cys Arg Val Thr Lys Glu Cys Gln Arg Phe Leu Glu Arg Val Val Asp
                465                 470                 475

ttg tca cgt ggt gct tag aaattgttac cgttttctag ctcttttatt            1551
Leu Ser Arg Gly Ala
            480

attagtggtt gaattatacg tgtcgttcct ctgttagtgt ataatataat aatcgattta   1611

ctctttgtaa tataatgatg tttttgatat ttttcaacta attttccatt gtaatattga   1671

ataatcgggt gttgttgtaa ttaataatga gaaacaattt gtt                     1714


<210> SEQ ID NO 28
<211> LENGTH: 481
<212> TYPE: PRT
<213> ORGANISM: Arabidopsis thaliana

<400> SEQUENCE: 28

Met His Ile Thr Lys Pro His Ala Ala Met Phe Ser Ser Pro Gly Met
1               5                   10                  15

Gly His Val Ile Pro Val Ile Glu Leu Gly Lys Arg Leu Ser Ala Asn
            20                  25                  30

Asn Gly Phe His Val Thr Val Phe Val Leu Glu Thr Asp Ala Ala Ser
        35                  40                  45

Ala Gln Ser Lys Phe Leu Asn Ser Thr Gly Val Asp Ile Val Lys Leu
    50                  55                  60

Pro Ser Pro Asp Ile Tyr Gly Leu Val Asp Pro Asp Asp His Val Val
65                  70                  75                  80

Thr Lys Ile Gly Val Ile Met Arg Ala Ala Val Pro Ala Leu Arg Ser
                85                  90                  95

Lys Ile Ala Ala Met His Gln Lys Pro Thr Ala Leu Ile Val Asp Leu
            100                 105                 110

Phe Gly Thr Asp Ala Leu Cys Leu Ala Lys Glu Phe Asn Met Leu Ser
        115                 120                 125

Tyr Val Phe Ile Pro Thr Asn Ala Arg Phe Leu Gly Val Ser Ile Tyr
    130                 135                 140

Tyr Pro Asn Leu Asp Lys Asp Ile Lys Glu Glu His Thr Val Gln Arg
145                 150                 155                 160

Asn Pro Leu Ala Ile Pro Gly Cys Glu Pro Val Arg Phe Glu Asp Thr
                165                 170                 175

Leu Asp Ala Tyr Leu Val Pro Asp Glu Pro Val Tyr Arg Asp Phe Val
            180                 185                 190

Arg His Gly Leu Ala Tyr Pro Lys Ala Asp Gly Ile Leu Val Asn Thr
        195                 200                 205

Trp Glu Glu Met Glu Pro Lys Ser Leu Lys Ser Leu Leu Asn Pro Lys
    210                 215                 220

Leu Leu Gly Arg Val Ala Arg Val Pro Val Tyr Pro Ile Gly Pro Leu
225                 230                 235                 240

Cys Arg Pro Ile Gln Ser Ser Glu Thr Asp His Pro Val Leu Asp Trp
                245                 250                 255

Leu Asn Glu Gln Pro Asn Glu Ser Val Leu Tyr Ile Ser Phe Gly Ser
            260                 265                 270
```

-continued

```
Gly Gly Cys Leu Ser Ala Lys Gln Leu Thr Glu Leu Ala Trp Gly Leu
        275                 280                 285

Glu Gln Ser Gln Gln Arg Phe Val Trp Val Val Arg Pro Pro Val Asp
    290                 295                 300

Gly Ser Cys Cys Ser Glu Tyr Val Ser Ala Asn Gly Gly Gly Thr Glu
305                 310                 315                 320

Asp Asn Thr Pro Glu Tyr Leu Pro Glu Gly Phe Val Ser Arg Thr Ser
                325                 330                 335

Asp Arg Gly Phe Val Val Pro Ser Trp Ala Pro Gln Ala Glu Ile Leu
            340                 345                 350

Ser His Arg Ala Val Gly Gly Phe Leu Thr His Cys Gly Trp Ser Ser
        355                 360                 365

Thr Leu Glu Ser Val Val Gly Gly Val Pro Met Ile Ala Trp Pro Leu
    370                 375                 380

Phe Ala Glu Gln Asn Met Asn Ala Ala Leu Leu Ser Asp Glu Leu Gly
385                 390                 395                 400

Ile Ala Val Arg Leu Asp Asp Pro Lys Glu Asp Ile Ser Arg Trp Lys
                405                 410                 415

Ile Glu Ala Leu Val Arg Lys Val Met Thr Glu Lys Glu Gly Glu Ala
            420                 425                 430

Met Arg Arg Lys Val Lys Lys Leu Arg Asp Ser Ala Glu Met Ser Leu
        435                 440                 445

Ser Ile Asp Gly Gly Gly Leu Ala His Glu Ser Leu Cys Arg Val Thr
    450                 455                 460

Lys Glu Cys Gln Arg Phe Leu Glu Arg Val Val Asp Leu Ser Arg Gly
465                 470                 475                 480

Ala


<210> SEQ ID NO 29
<211> LENGTH: 1993
<212> TYPE: DNA
<213> ORGANISM: Arabidopsis thaliana
<220> FEATURE:
<221> NAME/KEY: promoter
<222> LOCATION: (1)..(1993)
<223> OTHER INFORMATION: transcription regulating sequence from
      Arabidopsis thaliana gene At3g29630

<400> SEQUENCE: 29

gatcccacgg gacgggttgt tatataaaag tcgacttaga tcaattggta acagcttgtc      60

ttgtgggaac gttgtatagg gtgaggtctt gagttcgtgg aacgccaagc gcaccaataa     120

cctacctgtg ggcttaggtg gcccaaggag agaggttagg atcgatgcga gacagagcca     180

acatgatgcc acgtggagga gtatgtccac gtgggcgggt cccacgggac gggttgttat     240

agctctattg tgcaatctgt ggtagtcggc atcgccaaca gatgtattat gtattttgtt     300

actgagattg aggtcggtta attccgtgga ccgtacttct ttatcacctc gttaggggcc     360

agcatctcta tcgagtatat tatgtaaata ttctgttagt atatggtttg ggtcgactaa     420

tgctgcagtt gtaccattcc gacgtgcatt gatggataca tgctcgtttt gttctgaggt     480

tattattctg tctgatgata ttattatgtt cttatgattt aattatgtat tttgctagca     540

taagttctga tgtgctttac tttatttaaa attaattgaa ttgaaactat gtttgttagt     600

accaacacgt gaacattatt ttgtgcggga tcagaccgtg ttggtacttg ttcttcgggt     660

ttgtagtctc actgagcgat ttttcactca cataaattct gattccgtgc agagagcatt     720
```

-continued

```
gacgaggagc ggtatgcagc tgaggtttag agtttgttat tcgtagagcg agacttggta    780

gactttctaa agtttaattt attttgtttt taagatttgg agtttacaca agatttcaac    840

tttgtatatt ttgcaaattt tagtattttt attatagtaa tgcttcaaag attcttttga    900

attttcggag tgttactgtt caacttcagc atataataca ttttatttac gaaaatacct    960

ttgaattgaa gaaagcacat tgcttgtgga taacaaaaac ataattttat aaaattacgt   1020

gtttacactg tataaataat gtccatcttc ttcacttgaa agataaaaaa tttggaaact   1080

ttcaaaagct tttagaaatc ttttctaacg tttctagaaa aacatattgt gtttactcta   1140

caacaatgtt gtttttcttc atttgcaata ttattttctc atatctaaac cataattcca   1200

acatagtaaa cccttatcgt ggtcttaaac atttttttatt tgttaaagct gttaagttaa   1260

aactttcaat cacaaaatgt aaaccaaata atatattata atagaagaga tcatcagata   1320

acctcgatca cgtaggagaa aatacattgt cattaaaaag tttgagcgtg tacaaaatta   1380

tttactcttc aatgaataat ttctttccaa aatcccaatg tatccgtcga tagtaataaa   1440

gaaaacctca ttcgaatatc aaaaacaaaa ttgcgagaaa aagttaaaaa tacataacat   1500

ttaaatattt aaatacatta tattttatga ttaaaaatct tatacgtgtc tctatgcctt   1560

gttttttttt tgtcggccaa ttatcttatt atgtgataaa acgtatgcct tctttaaaat   1620

atgcaactat ttgacgtaat acattaatga aatttactca aacaattttt ctataaggac   1680

aaaaatgaaa aggcaaccac aaccattctt gacaaccaca ctaacacatg aaacaagtaa   1740

agtagtaaac caataatttg gttttatata ttaaagtaaa ctaataattc ccacctaatt   1800

caactaacca ttcactgata atcacactta acctaaaata ccattaaatt agtcgttcat   1860

tgcttcatgt agtggtatcc tgaatagacg agaagcatca atcacataac agtttttttct   1920

cttagaaaga aaatacaaag tttttatttc gtttgagttt cttgttttag gttttgacaa   1980

tttaggggaa agg                                                      1993
```

<210> SEQ ID NO 30
<211> LENGTH: 1909
<212> TYPE: DNA
<213> ORGANISM: Arabidopsis thaliana
<220> FEATURE:
<221> NAME/KEY: promoter
<222> LOCATION: (1)..(1909)
<223> OTHER INFORMATION: transcription regulating sequence from
      Arabidopsis thaliana gene At3g29630

<400> SEQUENCE: 30

```
gatcccacgg gacgggttgt tatataaaag tcgacttaga tcaattggta acagcttgtc     60

ttgtgggaac gttgtatagg gtgaggtctt gagttcgtgg aacgccaagc gcaccaataa    120

cctacctgtg ggcttaggtg gcccaaggag agaggttagg atcgatgcga gacagagcca    180

acatgatgcc acgtggagga gtatgtccac gtgggcgggt cccacgggac gggttgttat    240

agctctattg tgcaatctgt ggtagtcggc atcgccaaca gatgtattat gtattttgtt    300

actgagattg aggtcggtta attccgtgga ccgtacttct ttatcacctc gttaggggcc    360

agcatctcta tcgagtatat tatgtaaata ttctgttagt atatggtttg ggtcgactaa    420

tgctgcagtt gtaccattcc gacgtgcatt gatggataca tgctcgtttt gttctgaggt    480

tattattctg tctgatgata ttattatgtt cttatgattt aattatgtat tttgctagca    540

taagttctga tgtgctttac tttatttaaa attaattgaa ttgaaactat gtttgttagt    600

accaacacgt gaacattatt ttgtgcggga tcagaccgtg ttggtacttg ttcttcgggt    660
```

-continued

```
ttgtagtctc actgagcgat ttttcactca cataaattct gattccgtgc agagagcatt    720

gacgaggagc ggtatgcagc tgaggtttag agtttgttat tcgtagagcg agacttggta    780

gactttctaa agtttaattt attttgtttt taagatttgg agtttacaca agatttcaac    840

tttgtatatt ttgcaaattt tagtattttt attatagtaa tgcttcaaag attcttttga    900

attttcggag tgttactgtt caacttcagc atataataca ttttatttac gaaaatacct    960

ttgaattgaa gaaagcacat tgcttgtgga taacaaaaac ataattttat aaaattacgt   1020

gtttacactg tataaataat gtccatcttc ttcacttgaa agataaaaaa tttggaaact   1080

ttcaaaagct tttagaaatc ttttctaacg tttctagaaa aacatattgt gtttactcta   1140

caacaatgtt gtttttcttc atttgcaata ttattttctc atatctaaac cataattcca   1200

acatagtaaa cccttatcgt ggtcttaaac attttttatt tgttaaagct gttaagttaa   1260

aactttcaat cacaaaatgt aaaccaaata atatattata atagaagaga tcatcagata   1320

acctcgatca cgtaggagaa aatacattgt cattaaaaag tttgagcgtg tacaaaatta   1380

tttactcttc aatgaataat ttctttccaa aatcccaatg tatccgtcga tagtaataaa   1440

gaaaacctca ttcgaatatc aaaaacaaaa ttgcgagaaa aagttaaaaa tacataacat   1500

ttaaatattt aaatacatta tattttatga ttaaaaatct tatacgtgtc tctatgcctt   1560

gttttttttt tgtcggccaa ttatcttatt atgtgataaa acgtatgcct tctttaaaat   1620

atgcaactat ttgacgtaat acattaatga aatttactca aacaattttt ctataaggac   1680

aaaaatgaaa aggcaaccac aaccattctt gacaaccaca ctaacacatg aaacaagtaa   1740

agtagtaaac caataatttg gttttatata ttaaagtaaa ctaataattc ccacctaatt   1800

caactaacca ttcactgata atcacactta acctaaaata ccattaaatt agtcgttcat   1860

tgcttcatgt agtggtatcc tgaatagacg agaagcatca atcacataa               1909
```

<210> SEQ ID NO 31
<211> LENGTH: 1994
<212> TYPE: DNA
<213> ORGANISM: Arabidopsis thaliana
<220> FEATURE:
<221> NAME/KEY: promoter
<222> LOCATION: (1)..(1994)
<223> OTHER INFORMATION: transcription regulating sequence from
      Arabidopsis thaliana gene At3g29630

<400> SEQUENCE: 31

```
gatcccacgg gacgggttgt tatataaaag tcgacttaga tcaattggta acagcttgtc     60

ttgtgggaac gttgttatag ggtgaggtct tgagttcgtg gaacgccaag cgcaccaata    120

acctacctgt gggcttaggt ggcccaagga gagaggttag gatcgatgcg atacagagcc    180

aacatgatgc cacgtggagg agtatgtcca cgtgggcggg tcccacggga cgggttgtta    240

cagctctatt gtgcaatctg tggtagtcgg catcgccaac agattattat gtattttgtt    300

agtgggattg aggtcggtta attccgtgga ccgtacttct ttatcacctc gttaggggcc    360

aacatctcta tcgagtatat tatgtaaata ttctgtcagt atatggtttg ggtcgactaa    420

tgctgcagtt gtaccattcc gacgtgcatt gatggataca tgctcgtttt gttctgaggt    480

tattattctg tctgatgata ttattatgtt cttatgattt aattatgtat tttgctagca    540

taagttctga cgtgctttac tttatttaaa attaattgaa ttgaaactat gtttgttagt    600

accaacacgt aaatattatt ctgtgcggga tcagaccgtg ttggtacttg ttcttcgggt    660

ttgtagtctt actgagcgat ttttcactca cataagttct gattccgtgc agagagcatt    720
```

-continued

```
gacgagaagc ggtatgcagc tgaggtttag agtttgttat tcgtagagcg agacttggta    780

gactttctaa agtttaattt attttgtttt taagatttgg agtttacaca agatttcaac    840

tttgtatatt ttgcaaattt tagtattttt attatagtaa tgcttcaaag attcttttga    900

attttcggaa tgttactgtt caacttcagc atataataca ttttatttac gaaaatacct    960

ttgaattgaa gaaagcacat tgcttgtgga taacaaaaac ataattttat aaaattacgt   1020

gtttacactg tataaataat gtccatcttc ttcacttgaa agataaaaaa tttggaaact   1080

ttcaaaagct tttagaaatc ttttctaacg tttctagaaa aacatattgt gtttactcta   1140

caacaatgtt gtttttcttc atttgcaata ttattttctc atatctaaac cataattcca   1200

acatagtaaa cccttatcgt ggtcttaaac attttttatt tgttaaagct gttaagttaa   1260

aactttcaat cacaaaatgt aaaccaaata atatattata atagaagaga tcatcagata   1320

acctcgatca cgtaggagaa aatacattgt cattaaaaag tttgagcgtg tacaaaatta   1380

tttactcttc aatgaataat ttctttccaa aatcccaatg tatccgtcga tagtaataaa   1440

gaaaacctca ttcgaatatc aaaaacaaaa ttgcgagaaa aagttaaata tacataacat   1500

ttaaatattt aaatacatta tattttatga ttaaaaatct tatacgtgtc tctatgcctt   1560

gttttttttt tgtcggccaa ttatcttatt atgtgataaa acgtatgcct tctttaaaat   1620

atgcaactat ttgacgtaat acattaatga aatttactca aacaattttt ctataaggac   1680

aaaaatgaaa aggcaaccac aaccattctt gacaaccaca ctaacacatg aaacaagtaa   1740

agtagtaaac caataatttg gttttatata ttaaagtaaa ctaataattc ccacctaatt   1800

caactaacca ttcactgata atcacactta acctaaaata ccattaaatt agtcgttcat   1860

tgcttcatgt agtggtatcc tgaatagacg agaagcatca atcacataac agtttttttct  1920

cttagaaaga aaatacaaag tttttatttc gtttgagttt cttgttttag gttttgacaa   1980

tttaggggaa aggc                                                     1994
```

<210> SEQ ID NO 32
<211> LENGTH: 1582
<212> TYPE: DNA
<213> ORGANISM: Arabidopsis thaliana
<220> FEATURE:
<221> NAME/KEY: CDS
<222> LOCATION: (86)..(1432)
<223> OTHER INFORMATION: coding for UDP-glucose:flavonoid
      glucosyltransferase

<400> SEQUENCE: 32

```
gtttttctc ttagaaagaa aatacaaagt ttttatttcg tttgagtttc ttgttttagg      60

ttttgacaat ttaggggaaa ggaaa atg ggg tca aag ttt cat gct ttt ctt      112
                            Met Gly Ser Lys Phe His Ala Phe Leu
                            1               5

tat cca tgg ttt ggt ttt ggt cat atg att ccg tat ctt cat cta gct      160
Tyr Pro Trp Phe Gly Phe Gly His Met Ile Pro Tyr Leu His Leu Ala
10                  15                  20                  25

aac aaa tta gct gaa aaa ggt cat agg gtt act ttc ttg gct ccc aag      208
Asn Lys Leu Ala Glu Lys Gly His Arg Val Thr Phe Leu Ala Pro Lys
                30                  35                  40

aaa gct cag aaa caa ctc gaa cct ctc aac ttg ttc cca aac agc att      256
Lys Ala Gln Lys Gln Leu Glu Pro Leu Asn Leu Phe Pro Asn Ser Ile
            45                  50                  55

cac ttc gag aat gtt act ctt cct cat gtt gat ggt ctc cct gtt ggc      304
His Phe Glu Asn Val Thr Leu Pro His Val Asp Gly Leu Pro Val Gly
        60                  65                  70
```

-continued

```
gca gag aca acc gcg gat ctc ccg aac tca tct aag aga gtc ctc gct      352
Ala Glu Thr Thr Ala Asp Leu Pro Asn Ser Ser Lys Arg Val Leu Ala
    75                  80                  85

gat gcc atg gat ctt cta cgc gaa cag att gaa gtt aag att cgt tct      400
Asp Ala Met Asp Leu Leu Arg Glu Gln Ile Glu Val Lys Ile Arg Ser
90                  95                  100                 105

ttg aaa cct gac cta att ttc ttc gat ttt gtt gat tgg att cca caa      448
Leu Lys Pro Asp Leu Ile Phe Phe Asp Phe Val Asp Trp Ile Pro Gln
                110                 115                 120

atg gca aaa gaa tta gga atc aaa agt gta agt tac cag atc ata tcg      496
Met Ala Lys Glu Leu Gly Ile Lys Ser Val Ser Tyr Gln Ile Ile Ser
            125                 130                 135

gca gct ttt ata gct atg ttt ttc gct cct cgt gct gaa tta ggt tct      544
Ala Ala Phe Ile Ala Met Phe Phe Ala Pro Arg Ala Glu Leu Gly Ser
        140                 145                 150

cct cca cct ggg ttt cct tca tca aaa gta gca tta cgt gga cat gac      592
Pro Pro Pro Gly Phe Pro Ser Ser Lys Val Ala Leu Arg Gly His Asp
    155                 160                 165

gct aac atc tat tca ctc ttc gca aac acc cgc aaa ttt ctc ttt gat      640
Ala Asn Ile Tyr Ser Leu Phe Ala Asn Thr Arg Lys Phe Leu Phe Asp
170                 175                 180                 185

cga gtc acc aca ggc ctt aag aac tgc gac gtc att gcc ata agg aca      688
Arg Val Thr Thr Gly Leu Lys Asn Cys Asp Val Ile Ala Ile Arg Thr
                190                 195                 200

tgt gca gaa atc gaa ggt aac tta tgt gat ttc atc gaa aga caa tgt      736
Cys Ala Glu Ile Glu Gly Asn Leu Cys Asp Phe Ile Glu Arg Gln Cys
            205                 210                 215

cag aga aaa gtt ctc tta acc ggt cca atg ttc ctt gat cca caa ggg      784
Gln Arg Lys Val Leu Leu Thr Gly Pro Met Phe Leu Asp Pro Gln Gly
        220                 225                 230

aag agt ggt aag ccg cta gaa gat cga tgg aat aat tgg tta aac gga      832
Lys Ser Gly Lys Pro Leu Glu Asp Arg Trp Asn Asn Trp Leu Asn Gly
    235                 240                 245

ttt gaa cca agc tcg gta gtg tac tgt gcg ttt ggc acc cat ttc ttt      880
Phe Glu Pro Ser Ser Val Val Tyr Cys Ala Phe Gly Thr His Phe Phe
250                 255                 260                 265

ttc gag ata gat caa ttt caa gaa ctc tgt tta gga atg gag ctc acg      928
Phe Glu Ile Asp Gln Phe Gln Glu Leu Cys Leu Gly Met Glu Leu Thr
                270                 275                 280

ggt cta cct ttt ttg gta gcg gtt atg cca ccg aga ggg tct tca acg      976
Gly Leu Pro Phe Leu Val Ala Val Met Pro Pro Arg Gly Ser Ser Thr
            285                 290                 295

att caa gaa gca tta cca gaa ggg ttc gaa gaa cgg att aaa ggg cgt     1024
Ile Gln Glu Ala Leu Pro Glu Gly Phe Glu Glu Arg Ile Lys Gly Arg
        300                 305                 310

gga att gtt tgg gga gga tgg gtg gaa caa cct ttg ata ttg tct cat     1072
Gly Ile Val Trp Gly Gly Trp Val Glu Gln Pro Leu Ile Leu Ser His
    315                 320                 325

cca tca ata ggt tgc ttt gtg aac cat tgc ggg ttc ggt tca atg tgg     1120
Pro Ser Ile Gly Cys Phe Val Asn His Cys Gly Phe Gly Ser Met Trp
330                 335                 340                 345

gag tct ttg gtt agt gat tgc cag att gtg ttt att cca caa ttg gtt     1168
Glu Ser Leu Val Ser Asp Cys Gln Ile Val Phe Ile Pro Gln Leu Val
                350                 355                 360

gat caa gtt ctc aca acg aga ttg ttg acc gaa gaa ctc gag gtc tcc     1216
Asp Gln Val Leu Thr Thr Arg Leu Leu Thr Glu Glu Leu Glu Val Ser
            365                 370                 375

gtg aaa gta aag aga gat gaa att act ggt tgg ttt tcg aag gag agc     1264
Val Lys Val Lys Arg Asp Glu Ile Thr Gly Trp Phe Ser Lys Glu Ser
        380                 385                 390
```

```
ttg agg gat acg gtc aaa tct gtg atg gat aaa aat agt gag att ggg     1312
Leu Arg Asp Thr Val Lys Ser Val Met Asp Lys Asn Ser Glu Ile Gly
    395                 400                 405

aat cta gtg agg agg aat cat aag aaa ctg aag gaa act ttg gtt agt     1360
Asn Leu Val Arg Arg Asn His Lys Lys Leu Lys Glu Thr Leu Val Ser
410                 415                 420                 425

cct gga ttg ttg agt agt tat gct gat aag ttt gtt gac gaa tta gag     1408
Pro Gly Leu Leu Ser Ser Tyr Ala Asp Lys Phe Val Asp Glu Leu Glu
                430                 435                 440

aat cat atc cac agt aag aat tga aaacttgatc aaattaaaaa cttttttttt    1462
Asn His Ile His Ser Lys Asn
            445

tttgggtagc aaataatatt tcctctgttt tcaaatgaca atagtcgttt tactttcgta   1522

agatttaatg tttcagaccg tggactcatt attttctgaa ataaagtgtg aaatttgatt   1582


<210> SEQ ID NO 33
<211> LENGTH: 448
<212> TYPE: PRT
<213> ORGANISM: Arabidopsis thaliana

<400> SEQUENCE: 33

Met Gly Ser Lys Phe His Ala Phe Leu Tyr Pro Trp Phe Gly Phe Gly
1               5                   10                  15

His Met Ile Pro Tyr Leu His Leu Ala Asn Lys Leu Ala Glu Lys Gly
            20                  25                  30

His Arg Val Thr Phe Leu Ala Pro Lys Lys Ala Gln Lys Gln Leu Glu
        35                  40                  45

Pro Leu Asn Leu Phe Pro Asn Ser Ile His Phe Glu Asn Val Thr Leu
    50                  55                  60

Pro His Val Asp Gly Leu Pro Val Gly Ala Glu Thr Thr Ala Asp Leu
65                  70                  75                  80

Pro Asn Ser Ser Lys Arg Val Leu Ala Asp Ala Met Asp Leu Leu Arg
                85                  90                  95

Glu Gln Ile Glu Val Lys Ile Arg Ser Leu Lys Pro Asp Leu Ile Phe
            100                 105                 110

Phe Asp Phe Val Asp Trp Ile Pro Gln Met Ala Lys Glu Leu Gly Ile
        115                 120                 125

Lys Ser Val Ser Tyr Gln Ile Ile Ser Ala Ala Phe Ile Ala Met Phe
    130                 135                 140

Phe Ala Pro Arg Ala Glu Leu Gly Ser Pro Pro Pro Gly Phe Pro Ser
145                 150                 155                 160

Ser Lys Val Ala Leu Arg Gly His Asp Ala Asn Ile Tyr Ser Leu Phe
                165                 170                 175

Ala Asn Thr Arg Lys Phe Leu Phe Asp Arg Val Thr Thr Gly Leu Lys
            180                 185                 190

Asn Cys Asp Val Ile Ala Ile Arg Thr Cys Ala Glu Ile Glu Gly Asn
        195                 200                 205

Leu Cys Asp Phe Ile Glu Arg Gln Cys Gln Arg Lys Val Leu Leu Thr
    210                 215                 220

Gly Pro Met Phe Leu Asp Pro Gln Gly Lys Ser Gly Lys Pro Leu Glu
225                 230                 235                 240

Asp Arg Trp Asn Asn Trp Leu Asn Gly Phe Glu Pro Ser Ser Val Val
                245                 250                 255

Tyr Cys Ala Phe Gly Thr His Phe Phe Phe Glu Ile Asp Gln Phe Gln
            260                 265                 270
```

```
Glu Leu Cys Leu Gly Met Glu Leu Thr Gly Leu Pro Phe Leu Val Ala
        275                 280                 285

Val Met Pro Pro Arg Gly Ser Ser Thr Ile Gln Glu Ala Leu Pro Glu
    290                 295                 300

Gly Phe Glu Glu Arg Ile Lys Gly Arg Gly Ile Val Trp Gly Gly Trp
305                 310                 315                 320

Val Glu Gln Pro Leu Ile Leu Ser His Pro Ser Ile Gly Cys Phe Val
                325                 330                 335

Asn His Cys Gly Phe Gly Ser Met Trp Glu Ser Leu Val Ser Asp Cys
            340                 345                 350

Gln Ile Val Phe Ile Pro Gln Leu Val Asp Gln Val Leu Thr Thr Arg
        355                 360                 365

Leu Leu Thr Glu Glu Leu Glu Val Ser Val Lys Val Lys Arg Asp Glu
    370                 375                 380

Ile Thr Gly Trp Phe Ser Lys Glu Ser Leu Arg Asp Thr Val Lys Ser
385                 390                 395                 400

Val Met Asp Lys Asn Ser Glu Ile Gly Asn Leu Val Arg Arg Asn His
                405                 410                 415

Lys Lys Leu Lys Glu Thr Leu Val Ser Pro Gly Leu Leu Ser Ser Tyr
            420                 425                 430

Ala Asp Lys Phe Val Asp Glu Leu Glu Asn His Ile His Ser Lys Asn
        435                 440                 445
```

<210> SEQ ID NO 34
<211> LENGTH: 2535
<212> TYPE: DNA
<213> ORGANISM: Arabidopsis thaliana
<220> FEATURE:
<221> NAME/KEY: promoter
<222> LOCATION: (1)..(2535)
<223> OTHER INFORMATION: transcription regulating sequence from Arabidopsis thaliana gene At5g48070

<400> SEQUENCE: 34

```
tttgtagcca tatacatttt ttggtagtca attacataac tcatccttgg ccaaaaagaa     60

gtattgtgga cgtttttcgc tgactcgccg ttgagatttt tttgtaagag ggtttggacg    120

tttttcgggt atgctctgta agtctgtagt gagttccatg acttcaacga gattcttact    180

gcggaaaact ggatcgtcag aagattattt ggaacaagct aagaatgtga aacgaaagat    240

caaaaataag aatgtgattg atagttttat atcactaaca atgggtttaa aatagatcca    300

aatgttttca tgacaacaat tagattgata aaagaaaaga caaacaaaaa cagttagatt    360

gactaatgaa ttggtttgtc tctggaaatg cagcatcgcg taacatatta tattaattat    420

tatttttgga tcaactaaca tgttatatta attaaaacaa aattatatat atatatatac    480

cagaatttct attaactatt tcacttgttt gtttatgtag aatatttttc tcatagcatg    540

aatggctttt tcaaatttta ctattatatt ctcaacaaag cgatattcac tgattttcaa    600

aacttttccg gatattcatt ttttctagag aaaagtggct cacgaatatt ggtgtttcgc    660

aaaatatcta taacacaatc ctactatgtc gtgaaagatt aaaaaaagtt ttaacatacg    720

tttatgtctg atatattata tgtacttttg tttgttttta ccaaatatat atatatatac    780

atatatgtac ttttgtttta tagatttgga ataagataat caactctatt tctcttttgg    840

tagttcttaa acatgatatg ctaattcaga ttacaacttc tattatatgt acgtacatat    900

atacacatcg atgtatatta attttgttag taaatagaat gttgaaagtc ttaaaatatt    960
```

```
ttaaaacaga aataaaacat agaatgatta tgaagagata gtggagacct ttaaatttgt   1020

aaccgacaaa attttgcaaa tcaaaatatc agaaggaata atgctttcct aaaaaagaat   1080

gattactggt caaattagtc ggcaaccggt aagtaagcaa acaatcggga acgtgttact   1140

gttacagtgt taccataacg tgtaagttgg gtaacacaaa ggtaactgtg aattggcggg   1200

aacaaaaaaa caaaaagtta actttgaatt cttaggacat gttaagaaag ccaacataac   1260

atatttgttt agttctcaaa ttatgtccgt aattatagga aaataaactt tctggttttt   1320

atcaatcatc aaaatagaac acaacatagc tctttaacac atatatagtt gtaagaaaga   1380

tagtgctccg aattttcaaa gatttcataa tctatacagt gttgactgtt tgagaatatg   1440

aaaggatatg catcaaaata gtgaaactct aaacaccaaa ggtcaaagga aaagacttga   1500

aaccaaaaac aaagagttat atacactgcg agaagctgat cgagttaact tcgtcgctgg   1560

cgatggtacc ttttactcat gtcaccaaaa atcatgcaac aaggacgttt tctaacgatt   1620

gcatgtatat tgttttgatt tgaattgcta acgttaggca tttcaaacat atatattatc   1680

ttctaatttt ctgatagcat acttacttac gttgttatat agtataatta ttcaataaac   1740

tatatcttca gtatattcta aacactgttt tataatgtga aatatgatta tttttgttg    1800

tatataatat gattttctaa gatatgtatt tcttactata caccattaat tggatgattt   1860

atgtaattat cattcaattt gtagctagac gtttatagag cctaattttc aatcttggaa   1920

aacttatata tacttctaaa tgctagcttc tgcaaactcg attctgattt tatgtaacat   1980

attgctaatt tatgaacact gactgtcgag aatgatttta tattttttt ctatatacat    2040

atttaaacaa aaagtttttt gaccgacaaa attttgcaaa tgaaatatct aaatgaataa   2100

tgctttcaat ataaatatga tttatggtca aaatagccgg aaagtataaa acatccatag   2160

ggcactcata gttgtatgtt accatttacg agtaggtggt cctgattcta aattaacaaa   2220

catatactta agctctttat aaaaaacgcg acataccaac caaccaatta taaacgtaag   2280

tgtttctcgt attaattttt ttttctgccg gcatacaaac caagtaatgg agttatatat   2340

cttggtttca ctttctaaca atcaatatac tatcaaataa tgaatataca tattatcact   2400

tgtcagcctt attagtagac ccacacaaat tccttttcat ttccaacagc tatatatact   2460

aacgtccctt accttcattt tcacatcacc aatccatcta agatagtata actactcttt   2520

ccaaagcaat tttaa                                                    2535
```

```
<210> SEQ ID NO 35
<211> LENGTH: 3141
<212> TYPE: DNA
<213> ORGANISM: Arabidopsis thaliana
<220> FEATURE:
<221> NAME/KEY: promoter
<222> LOCATION: (1)..(3141)
<223> OTHER INFORMATION: transcription regulating sequence from
      Arabidopsis thaliana gene At5g48070

<400> SEQUENCE: 35
```

```
tttgtagcca tatacatttg ttggtagtca attacataac tcatccttgg ccaaaaagat     60

gtattgtgga cgtttttcgc tgacccgccg ttgagatttt tttgtaagag ggtttggacg    120

tttttcgggt atgctctgta gtgagttcca tgacttcatc gagattctta ctgcggaaaa    180

ctggtcgtca gaagattatt tggaacaagc taataatgtg aaaattgata aacgaaagat    240

caaaaataag aatgtgattg atagttttat atcactaaca atgagtttaa aatagatcca    300

aatgttttca tgacaacaat tagattgata aaagaaaaga caaacaaaaa cagttagatt    360
```

-continued

```
gactaatgaa ttggtttgtc tctggaaatg cagcatcgcg taacatatta tattaattat    420
tatttttgga tcaactaaca tgttatatta attaaaacaa aattatatat atatatacca    480
gaatttctat taactatttc acttattcac ttgtttgttt atgttgaata tttttctcat    540
aacatgaatg gctttttcaa atctatatat acatttttca gccattttgt gaaataaatc    600
ttggagttgg aacttattta caatggctgc cactggcttt taattattgt ttttttcagc    660
aataaattga ttaacaaact aaaaacattc caaatatatt ccaatcccat atatcacgca    720
gatttttcca aaatttgaac tagattttgg caactattta aaacaaaaat gtttgacaac    780
ccaaaagaca attgcaatcc cttaaaatga gcaaaacgca actaaataca tttattatca    840
attcactaaa tcttatttct ccaaaatttg aactagattt cgacaactat ttaaaacaaa    900
gttttgtttg acaaactaaa acacaattgc aatcccgtaa aatatttatt ttaattataa    960
atttaaatta gcggggtacc gcggtttttt cttacagaac gggtttgacg gaacgggttt   1020
ggaaggacgt tacttaataa caattgtaaa ctataaaata aaaatatttt atagataaat   1080
ataatttgca aaattttata tatactaatt taaaaaaata aattgtcggt taaaatctag   1140
ttttactatt atattctaaa caaagcgata ttcactgatt ttcaaaactt ttccggatat   1200
tcatttttttc tagagaaaag tggctcacga atattggtgt ttcgcaaaat atctataaca   1260
caatcctact atgtcgtgaa agattaaaag aagttttaac atacgtttat gtatgatata   1320
ttatatgtac ttttgtaaaa tatatatata tatatatata tatatatatg tacttttgtt   1380
ttatagattt ggaataagat aatcaactct atttctcttt tggtagttct taaacatgat   1440
atgctaattc agattacaac ttctattata tgtacgtaca tatatacaca tcgatgtata   1500
ttaattttgt tagtaaatag aatgttgaaa gtcttataat attttaaaac agaaataata   1560
catagaatga ttatgaagag atagtggaga ccttgaagtt tttaaccgac aaaattttgc   1620
aaatcaaaat atcaaaagga agaatgcttt cctaaaaaag aatgattact ggtcaaatta   1680
gtcggcaacc ggtaagtaag caaacaatcg ggaacgtgtt actgttacag tgttaccata   1740
acgtgtaggt tgggtaacac aaaggtaact gtgaattggc gggaacaaaa aaaaaacttt   1800
tgtcgtaaaa aaaacaacaa caaaaaagtt aactttgaat tcttaggaca tgttaagaaa   1860
gccttcataa catatttgtt tagttctcaa ataatgtccg taattatagg aaaataaact   1920
ttctggtttt tatcaatcat caaaatagaa cacaacatag ctctttaaca catagttgta   1980
agaaagatag tgctccgaat cttcatagat ttcataatct atacagtgtt gactgtttga   2040
gaatatgaaa ggatatgcat caaaatagtg aaactctaaa caccaaaggt caaaggaaaa   2100
gacttgaaac caaaaacaaa gagttatata cactgcgaga agctgatcga gttaacttcg   2160
tcgctggcga tggaaccttt tactcatgtc accaaaaatc atgcaacaag gacgttttct   2220
aacgattgca tgtatattgt tttgatttga attgttaacg ttaggcattt caaacatata   2280
tattatcttc taattttctg atagcatact tattacgttg ttatatagta taattattca   2340
ataaactata tcttcagtat attctaaaca ctgttttata atgtgaaata tgattatttt   2400
tgttgtttat aatatgattt tctaagatat gtatttctta ctatacacca ttaattggat   2460
gatttatgta attatcatgc aatttgtagc ttgacgttta tagagcctaa ttttcaatct   2520
tcgaaaactt atatatactt ctaattgcta gcttctgcaa actcgattct gattttacgt   2580
aacatatgct aatttatgaa cactgactgt cgagaatgat tttatatttt ctttctatat   2640
acatatttaa acaaaaagtt ttttgaccga caaaattttg caaatgaaat atctaaatga   2700
ataatgcttt caatataaat atgatttatg gtcaaaatag ccggaaagta taaaacaatc   2760
```

```
catagggcac tcatagttgt atgttaccat ttacgagtag gtggccctga ttctaaatta   2820

acaaacatat acttaagctc tttataaaaa acgcgacata ccaaccaacc aattataaac   2880

ataagtgttt ctcgtattaa tttttttctta tgccggcata caaaccaagt aatggagtta   2940

tatatcttgg tttcactttc taacaatcaa tatactatca aataatgaat atacatatta   3000

tcacttgtca gccttattag tagacccaca caaattcctt ttcatttcca acagctatat   3060

atactaacgt cctttacctt cattttcaca tcaccaatcc atctaagata ctataactac   3120

tctttccaaa agcaatttta a                                              3141
```

```
<210> SEQ ID NO 36
<211> LENGTH: 1309
<212> TYPE: DNA
<213> ORGANISM: Arabidopsis thaliana
<220> FEATURE:
<221> NAME/KEY: promoter
<222> LOCATION: (1)..(1309)
<223> OTHER INFORMATION: transcription regulating sequence from
      Arabidopsis thaliana gene At5g48070

<400> SEQUENCE: 36

aattcttagg acatgttaag aaagccaaca taacatattt gtttagttct caaattatgt     60

ccgtaattat aggaaaataa actttctggt ttttatcaat catcaaaata gaacacaaca    120

tagctcttta acacatatat agttgtaaga aagatagtgc tccgaatttt caaagatttc    180

ataatctata cagtgttgac tgtttgagaa tatgaaagga tatgcatcaa aatagtgaaa    240

ctctaaacac caaaggtcaa aggaaaagac ttgaaaccaa aaacaaagag ttatatacac    300

tgcgagaagc tgatcgagtt aacttcgccg ctggcgatgg aaccttttac tcatgtcacc    360

aaaaatcatg caacaaggac gttttctaac gattgcatgt atattgtttt gatttgaatt    420

gctaacgtta ggcatttcaa acatatatat tatcttctaa ttttctgata gcatacttac    480

ttacgttgtt atatagtata attattcaat aaactatatc ttcagtatat tctaaacact    540

gttttataat gtgaaatatg attatttttt gttgtatata atatgatttt ctaagatatg    600

tatttcttac tatacaccat taattggatg atttatgtaa ttatcattca atttgtagct    660

agacgtttat agagcctaat tttcaatctt ggaaaactta tatatacttc taaatgctag    720

cttctgcaaa ctcgattctg attttatgta acatattgct aatttatgaa cactgactgt    780

cgagaatgat tttatatttt ttttctatat acatatttaa acaaaaagtt ttttgaccga    840

caaaattttg caaatgaaat atctaaatga ataatgcttt caatataaat atgatttatg    900

gtcaaaatag ccggaaagta taaaacatcc atagggcact catagttgta tgttaccatt    960

tacgagtagg tggtcctgat tctaaattaa caaacatata cttaagctct ttataaaaaa   1020

cgcgacatac caaccaacca attataaacg taagtgtttc tcgtattaat ttttttttct   1080

gccggcatac aaaccaagta atggagttat atatcttggt ttcactttct aacaatcaat   1140

atactatcaa ataatgaata tacatattat cacttgtcag ccttattagt agacccacac   1200

aaattccttt tcatttccaa cagctatata tactaacgtc ccttaccttc attttcacat   1260

caccaatcca tctaagatag tataactact ctttccaaag caattttaa               1309
```

```
<210> SEQ ID NO 37
<211> LENGTH: 1304
<212> TYPE: DNA
<213> ORGANISM: Arabidopsis thaliana
<220> FEATURE:
<221> NAME/KEY: promoter
```

```
<222> LOCATION: (1)..(1304)
<223> OTHER INFORMATION: transcription regulating sequence from
      Arabidopsis thaliana gene At5g48070

<400> SEQUENCE: 37

aattcttagg acatgttaag aaagccttca taacatattt gtttagttct caaataatgt     60

ccgtaattat aggaaaataa actttctggt ttttatcaat catcaaaata gaacacaaca    120

tagctcttta acacatagtt gtaagaaaga tagtgctccg aatcttcata gatttcataa    180

tctatacagt gttgactgtt tgagaatatg aaaggatatg catcaaaata gtgaaactct    240

aaacaccaaa ggtcaaagga aaagacttga aaccaaaaac aaagagttat atacactgcg    300

agaagctgat cgagttaact tcgtcgctgg cgatggaacc ttttactcat gtcaccaaaa    360

atcatgcaac aaggacgttt tctaacgatt gcatgtatat tgttttgatt tgaattgtta    420

acgttaggca tttcaaacat atatattatc ttctaatttt ctgatagcat acttattacg    480

ttgttatata gtataattat tcaataaact atatcttcag tatattctaa acactgtttt    540

ataatgtgaa atatgattat ttttgttgtt tataatatga ttttctaaga tatgtatttc    600

ttactataca ccattaattg gatgatttat gtaattatca tgcaatttgt agcttgacgt    660

ttatagagcc taattttcaa tcttcgaaaa cttatatata cttctaattg ctagcttctg    720

caaactcgat tctgatttta cgtaacatat gctaatttat gaacactgac tgtcgagaat    780

gattttatat tttctttcta tatacatatt taaacaaaaa gtttttttgac cgacaaaatt    840

ttgcaaatga aatatctaaa tgaataatgc tttcaatata aatatgattt atggtcaaaa    900

tagccggaaa gtataaaaca atccataggg cactcatagt tgtatgttac catttacgag    960

taggtggccc tgattctaaa ttaacaaaca tatacttaag ctctttataa aaaacgcgac   1020

ataccaacca accaattata aacataagtg tttctcgtat taattttttc ttatgccggc   1080

atacaaacca agtaatggag ttatatatct tggtttcact ttctaacaat caatatacta   1140

tcaaataatg aatatacata ttatcacttg tcagccttat tagtagaccc acacaaattc   1200

cttttcattt ccaacagcta tatatactaa cgtcctttac cttcattttc acatcaccaa   1260

tccatctaag atactataac tactctttcc aaaagcaatt ttaa                    1304


<210> SEQ ID NO 38
<211> LENGTH: 1059
<212> TYPE: DNA
<213> ORGANISM: Arabidopsis thaliana
<220> FEATURE:
<221> NAME/KEY: CDS
<222> LOCATION: (27)..(875)
<223> OTHER INFORMATION: coding for xyloglucan endo-1,4-beta-D-glucanase

<400> SEQUENCE: 38

actactcttt ccaaaagcaa ttttaa atg gtg tca ttt tgc ggt aga agg ttc      53
                             Met Val Ser Phe Cys Gly Arg Arg Phe
                             1               5

gcc ttc ttg att atc ttt ctc ttt gca gca caa tat gag cgt gtc tac      101
Ala Phe Leu Ile Ile Phe Leu Phe Ala Ala Gln Tyr Glu Arg Val Tyr
10                  15                  20                  25

gct ggt agc ttt cac aag gac gtt cag ata cat tgg ggt gat ggc cgt      149
Ala Gly Ser Phe His Lys Asp Val Gln Ile His Trp Gly Asp Gly Arg
                30                  35                  40

gga aaa att ctc gac aat gtc gga aat ctt ctt tct ctc tcg ctc gac      197
Gly Lys Ile Leu Asp Asn Val Gly Asn Leu Leu Ser Leu Ser Leu Asp
            45                  50                  55

aaa ttc tct ggt tcc ggt ttt cag tcc cat caa gag ttt ctt tat ggc      245
```

-continued

```
Lys Phe Ser Gly Ser Gly Phe Gln Ser His Gln Glu Phe Leu Tyr Gly
        60                  65                  70

aaa gta gag gtt caa atg aaa ctt gta cct ggt aac tct gct gga aca      293
Lys Val Glu Val Gln Met Lys Leu Val Pro Gly Asn Ser Ala Gly Thr
    75                  80                  85

gtg aca aca ttc tat cta aaa tct cct gga act aca tgg gat gaa ata      341
Val Thr Thr Phe Tyr Leu Lys Ser Pro Gly Thr Thr Trp Asp Glu Ile
90                  95                  100                 105

gat ttt gag ttc ttg gga aac ata agt ggt cat cca tat act ctt cat      389
Asp Phe Glu Phe Leu Gly Asn Ile Ser Gly His Pro Tyr Thr Leu His
                110                 115                 120

act aat gtt tac aca aaa ggc aca gga gac aaa gaa caa cag ttt cat      437
Thr Asn Val Tyr Thr Lys Gly Thr Gly Asp Lys Glu Gln Gln Phe His
            125                 130                 135

cta tgg ttt gac cca act gtt gac ttt cac act tat tgt atc ata tgg      485
Leu Trp Phe Asp Pro Thr Val Asp Phe His Thr Tyr Cys Ile Ile Trp
        140                 145                 150

aat ccc caa agg gtc att ttt aca ata gat gga att ccg ata aga gaa      533
Asn Pro Gln Arg Val Ile Phe Thr Ile Asp Gly Ile Pro Ile Arg Glu
    155                 160                 165

ttc aag aac tcc gaa gcc ctt gga gtt ccc ttc cca aag cat caa cca      581
Phe Lys Asn Ser Glu Ala Leu Gly Val Pro Phe Pro Lys His Gln Pro
170                 175                 180                 185

atg agg ctc tat gct agc ctt tgg gaa gcc gag cat tgg gct aca aga      629
Met Arg Leu Tyr Ala Ser Leu Trp Glu Ala Glu His Trp Ala Thr Arg
                190                 195                 200

gga gga tta gag aaa aca gac tgg tcc aaa gct cct ttc acc gct ttc      677
Gly Gly Leu Glu Lys Thr Asp Trp Ser Lys Ala Pro Phe Thr Ala Phe
            205                 210                 215

tac aga aac tac aat gtg gat gca tgt gtg tgg tcc aat gga aaa tca      725
Tyr Arg Asn Tyr Asn Val Asp Ala Cys Val Trp Ser Asn Gly Lys Ser
        220                 225                 230

tca tgc tct gcg aat tcc tca tgg ttt act caa gta ctt gat ttc aaa      773
Ser Cys Ser Ala Asn Ser Ser Trp Phe Thr Gln Val Leu Asp Phe Lys
    235                 240                 245

ggc aag aat aga gtg aaa tgg gca cag aga aag tac atg gtc tac aac      821
Gly Lys Asn Arg Val Lys Trp Ala Gln Arg Lys Tyr Met Val Tyr Asn
250                 255                 260                 265

tat tgc act gat aag aaa aga ttt cct caa ggt gct cct cca gag tgc      869
Tyr Cys Thr Asp Lys Lys Arg Phe Pro Gln Gly Ala Pro Pro Glu Cys
                270                 275                 280

agt taa ataactgatt gcttgattca cgaattaatc acgtggcatt gtctttgtaa      925
Ser

cggaaatgat gtttatctat attttggcac tagctgagta tttgcgctaa ataaattact    985

tctctattag taattgtttt tttttgttct attatgttgt ttcttttata ttatttgtaa   1045

gtgtgatttg cgtt                                                     1059


<210> SEQ ID NO 39
<211> LENGTH: 282
<212> TYPE: PRT
<213> ORGANISM: Arabidopsis thaliana

<400> SEQUENCE: 39

Met Val Ser Phe Cys Gly Arg Arg Phe Ala Phe Leu Ile Ile Phe Leu
1               5                   10                  15

Phe Ala Ala Gln Tyr Glu Arg Val Tyr Ala Gly Ser Phe His Lys Asp
            20                  25                  30

Val Gln Ile His Trp Gly Asp Gly Arg Gly Lys Ile Leu Asp Asn Val
```

-continued

```
        35                  40                  45

Gly Asn Leu Leu Ser Leu Ser Leu Asp Lys Phe Ser Gly Ser Gly Phe
    50                  55                  60

Gln Ser His Gln Glu Phe Leu Tyr Gly Lys Val Glu Val Gln Met Lys
65                  70                  75                  80

Leu Val Pro Gly Asn Ser Ala Gly Thr Val Thr Thr Phe Tyr Leu Lys
                85                  90                  95

Ser Pro Gly Thr Thr Trp Asp Glu Ile Asp Phe Glu Phe Leu Gly Asn
            100                 105                 110

Ile Ser Gly His Pro Tyr Thr Leu His Thr Asn Val Tyr Thr Lys Gly
        115                 120                 125

Thr Gly Asp Lys Glu Gln Gln Phe His Leu Trp Phe Asp Pro Thr Val
    130                 135                 140

Asp Phe His Thr Tyr Cys Ile Ile Trp Asn Pro Gln Arg Val Ile Phe
145                 150                 155                 160

Thr Ile Asp Gly Ile Pro Ile Arg Glu Phe Lys Asn Ser Glu Ala Leu
                165                 170                 175

Gly Val Pro Phe Pro Lys His Gln Pro Met Arg Leu Tyr Ala Ser Leu
            180                 185                 190

Trp Glu Ala Glu His Trp Ala Thr Arg Gly Gly Leu Glu Lys Thr Asp
        195                 200                 205

Trp Ser Lys Ala Pro Phe Thr Ala Phe Tyr Arg Asn Tyr Asn Val Asp
    210                 215                 220

Ala Cys Val Trp Ser Asn Gly Lys Ser Ser Cys Ser Ala Asn Ser Ser
225                 230                 235                 240

Trp Phe Thr Gln Val Leu Asp Phe Lys Gly Lys Asn Arg Val Lys Trp
                245                 250                 255

Ala Gln Arg Lys Tyr Met Val Tyr Asn Tyr Cys Thr Asp Lys Lys Arg
            260                 265                 270

Phe Pro Gln Gly Ala Pro Pro Glu Cys Ser
        275                 280
```

<210> SEQ ID NO 40
<211> LENGTH: 3040
<212> TYPE: DNA
<213> ORGANISM: Arabidopsis thaliana
<220> FEATURE:
<221> NAME/KEY: promoter
<222> LOCATION: (1)..(3040)
<223> OTHER INFORMATION: transcription regulating sequence from Arabidopsis thaliana gene At4g17800

<400> SEQUENCE: 40

```
caacttcaat attacatggg caataaatta tatagaaact actttataat atatctaccg      60

acacaaatat acatgtttta ggtttatgca tgtattacgt gtgtaaaata tggttaccta     120

ccttgttaaa catatttagg acggcattgt gactaattta ataacttgaa gacccactta     180

cttcaaatat ctttgtaaaa gaagttctat gtgcctacac aatgctattg gataaggaac     240

catatatggc acaaacatcc ttaaaatata atatagaaaa taatgaatat acataaaaca     300

tacataaaat aaatgtatta acagtgtata ttatatatat ggctttgtca gacatcacta     360

cgttcgttcc aaaagtcgtc attgccaata ggttttcctt ttaaatttta gtggttacaa     420

ataaatcaac ctatcaagtt atttaaataa tatgttagat actataattt aaataatgga     480

agcgactcat acacatatac actaatttat attattactg tatacgtaaa actgaattaa     540

caacttttca ctgaaaaagc acacccttta atttatatat cagtgactaa gtcataacgt     600
```

-continued

```
gaaacaatta taaattctaa aggttaaaaa gatctaaaaa cttttgcacg tggaatgtgc    660
tatatattta ccctaaaata tcgaagccaa ctaaacaaat taatgaatta taaagacaca    720
ggttctttga tttgatggta atcattatgt catagaaact gttccataaa tttcatacta    780
tattatgcat ctagaaatca gataatgtag agtaagaaat aaatatacta tttcgaaatt    840
aagaaactcc aagttttgct atgatatctc aaccagttaa aattggttgt ttcagttcgg    900
tcttgacgat tttttacacg acatatgatg tagttatgtc tagcccatcc gttacattac    960
atatgtggta acagaatatt tcttggacct cttggtcgtc ttgaaaaaac tcttatgaac   1020
cggatgccaa aatactatat atcgtaaaca aaaacaaaat caagtaagtt ccaatatttt   1080
attcacttga aaaatcgcat actcgtataa ggaaacacta atcatagatg ttttcaatat   1140
ttcagttttt taaaatgacg actaacactt ggaaaccgat aatgatgaaa ctttatataa   1200
gaaaacaaag tttgtttcaa acatatcata gtcaacatac aaaaaaattg agtcatatta   1260
aaaaaaaaaa aaaaaaatct agaccaaatg attcacatgg caagaaattt aagtaatttc   1320
tgatgtaaac gcctgatcac taaattgagc ttctcatatt ttcttttttc ttttgagctt   1380
tatttaattc atacatgcat ctatataagg aaatcaaaaa tgttaatgca aaacgtaaat   1440
ttaatatgta ttgaatgtaa caacattaat aaaggcacga aattattggt ttgaaatgat   1500
tagatccaac taatttccaa ccaaagacgg tcaaagccaa ataaaaatgc ttagctctcc   1560
atgagcacca agagaaaccc atccaaatgg ttcagacaat cgtggacccc acgcgccgct   1620
tctcttctct ccccacttgc tattctctct ctctaattaa tttttaactt tgattagttt   1680
tggtcaactt tatagttaac catggttaac taataaaata tttatttatg tccaagatta   1740
attaatgaat aagtgattat ataggtatat gtgttagcct aagttttttt cttcaaaata   1800
gctttgttta tacacgttat ttttttttgt tgcaaggctt acatcttaat ttaggaaact   1860
gatatgattg ctatatatga ggcctgagtg tacaaaatat taattaagtt taaataaatt   1920
aaggcaaggc aatgatggtg gagaatgttt tgaaagacag aaaagaggaa gcatcttaat   1980
gaaacccaca agataacccc aaccacatat tatcatgatg gcttcattca tcttaattaa   2040
actttaacct ttcattttct ccaaatattt taacttatta taccaattag atcacaccca   2100
ctcacataca tctccttccc aatttctcac gctcctagaa tatgcgagga gactacttcc   2160
gttaggctac ttgatacaat cataacaatg tattgctaac tttggaactt tgtaatttat   2220
ctagttaaac caatcaacta tgagaagaag tgtagcggtt ttaaatgggg gtgtatatgt   2280
tcaaaaaaag agagaaggga attcatacct tgaaataatt aataatactt ttctagtcaa   2340
atatttgtat ggatcgtaaa catatacaaa catgttacaa acaagttttt tttgtaccaa   2400
taattgtcga ctaaaatact aaacataata ttttatttta ttataaatat cctatactat   2460
ataagttata aacatagcaa aaagaaaaac acaaaagcca acagtgaacc taaatatgtg   2520
tttgcttatg gtagccgcgt atattacacg ctctaactat tggagaagaa gaagaagagt   2580
ggagtttatt gtcgagtcca aaacacacaa aacgacataa aactcaacga gaacaaaatt   2640
tgaattgaag tcgataccaa attttatttt tatttttatt ttatttttat ttatcaatat   2700
ccattttgta agagtttagg ttagacaagt gactgcattt acatacatat atctatgtat   2760
atacaaacat tttttcttct tcattaatgc tttattttgg tctcaccttc tccttctact   2820
ttttatcatt tccctttctc ttcccatttt agtcttccta taacttcttc tcaatcctct   2880
ctcatatctt ttttcttagt ttaaatttca ataaaataga aaaaaacata tacaaatcta   2940
```

-continued

```
cagagaagag aagctttatt ttaatcttgt gtgtgtgtgt gttttatata atttttattt   3000

tttttcaaat taaaatctct tctttgcttt tgatgtgggc                         3040


<210> SEQ ID NO 41
<211> LENGTH: 2801
<212> TYPE: DNA
<213> ORGANISM: Arabidopsis thaliana
<220> FEATURE:
<221> NAME/KEY: promoter
<222> LOCATION: (1)..(2801)
<223> OTHER INFORMATION: transcription regulating sequence from
      Arabidopsis thaliana gene At4g17800

<400> SEQUENCE: 41

caacttcaat attacatggg caataaatta tatagaaact actttataat atatctaccg     60

acacaaatat acatgtttta ggtttatgca tgtattacgt gtgtaaaata tggttaccta    120

ccttgttaaa catatttagg acggcattgt gactaattta ataacttgaa gacccactta    180

cttcaaatat ctttgtaaaa gaagttctat gtgcctacac aatgctattg gataaggaac    240

catatatggc acaaacatcc ttaaaatata atatagaaaa taatgaatat acataaaaca    300

tacataaaat aaatgtatta acagtgtata ttatatatat ggctttgtca gacatcacta    360

cgttcgttcc aaaagtcgtc attgccaata ggttttcctt ttaaatttta gtggttacaa    420

ataaatcaac ctatcaagtt atttaaataa tatgttagat actataattt aaataatgga    480

agcgactcat acacatatac actaatttat attattactg tatacgtaaa actgaattaa    540

caacttttca ctgaaaaagc acacccttta atttatatat cagtgactaa gtcataacgt    600

gaaacaatta taaattctaa aggttaaaaa gatctaaaaa cttttgcacg tggaatgtgc    660

tatatattta ccctaaaata tcgaagccaa ctaaacaaat taatgaatta taaagacaca    720

ggttctttga tttgatggta atcattatgt catagaaact gttccataaa tttcatacta    780

tattatgcat ctagaaatca gataatgtag agtaagaaat aaatatacta tttcgaaatt    840

aagaaactcc aagttttgct atgatatctc aaccagttaa aattggttgt ttcagttcgg    900

tcttgacgat tttttacacg acatatgatg tagttatgtc tagcccatcc gttacattac    960

atatgtggta acagaatatt tcttggacct cttggtcgtc ttgaaaaaac tcttatgaac   1020

cggatgccaa aatactatat atcgtaaaca aaaacaaaat caagtaagtt ccaatatttt   1080

attcacttga aaaatcgcat actcgtataa ggaaacacta atcatagatg ttttcaatat   1140

ttcagttttt taaaatgacg actaacactt ggaaaccgat aatgatgaaa ctttatataa   1200

gaaaacaaag tttgtttcaa acatatcata gtcaacatac aaaaaaattg agtcatatta   1260

aaaaaaaaaa aaaaaaatct agaccaaatg attcacatgg caagaaattt aagtaatttc   1320

tgatgtaaac gcctgatcac taaattgagc ttctcatatt ttctttttttc ttttgagctt   1380

tatttaattc atacatgcat ctatataagg aaatcaaaaa tgttaatgca aaacgtaaat   1440

ttaatatgta ttgaatgtaa caacattaat aaaggcacga aattattggt ttgaaatgat   1500

tagatccaac taatttccaa ccaaagacgg tcaaagccaa ataaaaatgc ttagctctcc   1560

atgagcacca agagaaaccc atccaaatgg ttcagacaat cgtggacccc acgcgccgct   1620

tctcttctct ccccacttgc tattctctct ctctaattaa tttttaactt tgattagttt   1680

tggtcaactt tatagttaac catggttaac taataaaata tttatttatg tccaagatta   1740

attaatgaat aagtgattat ataggtatat gtgttagcct aagttttttt cttcaaaata   1800

gctttgttta tacacgttat ttttttttgt tgcaaggctt acatcttaat ttaggaaact   1860
```

-continued

```
gatatgattg ctatatatga ggcctgagtg tacaaaatat taattaagtt taaataaatt   1920

aaggcaaggc aatgatggtg gagaatgttt tgaaagacag aaaagaggaa gcatcttaat   1980

gaaacccaca agataacccc aaccacatat tatcatgatg gcttcattca tcttaattaa   2040

actttaacct ttcattttct ccaaatattt taacttatta taccaattag atcacaccca   2100

ctcacataca tctccttccc aatttctcac gctcctagaa tatgcgagga gactacttcc   2160

gttaggctac ttgatacaat cataacaatg tattgctaac tttggaactt tgtaatttat   2220

ctagttaaac caatcaacta tgagaagaag tgtagcggtt ttaaatgggg gtgtatatgt   2280

tcaaaaaaag agagaaggga attcatacct tgaaataatt aataatactt ttctagtcaa   2340

atatttgtat ggatcgtaaa catatacaaa catgttacaa acaagttttt tttgtaccaa   2400

taattgtcga ctaaaatact aaacataata ttttatttta ttataaatat cctatactat   2460

ataagttata aacatagcaa aaagaaaaac acaaaagcca acagtgaacc taaatatgtg   2520

tttgcttatg gtagccgcgt atattacacg ctctaactat tggagaagaa gaagaagagt   2580

ggagtttatt gtcgagtcca aaacacacaa aacgacataa aactcaacga gaacaaaatt   2640

tgaattgaag tcgataccaa attttatttt tatttttatt ttatttttat ttatcaatat   2700

ccattttgta agagtttagg ttagacaagt gactgcattt acatacatat atctatgtat   2760

atacaaacat tttttcttct tcattaatgc tttattttgg t                       2801
```

<210> SEQ ID NO 42
<211> LENGTH: 3041
<212> TYPE: DNA
<213> ORGANISM: Arabidopsis thaliana
<220> FEATURE:
<221> NAME/KEY: promoter
<222> LOCATION: (1)..(3041)
<223> OTHER INFORMATION: transcription regulating sequence from Arabidopsis thaliana gene At4g17800

<400> SEQUENCE: 42

```
caacttcaat attacatggg caataaatta tatagaaact actttataat atatctaccg     60

acacaaatat acatgtttta ggtttatgca tgtattacgt gtgtaaaata tggttaccta    120

ccttgttaaa catatttagg acggcactgt gactaattta ataacttgaa gacccactta    180

cttcaaatat ctttgtaaaa gaagttctat gtgcctacac aatgctattg gataaggaac    240

catatatggc acaaacatcc ttaaaatata atatagaaaa taatgaatat acataaaata    300

tacataaaat aaatgtatta acagtgtata ttatatatat ggctttgtca gacatcacta    360

cgttcgttcc aaaagtcgtc attgccaata ggttttcctt ttaaatttta gtggttacaa    420

ataaatcaac ctatcaagtt attaaaataa tatgtcagat actataattt aaataatgga    480

agcgactcat acacatatac actaatttat attattactg tatacgtaaa actgaattaa    540

caacttttca ctgaaaaagc acacccttta atttatatat cagtgactaa gtcataacgt    600

gaaacaatta taaattctaa aggttaaaaa gatctaaaaa cttttgcacg tggaatgtgc    660

tatatattta ccctaaaata tcgaagccaa ctaaacaaat taatgaatta taaagacaca    720

ggttctttga tttgatggta atcattatgt catagaaact gttctataaa tttcatacta    780

tattatgcat ctagaaatca gataatgtag agtaagaaat aaatatacta tttcgaaatt    840

aagaaactcc aagttttgct atgatatctc aaccagttaa aattggttgt ttcagttcgg    900

tcttgacgat tttttacacg acatatgatg tagttatgtc tagcccatcc gttacattac    960

atatgtggta acagaatatt tcttggacct cttggtcgtc ttgaaaaaac tcttatgaac   1020
```

-continued

```
cggatgccaa aatactatat atcgtaaaca aaaacaaaat caagtaagtt ccaatatttt   1080

attcacttga aaaatcgcat actcgtataa ggaaacacta atcatagatg ttttcaatat   1140

ttcagttttt taaaatgacg actaacactt ggaaaccgat aatgatgaaa ctttatataa   1200

gaaaacaaag tttgtttcaa acatatcata gtcaacatac aaaaaaaatg agtcatatta   1260

aaaaaaaaaa aaaaatctag accaaatgat tcacatggca agaaatttaa gtaatttctg   1320

atgtaaacgc ctgatcacta aattgagctt ctcatatttt ctttttttctt ttgagcttta   1380

tttaattcat acatgcatct atataaggaa atcaaaaatg ttaatgcaaa acgtaaattt   1440

aatatgtatt gaatgtaaca acattaataa aggcacgaaa ttattggttt gaaatgatta   1500

gatccaacta atttccaacc aaagacggtc aaagccaaat aaaaatgctt agctctccat   1560

gagcaccaag agaaacccat ccaaatggtt cagacaatcg tggaccccac gcgccgcttc   1620

tcttctctcc ccacttgcta ttctctctct ctaattaatt tttaactttg attagttttg   1680

gtcaacttta tagttaacca tggttaacta ataaaatatt tatttatgtc caagattaat   1740

taatgaataa gtgattatat aggtatatgt gttagcctaa gtttttttct tcaaaatagc   1800

tttgtttata cacgttattt tttttgttg caaggcttac atcttaattt aggaaactga   1860

tatgattgct atatataagg cctgagtgta caaaatatta attaagttta aataaattaa   1920

ggcaaggcaa tgatggtgga gaatgttttg aaagacagaa aagaggaagc atcttaatga   1980

aacccacaag ataaccccaa ccacatatta tcatgatggc ttcattcatc ttaattaaac   2040

tttaaccttt cattttctcc aaatatttta acttattata ccaattagat cacacccact   2100

cacatacatc tccttcccaa tttctcacgc tcctagaata tgcgtggaga ctacttccgt   2160

taggctactt gatacaatca taacaatgta ttgctaactt tggaactttg taatttatct   2220

agttaaacca atcaactatg agaagaagtg tagcggtttt aaatgggggt gtatatgttc   2280

aaaaaaagag agaagggaat tcataccttg aaataattaa taatactttt ctagtcaaat   2340

atttgtatgg atcgtaaaca tatacaaaca tgttacaaac aagttttttt tgtaccaata   2400

attatcgact aaaatactaa acataatatt ttattttatt ataaatatcc tatactatat   2460

aagttataaa catagcaaaa agaaaaacac aaaagccaac agtgaaacct aaatatgtgt   2520

ttgcttatgg tagccgcgta tattacacgc tctaactatt ggagaagaag aagaagagtg   2580

gagtttattg tcgagtccaa aacacacaaa acgacataaa actcaacgag aacaaaattt   2640

gaattgaagt cgataccaaa ttttattttt atttttattt tatttttatt tatcaatatc   2700

cattttgtaa gagtttaggt tagacaagtg actgcattta catacatata tctatatata   2760

tacaaacatt ttttcttctt cattaatgct ttattttagt ctcaccttct ccttctactt   2820

tttatcattt ccctttctct tcccatttta gtcttcctat aacttcttct caatcctctc   2880

tcatatcttt tttcttagtt taaatttcaa taaaatagaa aaaaacatat acaaatctac   2940

agagaagaga agctttattt taatcttgtg tgtgtgtgtg tgttttatat aatttttatt   3000

ttttttcaaa ttaaaatctc ttctttgctt ttgatgtggg c                       3041
```

<210> SEQ ID NO 43
<211> LENGTH: 1379
<212> TYPE: DNA
<213> ORGANISM: Arabidopsis thaliana
<220> FEATURE:
<221> NAME/KEY: CDS
<222> LOCATION: (242)..(1120)
<223> OTHER INFORMATION: coding for DNA-binding protein related protein

<400> SEQUENCE: 43

-continued

```
ctcaccttct ccttctactt tttatcattt ccctttctct tcccatttta gtcttcctat      60

aacttcttct caatcctctc tcatatcttt tttcttagtt taaatttcaa taaaatagaa     120

aaaaacatat acaaatctac agagaagaga agctttattt taatcttgtg tgtgtgtgtg     180

tgttttatat aatttttatt ttttttcaaa ttaaaatctc ttctttgctt ttgatgtggg     240

c atg gct ggt ctt gat cta ggc aca gct ttt cgt tac gtt aat cac cag     289
  Met Ala Gly Leu Asp Leu Gly Thr Ala Phe Arg Tyr Val Asn His Gln
  1               5                   10                  15

ctc cat cgt ccc gat ctc cac ctt cac cac aat tcc tcc tcc gat gac       337
Leu His Arg Pro Asp Leu His Leu His His Asn Ser Ser Ser Asp Asp
            20                  25                  30

gtc act ccc gga gcc ggg atg ggt cat ttc acc gtc gac gac gaa gac       385
Val Thr Pro Gly Ala Gly Met Gly His Phe Thr Val Asp Asp Glu Asp
        35                  40                  45

aac aac aac aac cat caa ggt ctt gac tta gcc tct ggt gga gga tca       433
Asn Asn Asn Asn His Gln Gly Leu Asp Leu Ala Ser Gly Gly Gly Ser
    50                  55                  60

gga agc tct gga gga gga gga ggt cac ggc ggg gga gga gac gtc gtt       481
Gly Ser Ser Gly Gly Gly Gly Gly His Gly Gly Gly Gly Asp Val Val
65                  70                  75                  80

ggt cgt cgt cca cgt ggc aga cca ccg gga tcc aag aac aaa ccg aaa       529
Gly Arg Arg Pro Arg Gly Arg Pro Pro Gly Ser Lys Asn Lys Pro Lys
                85                  90                  95

cct ccg gta att atc acg cgc gag agc gca aac act cta aga gct cac       577
Pro Pro Val Ile Ile Thr Arg Glu Ser Ala Asn Thr Leu Arg Ala His
            100                 105                 110

att ctt gaa gta aca aac ggc tgc gat gtt ttc gac tgc gtt gcg act       625
Ile Leu Glu Val Thr Asn Gly Cys Asp Val Phe Asp Cys Val Ala Thr
        115                 120                 125

tat gct cgt cgg aga cag cga ggg atc tgc gtt ctg agc ggt agc gga       673
Tyr Ala Arg Arg Arg Gln Arg Gly Ile Cys Val Leu Ser Gly Ser Gly
    130                 135                 140

acg gtc acg aac gtc agc ata cgt cag cca tct gcg gct gga gcg gtt       721
Thr Val Thr Asn Val Ser Ile Arg Gln Pro Ser Ala Ala Gly Ala Val
145                 150                 155                 160

gtg acg cta caa gga acg ttc gag att ctt tct ctc tcc gga tcg ttt       769
Val Thr Leu Gln Gly Thr Phe Glu Ile Leu Ser Leu Ser Gly Ser Phe
                165                 170                 175

ctt cct cct ccg gca cct ccc gga gca acg agt ttg aca att ttc tta       817
Leu Pro Pro Pro Ala Pro Pro Gly Ala Thr Ser Leu Thr Ile Phe Leu
            180                 185                 190

gcc gga gga caa ggt cag gtg gtt gga gga agc gtt gtg ggt gag ctt       865
Ala Gly Gly Gln Gly Gln Val Val Gly Gly Ser Val Val Gly Glu Leu
        195                 200                 205

acg gcg gct gga ccg gtg att gtg att gca gct tcg ttt act aat gtt       913
Thr Ala Ala Gly Pro Val Ile Val Ile Ala Ala Ser Phe Thr Asn Val
    210                 215                 220

gct tat gag aga ctt cct tta gaa gaa gat gag cag cag caa cag ctt       961
Ala Tyr Glu Arg Leu Pro Leu Glu Glu Asp Glu Gln Gln Gln Gln Leu
225                 230                 235                 240

gga gga gga tct aac ggc gga ggt aat ttg ttt ccg gag gtg gca gct      1009
Gly Gly Gly Ser Asn Gly Gly Gly Asn Leu Phe Pro Glu Val Ala Ala
                245                 250                 255

gga gga gga gga gga ctt ccg ttc ttt aat tta ccg atg aat atg caa      1057
Gly Gly Gly Gly Gly Leu Pro Phe Phe Asn Leu Pro Met Asn Met Gln
            260                 265                 270

cca aat gtg caa ctt ccg gtg gaa ggt tgg ccg ggg aat tcc ggt gga      1105
Pro Asn Val Gln Leu Pro Val Glu Gly Trp Pro Gly Asn Ser Gly Gly
```

-continued

```
        275                 280                 285

aga ggt cct ttc tga tgtgtatata ttgataatca ttatatatat accggcggag     1160
Arg Gly Pro Phe
    290

aagcttttcc ggcgaagaat ttgcgagagt gaagaaaggt tagaaaagct tttaatggac   1220

taatgaattt caaattatca tcgtgatttc ggacattgtc ttgttcatca tgttaagctt   1280

aggtttattt tttgtcgttt gtagaatttt atgtttgaat cctttttttt ttctgtgaaa   1340

ctctattgtg ttcgtctgcg aaggaaaaaa aaattctca                          1379


<210> SEQ ID NO 44
<211> LENGTH: 292
<212> TYPE: PRT
<213> ORGANISM: Arabidopsis thaliana

<400> SEQUENCE: 44

Met Ala Gly Leu Asp Leu Gly Thr Ala Phe Arg Tyr Val Asn His Gln
1               5                   10                  15

Leu His Arg Pro Asp Leu His Leu His His Asn Ser Ser Ser Asp Asp
            20                  25                  30

Val Thr Pro Gly Ala Gly Met Gly His Phe Thr Val Asp Asp Glu Asp
        35                  40                  45

Asn Asn Asn Asn His Gln Gly Leu Asp Leu Ala Ser Gly Gly Gly Ser
    50                  55                  60

Gly Ser Ser Gly Gly Gly Gly Gly His Gly Gly Gly Gly Asp Val Val
65                  70                  75                  80

Gly Arg Arg Pro Arg Gly Arg Pro Pro Gly Ser Lys Asn Lys Pro Lys
                85                  90                  95

Pro Pro Val Ile Ile Thr Arg Glu Ser Ala Asn Thr Leu Arg Ala His
            100                 105                 110

Ile Leu Glu Val Thr Asn Gly Cys Asp Val Phe Asp Cys Val Ala Thr
        115                 120                 125

Tyr Ala Arg Arg Arg Gln Arg Gly Ile Cys Val Leu Ser Gly Ser Gly
    130                 135                 140

Thr Val Thr Asn Val Ser Ile Arg Gln Pro Ser Ala Ala Gly Ala Val
145                 150                 155                 160

Val Thr Leu Gln Gly Thr Phe Glu Ile Leu Ser Leu Ser Gly Ser Phe
                165                 170                 175

Leu Pro Pro Pro Ala Pro Pro Gly Ala Thr Ser Leu Thr Ile Phe Leu
            180                 185                 190

Ala Gly Gly Gln Gly Gln Val Val Gly Gly Ser Val Val Gly Glu Leu
        195                 200                 205

Thr Ala Ala Gly Pro Val Ile Val Ile Ala Ala Ser Phe Thr Asn Val
    210                 215                 220

Ala Tyr Glu Arg Leu Pro Leu Glu Glu Asp Glu Gln Gln Gln Gln Leu
225                 230                 235                 240

Gly Gly Gly Ser Asn Gly Gly Gly Asn Leu Phe Pro Glu Val Ala Ala
                245                 250                 255

Gly Gly Gly Gly Gly Leu Pro Phe Phe Asn Leu Pro Met Asn Met Gln
            260                 265                 270

Pro Asn Val Gln Leu Pro Val Glu Gly Trp Pro Gly Asn Ser Gly Gly
        275                 280                 285

Arg Gly Pro Phe
    290
```

-continued

<210> SEQ ID NO 45
<211> LENGTH: 33
<212> TYPE: DNA
<213> ORGANISM: Artificial
<220> FEATURE:
<223> OTHER INFORMATION: oligonucleotide primer

<400> SEQUENCE: 45
cgctcgaggt ttggcctaaa tgtgtaatgc tgt 33

<210> SEQ ID NO 46
<211> LENGTH: 35
<212> TYPE: DNA
<213> ORGANISM: Artificial
<220> FEATURE:
<223> OTHER INFORMATION: oligonucleotide primer

<400> SEQUENCE: 46
gcggatccaa agcacattgc gactcactac tctcg 35

<210> SEQ ID NO 47
<211> LENGTH: 35
<212> TYPE: DNA
<213> ORGANISM: Artificial
<220> FEATURE:
<223> OTHER INFORMATION: oligonucleotide primer

<400> SEQUENCE: 47
gcggatcctt tctaattttt ggtcttttgg aagag 35

<210> SEQ ID NO 48
<211> LENGTH: 34
<212> TYPE: DNA
<213> ORGANISM: Artificial
<220> FEATURE:
<223> OTHER INFORMATION: oligonucleotide primer

<400> SEQUENCE: 48
gcggatcctt tacatctaaa cagagttctt aatt 34

<210> SEQ ID NO 49
<211> LENGTH: 33
<212> TYPE: DNA
<213> ORGANISM: Artificial
<220> FEATURE:
<223> OTHER INFORMATION: oligonucleotide primer

<400> SEQUENCE: 49
gcggatcccg aaacaagtag caaaacgaat aaa 33

<210> SEQ ID NO 50
<211> LENGTH: 37
<212> TYPE: DNA
<213> ORGANISM: Artificial
<220> FEATURE:
<223> OTHER INFORMATION: oligonucleotide primer

<400> SEQUENCE: 50
cgccatggtt ttttgtagaa tattgttcaa caagtag 37

<210> SEQ ID NO 51
<211> LENGTH: 27
<212> TYPE: DNA
<213> ORGANISM: Artificial
<220> FEATURE:
<223> OTHER INFORMATION: oligonucleotide primer

<400> SEQUENCE: 51
cgccatggga aggaaacaag tgaagtg 27

<210> SEQ ID NO 52
<211> LENGTH: 33
<212> TYPE: DNA
<213> ORGANISM: Artificial
<220> FEATURE:
<223> OTHER INFORMATION: oligonucleotide primer

<400> SEQUENCE: 52
gcggatcctc tttcctcata cacacaaaat gta 33

<210> SEQ ID NO 53
<211> LENGTH: 33
<212> TYPE: DNA
<213> ORGANISM: Artificial
<220> FEATURE:
<223> OTHER INFORMATION: oligonucleotide primer

<400> SEQUENCE: 53
gcggatccat ttgcagagat tatacttagc ctt 33

<210> SEQ ID NO 54
<211> LENGTH: 33
<212> TYPE: DNA
<213> ORGANISM: Artificial
<220> FEATURE:
<223> OTHER INFORMATION: oligonucleotide primer

<400> SEQUENCE: 54
cgccatggat gatgaaatga aagatatatg atc 33

<210> SEQ ID NO 55
<211> LENGTH: 31
<212> TYPE: DNA
<213> ORGANISM: Artificial
<220> FEATURE:
<223> OTHER INFORMATION: oligonucleotide primer

<400> SEQUENCE: 55
cgccatggat tgctatgatg attttagctt g 31

<210> SEQ ID NO 56
<211> LENGTH: 27
<212> TYPE: DNA
<213> ORGANISM: Artificial
<220> FEATURE:
<223> OTHER INFORMATION: oligonucleotide primer

<400> SEQUENCE: 56
agcgacgtaa ctcataggat ccaaatg 27

<210> SEQ ID NO 57
<211> LENGTH: 37
<212> TYPE: DNA
<213> ORGANISM: Artificial
<220> FEATURE:
<223> OTHER INFORMATION: oligonucleotide primer

<400> SEQUENCE: 57
cgccatggtc ttttgtctct gttttttgtg ctttctg 37

<210> SEQ ID NO 58

<211> LENGTH: 30
<212> TYPE: DNA
<213> ORGANISM: Artificial
<220> FEATURE:
<223> OTHER INFORMATION: oligonucleotide primer

<400> SEQUENCE: 58
cgccatggag agagagaagg tgataggacc 30

<210> SEQ ID NO 59
<211> LENGTH: 38
<212> TYPE: DNA
<213> ORGANISM: Artificial
<220> FEATURE:
<223> OTHER INFORMATION: oligonucleotide primer

<400> SEQUENCE: 59
cgctcgagtt cctccaaacc taaactcgga cccaatat 38

<210> SEQ ID NO 60
<211> LENGTH: 35
<212> TYPE: DNA
<213> ORGANISM: Artificial
<220> FEATURE:
<223> OTHER INFORMATION: oligonucleotide primer

<400> SEQUENCE: 60
cgggatccca ctacttcttc ttattcagtt agctt 35

<210> SEQ ID NO 61
<211> LENGTH: 32
<212> TYPE: DNA
<213> ORGANISM: Artificial
<220> FEATURE:
<223> OTHER INFORMATION: oligonucleotide primer

<400> SEQUENCE: 61
cgggatccgt ttctatggtc gttgtatatg gg 32

<210> SEQ ID NO 62
<211> LENGTH: 36
<212> TYPE: DNA
<213> ORGANISM: Artificial
<220> FEATURE:
<223> OTHER INFORMATION: oligonucleotide primer

<400> SEQUENCE: 62
ggcggatccc acgggacggg ttgttatata aaagtc 36

<210> SEQ ID NO 63
<211> LENGTH: 41
<212> TYPE: DNA
<213> ORGANISM: Artificial
<220> FEATURE:
<223> OTHER INFORMATION: oligonucleotide primer

<400> SEQUENCE: 63
cgccatggcc tttcccctaa attgtcaaaa cctaaaacaa g 41

<210> SEQ ID NO 64
<211> LENGTH: 31
<212> TYPE: DNA
<213> ORGANISM: Artificial
<220> FEATURE:
<223> OTHER INFORMATION: oligonucleotide primer

<400> SEQUENCE: 64

-continued

```
cgccatggtt atgtgattga tgcttctcgt c                                   31


<210> SEQ ID NO 65
<211> LENGTH: 26
<212> TYPE: DNA
<213> ORGANISM: Artificial
<220> FEATURE:
<223> OTHER INFORMATION: oligonucleotide primer

<400> SEQUENCE: 65

gcggatcctt tgtagccata tacatt                                         26


<210> SEQ ID NO 66
<211> LENGTH: 38
<212> TYPE: DNA
<213> ORGANISM: Artificial
<220> FEATURE:
<223> OTHER INFORMATION: oligonucleotide primer

<400> SEQUENCE: 66

cgccatggtt aaaattgctt tggaaagagt agttatag                            38


<210> SEQ ID NO 67
<211> LENGTH: 26
<212> TYPE: DNA
<213> ORGANISM: Artificial
<220> FEATURE:
<223> OTHER INFORMATION: oligonucleotide primer

<400> SEQUENCE: 67

cgctcgagca acttcaatat tacatg                                         26


<210> SEQ ID NO 68
<211> LENGTH: 37
<212> TYPE: DNA
<213> ORGANISM: Artificial
<220> FEATURE:
<223> OTHER INFORMATION: oligonucleotide primer

<400> SEQUENCE: 68

gcggatccgc ccacatcaaa agcaaagaag agatttt                             37


<210> SEQ ID NO 69
<211> LENGTH: 30
<212> TYPE: DNA
<213> ORGANISM: Artificial
<220> FEATURE:
<223> OTHER INFORMATION: oligonucleotide primer

<400> SEQUENCE: 69

gcgatccacc aaaataaagc attaatgaag                                     30
```

EXPRESSION CASSETTES FOR ROOT-PREFERENTIAL EXPRESSION IN PLANTS

FIELD OF THE INVENTION

The present invention relates to expression cassettes comprising transcription regulating sequences with root-preferential or root-specific expression profiles in plants obtainable from *Arabidopsis thaliana* genes At1g66280, At1g74500, At1g49570, At1g70710, At5g66690, At3g29630, At5g48070, or At4g17800.

BACKGROUND OF THE INVENTION

Manipulation of plants to alter and/or improve phenotypic characteristics (such as productivity or quality) requires the expression of heterologous genes in plant tissues. Such genetic manipulation relies on the availability of a means to drive and to control gene expression as required. For example, genetic manipulation relies on the availability and use of suitable promoters which are effective in plants and which regulate gene expression so as to give the desired effect(s) in the transgenic plant.

The root-preferential or root-specific promoters are useful for alteration of the function of root tissue, modification of growth rate, improvement of resistance to root preferred pathogens, pests, herbicides or adverse weather conditions, for detoxification of soil as well as for broadening the range of soils or environments in which said plant may grow. Root abundant or root specific gene expression would provide a mechanism according to which morphology and metabolism may be altered to improve the yield and to produce useful proteins in greater amounts. In particular, root specific promoters may be useful for expressing defense-related genes, including those conferring insectical resistance and stress tolerance, e.g. salt, cold or drought tolerance, and genes for altering nutrient uptake.

A limited number of examples of root preferred and root-specific promoters have been described. These include the RB7 promoter from *Nicotiana tabacum* (U.S. Pat. Nos. 5,459,252 and 5,750,386) the ARSKI promoter from *Arabidopsis thaliana* (Hwang and Goodman (1995) Plant J. 8:37:43), the MR7 promoter from *Zea mays* (U.S. Pat. No. 5,837,848), the ZRP2 promoter of *Zea mays* (U.S. Pat. No. 5,633,363), and the MTL promoter from *Zea mays* (U.S. Pat. Nos. 5,466,785 and 6,018,099). Many of these examples disclose promoters with expression patterns confined to a limited number of root tissues. Other fail to provide the root specificity needed for expression of selected genes. It is advantageous to have the choice of a variety of different promoters so that the most suitable promoter may be selected for a particular gene, construct, cell, tissue, plant or environment. Moreover, the increasing interest in cotransforming plants with multiple plant transcription units (PTU) and the potential problems associated with using common regulatory sequences for these purposes merit having a variety of promoter sequences available.

There is, therefore, a great need in the art for isolation and characterization of new root-specific or root-preferential transcription regulating sequences which offer a broad spectrum of breadth, expression level and specificity of root cell-type expression, that can be used for expression of selected transgenes in economically important plants. It is thus an objective of the present invention to provide new and alternative expression cassettes for root-preferential or root specific expression of transgenes in plants. The objective is solved by the present invention.

SUMMARY OF THE INVENTION

Accordingly, a first embodiment of the invention relates to a expression cassette for root-specific or root-preferential transcription of an operatively linked nucleic acid sequences in plants comprising i) at least one transcription regulating nucleotide sequence of a plant gene, said plant gene selected from the group of genes described by the GenBank *Arabidopsis thaliana* genome loci At1g66280, At1g74500, At1g49570, At1g70710, At5g66690, At3g29630, At5g48070, or At4g17800, or a functional equivalent thereof, and functionally linked thereto ii) at least one nucleic acid sequence which is heterologous in relation to said transcription regulating nucleotide sequence.

Preferably, the transcription regulating nucleotide sequence (or the functional equivalent thereof) is selected from the group of sequences consisting of i) the sequences described by SEQ ID NOs: 1, 2, 3, 4, 7, 8, 9, 10, 11, 14, 15, 16, 19, 20, 21, 24, 25, 26, 29, 30, 31, 34, 35, 36, 37, 40, 41, and 42, ii) a fragment of at least 50 consecutive bases of a sequence under i) which has substantially the same promoter activity as the corresponding transcription regulating nucleotide sequence described by SEQ ID NO: 1, 2, 3, 4, 7, 8, 9, 10, 11, 14, 15, 16, 19, 20, 21, 24, 25, 26, 29, 30, 31, 34, 35, 36, 37, 40, 41, or 42;

iii) a nucleotide sequence having substantial similarity (e.g., with a sequence identity of at least 40, 50, 60, to 70%, e.g., preferably 71%, 72%, 73%, 74%, 75%, 76%, 77%, 78%, to 79%, generally at least 80%, e.g., 81% to 84%, at least 85%, e.g., 86%, 87%, 88%, 89%, 90%, 91%, 92%, 93%, 94%, 95%, 96%, 97%, to 98% and 99%) to a transcription regulating nucleotide sequence described by SEQ ID NO: 1, 2, 3, 4, 7, 8, 9, 10, 11, 14, 15, 16, 19, 20, 21, 24, 25, 26, 29, 30, 31, 34, 35, 36, 37, 40, 41, or 42;

iv) a nucleotide sequence capable of hybridizing (preferably under conditions equivalent to hybridization in 7% sodium dodecyl sulfate (SDS), 0.5 M $NaPO_4$, 1 mM EDTA at 50° C. with washing in 2×SSC, 0.1% SDS at 50° C. (more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.) to a transcription regulating nucleotide sequence described by SEQ ID NO: 1, 2, 3, 4, 7, 8, 9, 10, 11, 14, 15, 16, 19, 20, 21, 24, 25, 26, 29, 30, 31, 34, 35, 36, 37, 40, 41, or 42, or the complement thereof;

v) a nucleotide sequence capable of hybridizing (preferably under conditions equivalent to hybridization in 7% sodium dodecyl sulfate (SDS), 0.5 M $NaPO_4$, 1 mM EDTA at 50° C. with washing in 2×SSC, 0.1% SDS at 50° C. (more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.) to a nucleic acid comprising 50 to 200 or more consecutive nucleotides of a transcription regulating nucleotide sequence described by SEQ ID NO: 1, 2, 3, 4, 7, 8, 9, 10, 11, 14, 15, 16, 19, 20, 21, 24, 25, 26, 29, 30, 31, 34, 35, 36, 37, 40, 41, and 42, or the complement thereof;

vi) a nucleotide sequence which is the complement or reverse complement of any of the previously mentioned nucleotide sequences under i) to v).

The functional equivalent of the transcription regulating nucleotide sequence is obtained or obtainable from plant genomic DNA from a gene encoding a polypeptide which has at least 70% amino acid sequence identity to a polypeptide selected from the group described by SEQ ID NO: 6, 13, 18, 23, 28, 33, 39, and 44, respectively.

The expression cassette may be employed for numerous expression purposes such as for example expression of a protein, or expression of a antisense RNA, sense or double-stranded RNA. Preferably, expression of the nucleic acid sequence confers to the plant an agronomically valuable trait.

Other embodiments of the invention relate to vectors comprising an expression cassette of the invention, and transgenic host cell or non-human organism comprising an expression cassette or a vector of the invention. Preferably the organism is a plant.

Another embodiment of the invention relates to a method for identifying and/or isolating a sequence with root-specific or root-preferential transcription regulating activity characterized that said identification and/or isolation utilizes a nucleic acid sequence encoding a amino acid sequence as described by SEQ ID NO: 6, 13, 18, 23, 28, 33, 39, or 44 or a part of at least 15 bases thereof. Preferably the nucleic acid sequences is described by SEQ ID NO: 5, 12, 17, 22, 27, 32, 38, or 43 or a part of at least 15 bases thereof. More preferably, identification and/or isolation is realized by a method selected from polymerase chain reaction, hybridization, and database screening.

Another embodiment of the invention relates to a method for providing a transgenic expression cassette for root-specific or root-preferential expression comprising the steps of:

I. isolating of a root-preferential or root-specific transcription regulating nucleotide sequence utilizing at least one nucleic acid sequence or a part thereof, wherein said sequence is encoding a polypeptide described by SEQ ID NO: 6, 13, 18, 23, 28, 33, 39, or 44, or a part of at least 15 bases thereof, and II. functionally linking said root-preferential or root-specific transcription regulating nucleotide sequence to another nucleotide sequence of interest, which is heterologous in relation to said root-preferential or root-specific transcription regulating nucleotide sequence.

DEFINITIONS

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention which will be limited only by the appended claims. It must be noted that as used herein and in the appended claims, the singular forms “a,” “and,” and “the” include plural reference unless the context clearly dictates otherwise. Thus, for example, reference to “a vector” is a reference to one or more vectors and includes equivalents thereof known to those skilled in the art, and so forth.

The term “about” is used herein to mean approximately, roughly, around, or in the region of. When the term “about” is used in conjunction with a numerical range, it modifies that range by extending the boundaries above and below the numerical values set forth. In general, the term “about” is used herein to modify a numerical value above and below the stated value by a variance of 20 per-cent up or down (higher or lower).

As used herein, the word “or” means any one member of a particular list and also includes any combination of members of that list.

The term “gene” is used broadly to refer to any segment of nucleic acid associated with a biological function. Thus, genes include coding sequences and/or the regulatory sequences required for their expression. For example, gene refers to a nucleic acid fragment that expresses mRNA or functional RNA, or encodes a specific protein, and which includes regulatory sequences. Genes also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

The term “native” or “wild type” gene refers to a gene that is present in the genome of an untransformed cell, i.e., a cell not having a known mutation.

A “marker gene” encodes a selectable or screenable trait.

The term “chimeric gene” refers to any gene that contains

1) DNA sequences, including regulatory and coding sequences, that are not found together in nature, or
2) sequences encoding parts of proteins not naturally adjoined, or
3) parts of promoters that are not naturally adjoined.

Accordingly, a chimeric gene may comprise regulatory sequences and coding sequences that are derived from different sources, or comprise regulatory sequences, and coding sequences derived from the same source, but arranged in a manner different from that found in nature.

A “transgene” refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term “endogenous gene” refers to a native gene in its natural location in the genome of an organism. A “foreign” gene refers to a gene not normally found in the host organism but that is introduced by gene transfer.

An “oligonucleotide” corresponding to a nucleotide sequence of the invention, e.g., for use in probing or amplification reactions, may be about 30 or fewer nucleotides in length (e.g., 9, 12, 15, 18, 20, 21 or 24, or any number between 9 and 30). Generally specific primers are upwards of 14 nucleotides in length. For optimum specificity and cost effectiveness, primers of 16 to 24 nucleotides in length may be preferred. Those skilled in the art are well versed in the design of primers for use processes such as PCR. If required, probing can be done with entire restriction fragments of the gene disclosed herein which may be 100's or even 1000's of nucleotides in length.

The terms "protein," "peptide" and "polypeptide" are used interchangeably herein.

The nucleotide sequences of the invention can be introduced into any plant. The genes to be introduced can be conveniently used in expression cassettes for introduction and expression in any plant of interest. Such expression cassettes will comprise the transcriptional initiation region of the invention linked to a nucleotide sequence of interest. Preferred promoters include constitutive, tissue-specific, developmental-specific, inducible and/or viral promoters, most preferred are the root-specific or root-preferential promoters of the invention. Such an expression cassette is provided with a plurality of restriction sites for insertion of the gene of interest to be under the transcriptional regulation of the regulatory regions. The expression cassette may additionally contain selectable marker genes. The cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such, as the octopine synthase and nopaline synthase termination regions (see also, Guerineau 1991; Proudfoot 1991; Sanfacon 1991; Mogen 1990; Munroe 1990; Ballas 1989; Joshi 1987).

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

A "functional RNA" refers to an antisense RNA, ribozyme, or other RNA that is not translated.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Transcription regulating nucleotide sequence", transcription regulating nucleotide sequence "regulatory sequences", and "suitable regulatory sequences", each refer to nucleotide sequences influencing the transcription, RNA processing or stability, or translation of the associated (or functionally linked) nucleotide sequence to be transcribed. The transcription regulating nucleotide sequence may have various localizations with the respect to the nucleotide sequences to be transcribed. The transcription regulating nucleotide sequence may be located upstream (5' non-coding sequences), within, or downstream (3' non-coding sequences) of the sequence to be transcribed (e.g., a coding sequence). The transcription regulating sequences may be selected from the group comprising enhancers, promoters, translation leader sequences, introns, 5'-untranslated sequences, 3'-untranslated sequences, and polyadenylation signal sequences. They include natural and synthetic sequences as well as sequences, which may be a combination of synthetic and natural sequences. As is noted above, the term "transcription regulating sequence" is not limited to promoters. However, preferably a transcription regulating nucleotide sequence of the invention comprises at least one promoter sequence (e.g., a sequence localized upstream of the transcription start of a gene capable to induce transcription of the downstream sequences). In one preferred embodiment the transcription regulating nucleotide sequence of the invention comprises the promoter sequence of the corresponding gene and optionally and preferably—the native 5'-untranslated region of said gene. Furthermore, the 3'-untranslated region and/or the polyadenylation region of said gene may also be employed.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner 1995).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., 1989.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide. The term "transit peptide" as used herein refers part of a expressed polypeptide (preferably to the amino terminal extension of a polypeptide), which is translated in conjunction with the polypeptide forming a precursor peptide and which is required for its entrance into a cell organelle (such as the plastids (e.g., chloroplasts) or mitochondria). The term "transit sequence" refers to a nucleotide sequence that encodes the transit peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements, derived from different promoters found in nature, or even be comprised of synthetic DNA segments. A promoter may also contain DNA sequences that are involved in the binding of protein factors which control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Constitutive promoter" refers to a promoter that is able to express the open reading frame (ORF) that it controls in all or nearly all of the plant tissues during all or nearly all developmental stages of the plant. Each of the transcription-activating elements do not exhibit an absolute tissue-specificity, but mediate transcriptional activation in most plant parts at a level of at least 1% of the level reached in the part of the plant in which transcription is most active.

"Regulated promoter" refers to promoters that direct gene expression not constitutively, but in a temporally- and/or spatially-regulated manner, and includes both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered, numerous examples may be found in the compilation by Okamuro et al. (1989). Typical regulated promoters useful in plants include but are not limited to safener-inducible promoters, promoters derived from the tetracycline-inducible system, promoters derived from salicylate-inducible systems, promoters derived from alcohol-inducible systems, promoters derived from glucocorticoid-inducible system, promoters derived from pathogen-inducible systems, and promoters derived from ecdysone-inducible systems.

"Tissue-specific promoter" refers to regulated promoters that are not expressed in all plant cells but only in one or more cell types in specific organs (such as leaves, roots, or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence.

"Inducible promoter" refers to those regulated promoters that can be turned on in one or more cell types by an external stimulus, such as a chemical, light, hormone, stress, or a pathogen.

"Operably-linked" or "functionally linked" refers preferably to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, ORF or portion thereof, or a transgene in plants. For example, in the case of antisense constructs, expression may refer to the transcription of the antisense DNA only. In addition, expression refers to the transcription and stable accumulation of sense (mRNA) or functional RNA. Expression may also refer to the production of protein.

"Specific expression" is the expression of gene products which is limited to one or a few plant tissues (spatial limitation) and/or to one or a few plant developmental stages (temporal limitation). It is acknowledged that hardly a true specificity exists: promoters seem to be preferably switch on in some tissues, while in other tissues there can be no or only little activity. This phenomenon is known as leaky expression. However, with specific expression in this invention is meant preferable expression in one or a few plant tissues.

The "expression pattern" of a promoter (with or without enhancer) is the pattern of expression levels which shows where in the plant and in what developmental stage transcription is initiated by said promoter. Expression patterns of a set of promoters are said to be complementary when the expression pattern of one promoter shows little overlap with the expression pattern of the other promoter. The level of expression of a promoter can be determined by measuring the 'steady state' concentration of a standard transcribed reporter mRNA. This measurement is indirect since the concentration of the reporter mRNA is dependent not only on its synthesis rate, but also on the rate with which the mRNA is degraded. Therefore, the steady state level is the product of synthesis rates and degradation rates.

The rate of degradation can however be considered to proceed at a fixed rate when the transcribed sequences are identical, and thus this value can serve as a measure of synthesis rates. When promoters are compared in this way techniques available to those skilled in the art are hybridization S1-RNAse analysis, northern blots and competitive RT-PCR. This list of techniques in no way represents all available techniques, but rather describes commonly used procedures used to analyze transcription activity and expression levels of mRNA.

The analysis of transcription start points in practically all promoters has revealed that there is usually no single base at which transcription starts, but rather a more or less clustered set of initiation sites, each of which accounts for some start points of the mRNA. Since this distribution varies from promoter to promoter the sequences of the reporter mRNA in each of the populations would differ from each other. Since each mRNA species is more or less prone to degradation, no single degradation rate can be expected for different reporter mRNAs. It has been shown for various eukaryotic promoter sequences that the sequence surrounding the initiation site ('initiator') plays an important role in determining the level of RNA expression directed by that specific promoter. This includes also part of the transcribed sequences. The direct fusion of promoter to reporter sequences would therefore lead to suboptimal levels of transcription.

A commonly used procedure to analyze expression patterns and levels is through determination of the 'steady state' level of protein accumulation in a cell. Commonly used candidates for the reporter gene, known to those skilled in the art are beta-glucuronidase (GUS), chloramphenicol acetyl transferase (CAT) and proteins with fluorescent properties, such as green fluorescent protein (GFP) from *Aequora victoria*. In principle, however, many more proteins are suitable for this purpose, provided the protein does not interfere with essential plant functions. For quantification and determination of localization a number of tools are suited. Detection systems can readily be created or are available which are based on, e.g., immunochemical, enzymatic, fluorescent detection and quantification. Protein levels can be determined in plant tissue extracts or in intact tissue using in situ analysis of protein expression.

Generally, individual transformed lines with one chimeric promoter reporter construct will vary in their levels of expression of the reporter gene. Also frequently observed is the phenomenon that such transformants do not express any detectable product (RNA or protein). The variability in expression is commonly ascribed to 'position effects', although the molecular mechanisms underlying this inactivity are usually not clear.

"Overexpression" refers to the level of expression in transgenic cells or organisms that exceeds levels of expression in normal or untransformed (non-transgenic) cells or organisms.

"Antisense inhibition" refers to the production of antisense RNA transcripts capable of suppressing the expression of protein from an endogenous gene or a transgene.

"Gene silencing" refers to homology-dependent suppression of viral genes, transgenes, or endogenous nuclear genes. Gene silencing may be transcriptional, when the suppression is due to decreased transcription of the affected genes, or post-transcriptional, when the suppression is due to increased turnover (degradation) of RNA species homologous to the affected genes (English 1996). Gene silencing includes virus-induced gene silencing (Ruiz et al. 1998).

The terms "heterologous DNA sequence," "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

"Homologous to" in the context of nucleotide sequence identity refers to the similarity between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art (as described in Haines and Higgins (eds.), Nucleic Acid Hybridization, IRL Press, Oxford, U.K.), or by the comparison of sequence similarity between two nucleic acids or proteins.

The term "substantially similar" refers to nucleotide and amino acid sequences that represent functional and/or structural equivalents of *Arabidopsis* sequences disclosed herein.

In its broadest sense, the term "substantially similar" when used herein with respect to a nucleotide sequence means that the nucleotide sequence is part of a gene which encodes a polypeptide having substantially the same structure and function as a polypeptide encoded by a gene for the reference nucleotide sequence, e.g., the nucleotide sequence comprises a promoter from a gene that is the ortholog of the gene corresponding to the reference nucleotide sequence, as well as promoter sequences that are structurally related the promoter sequences particularly exemplified herein, i.e., the substantially similar promoter sequences hybridize to the complement of the promoter sequences exemplified herein under high or very high stringency conditions. For example, altered nucleotide sequences which simply reflect the degeneracy of the genetic code but nonetheless encode amino acid sequences that are identical to a particular amino acid sequence are substantially similar to the particular sequences. The term "substantially similar" also includes nucleotide sequences wherein the sequence has been modified, for example, to optimize expression in particular cells, as well as nucleotide sequences encoding a variant polypeptide having one or more amino acid substitutions relative to the (unmodified) polypeptide encoded by the reference sequence, which substitution(s) does not alter the activity of the variant polypeptide relative to the unmodified polypeptide.

In its broadest sense, the term "substantially similar" when used herein with respect to polypeptide means that the polypeptide has substantially the same structure and function as the reference polypeptide. In addition, amino acid sequences that are substantially similar to a particular sequence are those wherein overall amino acid identity is at least 65% or greater to the instant sequences. Modifications that result in equivalent nucleotide or amino acid sequences are well within the routine skill in the art. The percentage of amino acid sequence identity between the substantially similar and the reference polypeptide is at least 65%, 66%, 67%, 68%, 69%, 70%, e.g., 71%, 72%, 73%, 74%, 75%, 76%, 77%, 78%, 79%, 80%, 81%, 82%, 83%, 84%, 85%, 86%, 87%, 88%, 89%, and even 90% or more, e.g., 91%, 92%, 93%, 94%, 95%, 96%, 97%, 98%, up to at least 99%, wherein the reference polypeptide is an *Arabidopsis* polypeptide encoded by a gene with a promoter having any one of SEQ ID NO: 1, 2, 3, 4, 7, 8, 9, 10, 11, 14, 15, 16, 19, 20, 21, 24, 25, 26, 29, 30, 31, 34, 35, 36, 37, 40, 41, or 42, a nucleotide sequence comprising an open reading frame having any one of SEQ ID NOs: 5, 12, 17, 22, 27, 32, 38, or 43, which encodes one of SEQ ID Nos: 6, 13, 18, 23, 28, 33, 39, or 44. One indication that two polypeptides are substantially similar to each other, besides having substantially the same function, is that an agent, e.g., an antibody, which specifically binds to one of the polypeptides, specifically binds to the other.

Sequence comparisons maybe carried out using a Smith-Waterman sequence alignment algorithm (see e.g., Waterman, 1995). The localS program, version 1.16, is preferably used with following parameters: match: 1, mismatch penalty: 0.33, open-gap penalty: 2, extended-gap penalty: 2.

Moreover, a nucleotide sequence that is "substantially similar" to a reference nucleotide sequence is said to be "equivalent" to the reference nucleotide sequence. The skilled artisan recognizes that equivalent nucleotide sequences encompassed by this invention can also be defined by their ability to hybridize, under low, moderate and/or stringent conditions (e.g., 0.1×SSC, 0.1% SDS, 65° C.), with the nucleotide sequences that are within the literal scope of the instant claims.

What is meant by "substantially the same activity" when used in reference to a polynucleotide or polypeptide fragment is that the fragment has at least 65%, 66%, 67%, 68%, 69%, 70%, e.g., 71%, 72%, 73%, 74%, 75%, 76%, 77%, 78%, 79%, 80%, 81%, 82%, 83%, 84%, 85%, 86%, 87%, 88%, 89%, and even 90% or more, e.g., 91%, 92%, 93%, 94%, 95%, 96%, 97%, 98%, up to at least 99% of the activity of the full length polynucleotide or full length polypeptide.

"Target gene" refers to a gene on the replicon that expresses the desired target coding sequence, functional RNA, or protein. The target gene is not essential for replicon replication. Additionally, target genes may comprise native non-viral genes inserted into a non-native organism, or chimeric genes, and will be under the control of suitable regulatory sequences. Thus, the regulatory sequences in the target gene may come from any source, including the virus. Target genes may include coding sequences that are either heterologous or homologous to the genes of a particular plant to be transformed. However, target genes do not include native viral genes.

Typical target genes include, but are not limited to genes encoding a structural protein, a seed storage protein, a protein that conveys herbicide resistance, and a protein that conveys insect resistance. Proteins encoded by target genes are known as "foreign proteins". The expression of a target gene in a plant will typically produce an altered plant trait.

The term "altered plant trait" means any phenotypic or genotypic change in a transgenic plant relative to the wild-type or non-transgenic plant host.

"Replication gene" refers to a gene encoding a viral replication protein. In addition to the ORF of the replication protein, the replication gene may also contain other overlapping or non-overlapping ORF(s), as are found in viral sequences in nature. While not essential for replication, these additional ORFs may enhance replication and/or viral DNA accumulation. Examples of such additional ORFs are AC3 and AL3 in ACMV and TGMV geminiviruses, respectively.

"Chimeric trans-acting replication gene" refers either to a replication gene in which the coding sequence of a replication protein is under the control of a regulated plant promoter other than that in the native viral replication gene, or a modified native viral replication gene, for example, in which a site specific sequence(s) is inserted in the 5' transcribed but untranslated region. Such chimeric genes also include insertion of the known sites of replication protein binding between the promoter and the transcription start site that attenuate transcription of viral replication protein gene.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms". Examples of methods of transformation of plants and plant cells include *Agrobacterium*-mediated transformation (De Blaere 1987) and particle bombardment technology (U.S. Pat. No. 4,945,050). Whole plants may be regenerated from transgenic cells by methods well known to the skilled artisan (see, for example, Fromm 1990).

"Transformed," "transgenic," and "recombinant" refer to a host organism such as a bacterium or a plant into which a heterologous nucleic acid molecule has been introduced. The nucleic acid molecule can be stably integrated into the genome generally known in the art and are disclosed (Sambrook 1989; Innis 1995; Gelfand 1995; Innis & Gelfand 1999. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" plants or calli have been through the transformation process and contain a foreign gene integrated into their chromosome. The term "untransformed" refers to normal plants that have not been through the transformation process.

"Transiently transformed" refers to cells in which transgenes and foreign DNA have been introduced (for example, by such methods as *Agrobacterium*-mediated transformation or biolistic bombardment), but not selected for stable maintenance.

"Stably transformed" refers to cells that have been selected and regenerated on a selection media following transformation.

"Transient expression" refers to expression in cells in which a virus or a transgene is introduced by viral infection or by such methods as *Agrobacterium*-mediated transformation, electroporation, or biolistic bombardment, but not selected for its stable maintenance.

"Genetically stable" and "heritable" refer to chromosomally-integrated genetic elements that are stably maintained in the plant and stably inherited by progeny through successive generations.

"Primary transformant" and "T0 generation" refer to transgenic plants that are of the same genetic generation as the tissue which was initially transformed (i.e., not having gone through meiosis and fertilization since transformation).

"Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

"Wild-type" refers to a virus or organism found in nature without any known mutation.

"Genome" refers to the complete genetic material of an organism.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer 1991; Ohtsuka 1985; Rossolini 1994). A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that, by the hand of man, exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein of interest chemicals.

The nucleotide sequences of the invention include both the naturally occurring sequences as well as mutant (variant) forms. Such variants will continue to possess the desired activity, i.e., either promoter activity or the activity of the product encoded by the open reading frame of the non-variant nucleotide sequence.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide sequence identity to the native (wild type or endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

The nucleic acid molecules of the invention can be "optimized" for enhanced expression in plants of interest (see, for example, WO 91/16432; Perlak 1991; Murray 1989). In this manner, the open reading frames in genes or gene fragments can be synthesized utilizing plant-preferred codons (see, for example, Campbell & Gowri, 1990 for a discussion of host-preferred codon usage). Thus, the nucleotide sequences can be optimized for expression in any plant. It is recognized that all or any part of the gene sequence may be optimized or synthetic. That is, synthetic or partially optimized sequences may also be used. Variant nucleotide sequences and proteins also encompass, sequences and protein derived from a mutagenic and recombinogenic procedure such as DNA shuffling. With such a procedure, one or more different coding sequences can be manipulated to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo, Strategies for such DNA shuffling are known in the art (see, for example, Stemmer 1994; Stemmer 1994; Crameri 1997; Moore 1997; Zhang 1997; Crameri 1998; and U.S. Pat. Nos. 5,605,793 and 5,837,458).

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

Thus, the polypeptides may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art (see, for example, Kunkel 1985; Kunkel 1987; U.S. Pat. No. 4,873,192; Walker & Gaastra, 1983 and the references cited therein). Guidance as to appropriate amino acid substitutions that do not affect biological activity of the protein of interest may be found in the model of Dayhoff et al. (1978). Conservative substitutions, such as exchanging one amino acid with another having similar properties, are preferred.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also, Creighton, 1984. In addition, individual substitutions, deletions or additions which alter, add or delete a single amino acid or a small percentage of amino acids in an encoded sequence are also "conservatively modified variations."

"Expression cassette" as used herein means a DNA sequence capable of directing expression of a particular nucleotide sequence in an appropriate host cell, comprising a promoter operably linked to a nucleotide sequence of interest, which is—optionally—operably linked to termination signals and/or other regulatory elements. An expression cassette may also comprise sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one, which is naturally occurring but has been obtained in a recombinant form useful for heterologous expression. An expression cassette may be assembled entirely extracellularly (e.g., by recombinant cloning techniques). However, an expression cassette may also be assembled using in part endogenous components. For example, an expression cassette may be obtained by placing (or inserting) a promoter sequence upstream of an endogenous sequence, which thereby becomes functionally linked and controlled by said promoter sequences. Likewise, a nucleic acid sequence to be expressed may be placed (or inserted) downstream of an endogenous promoter sequence thereby forming an expression cassette. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development (e.g., the root-specific or root-preferential promoters of the invention).

"Vector" is defined to include inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication).

Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

A "transgenic plant" is a plant having one or more plant cells that contain an expression vector.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, 1988; the local homology algorithm of Smith et al. 1981; the homology alignment algorithm of Needleman and Wunsch 1970; the search-for-similarity-method of Pearson and Lipman 1988; the algorithm of Karlin and Altschul, 1990, modified as in Karlin and Altschul, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.), the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described (Higgins 1988, 1989; Corpet 1988; Huang 1992; Pearson 1994). The ALIGN program is based on the algorithm of Myers and Miller, supra. The BLAST programs of Altschul et al., 1990, are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. 1997. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) (i) The term "substantial identity" or "substantial similarity" of polynucleotide sequences (preferably for a protein encoding sequence) means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. The term "substantial identity" or "substantial similarity" of polynucleotide sequences (preferably for a promoter sequence) means (as described above for variants) that a polynucleotide comprises a sequence that has at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(ii) The term "substantial identity" in the context of a peptide indicates that a peptide comprises a sequence with at least 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridization are sequence dependent, and are different under different environmental parameters. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, 1984:

$$T_m=81.5° \text{ C.}+16.6(\log_{10}M)+0.41(\%\ GC)-0.61(\%\ \text{form})-500/L$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point I for the specific sequence and its complement at a defined ionic strength and pH. However, severely stringent conditions can utilize a hybridization and/or wash at 1, 2, 3, or 4° C. lower than the thermal melting point I; moderately stringent conditions can utilize a hybridization and/or wash at 6, 7, 8, 9, or 10° C. lower than the thermal melting point I; low stringency conditions can utilize a hybridization and/or wash at 11, 12, 13, 14, 15, or 20° C. lower than the thermal melting point I. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, 1993. Generally, highly stringent hybridization and wash conditions are selected to be about 5° C. lower than the thermal melting point $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4 to 6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long robes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The following are examples of sets of hybridization/wash conditions that may be used to clone orthologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

"DNA shuffling" is a method to introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA preferably encodes a variant polypeptide modified with respect to the polypeptide encoded by the template DNA, and may have an altered biological activity with respect to the polypeptide encoded by the template DNA.

"Recombinant DNA molecule' is a combination of DNA sequences that are joined together using recombinant DNA technology and procedures used to join together DNA sequences as described, for example, in Sambrook et al., 1989.

The word "plant" refers to any plant, particularly to agronomically useful plants (e.g., seed plants), and "plant cell" is a structural and physiological unit of the plant, which comprises a cell wall but may also refer to a protoplast. The plant cell may be in form of an isolated single cell or a cultured cell, or as a part of higher organized unit such as, for example, a plant tissue, or a plant organ differentiated into a structure that is present at any stage of a plant's development. Such structures include one or more plant organs including, but are not limited to, fruit, shoot, stem, leaf, flower petal, etc. Preferably, the term "plant" includes whole plants, shoot vegetative organs/structures (e.g. leaves, stems and tubers), roots, flowers and floral organs/structures (e.g. bracts, sepals, petals, stamens, carpels, anthers and ovules), seeds (including embryo, endosperm, and seed coat) and fruits (the mature ovary), plant tissues (e.g. vascular tissue, ground tissue, and the like) and cells (e.g. guard cells, egg cells, trichomes and the like), and progeny of same.

The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous. Included within the scope of the invention are all genera and species of higher and lower plants of the plant kingdom. Included are furthermore the mature plants, seed, shoots and seedlings, and parts, propagation material (for example seeds and fruit) and cultures, for example cell cultures, derived therefrom. Preferred are plants and plant materials of the following plant families: Amaranthaceae, Brassicaceae, Carophyllaceae, Chenopodiaceae, Compositae, Cucurbitaceae, Labiatae, Leguminosae, Papilionoideae, Liliaceae, Linaceae, Malvaceae, Rosaceae, Saxifragaceae, Scrophulariaceae, Solanaceae, Tetragoniaceae.

Annual, perennial, monocotyledonous and dicotyledonous plants are preferred host organisms for the generation of transgenic plants. The use of the recombination system, or method according to the invention is furthermore advantageous in all ornamental plants, forestry, fruit, or ornamental trees, flowers, cut flowers, shrubs or turf. Said plant may include—but shall not be limited to—bryophytes such as, for example, Hepaticae (hepaticas) and Musci (mosses); pteridophytes such as ferns, horsetail and clubmosses; gymnosperms such as conifers, cycads, ginkgo and Gnetaeae; algae such as Chlorophyceae, Phaeophpyceae, Rhodophyceae, Myxophyceae, Xanthophyceae, Bacillariophyceae (diatoms) and Euglenophyceae.

Plants for the purposes of the invention may comprise the families of the Rosaceae such as rose, Ericaceae such as rhododendrons and azaleas, Euphorbiaceae such as poinsettias and croton, Caryophyllaceae such as pinks, Solanaceae such as petunias, Gesneriaceae such as African violet, Balsaminaceae such as touch-me-not, Orchidaceae such as orchids, Iridaceae such as gladioli, iris, freesia and crocus, Compositae such as marigold, Geraniaceae such as geraniums, Liliaceae such as Drachaena, Moraceae such as ficus, Araceae such as philodendron and many others.

The transgenic plants according to the invention are furthermore selected in particular from among dicotyledonous crop plants such as, for example, from the families of the Leguminosae such as pea, alfalfa and soybean; the family of the Umbelliferae, particularly the genus *Daucus* (very particularly the species *carota* (carrot)) and *Apium* (very particularly the species *graveolens* var. *dulce* (celery)) and many others; the family of the Solanaceae, particularly the genus *Lycopersicon*, very particularly the species *esculentum* (tomato) and the genus *Solanum*, very particularly the species *tuberosum* (potato) and *melongena* (aubergine), tobacco and many others; and the genus *Capsicum*, very particularly the species *annum* (pepper) and many others; the family of the Leguminosae, particularly the genus *Glycine*, very particularly the species *max* (soybean) and many others; and the family of the Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli); and the genus *Arabidopsis*, very particularly the species *thaliana* and many others; the family of the Compositae, particularly the genus *Lactuca*, very particularly the species *sativa* (lettuce) and many others.

The transgenic plants according to the invention may be selected among monocotyledonous crop plants, such as, for example, cereals such as wheat, barley, sorghum and millet, rye, triticale, maize, rice or oats, and sugarcane. Further preferred are trees such as apple, pear, quince, plum, cherry, peach, nectarine, apricot, papaya, mango, and other woody species including coniferous and deciduous trees such as poplar, pine, *sequoia*, cedar, oak, etc. Especially preferred are *Arabidopsis thaliana, Nicotiana tabacum*, oilseed rape, soybean, corn (maize), wheat, linseed, potato and tagetes.

"Significant increase" is an increase that is larger than the margin of error inherent in the measurement technique, preferably an increase by about 2-fold or greater.

"Significantly less" means that the decrease is larger than the margin of error inherent in the measurement technique, preferably a decrease by about 2-fold or greater.

DETAILED DESCRIPTION OF THE INVENTION

The present invention thus provides for isolated nucleic acid molecules comprising a plant nucleotide sequence that directs root-preferential or root-specific transcription of an operably linked nucleic acid fragment in a plant cell.

Specifically, the present invention provides transgenic expression cassettes for regulating root-preferential or root-specific expression in plants comprising i) at least one transcription regulating nucleotide sequence of a plant gene, said plant gene selected from the group of genes described by the GenBank *Arabidopsis thaliana* genome locii At1g66280, At1g74500, At1g49570, At1g70710, At5g66690, At3g29630, At5g48070, or At4g17800, or a functional equivalent thereof, and functionally linked thereto ii) at least one nucleic acid sequence which is heterologous in relation to said transcription regulating nucleotide sequence.

The root-preferential or root-specific promoters may be useful for alteration of the function of root tissue, modification of growth rate, improvement of resistance to root preferred pathogens, pests, herbicides or adverse weather conditions, for detoxification of soil as well as for broadening the range of soils or environments in which said plant may grow. Root abundant or root specific gene expression would provide a mechanism according to which morphology and metabolism may be altered to improve the yield and to produce useful proteins in greater amounts.

The term "root" in the context of the inventions means the usually underground organ of a plant that lacks buds or leaves or nodes, absorbs water and mineral salts and usually it anchors the plant to the ground. The plant root consists of many cell types such as epidermal, root cap, columella, cortex, pericycle, vascular and root hair forming trichoblasts, organized into tissues or regions of the root, for example, the root tip, root epidermis, meristematic zone, primary root, laternal root, root hair, and vascular tissue. Transcription regulatin sequences isolated as root-specific or root-preferred may regulated expression in one or a few of these cell types. This cell-specific activity can be useful for specific applications such as regulating meristematic activity in only meristematic cell zone or expression of a nematicidal gene in only the cell type that are contacted by the nematode pest.

"Root-specific transcription" in the context of this invention means the transcription of a nucleic acid sequence by a transcription regulating element in a way that transcription of said nucleic acid sequence in roots contribute to more than 90%, preferably more than 95%, more preferably more than 99% of the entire quantity of the RNA transcribed from said nucleic acid sequence in the entire plant during any of its developmental stage. For example, the transcription regulating sequenses designated with the following abreviations (and specified inmoe details in the examples) are considered to provide a root-specific expression profile: pSUH320, pSUH320S, pSUH320L, pSUH320GB, pSUH335S, pSUH335L, pSUH335GB, pSUH338, pSUH338GB, pSUH307, pSUH307S pSUH307GB, pSUH349, pSUH349S and pSUH349 GB "Root-preferential transcription" in the context of this invention means the transcription of a nucleic acid sequence by a transcription regulating element in a way that transcription of said nucleic acid sequence in roots contribute to more than 50%, preferably more than 70%, more preferably more than 80% of the entire quantity of the RNA transcribed from said nucleic acid sequence in the entire plant during any of its developmental stage. For example, the transcription regulating sequenses designated with the following abreviations (and specified inmoe details in the examples) are considered to provide a root-preferential expression profile: pSUH319, pSUH319S, pSUH319GB pSUH378, pSUH378GB, pSUH382, pSUH382GB, pSUH372, pSUH372S and pSUH372GB, pSUH379

Preferably a transcription regulating nucleotide sequence of the invention comprises at least one promoter sequence of the respective gene (e.g., a sequence localized upstream of the transcription start of the respective gene capable to induce transcription of the downstream sequences). The transcription regulating nucleotide sequence may comprise the promoter sequence of said genes but may further comprise other elements such as the 5'-untranslated sequence, enhancer, introns etc. Preferably, said promoter sequence directs root-preferential or root-specific transcription of an operably linked nucleic acid segment in a plant or plant cell e.g., a linked plant DNA comprising an open reading frame for a structural or regulatory gene. The following Table 1 illustrates the genes from which the promoters of the invention are preferably isolated, the function of said genes, the cDNA encoded by said genes, and the protein (ORF) encoded by said genes.

TABLE 1

Genes form which the promoters of the invention are preferably isolated, putative function of said genes, cDNA and the protein encoded by said genes.

| Gene Locus | Putative function | Promotor SEQ ID | mRNA locus ID cDNA SEQ ID | Proteine ID Protein SEQ ID |
|---|---|---|---|---|
| At1g66280 | glycosyl hydrolase family 1 | SEQ ID NO: 1, 2, 3, 4 | NM_105299 SEQ ID NO: 5 | NP_176802 SEQ ID NO: 6 |
| At1g74500 | bHLH family protein | SEQ ID NO: 7, 8, 9, 10, 11 | NM_106110 SEQ ID NO: 12 | NP_177590 SEQ ID NO: 13 |
| At1g49570 | peroxidase ATP5a | SEQ ID NO: 14, 15, 16 | NM_103845 SEQ ID NO: 17 | NP_175380 SEQ ID NO: 18 |
| At1g70710 | endo-1,4-beta-glucanase | SEQ ID NO: 19, 20, 21, | NM_105739 SEQ ID NO: 22 | NP_177228 SEQ ID NO: 23 |
| At5g66690 | UTP-glucose glucosyltransferase | SEQ ID NO: 24, 25, 26, | NM_126067 SEQ ID NO: 27 | NP_201470 SEQ ID NO: 28 |
| At3g29630 | UDP-glucose:flavonoid glucosyltransferase | SEQ ID NO: 29, 30, 31 | NM_113884 SEQ ID NO: 32 | NP_189604 SEQ ID NO: 33 |
| At5g48070 | Xyloglucan endo-1,4-beta-D-glucanase | SEQ ID NO: 34, 35, 36, 37 | NM_124181 SEQ ID NO: 38 | NP_199618 SEQ ID NO: 39 |
| At4g17800 | DNA-binding protein-related | SEQ ID NO: 40, 41, 42 | NM_117890 SEQ ID NO: 43 | NP_193515 SEQ ID NO: 44 |

Preferably the transcription regulating nucleotide sequence (or the functional equivalent thereof) is selected from the group of sequences consisting of i) the sequences described by SEQ ID NOs: 1, 2, 3, 4, 7, 8, 9, 10, 11, 14, 15, 16, 19, 20, 21, 24, 25, 26, 29, 30, 31, 34, 35, 36, 37, 40, 41, and 42, ii) a fragment of at least 50 consecutive bases of a sequence under i) which has substantially the same promoter activity as the corresponding transcription regulating nucleotide sequence described by SEQ ID NO: 1, 2, 3, 4, 7, 8, 9, 10, 11, 14, 15, 16, 19, 20, 21, 24, 25, 26, 29, 30, 31, 34, 35, 36, 37, 40, 41, or 42;

iii) a nucleotide sequence having substantial similarity (e.g., with a sequence identity of at least 40, 50, 60, to 70%, e.g., preferably 71%, 72%, 73%, 74%, 75%, 76%, 77%, 78%, to 79%, generally at least 80%, e.g., 81% to 84%, at least 85%, e.g., 86%, 87%, 88%, 89%, 90%, 91%, 92%, 93%, 94%, 95%, 96%, 97%, to 98% and 99%) to a transcription regulating nucleotide sequence described by SEQ ID NO: 1, 2, 3, 4, 7, 8, 9, 10, 11, 14, 15, 16, 19, 20, 21, 24, 25, 26, 29, 30, 31, 34, 35, 36, 37, 40, 41, or 42;

iv) a nucleotide sequence capable of hybridizing (preferably under conditions equivalent to hybridization in 7% sodium dodecyl sulfate (SDS), 0.5 M $NaPO_4$, 1 mM EDTA at 50° C. with washing in 2×SSC, 0.1% SDS at 50° C. (more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.) to a transcription regulating nucleotide sequence described by SEQ ID NO: 1, 2, 3, 4, 7, 8, 9, 10, 11, 14, 15, 16, 19, 20, 21, 24, 25, 26, 29, 30, 31, 34, 35, 36, 37, 40, 41, or 42, or the complement thereof;

v) a nucleotide sequence capable of hybridizing (preferably under conditions equivalent to hybridization in 7% sodium dodecyl sulfate (SDS), 0.5 M $NaPO_4$, 1 mM EDTA at 50° C. with washing in 2×SSC, 0.1% SDS at 50° C. (more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.) to a nucleic acid comprising 50 to 200 or more consecutive nucleotides of a transcription regulating nucleotide sequence described by SEQ ID NO: 1, 2, 3, 4, 7, 8, 9, 10, 11, 14, 15, 16, 19, 20, 21, 24, 25, 26, 29, 30, 31, 34, 35, 36, 37, 40, 41, or 42, or the complement thereof;

vi) a nucleotide sequence which is the complement or reverse complement of any of the previously mentioned nucleotide sequences under i) to v).

A functional equivalent of the transcription regulating nucleotide sequence can also be obtained or is obtainable from plant genomic DNA from a gene encoding a polypeptide which is substantially similar and preferably has at least 70%, preferably 80%, more preferably 90%, most preferably 95% amino acid sequence identity to a polypeptide encoded by an *Arabidopsis thaliana* gene comprising any one of SEQ ID NOs: 6, 13, 18, 23, 28, 33, 39, or 44, respectively, or a fragment of said transcription regulating nucleotide sequence which exhibits promoter activity in a root-preferential or root-specific fashion.

The activity of a transcription regulating nucleotide sequence is considered equivalent if transcription is initiated in a root-preferential or root-specific fashion (as defined above). Such expression profile is preferably demonstrated using reporter genes operably linked to said transcription regulating sequence. Preferred reporter genes (Schenborn 1999) in this context are green fluorescence protein (GFP) (Chui 1996; Leffel 1997), chloramphenicol transferase, luciferase (Millar 1992), β-glucuronidase or β-galactosidase. Especially preferred is β-glucuronidase (Jefferson 1987).

Beside this the transcription regulating activity of a function equivalent may vary from the activity of its parent sequence, especially with respect to expression level. The expression level may be higher or lower than the expression level of the parent sequence. Both derivations may be advantageous depending on the nucleic acid sequence of interest to be expressed. Preferred are such functional equivalent sequences which—in comparison with its parent sequence—does not derivate from the expression level of said parent sequence by more than 50%, preferably 25%, more preferably 10% (as to be preferably judged by either mRNA expression or protein (e.g., reporter gene) expression). Furthermore preferred are equivalent sequences which demonstrate an increased expression in comparison to its parent sequence, preferably an increase my at least 50%, more preferably by at least 100%, most preferably by at least 500%.

Preferably functional equivalent of the transcription regulating nucleotide sequence can be obtained or is obtainable from plant genomic DNA from a gene expressing a mRNA described by a cDNA which is substantially similar and preferably has at least 70%, preferably 80%, more preferably 90%, most preferably 95% sequence identity to a sequence described by any one of SEQ ID NOs: 5, 12, 17, 22, 27, 32, 38, or 43, respectively, or a fragment of said transcription regulating nucleotide sequence which exhibits promoter activity in a root-preferential or root-specific fashion.

Such functional equivalent of the transcription regulating nucleotide sequence may be obtained from other plant species by using the root-preferential or root-specific *Arabidopsis* promoter sequences described herein as probes to screen for homologous structural genes in other plants by hybridization under low, moderate or stringent hybridization conditions. Regions of the root-preferential or root-specific promoter sequences of the present invention which are conserved among species could also be used as PCR primers to amplify a segment from a species other than *Arabidopsis*, and that segment used as a hybridization probe (the latter approach permitting higher stringency screening) or in a transcription assay to determine promoter activity. Moreover, the root-preferential or root-specific promoter sequences could be employed to identify structurally related sequences in a database using computer algorithms.

More specifically, based on the *Arabidopsis* nucleic acid sequences of the present invention, orthologs may be identified or isolated from the genome of any desired organism, preferably from another plant, according to well known techniques based on their sequence similarity to the *Arabidopsis* nucleic acid sequences, e.g., hybridization, PCR or computer generated sequence comparisons. For example, all or a portion of a particular *Arabidopsis* nucleic acid sequence is used as a probe that selectively hybridizes to other gene sequences present in a population of cloned genomic DNA fragments or cDNA fragments (i.e., genomic or cDNA libraries) from a chosen source organism. Further, suitable genomic and cDNA libraries may be prepared from any cell or tissue of an organism. Such techniques include hybridization screening of plated DNA libraries (either plaques or colonies; see, e.g., Sambrook 1989) and amplification by PCR using oligonucleotide primers preferably corresponding to sequence domains conserved among related polypeptide or subsequences of the nucleotide sequences provided herein (see, e.g., Innis 1990). These methods are particularly well suited to the isolation of gene sequences from organisms closely related to the organism from which the probe sequence is derived. The application of these methods using the *Arabidopsis* sequences as probes is well suited for the isolation of gene sequences from any source organism, preferably other plant species. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the sequence of the invention. Methods for preparation of probes for hybridization and for construction of cDNA and genomic libraries are generally known in the art and are disclosed in Sambrook et al. (1989). In general, sequences that hybridize to the sequences disclosed herein will have at least 40% to 50%, about 60% to 70% and even about 80% 85%, 90%, 95% to 98% or more identity with the disclosed sequences.

That is, the sequence similarity of sequences may range, sharing at least about 40% to 50%, about 60% to 70%, and even about 80%, 85%, 90%, 95% to 98% sequence similarity.

The nucleic acid molecules of the invention can also be identified by, for example, a search of known databases for genes encoding polypeptides having a specified amino acid sequence identity or DNA having a specified nucleotide sequence identity. Methods of alignment of sequences for comparison are well known in the art and are described hereinabove.

Hence, the isolated nucleic acid molecules of the invention include the orthologs of the *Arabidopsis* sequences disclosed herein, i.e., the corresponding nucleotide sequences in organisms other than *Arabidopsis*, including, but not limited to, plants other than *Arabidopsis*, preferably dicotyledonous plants, e.g., *Brassica napus*, alfalfa, sunflower, soybean, cotton, peanut, tobacco or sugar beet, but also cereal plants such as corn, wheat, rye, turfgrass, sorghum, millet, sugarcane, barley and banana. An orthologous gene is a gene from a different species that encodes a product having the same or similar function, e.g., catalyzing the same reaction as a product encoded by a gene from a reference organism. Thus, an ortholog includes polypeptides having less than, e.g., 65% amino acid sequence identity, but which ortholog encodes a polypeptide having the same or similar function. Databases such GenBank may be employed to identify sequences related to the *Arabidopsis* sequences, e.g., orthologs in other dicotyledonous plants such as *Brassica napus* and others. Alternatively, recombinant DNA techniques such as hybridization or PCR may be employed to identify sequences related to the *Arabidopsis* sequences or to clone the equivalent sequences from different *Arabidopsis* DNAs.

The transcription regulating nucleotide sequences of the invention or their functional equivalents can be obtained or isolated from any plant or non-plant source, or produced synthetically by purely chemical means. Preferred sources include, but are not limited to the plants defined in the DEFINITION section above.

Thus, another embodiment of the invention relates to a method for identifying and/or isolating a sequence with root-preferential or root-specific transcription regulating activity utilizing a nucleic acid sequence encoding a amino acid sequence as described by SEQ ID NO: 6, 13, 18, 23, 28, 33, 39, or 44 or a part thereof. Preferred are nucleic acid sequences described by SEQ ID NO: 5, 12, 17, 22, 27, 32, 38, or 43 or parts thereof. "Part" in this context means a nucleic acid sequence of at least 15 bases preferably at least 25 bases, more preferably at least 50 bases. The method can be based on (but is not limited to) the methods described above such as polymerase chain reaction, hybridization or database screening. Preferably, this method of the invention is based on a polymerase chain reaction, wherein said nucleic acid sequence or its part is utilized as oligonucleotide primer. The person skilled in the art is aware of several methods to amplify and isolate the promoter of a gene starting from part of its coding sequence (such as, for example, part of a cDNA). Such methods may include but are not limited to method such as inverse PCR ("iPCR") or "thermal asymmetric interlaced PCR" ("TAIL PCR").

Another embodiment of the invention is related to a method for providing a transgenic expression cassette for root-preferential or root-specific expression comprising the steps of:

I. isolating of a root-preferential or root-specific transcription regulating nucleotide sequence utilizing at least one nucleic acid sequence or a part thereof, wherein said sequence is encoding a polypeptide described by SEQ ID NO: 6, 13, 18, 23, 28, 33, 39, or 44, or a part of at least 15 bases thereof, and II. functionally linking said root-preferential or root-specific transcription regulating nucleotide sequence to another nucleotide sequence of interest, which is heterologous in relation to said root-preferential or root-specific transcription regulating nucleotide sequence.

Preferably, the nucleic acid sequence employed for the isolation comprises at least 15 base, preferably at least 25 bases, more preferably at least 50 bases of a sequence described by SEQ ID NO: 5, 12, 17, 22, 27, 32, 38, or 43. Preferably, the isolation of the root-preferential or root-specific transcription regulating nucleotide sequence is realized by a polymerase chain reaction utilizing said nucleic acid sequence as a primer. The operable linkage can be realized by standard cloning method known in the art such as ligation-mediated cloning or recombination-mediated cloning.

Preferably, the transcription regulating nucleotide sequences and promoters of the invention include a consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, of any one of SEQ ID NO: 1, 2, 3, 4, 7, 8, 9, 10, 11, 14, 15, 16, 19, 20, 21, 24, 25, 26, 29, 30, 31, 34, 35, 36, 37, 40, 41, and 42, or the promoter orthologs thereof which include the minimal promoter region.

In a particular embodiment of the invention said consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, has at least 75%, preferably 80%, more preferably 90% and most preferably 95%, nucleic acid sequence identity with a corresponding consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, of any one of SEQ ID NOs: 1, 2, 3, 4, 7, 8, 9, 10, 11, 14, 15, 16, 19, 20, 21, 24, 25, 26, 29, 30, 31, 34, 35, 36, 37, 40, 41, and 42, or the promoter orthologs thereof, which include the minimal promoter region. The above defined stretch of contiguous nucleotides preferably comprises one or more promoter motifs selected from the group consisting of TATA box, GC-box, CMT-box and a transcription start site.

The transcription regulating nucleotide sequences of the invention or their functional equivalents are capable of driving root-preferential or root-specific expression of a coding sequence in a target cell, particularly in a plant cell. The promoter sequences and methods disclosed herein are useful in regulating root-preferential or root-specific expression, respectively, of any heterologous nucleotide sequence in a host plant in order to vary the phenotype of that plant. These promoters can be used with combinations of enhancer, upstream elements, and/or activating sequences from the 5' flanking regions of plant expressible structural genes. Similarly the upstream element can be used in combination with various plant promoter sequences.

The transcription regulating nucleotide sequences and promoters of the invention are useful to modify the phenotype of a plant. Various changes in the phenotype of a transgenic plant are desirable, i.e., modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in an alteration in the phenotype of the transformed plant.

Generally, the transcription regulating nucleotide sequences and promoters of the invention may be employed to express a nucleic acid segment that is operably linked to said promoter such as, for example, an open reading frame, or a portion thereof, an anti-sense sequence, a sequence encoding for a double-stranded RNA sequence, or a transgene in plants.

An operable linkage may—for example—comprise an sequential arrangement of the transcription regulating nucleotide sequence of the invention (for example a sequence as described by SEQ ID NO: 1, 2, 3, 4, 7, 8, 9, 10, 11, 14, 15, 16, 19, 20, 21, 24, 25, 26, 29, 30, 31, 34, 35, 36, 37, 40, 41, or 42) with a nucleic acid sequence to be expressed, and—optionally—additional regulatory elements such as for example polyadenylation or transcription termination elements, enhancers, introns etc, in a way that the transcription regulating nucleotide sequence can fulfill its function in the process of expression the nucleic acid sequence of interest under the appropriate conditions. the term “appropriate conditions” mean preferably the presence of the expression cassette in a plant cell. Preferred are arrangements, in which the nucleic acid sequence of interest to be expressed is placed down-stream (i.e., in 3'-direction) of the transcription regulating nucleotide sequence of the invention in a way, that both sequences are covalently linked. Optionally additional sequences may be inserted in-between the two sequences. Such sequences may be for example linker or multiple cloning sites. Furthermore, sequences can be inserted coding for parts of fusion proteins (in case a fusion protein of the protein encoded by the nucleic acid of interest is intended to be expressed). Preferably, the distance between the nucleic acid sequence of interest to be expressed and the transcription regulating nucleotide sequence of the invention is not more than 200 base pairs, preferably not more than 100 base pairs, more preferably no more than 50 base pairs.

An operable linkage in relation to any expression cassette or of the invention may be realized by various methods known in the art, comprising both in vitro and in vivo procedure. Thus, an expression cassette of the invention or an vector comprising such expression cassette may by realized using standard recombination and cloning techniques well known in the art (see e.g., Maniatis 1989; Silhavy 1984; Ausubel 1987).

An expression cassette may also be assembled by inserting a transcription regulating nucleotide sequence of the invention (for example a sequence as described by SEQ ID NO: 1, 2, 3, 4, 7, 8, 9, 10, 11, 14, 15, 16, 19, 20, 21, 24, 25, 26, 29, 30, 31, 34, 35, 36, 37, 40, 41, or 42) into the plant genome. Such insertion will result in an operable linkage to a nucleic acid sequence of interest which as such already existed in the genome. By the insertion the nucleic acid of interest is expressed in a root-preferential or root-specific way due to the transcription regulating properties of the transcription regulating sequence. The insertion may be directed or by chance. Preferably the insertion is directed and realized by for example homologous recombination. By this procedure a natural promoter may be exchanged against the transcription regulating nucleotide sequence of the invention, thereby modifying the expression profile of an endogenous gene. The transcription regulating nucleotide sequence may also be inserted in a way, that antisense mRNA of an endogenous gene is expressed, thereby inducing gene silencing.

Similar, a nucleic acid sequence of interest to be expressed may by inserted into a plant genome comprising the transcription regulating nucleotide sequence in its natural genomic environment (i.e. linked to its natural gene) in a way that the inserted sequence becomes operably linked to the transcription regulating sequence, thereby forming an expression cassette of the invention.

The open reading frame to be linked to the transcription regulating nucleotide sequence of the invention may be obtained from an insect resistance gene, a disease resistance gene such as, for example, a bacterial disease resistance gene, a fungal disease resistance gene, a viral disease resistance gene, a nematode disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker, a positive selectable marker, a gene affecting plant agronomic characteristics, i.e., yield, standability, and the like, or an environment or stress resistance gene, i.e., one or more genes that confer herbicide resistance or tolerance, insect resistance or tolerance, disease resistance or tolerance (viral, bacterial, fungal, oomycete, or nematode), stress tolerance or resistance (as exemplified by resistance or tolerance to drought, heat, chilling, freezing, excessive moisture, salt stress, or oxidative stress), increased yields, food content and makeup, physical appearance, male sterility, dry down, standability, prolificacy, starch properties or quantity, oil quantity and quality, amino acid or protein composition, and the like. By “resistant” is meant a plant which exhibits substantially no phenotypic changes as a consequence of agent administration, infection with a pathogen, or exposure to stress. By “tolerant” is meant a plant which, although it may exhibit some phenotypic changes as a consequence of infection, does not have a substantially decreased reproductive capacity or substantially altered metabolism.

Root-preferential or root-specific transcription regulating nucleotide sequences (e.g., promoters) are useful for expressing a wide variety of genes including those which alter metabolic pathways, confer disease resistance, for protein production, e.g., antibody production, or to improve nutrient uptake and the like. Root-preferential or root-specific transcription regulating nucleotide sequences (e.g., promoters) may be modified so as to be regulatable, e.g., inducible. The genes and s (e.g., promoters) described hereinabove can be used to identify orthologous genes and their transcription regulating nucleotide sequences (e.g., promoters) which are also likely expressed in a particular tissue and/or development manner. Moreover, the orthologous transcription regulating nucleotide sequences (e.g., promoters) are useful to express linked open reading frames. In addition, by aligning the transcription regulating nucleotide sequences (e.g., promoters) of these orthologs, novel cis elements can be identified that are useful to generate synthetic transcription regulating nucleotide sequences (e.g., promoters).

The expression regulating nucleotide sequences specified above may be optionally operably linked to other suitable regulatory sequences, e.g., a transcription terminator sequence, operator, repressor binding site, transcription factor binding site and/or an enhancer.

The present invention further provides a recombinant vector containing the expression cassette of the invention, and host cells comprising the expression cassette or vector, e.g., comprising a plasmid. The expression cassette or vector may augment the genome of a transformed plant or may be maintained extra chromosomally. The expression cassette or vector of the invention may be present in the nucleus, chloroplast, mitochondria and/or plastid of the cells of the plant. Preferably, the expression cassette or vector of the invention is comprised in the chromosomal DNA of the plant nucleus. The present invention also provides a transgenic plant prepared by this method, a seed from such a plant and progeny plants from such a plant including hybrids and inbreds. The expression cassette may be operatively linked to a structural gene, the open reading frame thereof, or a portion thereof. The expression cassette may further comprise a Ti plasmid and be contained in an *Agrobacterium tumefaciens* cell; it may be carried on a microparticle, wherein the microparticle is suitable for ballistic transformation of a plant cell; or it may be contained in a plant cell or protoplast. Further, the expression cassette or vector can be contained in a transformed plant or cells thereof, and the plant may be a dicot or a monocot. In particular, the plant may be a dicotyledonous plant. Preferred transgenic plants are transgenic maize, soybean, barley, alfalfa, sunflower, canola, soybean, cotton, peanut, sorghum, tobacco, sugarbeet, rice, wheat, rye, turfgrass, millet, sugarcane, tomato, or potato.

The invention also provides a method of plant breeding, e.g., to prepare a crossed fertile transgenic plant. The method comprises crossing a fertile transgenic plant comprising a particular expression cassette of the invention with itself or with a second plant, e.g., one lacking the particular expression cassette, to prepare the seed of a crossed fertile transgenic plant comprising the particular expression cassette. The seed is then planted to obtain a crossed fertile transgenic plant. The plant may be a monocot or a dicot. In a particular embodiment, the plant is a dicotyledonous plant. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants.

The transcription regulating sequences of the invention further comprise sequences which are complementary to one (hereinafter "test" sequence) which hybridizes under stringent conditions with a nucleic acid molecule as described by SEQ ID NO: 1, 2, 3, 4, 7, 8, 9, 10, 11, 14, 15, 16, 19, 20, 21, 24, 25, 26, 29, 30, 31, 34, 35, 36, 37, 40, 41, or 42, as well as RNA which is transcribed from the nucleic acid molecule. When the hybridization is performed under stringent conditions, either the test or nucleic acid molecule of invention is preferably supported, e.g., on a membrane or DNA chip. Thus, either a denatured test or nucleic acid molecule of the invention is preferably first bound to a support and hybridization is effected for a specified period of time at a temperature of, e.g., between 55 and 70° C., in double strength citrate buffered saline (SC) containing 0.1% SDS followed by rinsing of the support at the same temperature but with a buffer having a reduced SC concentration. Depending upon the degree of stringency required such reduced concentration buffers are typically single strength SC containing 0.1% SDS, half strength SC containing 0.1% SDS and one-tenth strength SC containing 0.1% SDS. More preferably hybridization is carried out under high stringency conditions (as defined above).

Virtually any DNA composition may be used for delivery to recipient plant cells, e.g., dicotyledonous cells, to ultimately produce fertile transgenic plants in accordance with the present invention. For example, DNA segments or fragments in the form of vectors and plasmids, or linear DNA segments or fragments, in some instances containing only the DNA element to be expressed in the plant, and the like, may be employed. The construction of vectors which may be employed in conjunction with the present invention will be known to those of skill of the art in light of the present disclosure (see, e.g., Sambrook 1989; Gelvin 1990).

Vectors, plasmids, cosmids, YACs (yeast artificial chromosomes), BACs (bacterial artificial chromosomes) and DNA segments for use in transforming such cells will, of course, generally comprise the cDNA, gene or genes which one desires to introduce into the cells. These DNA constructs can further include structures such as promoters, enhancers, polylinkers, or even regulatory genes as desired. The DNA segment, fragment or gene chosen for cellular introduction will often encode a protein which will be expressed in the resultant recombinant cells, such as will result in a screenable or selectable trait and/or which will impart an improved phenotype to the regenerated plant. However, this may not always be the case, and the present invention also encompasses transgenic plants incorporating non-expressed transgenes.

In certain embodiments, it is contemplated that one may wish to employ replication-competent viral vectors in monocot transformation. Such vectors include, for example, wheat dwarf virus (WDV) "shuttle" vectors, such as pW1-11 and PW1-GUS (Ugaki 1991). These vectors are capable of autonomous replication in maize cells as well as *E. coli*, and as such may provide increased sensitivity for detecting DNA delivered to transgenic cells. A replicating vector may also be useful for delivery of genes flanked by DNA sequences from transposable elements such as Ac, Ds, or Mu. It has been proposed (Laufs 1990) that transposition of these elements within the maize genome requires DNA replication. It is also contemplated that transposable elements would be useful for introducing DNA segments or fragments lacking elements necessary for selection and maintenance of the plasmid vector in bacteria, e.g., antibiotic resistance genes and origins of DNA replication. It is also proposed that use of a transposable element such as Ac, Ds, or Mu would actively promote integration of the desired DNA and hence increase the frequency of stably transformed cells. The use of a transposable element such as Ac, Ds, or Mu may actively promote integration of the DNA of interest and hence increase the frequency of stably transformed cells. Transposable elements may be useful to allow separation of genes of interest from elements necessary for selection and maintenance of a plasmid vector in bacteria or selection of a transformant. By use of a transposable element, desirable and undesirable DNA sequences may be transposed apart from each other in the genome, such that through genetic segregation in progeny, one may identify plants with either the desirable undesirable DNA sequences.

The nucleotide sequence of interest linked to one or more of the transcription regulating sequences of the invention can, for example, code for a ribosomal RNA, an antisense RNA or any other type of RNA that is not translated into protein. In another preferred embodiment of the invention, said nucleotide sequence of interest is translated into a protein product. The transcription regulating nucleotide sequence and/or nucleotide sequence of interest linked thereto may be of homologous or heterologous origin with respect to the plant to be transformed. A recombinant DNA molecule useful for introduction into plant cells includes that which has been derived or isolated from any source, that may be subsequently characterized as to structure, size and/or function, chemically altered, and later introduced into plants. An example of a nucleotide sequence or segment of interest "derived" from a source, would be a nucleotide sequence or segment that is identified as a useful fragment within a given organism, and which is then chemically synthesized in essentially pure form. An example of such a nucleotide sequence or segment of interest "isolated" from a source, would be nucleotide sequence or segment that is excised or removed from said source by chemical means, e.g., by the use of restriction endonucleases, so that it can be further manipulated, e.g., amplified, for use in the invention, by the methodology of genetic engineering. Such a nucleotide sequence or segment is commonly referred to as "recombinant."

Therefore a useful nucleotide sequence, segment or fragment of interest includes completely synthetic DNA, semi-synthetic DNA, DNA isolated from biological sources, and DNA derived from introduced RNA. Generally, the introduced DNA is not originally resident in the plant geno-type which is the recipient of the DNA, but it is within the scope of the invention to isolate a gene from a given plant genotype, and to subsequently introduce multiple copies of the gene into the same genotype, e.g., to enhance production of a given gene product such as a storage protein or a protein that confers tolerance or resistance to water deficit.

The introduced recombinant DNA molecule includes but is not limited to, DNA from plant genes, and non-plant genes such as those from bacteria, yeasts, animals or viruses. The introduced DNA can include modified genes, portions of genes, or chimeric genes, including genes from the same or different genotype. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of untransformed plant.

The introduced recombinant DNA molecule used for transformation herein may be circular or linear, double-stranded or single-stranded. Generally, the DNA is in the form of chimeric DNA, such as plasmid DNA, that can also contain coding regions flanked by regulatory sequences which promote the expression of the recombinant DNA present in the resultant plant. Generally, the introduced recombinant DNA molecule will be relatively small, i.e., less than about 30 kb to minimize any susceptibility to physical, chemical, or enzymatic degradation which is known to increase as the size of the nucleotide molecule increases. As noted above, the number of proteins, RNA transcripts or mixtures thereof which is introduced into the plant genome is preferably preselected and defined, e.g., from one to about 5-10 such products of the introduced DNA may be formed.

Two principal methods for the control of expression are known, viz.: overexpression and underexpression. Overexpression can be achieved by insertion of one or more than one extra copy of the selected gene. It is, however, not unknown for plants or their progeny, originally transformed with one or more than one extra copy of a nucleotide sequence, to exhibit the effects of underexpression as well as overexpression. For underexpression there are two principle methods which are commonly referred to in the art as "antisense downregulation" and "sense downregulation" (sense downregulation is also referred to as "cosuppression"). Generically these processes are referred to as "gene silencing". Both of these methods lead to an inhibition of expression of the target gene.

Obtaining sufficient levels of transgene expression in the appropriate plant tissues is an important aspect in the production of genetically engineered crops. Expression of heterologous DNA sequences in a plant host is dependent upon the presence of an operably linked promoter that is functional within the plant host. Choice of the promoter sequence will determine when and where within the organism the heterologous DNA sequence is expressed.

It is specifically contemplated by the inventors that one could mutagenize a promoter to potentially improve the utility of the elements for the expression of transgenes in plants. The mutagenesis of these elements can be carried out at random and the mutagenized promoter sequences screened for activity in a trial-by-error procedure. Alternatively, particular sequences which provide the promoter with desirable expression characteristics, or the promoter with expression enhancement activity, could be identified and these or similar sequences introduced into the sequences via mutation. It is further contemplated that one could mutagenize these sequences in order to enhance their expression of transgenes in a particular species.

The means for mutagenizing a DNA segment encoding a promoter sequence of the current invention are well-known to those of skill in the art. As indicated, modifications to promoter or other regulatory element may be made by random, or site-specific mutagenesis procedures. The promoter and other regulatory element may be modified by altering their structure through the addition or deletion of one or more nucleotides from the sequence which encodes the corresponding unmodified sequences.

Mutagenesis may be performed in accordance with any of the techniques known in the art, such as, and not limited to, synthesizing an oligonucleotide having one or more mutations within the sequence of a particular regulatory region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids also are routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the promoter. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and cells are selected which include recombinant vectors bearing the mutated sequence arrangement. Vector DNA can then be isolated from these cells and used for plant transformation. A genetic selection scheme was devised by Kunkel et al. (1987) to enrich for clones incorporating mutagenic oligonucleotides. Alternatively, the use of PCR with commercially available thermostable enzymes such as Taq polymerase may be used to incorporate a mutagenic oligonucleotide primer into an amplified DNA fragment that can then be cloned into an appropriate cloning or expression vector. The PCR-mediated mutagenesis procedures of Tomic et al. (1990) and Upender et al. (1995) provide two examples of such protocols. A PCR employing a thermostable ligase in addition to a thermostable polymerase also may be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected promoter-encoding DNA segments using site-directed mutagenesis is provided as a means of producing potentially useful species and is not meant to be limiting as there are other ways in which sequence variants of DNA sequences may be obtained. For example, recombinant vectors encoding the desired promoter sequence may be treated with mutagenic agents, such as hydroxylamine, to obtain sequence variants.

As used herein; the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing (see, for example, Watson and Rarnstad, 1987). Typically, vector mediated methodologies involve the introduction of the nucleic acid fragment into a DNA or RNA vector, the clonal amplification of the vector, and the recovery of the amplified nucleic acid fragment.

Examples of such methodologies are provided by U.S. Pat. No. 4,237,224. A number of template dependent processes are available to amplify the target sequences of interest present in a sample, such methods being well known in the art and specifically disclosed herein below.

Where a clone comprising a promoter has been isolated in accordance with the instant invention, one may wish to delimit the essential promoter regions within the clone. One efficient, targeted means for preparing mutagenizing promoters relies upon the identification of putative regulatory elements within the promoter sequence. This can be initiated by comparison with promoter sequences known to be expressed in similar tissue-specific or developmentally unique manner. Sequences which are shared among promoters with similar expression patterns are likely candidates for the binding of transcription factors and are thus likely elements which confer expression patterns. Confirmation of these putative regulatory elements can be achieved by deletion analysis of each putative regulatory region followed by functional analysis of each deletion construct by assay of a reporter gene which is functionally attached to each construct. As such, once a starting promoter sequence is provided, any of a number of different deletion mutants of the starting promoter could be readily prepared.

Functionally equivalent fragments of a transcription regulating nucleotide sequence of the invention can also be obtained by removing or deleting non-essential sequences without deleting the essential one. Narrowing the transcription regulating nucleotide sequence to its essential, transcription mediating elements can be realized in vitro by trial-and-arrow deletion mutations, or in silico using promoter element search routines. Regions essential for promoter activity often demonstrate clusters of certain, known promoter elements. Such analysis can be performed using available computer algorithms such as PLACE ("Plant Cis-acting Regulatory DNA Elements"; Higo 1999), the B10BASE database "Transfac" (Biologische Datenbanken GmbH, Braunschweig; Wingender 2001) or the database PlantCARE (Lescot 2002).

Preferably, functional equivalent fragments of one of the transcription regulating sequences of the invention comprises at least 100 base pairs, preferably, at least 200 base pairs, more preferably at least 500 base pairs of a transcription regulating nucleotide sequence as described by SEQ ID NO: 1, 2, 3, 4, 7, 8, 9, 10, 11, 14, 15, 16, 19, 20, 21, 24, 25, 26, 29, 30, 31, 34, 35, 36, 37, 40, 41, or 42. More preferably this fragment is starting from the 3'-end of the indicated sequences.

Especially preferred are equivalent fragments of transcription regulating sequences, which are obtained by deleting the region encoding the 5'-untranslated region of the mRNA, thus only providing the (untranscribed) promoter region. The 5'-untranslated region can be easily determined by methods known in the art (such as 5'-RACE analysis). Accordingly, some of the transcription regulating sequences of the invention are equivalent fragments of other sequences (see Table 2 below).

TABLE 2

Relationship of transcription regulating sequences of the invention

| Transcription regulating sequence | Equivalent sequence | Equivalent fragment |
|---|---|---|
| SEQ ID NO: 2 (3293 bp) | — | SEQ ID NO: 1 (1656 bp)<br>SEQ ID NO: 3 (3246 bp)<br>SEQ ID NO: 4 (1656 bp) |
| SEQ ID NO: 7 (3360 bp) | SEQ ID NO: 9 (3363 bp) | SEQ ID NO: 8 (3207 bp)<br>SEQ ID NO: 10 (1291 bp)<br>SEQ ID NO: 11 (1294 bp) |
| SEQ ID NO: 14 (2831 bp) | SEQ ID NO: 16 (2830 bp) | SEQ ID NO: 15 (2791 bp) |
| SEQ ID NO: 19 (3142 bp) | SEQ ID NO: 21 (3180 bp) | SEQ ID NO: 20 (3104 bp) |
| SEQ ID NO: 24 (3208 bp) | SEQ ID NO: 26 (3208 bp) | SEQ ID NO: 25 (3141 bp) |
| SEQ ID NO: 29 (1993 bp) | SEQ ID NO: 31 (1994 bp) | SEQ ID NO: 30 (1909 bp) |
| SEQ ID NO: 34 (2535 bp) | SEQ ID NO: 35 (3141 bp) | SEQ ID NO: 36 (1309 bp)<br>SEQ ID NO: 37 (1304 bp) |
| SEQ ID NO: 40 (3040 bp) | SEQ ID NO: 42 (3041 bp) | SEQ ID NO: 41 (2801 bp) |

As indicated above, deletion mutants, deletion mutants of the promoter of the invention also could be randomly prepared and then assayed. With this strategy, a series of constructs are prepared, each containing a different portion of the clone (a subclone), and these constructs are then screened for activity. A suitable means for screening for activity is to attach a deleted promoter or intron construct which contains a deleted segment to a selectable or screenable marker, and to isolate only those cells expressing the marker gene. In this way, a number of different, deleted promoter constructs are identified which still retain the desired, or even enhanced, activity. The smallest segment which is required for activity is thereby identified through comparison of the selected constructs. This segment may then be used for the construction of vectors for the expression of exogenous genes.

An expression cassette of the invention may comprise further regulatory elements. The term in this context is to be understood in the a broad meaning comprising all sequences which may influence construction or function of the expression cassette. Regulatory elements may for example modify transcription and/or translation in prokaryotic or eukaryotic organism. In an preferred embodiment the expression cassette of the invention comprised downstream (in 3'-direction) of the nucleic acid sequence to be expressed a transcription termination sequence and—optionally additional regulatory elements—each operably liked to the nucleic acid sequence to be expressed (or the transcription regulating sequence).

Additional regulatory elements may comprise additional promoter, minimal promoters, or promoter elements, which may modify the expression regulating properties. For example the expression may be made depending on certain stress factors such water stress, abscisin (Lam 1991) or heat stress (Schoffl 1989). Furthermore additional promoters or promoter elements may be employed, which may realized expression in other organisms (such as *E. coli* or *Agrobacterium*). Such regulatory elements can be find in the promoter sequences or bacteria such as amy and SPO2 or in the promoter sequences of yeast or fungal promoters (such as ADC1, MFa, AC, P-60, CYC1, GAPDH, TEF, rp28, and ADH).

Furthermore, it is contemplated that promoters combining elements from more than one promoter may be useful. For example, U.S. Pat. No. 5,491,288 discloses combining a Cauliflower Mosaic Virus promoter with a histone promoter. Thus, the elements from the promoters disclosed herein may be combined with elements from other promoters. Promoters which are useful for plant transgene expression include those that are inducible, viral, synthetic, constitutive (Odell 1985), temporally regulated, spatially regulated, tissue-specific, and spatial-temporally regulated.

Where expression in specific tissues or organs is desired, tissue-specific promoters may be used. In contrast, where gene expression in response to a stimulus is desired, inducible promoters are the regulatory elements of choice. Where continuous expression is desired throughout the cells of a plant, constitutive promoters are utilized. Additional regulatory sequences upstream and/or downstream from the core promoter sequence may be included in expression constructs of transformation vectors to bring about varying levels of expression of heterologous nucleotide sequences in a transgenic plant.

A variety of 5' and 3' transcriptional regulatory sequences are available for use in the present invention. Transcriptional terminators are responsible for the termination of transcription and correct mRNA polyadenylation. The 3' nontranslated regulatory DNA sequence preferably includes from about 50 to about 1,000, more preferably about 100 to about 1,000, nucleotide base pairs and contains plant transcriptional and translational termination sequences. Appropriate transcriptional terminators and those which are known to function in plants include the CaMV 35S terminator, the tml terminator, the nopaline synthase terminator, the pea rbcS E9 terminator, the terminator for the T7 transcript from the octopine synthase gene of *Agrobacterium tumefaciens*, and the 3' end of the protease inhibitor I or II genes from potato or tomato, although other 3' elements known to those of skill in the art can also be employed. Alternatively, one also could use a gamma coixin, oleosin 3 or other terminator from the genus *Coix*.

Preferred 3' elements include those from the nopaline synthase gene of *Agrobacterium tumefaciens* (Bevan 1983), the terminator for the T7 transcript from the octopine synthase gene of *Agrobacterium tumefaciens*, and the 3, end of the protease inhibitor I or II genes from potato or tomato.

As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will be most preferred.

Preferred regulatory elements also include the 5'-untranslated region, introns and the 3'-untranslated region of genes. Such sequences that have been found to enhance gene expression in transgenic plants include intron sequences (e.g., from Adh1, bronze1, actin1, actin 2 (WO 00/760067), or the sucrose synthase intron; see: The Maize Handbook, Chapter 116, Freeling and Walbot, Eds., Springer, N.Y. (1994)) and viral leader sequences (e.g., from TMV, MCMV and AMV; Gallie 1987). For example, a number of non-translated leader sequences derived from viruses are known to enhance expression. Specifically, leader sequences from Tobacco Mosaic Virus (TMV), Maize Chlorotic Mottle Virus (MCMV), and Alfalfa Mosaic Virus (AMV) have been shown to be effective in enhancing expression (e.g., Gallie 1987; Skuzeski 1990). Other leaders known in the art include but are not limited to: Picornavirus leaders, for example, EMCV leader (Encephalomyocarditis 5' noncoding region) (Elroy-Stein 1989); Potyvirus leaders, for example, TEV leader (Tobacco Etch Virus); MDMV leader (Maize Dwarf Mosaic Virus); Human immunoglobulin heavy-chain binding protein (BiP) leader, (Macejak 1991); Untranslated leader from the coat protein mRNA of alfalfa mosaic virus (AMV RNA 4), (Jobling 1987; Tobacco mosaic virus leader (TMV), (Gallie 1989; and Maize Chlorotic Mottle Virus leader (MCMV) (Lommel 1991. See also, Della-Cioppa 1987. Regulatory elements such as Adh intron 1 (Callis 1987), sucrose synthase intron (Vasil 1989) or TMV omega element (Gallie 1989), may further be included where desired. Especially preferred are the 5'-untranslated region, introns and the 3'-untranslated region from the genes described by the GenBank *Arabidopsis thaliana* genome locii At1g66280, At1g74500, At1g49570, At1g70710, At5g66690, At3g29630, At5g48070, or At4g17800, or of functional equivalent thereof.

Additional preferred regulatory elements are enhancer sequences or polyadenylation sequences. Preferred polyadenylation sequences are those from plant genes or *Agrobacterium* T-DNA genes (such as for example the terminator sequences of the OCS (octopine synthase) or NOS (nopaline synthase) genes).

Examples of enhancers include elements from the CaMV 35S promoter, octopine synthase genes (Ellis et al., 1987), the rice actin I gene, the maize alcohol dehydrogenase gene (Callis 1987), the maize shrunken I gene (Vasil 1989), TMV Omega element (Gallie 1989) and promoters from non-plant eukaryotes (e.g. yeast; Ma 1988). Vectors for use in accordance with the present invention may be constructed to include the ocs enhancer element. This element was first identified as a 16 bp palindromic enhancer from the octopine synthase (ocs) gene of ultilane (Ellis 1987), and is present in at least 10 other promoters (Bouchez 1989). The use of an enhancer element, such as the ocs elements and particularly multiple copies of the element, will act to increase the level of transcription from adjacent promoters when applied in the context of plant transformation.

An expression cassette of the invention (or a vector derived therefrom) may comprise additional functional elements, which are to be understood in the broad sense as all elements which influence construction, propagation, or function of an expression cassette or a vector or a transgenic organism comprising them. Such functional elements may include origin of replications (to allow replication in bacteria; for the ORI of pBR322 or the P15A ori; Sambrook 1989), or elements required for *Agrobacterium* T-DNA transfer (such as for example the left and/or rights border of the T-DNA).

Ultimately, the most desirable DNA segments for introduction into, for example, a dicot genome, may be homologous genes or gene families which encode a desired trait (e.g., increased yield per acre) and which are introduced under the control of novel promoters or enhancers, etc., or perhaps even homologous or tissue specific (e.g., root-, collar/sheath-, whorl-, stalk-, earshank-, kernel- or leaf-specific) promoters or control elements. Indeed, it is envisioned that a particular use of the present invention will be the expression of a gene in a root-preferential or root-specific manner.

Additionally, vectors may be constructed and employed in the intracellular targeting of a specific gene product within the cells of a transgenic plant or in directing a protein to the extracellular environment. This will generally be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane.

A particular example of such a use concerns the direction of a herbicide resistance gene, such as the EPSPS gene, to a particular organelle such as the chloroplast rather than to the cytoplasm. This is exemplified by the use of the rbcs transit peptide which confers plastid-specific targeting of proteins. In addition, it is proposed that it may be desirable to target certain genes responsible for male sterility to the mitochondria, or to target certain genes for resistance to phytopathogenic organisms to the extracellular spaces, or to target proteins to the vacuole.

By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. Targeting of certain proteins may be desirable in order to enhance the stability of the protein (U.S. Pat. No. 5,545,818).

It may be useful to target DNA itself within a cell. For example, it may be useful to target introduced DNA to the nucleus as this may increase the frequency of transformation. Within the nucleus itself it would be useful to target a gene in order to achieve site specific integration. For example, it would be useful to have an gene introduced through transformation replace an existing gene in the cell. Other elements include those that can be regulated by endogenous or exogenous agents, e.g., by zinc finger proteins, including naturally occurring zinc finger proteins or chimeric zinc finger proteins (see, e.g., U.S. Pat. No. 5,789,538, WO 99/48909; WO 99/45132; WO 98/53060; WO 98/53057; WO 98/53058; WO 00/23464; WO 95/19431; and WO 98/54311) or myb-like transcription factors. For example, a chimeric zinc finger protein may include amino acid sequences which bind to a specific DNA sequence (the zinc finger) and amino acid sequences that activate (e.g., GAL 4 sequences) or repress the transcription of the sequences linked to the specific DNA sequence.

It is one of the objects of the present invention to provide recombinant DNA molecules comprising a nucleotide sequence according to the invention operably linked to a nucleotide segment of interest.

A nucleotide segment of interest is reflective of the commercial markets and interests of those involved in the development of the crop. Crops and markets of interest changes, and as developing nations open up world markets, new crops and technologies will also emerge. In addition, as the understanding of agronomic traits and characteristics such as yield and heterosis increase, the choice of genes for transformation will change accordingly. General categories of nucleotides of interest include, for example, genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in starch, oil, carbohydrate, or nutrient metabolism, as well as those affecting kernel size, sucrose loading, zinc finger proteins, see, e.g., U.S. Pat. No. 5,789,538, WO 99/48909; WO 99/45132; WO 98/53060; WO 98/53057; WO 98/53058; WO 00/23464; WO 95/19431; and WO 98/54311, and the like.

One skilled in the art recognizes that the expression level and regulation of a transgene in a plant can vary significantly from line to line. Thus, one has to test several lines to find one with the desired expression level and regulation. Once a line is identified with the desired regulation specificity of a chimeric Cre transgene, it can be crossed with lines carrying different inactive replicons or inactive transgene for activation.

Other sequences which may be linked to the gene of interest which encodes a polypeptide are those which can target to a specific organelle, e.g., to the mitochondria, nucleus, or plastid, within the plant cell. Targeting can be achieved by providing the polypeptide with an appropriate targeting peptide sequence, such as a secretory signal peptide (for secretion or cell wall or membrane targeting, a plastid transit peptide, a chloroplast transit peptide, e.g., the chlorophyll a/b binding protein, a mitochondrial target peptide, a vacuole targeting peptide, or a nuclear targeting peptide, and the like. For example, the small subunit of ribulose bisphosphate carboxylase transit peptide, the EPSPS transit peptide or the dihydrodipicolinic acid synthase transit peptide may be used. For examples of plastid organelle targeting sequences (see WO 00/12732). Plastids are a class of plant organelles derived from proplastids and include chloroplasts, leucoplasts, amyloplasts, and chromoplasts. The plastids are major sites of biosynthesis in plants. In addition to photosynthesis in the chloroplast, plastids are also sites of lipid biosynthesis, nitrate reduction to ammonium, and starch storage. And while plastids contain their own circular, genome, most of the proteins localized to the plastids are encoded by the nuclear genome and are imported into the organelle from the cytoplasm.

Transgenes used with the present invention will often be genes that direct the expression of a particular protein or polypeptide product, but they may also be non-expressible DNA segments, e.g., transposons such as Ds that do no direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The invention also contemplates that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

The choice of the particular DNA segments to be delivered to the recipient cells will often depend on the purpose of the transformation. One of the major purposes of transformation of crop plants is to add some commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; dry down; standability; prolificacy; starch properties; oil quantity and quality; and the like. One may desire to incorporate one or more genes conferring any such desirable trait or traits, such as, for example, a gene or genes encoding pathogen resistance.

In certain embodiments, the present invention contemplates the transformation of a recipient cell with more than one advantageous transgene. Two or more transgenes can be supplied in a single transformation event using either distinct transgene-encoding vectors, or using a single vector incorporating two or more gene coding sequences. For example, plasmids bearing the bar and aroA expression units in either convergent, divergent, or colinear orientation, are considered to be particularly useful. Further preferred combinations are those of an insect resistance gene, such as a Bt gene, along with a protease inhibitor gene such as pinII, or the use of bar in combination with either of the above genes. Of course, any two or more transgenes of any description, such as those conferring herbicide, insect, disease (viral, bacterial, fungal, nematode) or drought resistance, male sterility, dry down, standability, prolificacy, starch properties, oil quantity and quality, or those increasing yield or nutritional quality may be employed as desired.

1. Exemplary Transgenes 1.1. Herbicide Resistance

The genes encoding phosphinothricin acetyltransferase (bar and pat), glyphosate tolerant EPSP synthase genes, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvylshikimate 3-phosphate synthase (EPSP Synthase), is normally inhibited by the herbicide N-(phosphonomethyl)glycine(glyphosate). However, genes are known that encode glyphosate-resistant EPSP Synthase enzymes. The deh gene encodes the enzyme dalapon dehalogenase and confers resistance to the herbicide dalapon. The bxn gene codes for a specific nitrilase enzyme that converts bromoxynil to a non-herbicidal degradation product.

1.2 Insect Resistance

An important aspect of the present invention concerns the introduction of insect resistance-conferring genes into plants. Potential insect resistance genes which can be introduced include *Bacillus thuringiensis* crystal toxin genes or Bt genes (Watrud 1985). Bt genes may provide resistance to lepidopteran or coleopteran pests such as European Corn Borer (ECB) and corn rootworm (CRW). Preferred Bt toxin genes for use in such embodiments include the CryIA(b) and CryIA(c) genes. Endotoxin genes from other species of *B. thuringiensis* which affect insect growth or development may also be employed in this regard. Protease inhibitors may also provide insect resistance (Johnson 1989), and will thus have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered by the present inventors to produce synergistic insecticidal activity. Other genes which encode inhibitors of the insects' digestive system, or those that encode enzymes or co-factors that facilitate the production of inhibitors, may also be useful. This group may be exemplified by cystatin and amylase inhibitors, such as those from wheat and barley.

Also, genes encoding lectins may confer additional or alternative insecticide properties. Lectins (originally termed phytohemagglutinins) are multivalent carbohydrate-binding proteins which have the ability to agglutinate red blood cells from a range of species. Lectins have been identified recently as insecticidal agents with activity against weevils, ECB and rootworm (Murdock 1990; Czapla & Lang, 1990). Lectin genes contemplated to be useful include, for example, barley and wheat germ agglutinin (WGA) and rice lectins (Gatehouse 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated, that the expression of juvenile hormone esterase, directed towards specific insect pests, may also result in insecticidal activity, or perhaps cause cessation of metamorphosis (Hammock 1990).

Transgenic plants expressing genes which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant maize plants. Genes that code for activities that affect insect molting, such those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests are also encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity which may be resistant to insect feeding.

The present invention also provides methods and compositions by which to achieve qualitative or quantitative changes in plant secondary metabolites. One example concerns transforming plants to produce DIMBOA which, it is contemplated, will confer resistance to European corn borer, root worm and several other maize insect pests. Candidate genes that are particularly considered for use in this regard include those genes at the bx locus known to be involved in the synthetic DIMBOA pathway (Dunn 1981). The introduction of genes that can regulate the production of maysin, and genes involved in the production of dhurrin in sorghum, is also contemplated to be of use in facilitating resistance to ear worm and root worm, respectively.

*Tripsacum dactyloides* is a species of grass that is resistant to certain insects, including corn root worm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson & Guss, 1972).

Further genes encoding proteins characterized as having potential insecticidal activity may also be used as transgenes in accordance herewith. Such genes include, for example, the cowpea trypsin inhibitor (CpTI; Hilder 1987) which may be used as a root worm deterrent; genes encoding avermectin (Campbell 1989; Ikeda 1987) which may prove particularly useful as a corn root worm deterrent; ribosome inactivating protein genes; and even genes that regulate plant structures. Transgenic maize including anti-insect antibody genes and genes that code for enzymes that can covert a non-toxic insecticide (pro-insecticide) applied to the outside of the plant into an insecticide inside the plant are also contemplated.

1.3 Environment or Stress Resistance

Improvement of a plant's ability to tolerate various environmental stresses such as, but not limited to, drought, excess moisture, chilling, freezing, high temperature, salt, and oxidative stress, can also be effected through expression of heterologous, or overexpression of homologous genes. Benefits may be realized in terms of increased resistance to freezing temperatures through the introduction of an "antifreeze" protein such as that of the Winter Flounder (Cutler 1989) or synthetic gene derivatives thereof. Improved chilling tolerance may also be conferred through increased expression of glycerol-3-phosphate acetyltransferase in chloroplasts (Murata 1992; Wolter 1992). Resistance to oxidative stress (often exacerbated by conditions such as chilling temperatures in combination with high light intensities) can be conferred by expression of superoxide dismutase (Gupta 1993), and may be improved by glutathione reductase (Bowler 1992). Such strategies may allow for tolerance to freezing in newly emerged fields as well as extending later maturity higher yielding varieties to earlier relative maturity zones.

Expression of novel genes that favorably effect plant water content, total water potential, osmotic potential, and turgor can enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments, and perform in a relatively superior manner. In this aspect of the invention it is proposed, for example, that the expression of a gene encoding the biosynthesis of osmotically active solutes can impart protection against drought. Within this class of genes are DNAs encoding mannitol dehydrogenase (Lee and Saier, 1982) and trehalose-6-phosphate synthase (Kaasen 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski 1992).

Similarly, the efficacy of other metabolites in protecting either enzyme function (e.g. alanopine or propionic acid) or membrane integrity (e.g., alanopine) has been documented (Loomis 1989), and therefore expression of gene encoding the biosynthesis of these compounds can confer drought resistance in a manner similar to or complimentary to mannitol. Other examples of naturally occurring metabolites that are osmotically active and/or provide some direct protective effect during drought and/or desiccation include sugars and sugar derivatives such as fructose, erythritol (Coxson 1992), sorbitol, dulcitol (Karsten 1992), glucosylglycerol (Reed 1984; Erdmann 1992), sucrose, stachyose (Koster & Leopold 1988; Blackman 1992), ononitol and pinitol (Vernon & Bohnert 1992), and raffinose (Bernal-Lugo & Leopold 1992). Other osmotically active solutes which are not sugars include, but are not limited to, proline and glycine-betaine (Wyn-Jones and Storey, 1981). Continued canopy growth and increased reproductive fitness during times of stress can be augmented by introduction and expression of genes such as those controlling the osmotically active compounds discussed above and other such compounds, as represented in one exemplary embodiment by the enzyme myoinositol O-methyltransferase.

It is contemplated that the expression of specific proteins may also increase drought tolerance. Three classes of Late Embryogenic Proteins have been assigned based on structural similarities (see Dure 1989). All three classes of these proteins have been demonstrated in maturing (i.e., desiccating) seeds. Within these 3 types of proteins, the Type-II (dehydrin-type) have generally been implicated in drought and/or desiccation tolerance in vegetative plant parts (e.g. Mundy and Chua, 1988; Piatkowski 1990; Yamaguchi-Shinozaki 1992). Recently, expression of a Type-III LEA (HVA-1) in tobacco was found to influence plant height, maturity and drought tolerance (Fitzpatrick, 1993). Expression of structural genes from all three groups may therefore confer drought tolerance. Other types of proteins induced during water stress include thiol proteases, aldolases and transmembrane transporters (Guerrero 1990), which may confer various protective and/or repair-type functions during drought stress. The expression of a gene that effects lipid biosynthesis and hence membrane composition can also be useful in conferring drought resistance on the plant.

Many genes that improve drought resistance have complementary modes of action. Thus, combinations of these genes might have additive and/or synergistic effects in improving drought resistance in maize. Many of these genes also improve freezing tolerance (or resistance); the physical stresses incurred during freezing and drought are similar in nature and may be mitigated in similar fashion. Benefit may be conferred via constitutive expression or tissue-specific of these genes, but the preferred means of expressing these novel genes may be through the use of a turgor-induced promoter (such as the promoters for the turgor-induced genes described in Guerrero et al. 1990 and Shagan 1993). Spatial and temporal expression patterns of these genes may enable maize to better withstand stress.

Expression of genes that are involved with specific morphological traits that allow for increased water extractions from drying soil would be of benefit. For example, introduction and expression of genes that alter root characteristics may enhance water uptake. Expression of genes that enhance reproductive fitness during times of stress would be of significant value. For example, expression of DNAs that improve the synchrony of pollen shed and receptiveness of the female flower parts, i.e., silks, would be of benefit. In addition, expression of genes that minimize kernel abortion during times of stress would increase the amount of grain to be harvested and hence be of value. Regulation of cytokinin levels in monocots, such as maize, by introduction and expression of an isopentenyl transferase gene with appropriate regulatory sequences can improve monocot stress resistance and yield (Gan 1995).

Given the overall role of water in determining yield, it is contemplated that enabling plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

Improved protection of the plant to abiotic stress factors such as drought, heat or chill, can also be achieved—for example—by overexpressing antifreeze polypeptides from Myoxocephalus Scorpius (WO 00/00512), Myoxocephalus octodecemspinosus, the *Arabidopsis thaliana* transcription activator CBFI, glutamate dehydrogenases (WO 97/12983, WO 98/11240), calcium-dependent protein kinase genes (WO 98/26045), calcineurins (WO 99/05902), casein kinase from yeast (WO 02/052012), farnesyltransferases (WO 99/06580; Pei Z M et al. (1998) Science 282:287-290), ferritin (Deak M et al. (1999) Nature Biotechnology 17:192-196), oxalate oxidase (WO 99/04013; Dunwell J M (1998) Biotechn Genet Eng Rev 15:1-32), DREB1A factor ("dehydration response element B 1A"; Kasuga M et al. (1999) Nature Biotech 17:276-286), genes of mannitol or trehalose synthesis such as trehalose-phosphate synthase or trehalose-phosphate phosphatase (WO 97/42326) or by inhibiting genes such as trehalase (WO 97/50561).

1.4 Disease Resistance

It is proposed that increased resistance to diseases may be realized through introduction of genes into plants period. It is possible to produce resistance to diseases caused, by viruses, bacteria, fungi, root pathogens, insects and nematodes. It is also contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo 1988, Hemenway 1988, Abel 1986). It is contemplated that expression of antisense genes targeted at essential viral functions may impart resistance to said virus. For example, an antisense gene targeted at the gene responsible for replication of viral nucleic acid may inhibit said replication and lead to resistance to the virus. It is believed that interference with other viral functions through the use of antisense genes may also increase resistance to viruses. Further it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of many species of bacteria and fungi. It is proposed that expression of PR proteins in plants may be useful in conferring resistance to bacterial disease. These genes are induced following pathogen attack on a host plant and have been divided into at least five classes of proteins (Bol 1990). Included amongst the PR proteins are beta-1,3-glucanases, chitinases, and osmotin and other proteins that are believed to function in plant resistance to disease organisms. Other genes have been identified that have antifungal properties, e.g., UDA (stinging nettle lectin) and hevein (Broakgert 1989; Barkai-Golan 1978). It is known that certain plant diseases are caused by the production of phytotoxins. Resistance to these diseases could be achieved through expression of a novel gene that encodes an enzyme capable of degrading or otherwise inactivating the phytotoxin. Expression novel genes that alter the interactions between the host plant and pathogen may be useful in reducing the ability the disease organism to invade the tissues of the host plant, e.g., an increase in the waxiness of the leaf cuticle or other morphological characteristics.

Plant parasitic nematodes are a cause of disease in many plants. It is proposed that it would be possible to make the plant resistant to these organisms through the expression of novel genes. It is anticipated that control of nematode infestations would be accomplished by altering the ability of the nematode to recognize or attach to a host plant and/or enabling the plant to produce nematicidal compounds, including but not limited to proteins.

Furthermore, a resistance to fungi, insects, nematodes and diseases, can be achieved by targeted accumulation of certain metabolites or proteins. Such proteins include but are not limited to glucosinolates (defense against herbivores), chitinases or glucanases and other enzymes which destroy the cell wall of parasites, ribosome-inactivating proteins (RIPS) and other proteins of the plant resistance and stress reaction as are induced when plants are wounded or attacked by microbes, or chemically, by, for example, salicylic acid, jasmonic acid or ethylene, or lysozymes from nonplant sources such as, for example, T4-lysozyme or lysozyme from a variety of mammals, insecticidal proteins such as *Bacillus thuringiensis* endotoxin, a-amylase inhibitor or protease inhibitors (cowpea trypsin inhibitor), lectins such as wheatgerm agglutinin, RNAses or ribozymes. Further examples are nucleic acids which encode the *Trichoderma harzianum* chit42 endochitinase (GenBank Acc. No.: S78423) or the N-hydroxylating, multi-functional cytochrome P-450 (CYP79) protein from *Sorghum bicolor* (GenBank Acc. No.: U32624), or functional equivalents of these. The accumulation of glucosinolates as protection from pests (Rask L et al. (2000) Plant Mol Biol 42:93-113; Menard R et al. (1999) Phytochemistry 52:29-35), the expression of *Bacillus thuringiensis* endotoxins (Vaeck et al. (1987) Nature 328:33-37) or the protection against attack by fungi, by expression of chitinases, for example from beans (Brogue et al. (1991) Science 254:1194-1197), is advantageous. Resistance to pests such as, for example, the rice pest *Nilaparvata lugens* in rice plants can be achieved by expressing the snowdrop (*Galanthus nivalis*) lectin agglutinin (Rao et al. (1998) Plant J 15(4):469-77). The expression of synthetic cryIA(b) and cryIA(c) genes, which encode lepidoptera-specific *Bacillus thuringiensis* D-endotoxins can bring about a resistance to insect pests in various plants (Goyal R K et al. (2000) Crop Protection 19(5):307-312). Further target genes which are suitable for pathogen defense comprise "polygalacturonase-inhibiting protein" (PGIP), thaumatine, invertase and antimicrobial peptides such as lactoferrin (Lee T J et al. (2002) J Amer Soc Horticult Sci 127(2):158-164).

1.5 Mycotoxin Reduction/Elimination

Production of mycotoxins, including aflatoxin and fumonisin, by fungi associated with plants is a significant factor in rendering the grain not useful. These fungal organisms do not cause disease symptoms and/or interfere with the growth of the plant, but they produce chemicals (mycotoxins) that are toxic to animals. Inhibition of the growth of these fungi would reduce the synthesis of these toxic substances and, therefore, reduce grain losses due to mycotoxin contamination. Novel genes may be introduced into plants that would inhibit synthesis of the mycotoxin without interfering with fungal growth. Expression of a novel gene which encodes an enzyme capable of rendering the mycotoxin nontoxic would be useful in order to achieve reduced mycotoxin contamination of grain. The result of any of the above mechanisms would be a reduced presence of mycotoxins on grain.

1.6 Plant Agronomic Characteristics

Two of the factors determining where plants can be grown are the average daily temperature during the growing season and the length of time between frosts. Within the areas where it is possible to grow a particular plant, there are varying limitations on the maximal time it is allowed to grow to maturity and be harvested. The plant to be grown in a particular area is selected for its ability to mature and dry down to harvestable moisture content within the required period of time with maximum possible yield. Therefore, plant of varying maturities are developed for different growing locations. Apart from the need to dry down sufficiently to permit harvest is the desirability of having maximal drying take place in the field to minimize the amount of energy required for additional drying post-harvest. Also the more readily the grain can dry down, the more time there is available for growth and kernel fill. Genes that influence maturity and/or dry down can be identified and introduced into plant lines using transformation techniques to create new varieties adapted to different growing locations or the same growing location but having improved yield to moisture ratio at harvest. Expression of genes that are involved in regulation of plant development may be especially useful, e.g., the liguleless and rough sheath genes that have been identified in plants.

Genes may be introduced into plants that would improve standability and other plant growth characteristics. For example, expression of novel genes which confer stronger stalks, improved root systems, or prevent or reduce ear droppage would be of great value to the corn farmer. Introduction and expression of genes that increase the total amount of photoassimilate available by, for example, increasing light distribution and/or interception would be advantageous. In addition the expression of genes that increase the efficiency of photosynthesis and/or the leaf canopy would further increase gains in productivity. Such approaches would allow for increased plant populations in the field.

Delay of late season vegetative senescence would increase the flow of assimilate into the grain and thus increase yield. Overexpression of genes within plants that are associated with "stay green" or the expression of any gene that delays senescence would be advantageous. For example, a non-yellowing mutant has been identified in *Festuca pratensis* (Davies 1990). Expression of this gene as well as others may prevent premature breakdown of chlorophyll and thus maintain canopy function.

1.7 Nutrient Utilization

The ability to utilize available nutrients and minerals may be a limiting factor in growth of many plants. It is proposed that it would be possible to alter nutrient uptake, tolerate pH extremes, mobilization through the plant, storage pools, and availability for metabolic activities by the introduction of novel genes. These modifications would allow a plant to more efficiently utilize available nutrients. It is contemplated that an increase in the activity of, for example, an enzyme that is normally present in the plant and involved in nutrient utilization would increase the availability of a nutrient. An example of such an enzyme would be phytase. It is also contemplated that expression of a novel gene may make a nutrient source available that was previously not accessible, e.g., an enzyme that releases a component of nutrient value from a more complex molecule, perhaps a macromolecule.

1.8 Non-Protein-Expressing Sequences 1.8.1 RNA-Expressing

DNA may be introduced into plants for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes.

Genes may be constructed or isolated, which when transcribed, produce antisense RNA or double-stranded RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction which include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition or plant morphological changes respectively. The possibilities cited above are provided only by way of example and do not represent the full range of applications.

Expression of antisense-RNA or double-stranded RNA by one of the expression cassettes of the invention is especially preferred. Also expression of sense RNA can be employed for gene silencing (co-suppression). This RNA is preferably a non-translatable RNA. Gene regulation by double-stranded RNA ("double-stranded RNA interference"; dsRNAi) is well known in the arte and described for various organism including plants (e.g., Matzke 2000; Fire A et al 1998; WO 99/32619; WO 99/53050; WO 00/68374; WO 00/44914; WO 00/44895; WO 00/49035; WO 00/63364).

Genes may also be constructed or isolated, which when transcribed produce RNA enzymes, or ribozymes, which can act as endoribonucleases and catalyze the cleavage of RNA molecules with selected sequences. The cleavage of selected messenger RNA's can result in the reduced production of their encoded polypeptide products. These genes may be used to prepare novel transgenic plants which possess them. The transgenic plants may possess reduced levels of polypeptides including but not limited to the polypeptides cited above that may be affected by antisense RNA.

It is also possible that genes may be introduced to produce novel transgenic plants which have reduced expression of a native gene product by a mechanism of cosuppression. It has been demonstrated in tobacco, tomato, and petunia (Goring 1991; Smith 1990; Napoli 1990; van der Krol 1990) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

1.8.2 Non-RNA-Expressing

For example, DNA elements including those of transposable elements such as Ds, Ac, or Mu, may be, inserted into a gene and cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta 1988). Once identified, the entire gene(s) for the particular trait, including control or regulatory regions where desired may be isolated, cloned and manipulated as desired. The utility of DNA elements introduced into an organism for purposed of gene tagging is independent of the DNA sequence and does not depend on any biological activity of the DNA sequence, i.e., transcription into RNA or translation into protein. The sole function of the DNA element is to disrupt the DNA sequence of a gene.

It is contemplated that unexpressed DNA sequences, including novel synthetic sequences could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Another possible element which may be introduced is a matrix attachment region element (MAR), such as the chicken lysozyme A element (Stief 1989), which can be positioned around an expressible gene of interest to effect an increase in overall expression of the gene and diminish position dependant effects upon incorporation into the plant genome (Stief 1989; Phi-Van 1990).

Further nucleotide sequences of interest that may be contemplated for use within the scope of the present invention in operable linkage with the promoter sequences according to the invention are isolated nucleic acid molecules, e.g., DNA or RNA, comprising a plant nucleotide sequence according to the invention comprising an open reading frame that is preferentially expressed in a specific tissue, i.e., seed-, root, green tissue (leaf and stem), panicle-, or pollen, or is expressed constitutively.

2. Marker Genes

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait, the green fluorescent protein (GFP)). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., alpha-amylase, beta-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). For example, the maize HPRG (Steifel 1990) molecule is well characterized in terms of molecular biology, expression and protein structure. However, any one of a variety of ultilane and/or glycine-rich wall proteins (Keller 1989) could be modified by the addition of an antigenic site to create a screenable marker.

One exemplary embodiment of a secretable screenable marker concerns the use of a maize sequence encoding the wall protein HPRG, modified to include a 15 residue epitope from the pro-region of murine interleukin, however, virtually any detectable epitope may be employed in such embodiments, as selected from the extremely wide variety of antigen-antibody combinations known to those of skill in the art. The unique extracellular epitope can then be straightforwardly detected using antibody labeling in conjunction with chromogenic or fluorescent adjuncts.

Elements of the present disclosure may be exemplified in detail through the use of the bar and/or GUS genes, and also through the use of various other markers. Of course, in light of this disclosure, numerous other possible selectable and/or screenable marker genes will be apparent to those of skill in the art in addition to the one set forth herein below. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed plant.

2.1 Selectable Markers

Various selectable markers are known in the art suitable for planttransformation. Such markers may include but are not limited to:

2.1.1 Negative selection markers

Negative selection markers confer a resistance to a biocidal compound such as a metabolic inhibitor (e.g., 2-deoxyglucose-6-phosphate, WO 98/45456), antibiotics (e.g., kanamycin, G 418, bleomycin or hygromycin) or herbicides (e.g., phosphinothricin or glyphosate). Transformed plant material (e.g., cells, tissues or plantlets), which express marker genes, are capable of developing in the presence of concentrations of a corresponding selection compound (e.g., antibiotic or herbicide) which suppresses growth of an untransformed wild type tissue. Especially preferred negative selection markers are those which confer resistance to herbicides. Examples which may be mentioned are:

- Phosphinothricin acetyltransferases (PAT; also named Bialophos® resistance; bar; de Block 1987; Vasil 1992, 1993; Weeks 1993; Becker 1994; Nehra 1994; Wan & Lemaux 1994; EP 0 333 033; U.S. Pat. No. 4,975,374). Preferred are the bar gene from *Streptomyces hygroscopicus* or the pat gene from *Streptomyces viridochromogenes*. PAT inactivates the active ingredient in the herbicide bialaphos, phosphinothricin (PPT). PPT inhibits glutamine synthetase, (Murakami 1986; Twell 1989) causing rapid accumulation of ammonia and cell death.
- altered 5-enolpyruvylshikimate-3-phosphate synthase (EPSPS) conferring resistance to Glyphosate® (N-(phosphonomethyl)glycine) (Hinchee 1988; Shah 1986; Della-Cioppa 1987). Where a mutant EPSP synthase gene is employed, additional benefit may be realized through the incorporation of a suitable chloroplast transit peptide, CTP (EP-A1 0 218 571).
- Glyphosate® degrading enzymes (Glyphosate® oxidoreductase; gox),
- Dalapon® inactivating dehalogenases (deh)
- sulfonylurea- and/or imidazolinone-inactivating acetolactate synthases (ahas or ALS; for example mutated ahas/ALS variants with, for example, the S4, XI12, XA17, and/or Hra mutation (EP-A1 154 204)
- Bromoxynil® degrading nitrilases (bxn; Stalker 1988)
- Kanamycin- or geneticin (G418) resistance genes (NPTII; NPT or neo; Potrykus 1985) coding e.g., for neomycin phosphotransferases (Fraley 1983; Nehra 1994)
- 2-Desoxyglucose-6-phosphate phosphatase ($DOG^R$1-Gene product; WO 98/45456; EP 0 807 836) conferring resistance against 2-desoxyglucose (Randez-Gil 1995).
- hygromycin phosphotransferase (HPT), which mediates resistance to hygromycin (Vanden Elzen 1985).
- altered dihydrofolate reductase (Eichholtz 1987) conferring resistance against methotrexat (Thillet 1988);
- mutated anthranilate synthase genes that confers resistance to 5-methyl tryptophan.

Additional negative selectable marker genes of bacterial origin that confer resistance to antibiotics include the aadA gene, which confers resistance to the antibiotic spectinomycin, gentamycin acetyl transferase, streptomycin phosphotransferase (SPT), aminoglycoside-3-adenyl transferase and the bleomycin resistance determinant (Hayford 1988; Jones 1987; Svab 1990; Hille 1986).

Especially preferred are negative selection markers that confer resistance against the toxic effects imposed by D-amino acids like e.g., D-alanine and D-serine (WO 03/060133; Erikson 2004). Especially preferred as negative selection marker in this contest are the dao1 gene (EC: 1.4. 3.3: GenBank Acc.-No.: U60066) from the yeast *Rhodotorula gracilis* (*Rhodosporidium toruloides*) and the *E. coli* gene dsdA (D-serine dehydratase (D-serine deaminase) [EC: 4.3. 1.18; GenBank Acc.-No.: J01603).

Transformed plant material (e.g., cells, embryos, tissues or plantlets) which express such marker genes are capable of developing in the presence of concentrations of a corresponding selection compound (e.g., antibiotic or herbicide) which suppresses growth of an untransformed wild type tissue. The resulting plants can be bred and hybridized in the customary fashion. Two or more generations should be grown in order to ensure that the genomic integration is stable and hereditary. Corresponding methods are described (Jenes 1993; Potrykus 1991).

Furthermore, reporter genes can be employed to allow visual screening, which may or may not (depending on the type of reporter gene) require supplementation with a substrate as a selection compound.

Various time schemes can be employed for the various negative selection marker genes. In case of resistance genes (e.g., against herbicides or D-amino acids) selection is preferably applied throughout callus induction phase for about 4 weeks and beyond at least 4 weeks into regeneration. Such a selection scheme can be applied for all selection regimes. It is furthermore possible (although not explicitly preferred) to remain the selection also throughout the entire regeneration scheme including rooting.

For example, with the phosphinotricin resistance gene (bar) as the selective marker, phosphinotricin at a concentration of from about 1 to 50 mg/l may be included in the medium. For example, with the dao1 gene as the selective marker, D-serine or D-alanine at a concentration of from about 3 to 100 mg/l may be included in the medium. Typical concentrations for selection are 20 to 40 mg/l. For example, with the mutated ahas genes as the selective marker, PURSUIT™ at a concentration of from about 3 to 100 mg/l may be included in the medium. Typical concentrations for selection are 20 to 40 mg/l.

2.1.2 Positive selection marker

Furthermore, positive selection marker can be employed. Genes like isopentenyltransferase from *Agrobacterium tumefaciens* (strain: PO22; Genbank Acc.-No.: AB025109) may—as a key enzyme of the cytokinin biosynthesis—facilitate regeneration of transformed plants (e.g., by selection on cytokinin-free medium). Corresponding selection methods are described (Ebinuma 2000a,b). Additional positive selection markers, which confer a growth advantage to a transformed plant in comparison with a non-transformed one, are described e.g., in EP-A 0 601 092. Growth stimulation selection markers may include (but shall not be limited to) β-Glucuronidase (in combination with e.g., a cytokinin glucuronide), mannose-6-phosphate isomerase (in combination with mannose), UDP-galactose-4-epimerase (in combination with e.g., galactose), wherein mannose-6-phosphate isomerase in combination with mannose is especially preferred.

2.1.3 Counter-Selection Marker

Counter-selection markers are especially suitable to select organisms with defined deleted sequences comprising said marker (Koprek 1999). Examples for counter-selection marker comprise thymidin kinases (TK), cytosine deaminases (Gleave 1999; Perera 1993; Stougaard 1993), cytochrom P450 proteins (Koprek 1999), haloalkan dehalogenases (Naested 1999), iaaH gene products (Sundaresan 1995), cytosine deaminase codA (Schlaman & Hooykaas 1997), tms2 gene products (Fedoroff & Smith 1993), or α-naphthalene acetamide (NAM; Depicker 1988). Counter selection markers may be useful in the construction of transposon tagging lines. For example, by marking an autonomous transposable element such as Ac, Master Mu, or En/Spn with a counter selection marker, one could select for transformants in which the autonomous element is not stably integrated into the genome. This would be desirable, for example, when transient expression of the autonomous element is desired to activate in trans the transposition of a defective transposable element, such as Ds, but stable integration of the autonomous element is not desired. The presence of the autonomous element may not be desired in order to stabilize the defective element, i.e., prevent it from further transposing. However, it is proposed that if stable integration of an autonomous transposable element is desired in a plant the presence of a negative selectable marker may make it possible to eliminate the autonomous element during the breeding process.

2.2. Screenable Markers

Screenable markers that may be employed include, but are not limited to, a beta-glucuronidase (GUS) or uidA gene which encodes an enzyme for which various chromogenic substrates are known; an R-locus gene, which encodes a product that regulates the production of anthocyanin pigments (red color) in plant tissues (Dellaporta 1988); a beta-lactamase gene (Sutcliffe 1978), which encodes an enzyme for which various chromogenic substrates are known (e.g., PADAC, a chromogenic cephalosporin); a xylE gene (Zukowsky 1983) which encodes a catechol dioxygenase that can convert chromogenic catechols; an α-amylase gene (Ikuta 1990); a tyrosinase gene (Katz 1983) which encodes an enzyme capable of oxidizing tyrosine to DOPA and dopaquinone which in turn condenses to form the easily detectable compound melanin; β-galactosidase gene, which encodes an enzyme for which there are chromogenic substrates; a luciferase (lux) gene (Ow 1986), which allows for bioluminescence detection; or even an aequorin gene (Prasher 1985), which may be employed in calcium-sensitive bioluminescence detection, or a green fluorescent protein gene (Niedz 1995).

Genes from the maize R gene complex are contemplated to be particularly useful as screenable markers. The R gene complex in maize encodes a protein that acts to regulate the production of anthocyanin pigments in most seed and plant tissue. A gene from the R gene complex was applied to maize transformation, because the expression of this gene in transformed cells does not harm the cells. Thus, an R gene introduced into such cells will cause the expression of a red pigment and, if stably incorporated, can be visually scored as a red sector. If a maize line carries dominant genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together.

It is further proposed that R gene regulatory regions may be employed in chimeric constructs in order to provide mechanisms for controlling the expression of chimeric genes. More diversity of phenotypic expression is known at the R locus than at any other locus (Coe 1988). It is contemplated that regulatory regions obtained from regions 5' to the structural R gene would be valuable in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bol3). Sn is a dominant member of the P gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening. Where use of a screenable marker gene such as lux or GFP is desired, benefit may be realized by creating a gene fusion between the screenable marker gene and a selectable marker gene, for example, a GFP-NPTII gene fusion. This could allow, for example, selection of transformed cells followed by screening of transgenic plants or seeds.

3. Exemplary DNA Molecules

The invention provides an isolated nucleic acid molecule, e.g., DNA or RNA, comprising a plant nucleotide sequence comprising an open reading frame that is preferentially expressed in a specific plant tissue, i.e., in seeds, roots, green tissue (leaf and stem), panicles or pollen, or is expressed constitutively, or a promoter thereof.

These promoters include, but are not limited to, constitutive, inducible, temporally regulated, developmentally regulated, spatially-regulated, chemically regulated, stress-responsive, tissue-specific, viral and synthetic promoters. Promoter sequences are known to be strong or weak. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. A bacterial promoter such as the $P_{tac}$ promoter can be induced to varying levels of gene expression depending on the level of isothiopropylgalactoside added to the transformed bacterial cells. An isolated promoter sequence that is a strong promoter for heterologous nucleic acid is advantageous because it provides for a sufficient level of gene expression to allow for easy detection and selection of transformed cells and provides for a high level of gene expression when desired.

Within a plant promoter region there are several domains that are necessary for full function of the promoter. The first of these domains lies immediately upstream of the structural gene and forms the "core promoter region" containing consensus sequences, normally 70 base pairs immediately upstream of the gene. The core promoter region contains the characteristic CAAT and TATA boxes plus surrounding sequences, and represents a transcription initiation sequence that defines the transcription start point for the structural gene.

The presence of the core promoter region defines a sequence as being a promoter: if the region is absent, the promoter is non-functional. Furthermore, the core promoter region is insufficient to provide full promoter activity. A series of regulatory sequences upstream of the core constitute the remainder of the promoter. The regulatory sequences determine expression level, the spatial and temporal pattern of expression and, for an important subset of promoters, expression under inductive conditions (regulation by external factors such as light, temperature, chemicals, hormones).

Regulated expression of the chimeric transacting viral replication protein can be further regulated by other genetic strategies. For example, Cre-mediated gene activation as described by Odell et al. 1990. Thus, a DNA fragment containing 3' regulatory sequence bound by lox sites between the promoter and the replication protein coding sequence that blocks the expression of a chimeric replication gene from the promoter can be removed by Cre-mediated excision and result in the expression of the trans-acting replication gene. In this case, the chimeric Cre gene, the chimeric trans-acting replication gene, or both can be under the control of tissue- and developmental-specific or inducible promoters. An alternate genetic strategy is the use of tRNA suppressor gene. For example, the regulated expression of a tRNA suppressor gene can conditionally control expression of a trans-acting replication protein coding sequence containing an appropriate termination codon as described by Ulmasov et al. 1997. Again, either the chimeric tRNA suppressor gene, the chimeric transacting replication gene, or both can be under the control of tissue- and developmental-specific or inducible promoters.

Frequently it is desirable to have continuous or inducible expression of a DNA sequence throughout the cells of an organism in a tissue-independent manner. For example, increased resistance of a plant t6 infection by soil- and airborne-pathogens might be accomplished by genetic manipulation of the plant's genome to comprise a continuous promoter operably linked to a heterologous pathogen-resistance gene such that pathogen-resistance proteins are continuously expressed throughout the plant's tissues.

Alternatively, it might be desirable to inhibit expression of a native DNA sequence within the seeds of a plant to achieve a desired phenotype. In this case, such inhibition might be accomplished with transformation of the plant to comprise a promoter operably linked to an antisense nucleotide sequence, such that root-preferential or root-specific expression of the antisense sequence produces an RNA transcript that interferes with translation of the mRNA of the native DNA sequence.

To define a minimal promoter region, a DNA segment representing the promoter region is removed from the 5' region of the gene of interest and operably linked to the coding sequence of a marker (reporter) gene by recombinant DNA techniques well known to the art. The reporter gene is operably linked downstream of the promoter, so that transcripts initiating at the promoter proceed through the reporter gene. Reporter genes generally encode proteins which are easily measured, including, but not limited to, chloramphenicol acetyl transferase (CAT), beta-glucuronidase (GUS), green fluorescent protein (GFP), beta-galactosidase (beta-GAL), and luciferase.

The construct containing the reporter gene under the control of the promoter is then introduced into an appropriate cell type by transfection techniques well known to the art. To assay for the reporter protein, cell lysates are prepared and appropriate assays, which are well known in the art, for the reporter protein are performed. For example, if CAT were the reporter gene of choice, the lysates from cells transfected with constructs containing CAT under the control of a promoter under study are mixed with isotopically labeled chloramphenicol and acetyl-coenzyme A (acetyl-CoA). The CAT enzyme transfers the acetyl group from acetyl-CoA to the 2- or 3-position of chloramphenicol. The reaction is monitored by thin-layer chromatography, which separates acetylated chloramphenicol from unreacted material. The reaction products are then visualized by autoradiography.

The level of enzyme activity corresponds to the amount of enzyme that was made, which in turn reveals the level of expression from the promoter of interest. This level of expression can be compared to other promoters to determine the relative strength of the promoter under study. In order to be sure that the level of expression is determined by the promoter, rather than by the stability of the mRNA, the level of the reporter mRNA can be measured directly, such as by Northern blot analysis.

Once activity is detected, mutational and/or deletional analyses may be employed to determine the minimal region and/or sequences required to initiate transcription. Thus, sequences can be deleted at the 5' end of the promoter region and/or at the 3' end of the promoter region, and nucleotide substitutions introduced. These constructs are then introduced to cells and their activity determined.

In one embodiment, the promoter may be a gamma zein promoter, an oleosin ole16 promoter, a globulins promoter, an actin I promoter an actin cI promoter, a sucrose synthetase promoter, an INOPS promoter, an EXM5 promoter, a globulin2 promoter, a b-32, ADPG-pyrophosphorylase promoter, an Ltp1 promoter, an Ltp2 promoter, an oleosin ole17 promoter, an oleosin ole18 promoter, an actin 2 promoter, a pollen-specific protein promoter, a pollen-specific pectate lyase promoter, an anther-specific protein promoter, an anther-specific gene RTS2 promoter, a pollen-specific gene promoter, a tape turn-specific gene promoter, tape turn-specific gene RAB24 promoter, a anthranilate synthase alpha subunit promoter, an alpha zein promoter, an anthranilate synthase beta subunit promoter, a dihydrodipicolinate synthase promoter, a Thil promoter, an alcohol dehydrogenase promoter, a cab binding protein promoter, an H3C4 promoter, a RUBISCO SS starch branching enzyme promoter, an ACCase promoter, an actin3 promoter, an actin7 promoter, a regulatory protein GF14-12 promoter, a ribosomal protein L9 promoter, a cellulose biosynthetic enzyme promoter, an S-adenosyl-L-homocysteine hydrolase promoter, a superoxide dismutase promoter, a C-kinase receptor promoter, a phosphoglycerate mutase promoter, a root-specific RCc3 mRNA promoter, a glucose-6 phosphate isomerase promoter, a pyrophosphate-fructose 6-phosphatelphosphotransferase promoter, an ubiquitin promoter, a beta-ketoacyl-ACP synthase promoter, a 33 kDa photosystem 11 promoter, an oxygen evolving protein promoter, a 69 kDa vacuolar ATPase subunit promoter, a metallothionein-like protein promoter, a glyceraldehyde-3-phosphate dehydrogenase promoter, an ABA- and ripening-inducible-like protein promoter, a phenylalanine ammonia lyase promoter, an adenosine triphosphatase S-adenosyl-L-homocysteine hydrolase promoter, an α-tubulin promoter, a cab promoter, a PEPCase promoter, an R gene promoter, a lectin promoter, a light harvesting complex promoter, a heat shock protein promoter, a chalcone synthase promoter, a zein promoter, a globulin-1 promoter, an ABA promoter, an auxin-binding protein promoter, a UDP glucose flavonoid glycosyl-transferase gene promoter, an NTI promoter, an actin promoter, an opaque 2 promoter, a b70 promoter, an oleosin promoter, a CaMV 35S promoter, a CaMV 34S promoter, a CaMV 19S promoter, a histone promoter, a turgor-inducible promoter, a pea small subunit RuBP carboxylase promoter, a Ti plasmid mannopine synthase promoter, Ti plasmid nopaline synthase promoter, a petunia chalcone isomerase promoter, a bean glycine rich protein I promoter, a CaMV 35S transcript promoter, a potato patatin promoter, or a S-E9 small subunit RuBP carboxylase promoter.

4. Transformed (Transgenic) Plants of the Invention and Methods of Preparation

Plant species may be transformed with the DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, mega-gametophytes, callus tissue, existing meristematic tissue (e.g., apical meristems, axillary buds, and root meristems), and induced meristem tissue (e.g., cotyledon meristem and ultilane meristem).

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the expression cassette to assist in breeding.

Thus, the present invention provides a transformed (transgenic) plant cell, in planta or ex planta, including a transformed plastid or other organelle, e.g., nucleus, mitochondria or chloroplast. The present invention may be used for transformation of any plant species, including, but not limited to, cells from the plant species specified above in the DEFINITION section. Preferably, transgenic plants of the present invention are crop plants and in particular cereals (for example, corn, alfalfa, sunflower, rice, *Brassica*, canola, soybean, barley, soybean, sugarbeet, cotton, safflower, peanut, sorghum, wheat, millet, tobacco, etc.), and even more preferably corn, rice and soybean. Other embodiments of the invention are related to cells, cell cultures, tissues, parts (such as plants organs, leaves, roots, etc.) and propagation material (such as seeds) of such plants.

The transgenic expression cassette of the invention may not only be comprised in plants or plant cells but may advantageously also be containing in other organisms such for example bacteria. Thus, another embodiment of the invention relates to transgenic cells or non-human, transgenic organisms comprising an expression cassette of the invention. Preferred are prokaryotic and eukaryotic organism. Both microorganism and higher organisms are comprised. Preferred microorganism are bacteria, yeast, algae, and fungi. Preferred bacteria are those of the genus *Escherichia, Erwinia, Agrobacterium, Flavobacterium, Alcaligenes, Pseudomonas, Bacillus* or *Cyanobacterim* such as—for example—*Synechocystis* and other bacteria described in Brock Biology of Microorganisms Eighth Edition (pages A-8, A-9, A10 and A11).

Especially preferred are microorganisms capable to infect plants and to transfer DNA into their genome, especially bacteria of the genus *Agrobacterium*, preferably *Agrobacterium tumefaciens* and *rhizogenes*. Preferred yeasts are *Candida, Saccharomyces, Hansenula* and *Pichia*. Preferred Fungi are *Aspergillus, Trichoderma, Ashbya, Neurospora, Fusarium*, and *Beauveria*. Most preferred are plant organisms as defined above.

Transformation of plants can be undertaken with a single DNA molecule or multiple DNA molecules (i.e., co-transformation), and both these techniques are suitable for use with the expression cassettes of the present invention. Numerous transformation vectors are available for plant transformation, and the expression cassettes of this invention can be used in conjunction with any such vectors. The selection of vector will depend upon the preferred transformation technique and the target species for transformation.

A variety of techniques are available and known to those skilled in the art for introduction of constructs into a plant cell host. These techniques generally include transformation with DNA employing *A. tumefaciens* or *A. rhizogenes* as the transforming agent, liposomes, PEG precipitation, electroporation, DNA injection, direct DNA uptake, microprojectile bombardment, particle acceleration, and the like (See, for example, EP 295959 and EP 138341) (see below). However, cells other than plant cells may be transformed with the expression cassettes of the invention. The general descriptions of plant expression vectors and reporter genes, and *Agrobacterium* and *Agrobacterium*-mediated gene transfer, can be found in Gruber et al. (1993).

Expression vectors containing genomic or synthetic fragments can be introduced into protoplasts or into intact tissues or isolated cells. Preferably expression vectors are introduced into intact tissue. General methods of culturing plant tissues are provided for example by Maki et al., (1993); and by Phillips et al. (1988). Preferably, expression vectors are introduced into maize or other plant tissues using a direct gene transfer method such as microprojectile-mediated delivery, DNA injection, electroporation and the like. More preferably expression vectors are introduced into plant tissues using the microprojectile media delivery with the biolistic device. See, for example, Tomes et al. (1995). The vectors of the invention can not only be used for expression of structural genes but may also be used in exon-trap cloning, or promoter trap procedures to detect differential gene expression in varieties of tissues (Lindsey 1993; Auch & Reth 1990).

It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciotti 1985: Byrne 1987; Sukhapinda 1987; Lorz 1985; Potrykus, 1985; Park 1985: Hiei 1994). The use of T-DNA to transform plant cells has received extensive study and is amply described (EP 120516; Hoekema, 1985; Knauf, 1983; and An 1985). For introduction into plants, the chimeric genes of the invention can be inserted into binary vectors as described in the examples.

Other transformation methods are available to those skilled in the art, such as direct uptake of foreign DNA constructs (see EP 295959), techniques of electroporation (Fromm 1986) or high velocity ballistic bombardment with metal particles coated with the nucleic acid constructs (Kline 1987, and U.S. Pat. No. 4,945,050). Once transformed, the cells can be regenerated by those skilled in the art. Of particular relevance are the recently described methods to transform foreign genes into commercially important crops, such as rapeseed (De Block 1989), sunflower (Everett 1987), soybean (McCabe 1988; Hinchee 1988; Chee 1989; Christou 1989; EP 301749), rice (Hiei 1994), and corn (Gordon-Kamm 1990; Fromm 1990).

Those skilled in the art will appreciate that the choice of method might depend on the type of plant, i.e., monocotyledonous or dicotyledonous, targeted for transformation. Suitable methods of transforming plant cells include, but are not limited to, microinjection (Crossway 1986), electroporation (Riggs 1986), *Agrobacterium*-mediated transformation (Hinchee 1988), direct gene transfer (Paszkowski 1984), and ballistic particle acceleration using devices available from Agracetus, Inc., Madison, Wis. And BioRad, Hercules, Calif. (see, for example, U.S. Pat. No. 4,945,050; and McCabe 1988). Also see, Weissinger 1988; Sanford 1987 (onion); Christou 1988 (soybean); McCabe 1988 (soybean); Datta 1990 (rice); Klein 1988 (maize); Klein 1988 (maize); Klein 1988 (maize); Fromm 1990 (maize); and Gordon-Kamm 1990 (maize); Svab 1990 (tobacco chloroplast); Koziel 1993 (maize); Shimamoto 1989 (rice); Christou 1991 (rice); European Patent Application EP 0 332 581 (orchardgrass and other Pooideae); Vasil 1993 (wheat); Weeks 1993 (wheat).

In another embodiment, a nucleotide sequence of the present invention is directly transformed into the plastid genome. Plastid transformation technology is extensively described in U.S. Pat. Nos. 5,451,513, 5,545,817, and 5,545,818, in PCT application no. WO 95/16783, and in McBride et al., 1994. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate orthologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab 1990; Staub 1992). This resulted in stable homoplasmic transformants at a frequency of approximately one per 100 bombardments of target leaves. The presence of cloning sites between these markers allowed creation of a plastid targeting vector for introduction of foreign genes (Staub 1993). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3N-adenyltransferase (Svab 1993). Other selectable markers useful for plastid transformation are known in the art and encompassed within the scope of the invention. Typically, approximately 15-20 cell division cycles following transformation are required to reach a homoplastidic state. Plastid expression, in which genes are inserted by orthologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid targeting vector and transformed into the plastid genome of a desired plant host. Plants homoplastic for plastid genomes containing a nucleotide sequence of the present invention are obtained, and are preferentially capable of high expression of the nucleotide sequence.

*Agrobacterium tumefaciens* cells containing a vector comprising an expression cassette of the present invention, wherein the vector comprises a Ti plasmid, are useful in methods of making transformed plants. Plant cells are infected with an *Agrobacterium tumefaciens* as described above to produce a transformed plant cell, and then a plant is regenerated from the transformed plant cell. Numerous *Agrobacterium* vector systems useful in carrying out the present invention are known.

Various *Agrobacterium* strains can be employed, preferably disarmed *Agrobacterium tumefaciens* or *rhizogenes* strains. In a preferred embodiment, *Agrobacterium* strains for use in the practice of the invention include octopine strains, e.g., LBA4404 or agropine strains, e.g., EHA101 or EHA105. Suitable strains of *A. tumefaciens* for DNA transfer are for example EHA101[pEHA101] (Hood 1986), EHA105[pEHA105] (Li 1992), LBA4404[pAL4404] (Hoekema 1983), C58C1[pMP90] (Koncz & Schell 1986), and C58C1[pGV2260] (Deblaere 1985). Other suitable strains are *Agrobacterium tumefaciens* C58, a nopaline strain. Other suitable strains are *A. tumefaciens* C58C1 (Van Larebeke 1974), A136 (Watson 1975) or LBA4011 (Kiapwijk 1980). In another preferred embodiment the soil-borne bacterium is a disarmed variant of *Agrobacterium rhizogenes* strain K599 (NCPPB 2659). Preferably, these strains are comprising a disarmed plasmid variant of a Ti- or Ri-plasmid providing the functions required for T-DNA transfer into plant cells (e.g., the vir genes). In a preferred embodiment, the *Agrobacterium* strain used to transform the plant tissue pre-cultured with the plant phenolic compound contains a L,L-succinamopine type Ti-plasmid, preferably disarmed, such as pEHA101. In another preferred embodiment, the *Agrobacterium* strain used to transform the plant tissue pre-cultured with the plant phenolic compound contains an octopine-type Ti-plasmid, preferably disarmed, such as pAL4404. Generally, when using octopine-type Ti-plasmids or helper plasmids, it is preferred that the virF gene be deleted or inactivated (Jarschow 1991).

The method of the invention can also be used in combination with particular *Agrobacterium* strains, to further increase the transformation efficiency, such as *Agrobacterium* strains wherein the vir gene expression and/or induction thereof is altered due to the presence of mutant or chimeric virA or virG genes (e.g. Hansen 1994; Chen and Winans 1991; Scheeren-Groot, 1994). Preferred are further combinations of *Agrobacterium tumefaciens* strain LBA4404 (Hiei 1994) with super-virulent plasmids. These are preferably pTOK246-based vectors (Ishida 1996).

A binary vector or any other vector can be modified by common DNA recombination techniques, multiplied in *E. coli*, and introduced into *Agrobacterium* by e.g., electroporation or other transformation techniques (Mozo & Hooykaas 1991).

*Agrobacterium* is grown and used in a manner similar to that described in Ishida (1996). The vector comprising *Agrobacterium* strain may, for example, be grown for 3 days on YP medium (5 g/l yeast extract, 10 g/l peptone, 5 g/l NaCl, 15 g/l agar, pH 6.8) supplemented with the appropriate antibiotic (e.g., 50 mg/l spectinomycin). Bacteria are collected with a loop from the solid medium and resuspended. In a preferred embodiment of the invention, *Agrobacterium* cultures are started by use of aliquots frozen at −80° C.

The transformation of the target tissue (e.g., an immature embryo) by the *Agrobacterium* may be carried out by merely contacting the target tissue with the *Agrobacterium*. The concentration of *Agrobacterium* used for infection and co-cultivation may need to be varied. For example, a cell suspension of the *Agrobacterium* having a population density of approximately from 105-$10^{11}$, preferably $10^6$ to $10^{10}$, more preferably about $10^8$ cells or cfu/ml is prepared and the target tissue is immersed in this suspension for about 3 to 10 minutes. The resulting target tissue is then cultured on a solid medium for several days together with the *Agrobacterium*.

Preferably, the bacterium is employed in concentration of $10^6$ to $10^{10}$ cfu/ml. In a preferred embodiment for the co-cultivation step about 1 to 10 μl of a suspension of the soil-borne bacterium (e.g., *Agrobacteria*) in the co-cultivation medium are directly applied to each target tissue explant and air-dried. This is saving labor and time and is reducing unintended *Agrobacterium*-mediated damage by excess *Agrobacterium* usage.

For *Agrobacterium* treatment, the bacteria are resuspended in a plant compatible co-cultivation medium. Supplementation of the co-culture medium with antioxidants (e.g., silver nitrate), phenol-absorbing compounds (like polyvinylpyrrolidone, Perl 1996) or thiol compounds (e.g., dithiothreitol, L-cysteine, Olhoft 2001) which can decrease tissue necrosis due to plant defense responses (like phenolic oxidation) may further improve the efficiency of *Agrobacterium*-mediated transformation. In another preferred embodiment, the co-cultivation medium of comprises least one thiol compound, preferably selected from the group consisting of sodium thiosulfate, dithiotrietol (DTT) and cysteine. Preferably the concentration is between about 1 mM and 10 mM of L-Cysteine, 0.1 mM to 5 mM DTT, and/or 0.1 mM to 5 mM sodium thiosulfate. Preferably, the medium employed during co-cultivation comprises from about 1 μM to about 10 μM of silver nitrate and from about 50 mg/L to about 1,000 mg/L of L-Cystein. This results in a highly reduced vulnerability of the target tissue against *Agrobacterium*-mediated damage (such as induced necrosis) and highly improves overall transformation efficiency.

Various vector systems can be used in combination with *Agrobacteria*. Preferred are binary vector systems. Common binary vectors are based on "broad host range"-plasmids like pRK252 (Bevan 1984) or pTJS75 (Watson 1985) derived from the P-type plasmid RK2. Most of these vectors are derivatives of pBIN19 (Bevan 1984). Various binary vectors are known, some of which are commercially available such as, for example, pBI101.2 or pBIN19 (Clontech Laboratories, Inc. USA). Additional vectors were improved with regard to size and handling (e.g. pPZP; Hajdukiewicz 1994). Improved vector systems are described also in WO 02/00900.

Methods using either a form of direct gene transfer or *Agrobacterium*-mediated transfer usually, but not necessarily, are undertaken with a selectable marker which may provide resistance to an antibiotic (e.g., kanamycin, hygromycin or methotrexate) or a herbicide (e.g., phosphinothricin). The choice of selectable marker for plant transformation is not, however, critical to the invention.

For certain plant species, different antibiotic or herbicide selection markers may be preferred. Selection markers used routinely in transformation include the nptII gene which confers resistance to kanamycin and related antibiotics (Messing & Vierra, 1982; Bevan 1983), the bar gene which confers resistance to the herbicide phosphinothricin (White 1990, Spencer 1990), the hph gene which confers resistance to the antibiotic hygromycin (Blochlinger & Diggelmann), and the dhfr gene, which confers resistance to methotrexate (Bourouis 1983).

5. Production and Characterization of Stably Transformed Plants

Transgenic plant cells are then placed in an appropriate selective medium for selection of transgenic cells which are then grown to callus. Shoots are grown from callus and plantlets generated from the shoot by growing in rooting medium. The various constructs normally will be joined to a marker for selection in plant cells. Conveniently, the marker may be resistance to a biocide (particularly an antibiotic, such as kanamycin, G418, bleomycin, hygromycin, chloramphenicol, herbicide, or the like). The particular marker used will allow for selection of transformed cells as compared to cells lacking the DNA which has been introduced. Components of DNA constructs including transcription cassettes of this invention may be prepared from sequences which are native (endogenous) or foreign (exogenous) to the host. By "foreign" it is meant that the sequence is not found in the wild-type host into which the construct is introduced.

Heterologous constructs will contain at least one region which is not native to the gene from which the transcription-initiation-region is derived.

To confirm the presence of the transgenes in transgenic cells and plants, a variety of assays may be performed. Such assays include, for example, "molecular biological" assays well known to those of skill in the art, such as Southern and Northern blotting, in situ hybridization and nucleic acid-based amplification methods such as PCR or RT-PCR; "biochemical" assays, such as detecting the presence of a protein product, e.g., by immunological means (ELISAs and Western blots) or by enzymatic function; plant part assays, such as seed assays; and also, by analyzing the phenotype of the whole regenerated plant, e.g., for disease or pest resistance.

DNA may be isolated from cell lines or any plant parts to determine the presence of the preselected nucleic acid segment through the use of techniques well known to those skilled in the art. Note that intact sequences will not always be present, presumably due to rearrangement or deletion of sequences in the cell.

The presence of nucleic acid elements introduced through the methods of this invention may be determined by potymerase chain reaction (PCR). Using this technique discreet fragments of nucleic acid are amplified and detected by gel electrophoresis. This type of analysis permits one to determine whether a preselected nucleic acid segment is present in a stable transformant, but does not prove integration of the introduced preselected nucleic acid segment into the host cell genome. In addition, it is not possible using PCR techniques to determine whether transformants have exogenous genes introduced into different sites in the, genome, i.e., whether transformants are of independent origin. It is contemplated that using PCR techniques it would be possible to clone fragments of the host genomic DNA adjacent to an introduced preselected DNA segment.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced preselected DNA segments in high molecular weight DNA, i.e., confirm that the introduced preselected, DNA segment has been integrated into the host cell genome. The technique of Southern hybridization provides information that is obtained using PCR, e.g., the presence of a preselected DNA segment, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a preselected DNA segment.

Both PCR and Southern hybridization techniques can be used to demonstrate transmission of a preselected DNA segment to progeny. In most instances the characteristic Southern hybridization pattern for a given transformant will segregate in progeny as one or more Mendelian genes (Spencer 1992); Laursen 1994) indicating stable inheritance of the gene. The non-chimeric nature of the callus and the parental transformants ($R_0$) was suggested by germline transmission and the identical Southern blot hybridization patterns and intensities of the transforming DNA in callus, $R_0$ plants and $R_1$ progeny that segregated for the transformed gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced preselected DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the protein products of the introduced preselected DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed.

Very frequently the expression of a gene product is determined by evaluating the phenotypic results of its expression. These assays also may take many forms including but not limited to analyzing changes in the chemical composition, morphology, or physiological properties of the plant. Morphological changes may include greater stature or thicker stalks. Most often changes in response of plants or plant parts to imposed treatments are evaluated under carefully controlled conditions termed bioassays.

6. Uses of Transgenic Plants

Once an expression cassette of the invention has been transformed into a particular plant species, it may be propagated in that species or moved into other varieties of the same species, particularly including commercial varieties, using traditional breeding techniques. Particularly preferred plants of the invention include the agronomically important crops listed above. The genetic properties engineered into the transgenic seeds and plants described above are passed on by sexual reproduction and can thus be maintained and propagated in progeny plants. The present invention also relates to a transgenic plant cell, tissue, organ, seed or plant part obtained from the transgenic plant. Also included within the invention are transgenic descendants of the plant as well as transgenic plant cells, tissues, organs, seeds and plant parts obtained from the descendants.

Preferably, the expression cassette in the transgenic plant is sexually transmitted. In one preferred embodiment, the coding sequence is sexually transmitted through a complete normal sexual cycle of the R0 plant to the R1 generation. Additionally preferred, the expression cassette is expressed in the cells, tissues, seeds or plant of a transgenic plant in an amount that is different than the amount in the cells, tissues, seeds or plant of a plant which only differs in that the expression cassette is absent.

The transgenic plants produced herein are thus expected to be useful for a variety of commercial and research purposes. Transgenic plants can be created for use in traditional agriculture to possess traits beneficial to the grower (e.g., agronomic traits such as resistance to water deficit, pest resistance, herbicide resistance or increased yield), beneficial to the consumer of the grain harvested from the plant (e.g., improved nutritive content in human food or animal feed; increased vitamin, amino acid, and antioxidant content; the production of antibodies (passive immunization) and nutriceuticals), or beneficial to the food processor (e.g., improved processing traits). In such uses, the plants are generally grown for the use of their grain in human or animal foods. Additionally, the use of root-specific promoters in transgenic plants can provide beneficial traits that are localized in the consumable (by animals and humans) roots of plants such as carrots, parsnips, and beets. However, other parts of the plants, including stalks, husks, vegetative parts, and the like, may also have utility, including use as part of animal silage or for ornamental purposes. Often, chemical constituents (e.g., oils or starches) of maize and other crops are extracted for foods or industrial use and transgenic plants may be created which have enhanced or modified levels of such components.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules. The transgenic plants may also be used in commercial breeding programs, or may be crossed or bred to plants of related crop species. Improvements encoded by the expression cassette may be transferred, e.g., from maize cells to cells of other species, e.g., by protoplast fusion.

The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences which can be used to identify proprietary lines or varieties.

Thus, the transgenic plants and seeds according to the invention can be used in plant breeding which aims at the development of plants with improved properties conferred by the expression cassette, such as tolerance of drought, disease, or other stresses. The various breeding steps are characterized by well-defined human intervention such as selecting the lines to be crossed, directing pollination of the parental lines, or selecting appropriate descendant plants. Depending on the desired properties different breeding measures are taken. The relevant techniques are well known in the art and include but are not limited to hybridization, inbreeding, backcross breeding, multilane breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines which for example increase the effectiveness of conventional methods such as herbicide or pesticide treatment or allow to dispense with said methods due to their modified genetic properties. Alternatively new crops with improved stress tolerance can be obtained which, due to their optimized genetic "equipment", yield harvested product of better quality than products which were not able to tolerate comparable adverse developmental conditions.

EXAMPLES

Materials and General Methods

Unless indicated otherwise, chemicals and reagents in the Examples were obtained from Sigma Chemical Company (St. Louis, Mo.), restriction endonucleases were from New England Biolabs (Beverly, Mass.) or Roche (Indianapolis, Ind.), oligonucleotides were synthesized by MWG Biotech Inc. (High Point, N.C.), and other modifying enzymes or kits regarding biochemicals and molecular biological assays were from Clontech (Palo Alto, Calif.), Pharmacia Biotech (Piscataway, N.J.), Promega Corporation (Madison, Wis.), or Stratagene (La Jolla, Calif.). Materials for cell culture media were obtained from Gibco/BRL (Gaithersburg, Md.) or DIFCO (Detroit, Mich.). The cloning steps carried out for the purposes of the present invention, such as, for example, restriction cleavages, agarose gel electrophoresis, purification of DNA fragments, transfer of nucleic acids to nitrocellulose and nylon membranes, linking DNA fragments, transformation of *E. coli* cells, growing bacteria, multiplying phages and sequence analysis of recombinant DNA, are carried out as described by Sambrook (1989). The sequencing of recombinant DNA molecules is carried out using ABI laser fluorescence DNA sequencer following the method of Sanger (Sanger 1977).

For generating transgenic *Arabidopsis* plants *Agrobacterium tumefaciens* (strain C58C1[pMP90]) is transformed with the various promoter:GUS vector constructs (see below). Resulting *Agrobacterium* strains are subsequently employed to obtain transgenic plants. For this purpose a isolated transformed *Agrobacterium* colony is incubated in 4 ml culture (Medium: YEB medium with 50 μg/ml Kanamycin and 25 μg/ml Rifampicin) over night at 28° C. With this culture a 400 ml culture of the same medium is inoculated and incubated over night (28° C., 220 rpm). The bacteria a precipitated by centrifugation (GSA-Rotor, 8.000 U/min, 20 min) and the pellet is resuspended in infiltration medium (½ MS-Medium; 0.5 g/l MES, pH 5.08; 50 g/l sucrose). The suspension is placed in a plant box (Duchefa) and 100 ml SILVET L-77 (Osi Special-ties Inc, Cat. P030196) are added to a final concentration of 0.02%. The plant box with 8 to 12 Plants is placed into an exsiccator for 10 to 15 min. under vacuum with subsequent, spontaneous ventilation (expansion). This process is repeated 2-3 times. Thereafter all plants are transferred into pods with wet-soil and grown under long daytime conditions (16 h light; day temperature 22-24° C., night temperature 19° C.; 65% rel. humidity). Seeds are harvested after 6 weeks.

Example 1

Growth Conditions for Plants for Tissue-Specific Expression Analysis

To obtain 4 and 7 days old seedlings, about 400 seeds (*Arabidopsis thaliana* ecotype Columbia) are sterilized with a 80% (v/v) ethanol:water solution for 2 minutes, treated with a sodium hypochlorite solution (0.5% v/v) for 5 minutes, washed three times with distillated water and incubated at 4° C. for 4 days to ensure a standardized germination. Subsequently, seeds are incubated on Petri dishes with MS medium (Sigma M5519) supplemented with 1% sucrose, 0.5 g/l MES (Sigma M8652), 0.8% Difco-BactoAgar (Difco 0140-01), adjusted to pH 5.7. The seedlings are grown under 16 h light/8 h dark cyklus (Philips 58W/33 white light) at 22° C. and harvested after 4 or 7 days, respectively.

To obtain root tissue, 100 seeds are sterilized as described above, incubated at 4° C. for 4 days, and transferred into 250 ml flasks with MS medium (Sigma M5519) supplemented with additional 3% sucrose and 0.5 g/l MES (Sigma M8652), adjusted to pH 5.7 for further growing. The seedlings are grown at a 16 h light/8 h dark cycle (Philips 58W/33 white light) at 22° C. and 120 rpm and harvested after 3 weeks. For all other plant organs employed, seeds are sown on standard soil (Type VM, Manna-Italia, Via S. Giacomo 42, 39050 San Giacomo/Laives, Bolzano, Italien), incubated for 4 days at 4° C. to ensure uniform germination, and subsequently grown under a 16 h light/8 darkness regime (OSRAM Lumi-lux Daylight 36W/12) at 22° C. Young rosette leaves are harvested at the 8-leaf stage (after about 3 weeks), mature rosette leaves are harvested after 8 weeks briefly before stem formation. Apices of out-shooting stems are harvested briefly after out-shooting. Stems stem leaves, and flower buds are harvested in development stage 12 (Bowmann J (ed.), *Arabidopsis*, Atlas of Morphology, Springer N.Y., 1995) prior to stamen development. Open flowers are harvested in development stage 14 immediately after stamen development. Wilting flowers are harvested in stage 15 to 16. Green and yellow shoots used for the analysis have a length of 10 to 13 mm.

Example 2

Demonstration of Expression Profile

To demonstrate and analyze the transcription regulating properties of a promoter of the useful to operably link the promoter or its fragments to a reporter gene, which can be employed to monitor its expression both qualitatively and quantitatively. Preferably bacterial β-glucuronidase is used (Jefferson 1987). β-glucuronidase activity can be monitored in planta with chromogenic substrates such as 5-bromo-4-Chloro-3-indolyl-β-D-glucuronic acid during corresponding activity assays (Jefferson 1987). For determination of promoter activity and tissue specificity plant tissue is dissected, embedded, stained and analyzed as described (e.g., Bäumlein 1991).

For quantitative β-glucuronidase activity analysis MUG (methylumbelliferyl glucuronide) is used as a substrate, which is converted into MU (methylumbelliferone) and glucuronic acid. Under alkaline conditions this conversion can be quantitatively monitored fluorometrically (excitation at 365 nm, measurement at 455 nm; SpectroFluorimeter Thermo Life Sciences Fluoroscan) as described (Bustos 1989).

Example 3

Cloning of the Promoter Fragments

To isolate the promoter fragments described by SEQ ID NO: 1, 2, 3, 4, 7, 8, 9, 10, 11, 14, 15, 16, 19, 20, 21, 24, 25, 26, 29, 30, 31, 34, 35, 36, 37, 40, 41, and 42, genomic DNA is isolated from *Arabidopsis thaliana* (ecotype Columbia) as described (Galbiati 2000). The isolated genomic DNA is employed as matrix DNA for a polymerase chain reaction (PCR) mediated amplification using the oligonucleotide primers and protocols indicated below (Table 3).

TABLE 3

PCR conditions and oligonucleotide primers for amplification of the various transcription regulating sequences

| SEQ ID | Promoter | Forward Primer | Reverse Primer | Restriction enzymes |
|---|---|---|---|---|
| SEQ ID NO: 1 | pSUK320 | UH320for SEQ ID NO: 45 | UH320rev SEQ ID NO: 46 | XhoI/BamHI |
| SEQ ID NO: 2 | pSUH320L | UH320for SEQ ID NO: 45 | UH320Lrev SEQ ID NO: 47 | XhoI/BamHI |
| SEQ ID NO: 3 | pSUH320S | UH320for SEQ ID NO: 45 | UH320Srev SEQ ID NO: 48 | XhoI/BamHI |
| SEQ ID NO: 4 | pSUK320GB | UH320for SEQ ID NO: 45 | UH320rev SEQ ID NO: 46 | XhoI/BamHI |

TABLE 3-continued

PCR conditions and oligonucleotide primers for amplification of the various transcription regulating sequences

| SEQ ID | Promoter | Forward Primer | Reverse Primer | Restriction enzymes |
|---|---|---|---|---|
| SEQ ID NO: 7 | pSUH335L | UH335for SEQ ID NO: 49 | UH335rev SEQ ID NO: 50 | BamHI/NcoI |
| SEQ ID NO: 8 | pSUH335S | UH335for SEQ ID NO: 49 | UH335Srev SEQ ID NO: 51 | BamHI/NcoI |
| SEQ ID NO: 9 | pSUH335GB | UH335for SEQ ID NO: 49 | UH335rev SEQ ID NO: 50 | BamHI/NcoI |
| SEQ ID NO: 10 | pSUH338 | UH338for SEQ ID NO: 52 | UH335rev SEQ ID NO: 50 | BamHI/NcoI |
| SEQ ID NO: 11 | pSUH338GB | UH338for SEQ ID NO: 52 | UH335rev SEQ ID NO: 50 | BamHI/NcoI |
| SEQ ID NO: 14 | pSUH307 | UH307for SEQ ID NO: 53 | UH307rev SEQ ID NO: 54 | BamHI/NcoI |
| SEQ ID NO: 15 | pSUH307S | UH307for SEQ ID NO: 53 | UH307Srev SEQ ID NO: 55 | BamHI/NcoI |
| SEQ ID NO: 16 | pSUH307GB | UH307for SEQ ID NO: 53 | UH307rev SEQ ID NO: 54 | BamHI/NcoI |
| SEQ ID NO: 19 | pSUH319 | UH319for SEQ ID NO: 56 | UH319rev SEQ ID NO: 57 | BamHI/NcoI |
| SEQ ID NO: 20 | pSUH319S | UH319for SEQ ID NO: 56 | UH319Srev SEQ ID NO: 58 | BamHI/NcoI |
| SEQ ID NO: 21 | pSUH319GB | UH319for SEQ ID NO: 56 | UH319rev SEQ ID NO: 57 | BamHI/NcoI |
| SEQ ID NO: 24 | pSUH349 | UH349for SEQ ID NO: 59 | UH349rev SEQ ID NO: 60 | XhoI/BamHI |
| SEQ ID NO: 25 | pSUH349S | UH349for SEQ ID NO: 59 | UH349Srev SEQ ID NO: 61 | XhoI/BamHI |
| SEQ ID NO: 26 | pSUH349GB | UH349for SEQ ID NO: 59 | UH349rev SEQ ID NO: 60 | XhoI/BamHI |
| SEQ ID NO: 29 | pSUH372 | UH372for SEQ ID NO: 62 | UH372rev SEQ ID NO: 63 | BamHI/NcoI |
| SEQ ID NO: 30 | pSUH372S | UH372for SEQ ID NO: 62 | UH372Srev SEQ ID NO: 64 | BamHI/NcoI |
| SEQ ID NO: 31 | pSUH372GB | UH372for SEQ ID NO: 62 | UH372rev SEQ ID NO: 63 | BamHI/NcoI |
| SEQ ID NO: 34 | pSUH378 | UH378for SEQ ID NO: 65 | UH378rev SEQ ID NO: 66 | BamHI/NcoI |
| SEQ ID NO: 35 | pSUH378GB | UH378for SEQ ID NO: 65 | UH378rev SEQ ID NO: 66 | BamHI/NcoI |
| SEQ ID NO: 36 | pSUH382 | UH378for SEQ ID NO: 65 | UH378rev SEQ ID NO: 66 | EcoRI/NcoI |
| SEQ ID NO: 37 | pSUH382GB | UH378for SEQ ID NO: 65 | UH378rev SEQ ID NO: 66 | EcoRI/NcoI |
| SEQ ID NO: 40 | pSUH379 | UH379for SEQ ID NO: 67 | UH379rev SEQ ID NO: 68 | XhoI/BamHI |
| SEQ ID NO: 41 | pSUH379S | UH379for SEQ ID NO: 67 | UH379Srev SEQ ID NO: 69 | XhoI/BamHI |
| SEQ ID NO: 42 | pSUH379GB | UH379for SEQ ID NO: 67 | UH379rev SEQ ID NO: 68 | XhoI/BamHI |

Amplification is carried out as follows:

100 ng genomic DNA

1×PCR buffer 2.5 mM MgCl2,

200 μM each of dATP, dCTP, dGTP und dTTP 10 pmol of each oligonucleotide primers 2.5 Units Pfu DNA Polymerase (Stratagene)

in a final volume of 50 μl

The following temperature program is employed for the various amplifications (BIORAD Thermocycler). The annealing temperature (Ta) is specific for the primer pairs and given in the Table above.

1. 95° C. for 5 min 2. 54° C. for 1 min, followed by 72° C. for 5 min and 95° C. for 30 sec. Repeated 25 times 3. 54° C. for 1 min, followed by 72° C. for 10 min.

4. Storage at 4° C.

The resulting PCR-products are digested with the restriction endonucleases specified in the Table above and cloned into the vector pSUN0301 (SEQ ID NO: 68) (pre-digested with the same enzymes) upstream and in operable linkage to the glucuronidase (GUS) gene. Following stable transformation of each of these constructs into *Arabidopsis thaliana* tissue specificity and expression profile was analyzed by a histochemical and quantitative GUS-assay, respectively.

Example 4

Expression Profile of the Various Promoter:GUS Constructs in Stably Transformed *A. thaliana* Plants 4.1 pSUH320, pSUH320S, pSUH320L and pSUH320GB The promoter sequences derived from gene At1g66280 confer a strong and highly specific expression in roots and in particular in vascular bundles. No expression is observed in root tips, root epidermis and in all other tissues analyzed (seedlings, leaves, stem, flowers, shoots, seeds).

4.2 pSUH335S, pSUH335L, pSUH335GB, pSUH338, and pSUH338GB

The promoter sequences derived from gene At1g74500 confer a medium to strong and highly specific expression in roots and in particular in root tips and growing roots. No expression is observed in all other tissues analyzed (seedlings, leaves, stem, flowers, shoots, seeds).

4.3 pSUH307, pSUH307S and pSUH307GB

The promoter sequences derived from gene At1g49570 demonstrate an extraordinary strong and uniform expression in roots except root tips of seedlings and adult plants. During flower development weak side activities are observed in flower buds and immature anthers.

4.4 pSUH349, pSUH349S and pSUH349GB

The promoter sequences derived from gene At5g66690 confer a very strong expression in growing roots. There are weak side activities in young flower buds and sometimes in stems.

4.5 pSUH372, pSUH372S and pSUH372GB

The promoter sequences derived from gene At3g26930 drive preferentially expression in roots. Expression in roots is very strong except in root tips. Weak side activities are seen in vascular tissues of siliques, leaves, stems and seed coats.

4.6 pSUH378, pSUH378GB, pSUH382 and pSUH382GB

The promoter sequences derived from gene At5g48070 drive preferentially expression in roots. Expression in roots is medium to strong and mainly localized in central cylinder. Weak side activities are seen in tips and basis of young siliques as well as in vascular tissue of leaves and stems.

4.7 pSUH319, pSUH319S and pSUH319GB

The promoter sequences derived from gene At1g70710 drive preferentially expression in roots. The medium expression is mainly localized in central cylinder of roots. There are side activities in stem, siliques, seeds as well as in guard cells of leaves.

4.8 pSUH379

The promoter sequences derived from gene At4g17800 drive preferentially expression in roots. Expression in roots is uniform with medium strength except in root tips of adult plants. Weak side activities are observed in leaf tips, stamen and trichomes.

Example 5

Vector Construction for Overexpression and Gene "Knockout" Experiments 5.1 Overexpression Vectors used for expression of full-length "candidate genes" of interest in plants (overexpression) are designed to overexpress the protein of interest and are of two general types, biolistic and binary, depending on the plant transformation method to be used.

For biolistic transformation (biolistic vectors), the requirements are as follows:

1. a backbone with a bacterial selectable marker (typically, an antibiotic resistance gene) and origin of replication functional in *Escherichia coli* (*E. coli*; e.g., ColE1), and
2. a plant-specific portion consisting of:
    a. a gene expression cassette consisting of a promoter (eg. ZmUBlint MOD), the gene of interest (typically, a full-length cDNA) and a transcriptional terminator (e.g., *Agrobacterium tumefaciens* nos terminator);
    b. a plant selectable marker cassette, consisting of a suitable promoter, selectable marker gene (e.g., D-amino acid oxidase; dao1) and transcriptional terminator (eg. nos terminator).

Vectors designed for transformation by *Agrobacterium tumefaciens* (*A. tumefaciens*; binary vectors) consist of:

1. a backbone with a bacterial selectable marker functional in both *E. coli* and *A. tumefaciens* (e.g., spectinomycin resistance mediated by the aadA gene) and two origins of replication, functional in each of aforementioned bacterial hosts, plus the *A. tumefaciens* virG gene;
2. a plant-specific portion as described for biolistic vectors above, except in this instance this portion is flanked by *A. tumefaciens* right and left border sequences which mediate transfer of the DNA flanked by these two sequences to the plant.

5.2 Gene Silencing Vectors

Vectors designed for reducing or abolishing expression of a single gene or of a family or related genes (gene silencing vectors) are also of two general types corresponding to the methodology used to down regulate gene expression: antisense or double-stranded RNA interference (dsRNAi).

(a) Anti-Sense

For antisense vectors, a full-length or partial gene fragment (typically, a portion of the cDNA) can be used in the same vectors described for full-length expression, as part of the gene expression cassette. For antisense-mediated down-regulation of gene expression, the coding region of the gene or gene fragment will be in the opposite orientation relative to the promoter; thus, mRNA will be made from the non-coding (antisense) strand in planta.

(b) dsRNAi

For dsRNAi vectors, a partial gene fragment (typically, 300 to 500 base pairs long) is used in the gene expression cassette, and is expressed in both the sense and antisense orientations, separated by a spacer region (typically, a plant intron, eg. the OsSH1 intron 1, or a selectable marker, eg. conferring kanamycin resistance). Vectors of this type are designed to form a double-stranded mRNA stem, resulting from the base pairing of the two complementary gene fragments in planta.

Biolistic or binary vectors designed for overexpression or knockout can vary in a number of different ways, including eg. the selectable markers used in plant and bacteria, the transcriptional terminators used in the gene expression and plant selectable marker cassettes, and the methodologies used for cloning in gene or gene fragments of interest (typically, conventional restriction enzyme-mediated or Gateway™ recombinase-based cloning).

REFERENCES

1. Abel et al., Science, 232:738 (1986).
2. Altschul et al., Nucleic Acids Res., 25:3389 (1997).
3. Altschul et al., J. Mol. Biol., 215:403 (1990).
4. An et al., EMBO J., 4:277 (1985).
5. Auch & Reth, Nucleic Acids Research, 18:6743 (1990).

6. Ausubel et al. (1987) Current Protocols in Molecular Biology, Greene Publishing Assoc. and Wiley Interscience
7. Ballas et al., Nucleic Acids Res., 17:7891 (1989).
8. Barkai-Golan et al., Arch. Microbiol., 116:119 (1978).
9. Batzer et al., Nucleic Acid Res., 19:5081 (1991).
10. Bäumlein et al. Mol Gen Genet 225:121-128 (1991)
11. Becker et al. (1994) Plant J., 5:299-307,
12. Bernal-Lugo and Leopold, Plant Physiol., 98:1207 (1992).
13. Bevan et al., Nature, 304:184 (1983).
14. Bevan et al., Nucl. Acids Res., 11:369 (1983).
15. Bevan, Nucl. Acids Res., 12:8711 (1984).
16. Blackman et al., Plant Physiol., 100:225 (1992).
17. Blochlinger & Diggelmann, Mol Cell Biol, 4:2929 (1984).
18. Bol et al., Ann. Rev. Phytopath., 28:113 (1990).
19. Bouchez et al., EMBO J., 8:4197 (1989).
20. Bourouis et al., EMBO J., 2:1099 (1983).
21. Bowler et al., Ann. Rev. Plant Physiol., 43:83 (1992).
22. Branson and Guss, Proc. North Central Branch Entomological Society of America (1972).
23. Broakgert et al., Science, 245:110 (1989).
24. Bustos M M et al. (1989) Plant Gell 1:839-853
25. Byrne et al. Plant Cell Tissue and Organ Culture, 8:3 (1987).
26. Callis et al., Genes and Develop., 1:1183 (1987).
27. Campbell and Gowri, Plant Physiol., 92:1 (1990).
28. Campbell, W. C., ed Ivermectin and Abamectin, Springer-Verlag, New York, 1989.
29. Chee et al. Plant Physiol., 91:1212 (1989).
30. Chen and Winans (1991) J. Bacteriol. 173: 1139-1144
31. Christou et al. Proc. Natl. Acad. Sci USA, 86:7500 (1989).
32. Christou et al., Biotechnology, 9:957 (1991).
33. Christou et al., Plant Physiol., 87:671 (1988).
34. Chui et al. (1996) Curr Biol 6:325-330
35. Coe et al., In: Corn and Corn Improvement, Sprague et al. (eds.) pp. 81-258 (1988).
36. Corpet et al. Nucleic Acids Res., 16:10881 (1988).
37. Coxson et al., Biotropica, 24:121 (1992).
38. Crameri et al., Nature Biotech., 15:436 (1997).
39. Crameri et al., Nature, 391:288 (1998).
40. Crossway et al., BioTechniques, 4:320 (1986).
41. Cuozzo et al., Bio/Technology, 6:549 (1988).
42. Cutler et al, J. Plant Physiol., 135:351 (1989).
43. Czapla and Lang, J. Econ. Entomol., 83:2480 (1990).
44. Datta et al., Bio/Technology, 8:736 (1990).
45. Davies et al., Plant Physiol., 93:588 (1990).
46. Dayhoff et al., Atlas of Protein Sequence and Structure, Natl. Biomed. Res. Found., ashington, C. D. (1978).
47. De Blaere et al., Meth. Enzymol., 143:277 (1987).
48. De Block et al. Plant Physiol., 91:694 (1989).
49. De Block et al., EMBO Journal, 6:2513 (1987).
50. Deblaere et al. Nucl Acids Res 13:4777-4788 (1985)
51. Della-Cioppa et al. Bio/Technology 5:579-584 (1987)
52. Della-Cioppa et al., Plant Physiology, 84:965-968 (1987).
53. Dellaporta et al., in Chromosome Structure and Function, Plenum Press, 263-282 (1988).
54. Depicker et al., Plant Cell Reports, 7:63 (1988).
55. Dunn et al., Can. J. Plant Sci., 61:583 (1981).
56. Dure et al., Plant Mol. Biol., 12:475 (1989),
57. Ebinuma et al. Proc Natl Acad Sci USA 94:2117-2121 (2000a)
58. Ebinuma et al. Selection of Marker-free transgenic plants using the oncogenes (ipt, rot A, B, C) of *Agrobacterium* as selectable markers, In Molecular Biology of Woody Plants. Kluwer Academic Publishers (2000b)
59. Eichholtz et al. Somatic Cell and Molecular Genetics 13, 67-76 (1987)
60. Ellis et al., EMBO Journal, 6:3203 (1987).
61. Elroy-Stein et al., Proc. Natl. Acad. Sci. U.S.A., 86:6126 (1989).
62. English et al., Plant Cell, 8:179 (1996).
63. Erdmann et al., J. Gen. Microbiol., 138:363 (1992).
64. Erikson et al. Nat Biotechnol. 22(4):455-8 (2004)
65. Everett et al., Bio/Technology, 5:1201 (1987).
66. Fedoroff N V & Smith D L Plant J 3:273-289 (1993)
67. Fire A et al Nature 391:806-811 (1998)
68. Fitzpatrick, Gen. Engineering News, 22:7 (1993).
69. Fraley et al. Proc Natl Acad Sci USA 80:4803 (1983)
70. Fromm et al., Bio/Technology, 8:833 (1990).
71. Fromm et al., Nature (London), 319:791 (1986).
72. Galbiati et al. Funct. Integr Genozides 2000, 20 1:25-34
73. Gallie et al. Nucl Acids Res 15:8693-8711 (1987)
74. Gallie et al., Nucleic Acids Res., 15:3257 (1987).
75. Gallie et al., The Plant Cell, 1:301 (1989).
76. Gan et al., Science, 270:1986 (1995).
77. Gatehouse et al., J. Sci. Food Agric., 35:373 (1984).
78. Gelfand, eds., PCR Strategies Academic Press, New York (1995).
79. Gelvin et al., Plant Molecular Biology Manual, (1990).
80. Gleave et al. Plant Mol Biol. 40(2):223-35 (1999)
81. Gordon-Kamm et al., Plant Cell, 2:603 (1990).
82. Goring et al, PNAS, 88:1770 (1991).
83. Gruber, et al., Vectors for Plant Transformation, in: Methods in Plant Molecular Biology & Biotechnology" in Glich et al., (Eds. pp. 89-119, CRC Press, 1993).
84. Guerineau et al., Mol. Gen. Genet., 262:141 (1991).
85. Guerrero et al., Plant Mol. Biol., 15:11 (1990).
86. Gupta et al., PNAS, 90:1629 (1993).
87. Haines and Higgins (eds.), Nucleic Acid Hybridization, IRL Press, Oxford, U.K.
88. Hajdukiewicz et al. Plant Mol Biol 25:989-994 (1994)
89. Hammock et al., Nature, 344:458 (1990).
90. Hansen et al. Proc. Natl. Acad. Sci. USA 91:7603-7607 (1994)
91. Hayford et al. Plant Physiol. 86:1216 (1988)
92. Hemenway et al., EMBO Journal, 7:1273 (1988).
93. Henikoff & Henikoff, Proc. Natl. Acad. Sci. USA, 89:10915 (1989).
94. Hiei et al. Plant J 6: 271-282 (1994)
95. Higgins et al., Gene, 73:237 (1988).
96. Higo et al. (1999) Nucl Acids Res 27(1): 297-300
97. Hilder et al., Nature, 330:160 (1987).
98. Hille et al. Plant Mol. Biol. 7:171 (1986)
99. Hinchee et al. Bio/Technology 6:915 (1988).
100. Hoekema et al. (1983) Nature 303:179-181
101. Hoekema, In: The Binary Plant Vector System. Offset-drukkerij Kanters B. V.; Alblasserdam (1985).
102. Hood et al. J Bacteriol 168:1291-1301 (1986)
103. Huang et al., CABIOS, 8:155 (1992).
104. Ikeda et al., J. Bacteriol., 169:5612 (1987).
105. Ikuta et al., Biotech., 8:241 (1990).
106. Ingelbrecht et al., Plant Cell, 1:671 (1989).
107. Innis and Gelfand, eds., PCR Methods Manual (Academic Press, New York) (1999).
108. Innis et al., eds., PCR Protocols: A Guide to Methods and Applications (Academic Press, New York (1995).
109. Innis et al., PCR Protocols: A Guide to Methods and Applications, Academic Press, Inc., San Diego, Calif. (1990).

110. Ishida Y et al. Nature Biotech 745-750 (1996)
111. Jefferson et al. EMBO J 6:3901-3907 (1987)
112. Jefferson et al. Plant Mol Biol Rep 5:387-405 (1987)
113. Jenes B et al. Techniques for Gene Transfer, in: Recombinant Plants, Vol. 1, Engineering and Utilization, edited by S D Kung and R Wu, Academic Press, pp. 128-143 (1993)
114. Jobling et al., Nature, 325:622 (1987).
115. Johnson et al., PNAS USA, 86:9871 (1989)
116. Jones et al. Mol. Gen. Genet., 210:86 (1987)
117. Joshi et al., Nucleic Acid Res., 15:9627 (1987).
118. Kaasen et al., J. Bacteriol., 174:889 (1992).
119. Karlin and Altschul, Proc. Natl. Acad Sci. USA, 87:2264 (1990).
120. Karlin and Altschul, Proc. Natl. Acad. Sci. USA, 90:5873 (1993),
121. Karsten et al., Botanica Marina, 35:11 (1992).
122. Katz et al., J. Gen. Microbiol., 129:2703 (1983).
123. Keller et al., EMBO Journal, 8:1309 (1989).
124. Keller et al., Genes Dev., 3:1639 (1989).
125. Klapwijk et al. J. Bacteriol., 141, 128-136 (1980)
126. Klein et al., Bio/Technology, 6:559 (1988).
127. Klein et al., Plant Physiol., 91:440 (1988).
128. Klein et al., Proc. Natl. Acad. Sci. USA, 85:4305 (1988).
129. Knauf, et al., Genetic Analysis of Host Range Expression by *Agrobacterium* In: Molecular Genetics of the Bacteria-Plant Interaction, Puhler, A. ed., Springer-Verlag, New York, 1983.
130. Koncz & Schell Mol Gen Genet 204:383-396 (1986)
131. Koprek T et al. Plant J 19(6): 719-726 (1999)
132. Koster and Leopold, Plant Physiol., 88:829 (1988).
133. Koziel et al., Biotechnology, 11:194 (1993).
134. Kunkel et al., Methods in Enzymol., 154:367 (1987).
135. Kunkel, Proc. Natl. Acad. Sci. USA, 82:488 (1985).
136. Lam E und Chua N H, J Biol Chem; 266(26):17131-17135 (1991)
137. Laufs et al., PNAS, 87:7752 (1990).
138. Lawton et al., Mol. Cell Biol., 7:335 (1987).
139. Lee and Saier, J. Bacteriol., 153 (1982).
140. Leffel et al. Biotechniques 23(5):912-8 (1997)
141. Lescot et al. Nucleic Acids Res 30(1):325-7 (2002)
142. Levings, Science, 250:942 (1990).
143. Li et al. Plant Mol Biol 20:1037-1048 (1992)
144. Lindsey et al., Transgenic Research, 2:3347 (1993).
145. Liu et al., Plant J. 8, 457-463 (1995)
146. Lommel et al., Virology, 181:382 (1991).
147. Loomis et al., J. Expt. Zool., 252:9 (1989).
148. Lorz et al., Mot. Gen. Genet., 199:178 (1985).
149. Ma et al., Nature, 334:631 (1988).
150. Macejak et al., Nature, 353:90 (1991).
151. Maki et al., Methods in Plant Molecular Biology & Biotechnology, Glich et al., 67-88 CRC Press, (1993).
152. Maniatis T, Fritsch E F, and Sambrook J Molecular Cloning: A Laboratory Manual, Cold Spring Harbor Laboratory, Cold Spring Harbor (N.Y.), (1989)
153. Mariani et al, Nature, 347:737 (1990).
154. Matzke et al. (2000) Plant Mol Biol 43:401-415;
155. McBride et al., PNAS USA, 91:7301 (1994).
156. McCabe et al., Bio/Technology, 6:923 (1988).
157. Meinkoth and Wahl, Anal. Biochem., 138:267 (1984).
158. Messing and Vierra, Gene, 19:259 (1982).
159. Michael et al., J. Mol. Biol., 26: 585 (1990). (im Text steht: Michael et al. 1994)
160. Millar et al. Plant Mol Biol Rep 10:324-414 (1992)
161. Mogen et al., Plant Cell, 2:1261 (1990).
162. Moore et al., J. Mot. Biol., 272:336 (1997).
163. Mozo & Hooykaas Plant Mol. Biol. 16:917-918 (1991)
164. Mundy and Chua, EMBO J., 7:2279 (1988).
165. Munroe et al., Gene, 91:151 (1990).
166. Murakami et al., Mot. Gen. Genet., 205:42 (1986).
167. Murata et al., FEBS Lett., 296:187 (1992).
168. Murdock et al., Phytochemistry, 29:85 (1990).
169. Murray et al., Nucleic Acids Res., 17:477 (1989).
170. Myers and Miller, CABIOS, 4:11 (1988).
171. Naested H Plant J 18:571-576 (1999)
172. Napoli et al., Plant Cell, 2:279 (1990).
173. Needleman and Wunsch, J. Mot. Biol., 48:443-453 (1970).
174. Nehra et al. Plant J. 5:265-297 (1994)
175. Niedz et al., Plant Cell Reports, 14:403 (1995).
176. Odell et al., Mol. Gen. Genet, 113:369 (1990).
177. Odell et al., Nature, 313:810 (1985).
178. Ohtsuka et al., J. Biol. Chem., 260:2605 (1985)
179. Olhoft et al. Plant Cell Rep 20: 706-711 (2001)
180. Ow et al., Science, 234:856 (1986).
181. Pacciotti et al., Bio/Technology, 3:241 (1985).
182. Park et al., J. Plant Biol., 38:365 (1985).
183. Paszkowski et al., EMBO J., 3:2717 (1984).
184. Pearson and Lipman, Proc. Natl. Acad. Sci., 85:2444 (1988).
185. Pearson et al., Meth. Mol. Biol., 24:307 (1994).
186. Perera R J et al. Plant Mol. Biol 23(4): 793-799 (1993)
187. Perlak et al., Proc. Natl. Acad. Sci. USA, 88:3324 (1991).
188. Phillips et al., In Corn & Corn Improvement, 3rd Edition 10 Sprague et al. (Eds. pp. 345-387)(1988).
189. Phi-Van et al., Mol. Cell. Biol., 10:2302 (1990).
190. Piatkowski et al., Plant Physiol., 94:1682 (1990).
191. Potrykus et al., Mol. Gen. Genet., 199:183 (1985).
192. Potrykus, Trends Biotech., 7:269 (1989).
193. Prasher et al., Biochem. Biophys. Res. Comm., 126: 1259 (1985).
194. Proudfoot, Cell, 64:671 (1991).
195. Reed et al., J. Gen. Microbiol., 130:1 (1984).
196. Riggs et al., Proc. Natl. Acad. Sci. USA, 83:5602 (1986).
197. Rossolini et al., Mol. Cell. Probes, 8:91 (1994).
198. Ruiz, Plant Cell, 10:937 (1998).
199. Sambrook et al., Molecular Cloning: A Laboratory Manual (2d ed., Cold Spring Harbor Laboratory Press, Plainview, N.Y.) (1989).
200. Sanfacon et al., Genes Dev., 5:141 (1991).
201. Sanford et al., Particulate Science and Technology, 5:27 (1987).
202. Scheeren-Groot et al. J. Bacteriol 176: 6418-6426 (1994)
203. Schenborn and Groskreutz Mol Biotechnol 13(1): 29-44 (1999)
204. Schlaman and Hooykaas Plant J 11:1377-1385 (1997)
205. Schoffl F et al. (1989) Mol Gen Genetics 217(2-3): 246-53
206. Shagan et al., Plant Physiol., 101:1397 (1993).
207. Shah et al. Science 233: 478 (1986)
208. Shapiro, Mobile Genetic Elements, Academic Press, N.Y. (1983).
209. Shimamoto et al., Nature, 338:274 (1989).
210. Silhavy T J, Berman M L, and Enquist L W Experiments with Gene Fusions, Cold Spring Harbor Laboratory Press, Cold Spring Harbor (N.Y.), (1984)
211. Skuzeski et al., Plant Molec. Biol. 15: 65-79 (1990).
212. Smith et al., Adv. Appl. Math., 2:482 (1981).
213. Smith et al., Mol. Gen. Genet., 224:447 (1990).

214. Spencer et al., Theor. Appl. Genet, 79:625 (1990). Spencer 1992 Referenz fehit
215. Stalker et al., Science, 242:419 (1988).
216. Staub et al., EMBO J., 12:601 (1993).
217. Staub et al., Plant Cell, 4:39 (1992).
218. Steifel et al., The Plant Cell, 2:785 (1990).
219. Stemmer, Nature, 370:389 (1994).
220. Stemmer, Proc. Natl. Acad. Sci. USA, 91:10747 (1994).
221. Stief et al., Nature, 341:343 (1989).
222. Stougaard Plant J 3:755-761 (1993)
223. Sukhapinda et al., Plant Mol. Biol., 8:209 (1987).
224. Sundaresan et al. Gene Develop 9: 1797-1810 (1995)
225. Sutcliffe, PNAS USA, 75:3737 (1978).
226. Svab et al., Plant Mol. Biol. 14:197 (1990)
227. Svab et al., Proc. Natl. Acad. Sci. USA, 87:8526 (1990).
228. Svab et al., Proc. Natl. Acad. Sci. USA, 90:913 (1993).
229. Tarczynski et al., PNAS USA, 89:2600 (1992).
230. Thillet et al., J. Biol. Chem., 263:12500 (1988).
231. Tijssen, Laboratory Techniques in Biochemistry and Molecular Biology-Hybridization with Nucleic Acid Probes, Elsevier, N.Y. (1993).
232. Tomes et al., Plant Cell, Tissue and Organ Culture: Fundamental Methods, Springer Verlag, Berlin (1995).
233. Tomic et al., NAR, 12:1656 (1990).
234. Turner et al., Molecular Biotechnology, 3:225 (1995).
235. Twell et al., Plant Physiol., 91:1270 (1989).
236. Ugaki et al., Nucl. Acids Res., 19:371 (1991).
237. Ulmasov et al., Plant Mol. Biol., 35:417 (1997).
238. Upender et al., Biotechniques, 18:29 (1995).
239. van der Krol et al., Plant Cell, 2:291 (1990).
240. Vanden Eizen et al., Plant Mol Biol. 5:299 (1985)
241. Vasil et al. Bio/Technology, 10:667-674 (1992)
242. Vasil et al. Bio/Technology, 11:1153-1158 (1993)
243. Vasil et al., Mol. Microbiol., 3:371 (1989).
244. Vasil et al., Plant Physiol., 91:1575 (1989).
245. Vernon and Bohnert, EMBO J., 11:2077 (1992).
246. Walker and Gaastra, eds., Techniques in Molecular Biology, MacMillan Publishing Company, New York (1983).
247. Wan & Lemaux (1994) Plant Physiol., 104:3748
248. Wang et al., Mol. Cell. Biol., 12:3399 (1992).
249. Waterman, M. S. Introduction to Computational Biology: Maps, sequences and genomes. Chapman & Hall. London (1995).
250. Watrud et al., in Engineered Organisms and the Environment (1985).
251. Watson et al. J. Bacteriol 123, 255-264 (1975)
252. Watson et al., Corn: Chemistry and Technology (1987).
253. Weeks et al. Plant Physiol 102:1077-1084 (1993)
254. Weissinger et al., Annual Rev. Genet., 22:421 (1988).
255. White et al, Nucl Acids Res, 18, 1062 (1990).
256. Wingender E et al. Nucleic Acids Res 29(1):281-3 (2001)
257. Wolter et al., EMBO Journal, 11:4685 (1992).
258. Wyn-Jones and Storey, Physiology and Biochemistry of Drought Resistance in Plants, Paleg et al. (eds.), pp. 171-204 (1981).
259. Yamaguchi-Shinozaki et al., Plant Cell Physiol., 33:217 (1992).
260. Zhang et al., Proc. Natl. Acad. Sci. USA, 94:4504 (1997).
261. Zukowsky et al., PNAS USA, 80:1101 (1983).

All publications, patents and patent applications are incorporated herein by reference. While in the foregoing specification this invention has been described in relation to certain preferred embodiments thereof and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. An expression cassette for regulating root-preferential or root-specific expression in a plant comprising:

i) at least one transcription regulating nucleotide sequence of a plant gene, and ii) at least one nucleic acid sequence which is operably linked to and heterologous in relation to said transcription regulating nucleotide sequence;

wherein the plant gene comprises the nucleic acid sequence as set forth in SEQ ID NO: 12 and wherein the transcription regulating nucleotide sequence has root-preferential or root-specific expression activity.

2. The expression cassette of claim 1, wherein expression of the nucleic acid sequence results in expression of a protein, or expression of an antisense RNA, a sense RNA, or a double-stranded RNA.

3. The expression cassette of claim 1, wherein expression of the nucleic acid sequence confers to the plant an agronomically valuable trait.

4. A transgenic plant cell or microorganism comprising the expression cassette of claim 1.

5. A transgenic plant comprising the expression cassette of claim 1.

6. An expression cassette for regulating root-preferential or root-specific expression in a plant comprising:

i) at least one transcription regulating nucleotide sequence; and ii) at least one nucleic acid sequence which is operably linked to and heterologous in relation to said transcription regulating nucleotide sequence;

wherein the transcription regulating nucleotide sequence comprises the nucleotide sequence of SEQ ID NO: 7, 8, 9, 10, or 11, or a nucleotide sequence having at least 99% identity to the nucleotide sequence of SEQ ID NO: 7, 8, 9, 10, or 11, and wherein the transcription regulating nucleotide sequence has root-preferential or root-specific expression activity.

7. The expression cassette of claim 6 wherein expression of the nucleic acid sequence results in expression of a protein, or expression of an antisense RNA, a sense RNA, or a double-stranded RNA.

8. The expression cassette of claim 6, wherein expression of the nucleic acid sequence confers to the plant an agronomically valuable trait.

9. A transgenic plant cell or microorganism comprising the expression cassette of claim 6.

10. A transgenic plant comprising the expression cassette of claim 6.

11. An expression cassette for regulating root-preferential or root-specific expression in a plant comprising:

i) at least one transcription regulating nucleotide sequence; and ii) at least one nucleic acid sequence which is operably linked to and heterologous in relation to said transcription regulating nucleotide sequence;

wherein the transcription regulating nucleotide sequence comprises a fragment of SEQ ID NO: 7, 8, 9, 10, or 11, and wherein the fragment has root-preferential or root-specific expression activity.

12. The expression cassette of claim 11 wherein expression of the nucleic acid sequence results in expression of a protein, or expression of an antisense RNA, a sense RNA, or a double-stranded RNA.

13. The expression cassette of claim 11, wherein expression of the nucleic acid sequence confers to the plant an agronomically valuable trait.

14. A transgenic plant cell or microorganism comprising the expression cassette of claim 11.

15. A transgenic plant comprising the expression cassette of claim 11.

* * * * *